(12) United States Patent
Robl et al.

(10) Patent No.: US 7,807,863 B2
(45) Date of Patent: *Oct. 5, 2010

(54) TRANSGENIC BOVINE HAVING REDUCED PRION PROTEIN ACTIVITY AND USES THEREOF

(75) Inventors: James M. Robl, Brandon, SD (US); Yoshimi Kuroiwa, Sioux Falls, SD (US); Kazuma Tomizuka, Takasaki (JP); Isao Ishida, Isehara (JP)

(73) Assignee: Kyowa Hakko Kirin Co., Ltd., Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 12/231,873

(22) Filed: Sep. 5, 2008

(65) Prior Publication Data
US 2009/0165154 A1    Jun. 25, 2009

Related U.S. Application Data

(63) Continuation of application No. 10/705,519, filed on Nov. 10, 2003, now Pat. No. 7,429,690.

(60) Provisional application No. 60/425,056, filed on Nov. 8, 2002, provisional application No. 60/506,901, filed on Sep. 26, 2003.

(51) Int. Cl.
A01K 67/027   (2006.01)
C12N 15/00    (2006.01)
C12N 5/00     (2006.01)

(52) U.S. Cl. .................... 800/15; 800/24; 435/325

(58) Field of Classification Search ........... None
See application file for complete search history.

(56) References Cited

U.S. PATENT DOCUMENTS

| | | | |
|---|---|---|---|
| 4,797,356 A | 1/1989 | Brandt et al. |
| 4,847,081 A | 7/1989 | Rice |
| 4,873,316 A | 10/1989 | Meade et al. |
| 4,959,317 A | 9/1990 | Sauer |
| 4,994,384 A | 2/1991 | Prather et al. |
| 5,021,244 A | 6/1991 | Spaulding |

(Continued)

FOREIGN PATENT DOCUMENTS

EP    0773288 A2    5/1997

(Continued)

OTHER PUBLICATIONS

Muramoto et al. Heritable Disorder Resembling Neuronal Storage Disease in in Mice Expressing Prion Protein with the Deletion of an Alpha-Helix. Nature Med. 1997, vol. 3, pp. 750-755.*

(Continued)

*Primary Examiner*—Deborah Crouch
(74) *Attorney, Agent, or Firm*—Clark & Elbing LLP

(57) ABSTRACT

The invention provides cloned transgenic ungulates (e.g., bovines) in which prion protein activity is reduced by one or more genetically engineered mutations. Desirably, these transgenic bovines are also genetically modified to express xenogenous (e.g., human) antibodies. Because of their resistance to prion-related diseases such as bovine spongiform encephalopy (also known as mad cow disease), these bovines are a safer source of human antibodies for pharmaceutical uses and a safer source of agricultural products.

14 Claims, 74 Drawing Sheets

U.S. PATENT DOCUMENTS

| | | |
|---|---|---|
| 5,057,420 A | 10/1991 | Massey |
| 5,096,822 A | 3/1992 | Rosenkrans, Jr. et al. |
| 5,160,312 A | 11/1992 | Voelkel |
| 5,175,384 A | 12/1992 | Krimpenfort et al. |
| 5,213,979 A | 5/1993 | First et al. |
| 5,320,952 A | 6/1994 | Deutch et al. |
| 5,346,990 A | 9/1994 | Spaulding |
| 5,374,544 A | 12/1994 | Schwartz et al. |
| 5,434,066 A | 7/1995 | Bebee et al. |
| 5,434,340 A | 7/1995 | Krimpenfort et al. |
| 5,453,366 A | 9/1995 | Sims et al. |
| 5,464,764 A | 11/1995 | Capecchi et al. |
| 5,470,560 A | 11/1995 | Martin, Jr. |
| 5,482,856 A | 1/1996 | Fell, Jr. et al. |
| 5,487,992 A | 1/1996 | Capecchi et al. |
| 5,496,720 A | 3/1996 | Susko-Parrish et al. |
| 5,527,674 A | 6/1996 | Guerra et al. |
| 5,545,806 A | 8/1996 | Lonberg et al. |
| 5,545,807 A | 8/1996 | Surani et al. |
| 5,565,186 A | 10/1996 | Prusiner et al. |
| 5,565,350 A | 10/1996 | Kmiec |
| 5,565,362 A | 10/1996 | Rosen |
| 5,569,825 A | 10/1996 | Lonberg et al. |
| 5,583,016 A | 12/1996 | Villeponteau et al. |
| 5,591,669 A | 1/1997 | Krimpenfort et al. |
| 5,612,205 A | 3/1997 | Kay et al. |
| 5,614,396 A | 3/1997 | Bradley et al. |
| 5,618,686 A | 4/1997 | Kojima et al. |
| 5,625,126 A | 4/1997 | Lonberg et al. |
| 5,627,059 A | 5/1997 | Capecchi et al. |
| 5,631,153 A | 5/1997 | Capecchi et al. |
| 5,633,076 A | 5/1997 | DeBoer et al. |
| 5,633,425 A | 5/1997 | Lonberg et al. |
| 5,639,457 A | 6/1997 | Brem et al. |
| 5,652,373 A | 7/1997 | Reisner |
| 5,654,182 A | 8/1997 | Wahl et al. |
| 5,660,997 A | 8/1997 | Spaulding |
| 5,661,016 A | 8/1997 | Lonberg et al. |
| 5,677,177 A | 10/1997 | Wahl et al. |
| 5,679,523 A | 10/1997 | Li et al. |
| 5,695,977 A | 12/1997 | Jurka |
| 5,698,763 A | 12/1997 | Weissmann et al. |
| 5,721,367 A | 2/1998 | Kay et al. |
| 5,733,730 A | 3/1998 | De Lange |
| 5,741,957 A | 4/1998 | Deboer et al. |
| 5,750,172 A | 5/1998 | Meade et al. |
| 5,756,325 A | 5/1998 | Kmiec |
| 5,763,240 A | 6/1998 | Zarling et al. |
| 5,770,422 A | 6/1998 | Collins |
| 5,770,429 A | 6/1998 | Lonberg et al. |
| 5,776,744 A | 7/1998 | Glazer et al. |
| 5,780,009 A | 7/1998 | Karatzas et al. |
| 5,780,296 A | 7/1998 | Holloman et al. |
| 5,789,215 A | 8/1998 | Berns et al. |
| 5,789,650 A | 8/1998 | Lonberg et al. |
| 5,789,655 A | 8/1998 | Prusiner et al. |
| 5,801,030 A | 9/1998 | McVey et al. |
| 5,814,318 A | 9/1998 | Lonberg et al. |
| 5,821,117 A | 10/1998 | Sandrin et al. |
| 5,827,690 A | 10/1998 | Meade et al. |
| 5,830,698 A | 11/1998 | Reff et al. |
| 5,837,857 A | 11/1998 | Villeponteau et al. |
| 5,843,643 A | 12/1998 | Ratner |
| 5,843,754 A | 12/1998 | Susko-Parrish et al. |
| 5,849,991 A | 12/1998 | d'Apice et al. |
| 5,849,992 A | 12/1998 | Meade et al. |
| 5,874,299 A | 2/1999 | Lonberg et al. |
| 5,876,979 A | 3/1999 | Andrews et al. |
| 5,877,397 A | 3/1999 | Lonberg et al. |
| 5,891,698 A | 4/1999 | Prieto et al. |
| 5,945,577 A | 8/1999 | Stice et al. |
| 5,952,222 A | 9/1999 | Rosenkrans, Jr. et al. |
| 6,011,197 A | 1/2000 | Strelchenko et al. |
| 6,023,010 A | 2/2000 | Krimpenfort et al. |
| 6,030,833 A | 2/2000 | Seebach et al. |
| 6,054,632 A | 4/2000 | Reid |
| 6,066,719 A | 5/2000 | Zapata |
| 6,074,853 A | 6/2000 | Pati et al. |
| 6,077,710 A | 6/2000 | Susko-Parrish et al. |
| 6,091,001 A | 7/2000 | Jakobovits et al. |
| 6,133,503 A | 10/2000 | Scheffler |
| 6,147,276 A | 11/2000 | Campbell et al. |
| 6,153,428 A | 11/2000 | Gustafsson et al. |
| 6,166,288 A | 12/2000 | Diamond et al. |
| 6,183,993 B1 | 2/2001 | Boyce et al. |
| 6,194,202 B1 | 2/2001 | Susko-Parrish et al. |
| 6,204,061 B1 | 3/2001 | Capecchi et al. |
| 6,204,431 B1 | 3/2001 | Prieto et al. |
| 6,252,133 B1 | 6/2001 | Campbell et al. |
| 6,258,998 B1 | 7/2001 | Damiani et al. |
| 6,271,436 B1 | 8/2001 | Piedrahita et al. |
| 6,300,129 B1 | 10/2001 | Lonberg et al. |
| 6,395,958 B1 | 5/2002 | Strelchenko et al. |
| 6,753,457 B2 | 6/2004 | Wangh et al. |
| 7,074,983 B2 | 7/2006 | Robl et al. |
| 7,253,334 B2 | 8/2007 | Collas et al. |
| 7,414,170 B2 | 8/2008 | Robl et al. |
| 7,420,099 B2 | 9/2008 | Robl et al. |
| 2002/0001842 A1 | 1/2002 | Chapman |
| 2002/0012660 A1 | 1/2002 | Colman et al. |
| 2002/0069423 A1* | 6/2002 | Good et al. ............ 800/15 |
| 2002/0108132 A1 | 8/2002 | Rapp |
| 2002/0194635 A1 | 12/2002 | Dunne et al. |
| 2003/0046722 A1* | 3/2003 | Collas et al. ........... 800/21 |
| 2004/0068760 A1 | 4/2004 | Robl et al. |
| 2004/0131620 A1 | 7/2004 | Maeda et al. |
| 2005/0097627 A1 | 5/2005 | Robl et al. |
| 2005/0183145 A1 | 8/2005 | Goldsby et al. |
| 2006/0041945 A1 | 2/2006 | Robl et al. |
| 2006/0117394 A1 | 6/2006 | Robl et al. |
| 2006/0117395 A1 | 6/2006 | Robl et al. |
| 2006/0130157 A1 | 6/2006 | Wells et al. |

FOREIGN PATENT DOCUMENTS

| | | |
|---|---|---|
| EP | 0546073 B1 | 9/1997 |
| EP | 0843961 A1 | 5/1998 |
| EP | 1106061 A1 | 6/2001 |
| EP | 1563084 A2 | 8/2005 |
| WO | WO 92/03918 A1 | 3/1992 |
| WO | WO 93/10227 A1 | 5/1993 |
| WO | WO 94/02602 A1 | 2/1994 |
| WO | WO 95/23868 A1 | 9/1995 |
| WO | WO 95/33828 A1 | 12/1995 |
| WO | WO 96/33735 A1 | 10/1996 |
| WO | WO 97/07668 A1 | 3/1997 |
| WO | WO 97/07669 A1 | 3/1997 |
| WO | WO 97/07671 A1 | 3/1997 |
| WO | WO 97/13852 A1 | 4/1997 |
| WO | WO 98/14593 A2 | 4/1998 |
| WO | WO 98/24884 A1 | 6/1998 |
| WO | WO 98/24893 A2 | 6/1998 |
| WO | WO 98/30683 A2 | 7/1998 |
| WO | WO 98/37183 A1 | 8/1998 |
| WO | WO 98/39416 A1 | 9/1998 |
| WO | WO 99/21415 A1 | 5/1999 |
| WO | WO 99/60108 A2 | 11/1999 |
| WO | WO 00/10383 A1 | 3/2000 |
| WO | WO 00/42174 A1 | 7/2000 |
| WO | WO 00/46251 A2 | 8/2000 |
| WO | WO 00/51424 A2 | 9/2000 |
| WO | WO 00/67568 A1 | 11/2000 |
| WO | WO 00/67569 A1 | 11/2000 |
| WO | WO 00/74477 A1 | 12/2000 |

| WO | WO 01/23541 A2 | 4/2001 |
| WO | WO 01/30992 A2 | 5/2001 |
| WO | WO 01/35735 A1 | 5/2001 |
| WO | WO 01/73107 A1 | 10/2001 |
| WO | WO 02/12437 A2 | 2/2002 |
| WO | WO 02/051997 A1 | 7/2002 |
| WO | WO 02/070648 A2 | 9/2002 |
| WO | WO 02/079416 A2 | 10/2002 |
| WO | WO 02/079418 A2 | 10/2002 |
| WO | WO 2004/044156 A2 | 5/2004 |

OTHER PUBLICATIONS

Aguzzi et al., "The Prion's Perplexing Persistence," *Nature* 392:763-764, 1998.

Ahearn et al., "Disruption of the Cr2 Locus Results in a Reduction in B-1a Cells and in an Impaired B Cell Response to T-Dependent Antigen," *Immunity* 4:251-262, 1996.

Baguisi et al., "Production of Goats by Somatic Cell Nuclear Transfer," *Nature Biotechnol.* 17:456-461, 1999.

Bondioli et al., "Cloned Pigs Generated from Cultured Skin Fibroblasts Derived from a H-Transferase Transgenic Boar," *Mol. Reproduct. Develop.* 60:189-195, 2001.

Bosch et al., "Isolation, Characterization, Gene Modification, and Nuclear Reprogramming of Porcine Mesenchymal Stem Cells," *Biol. Reproduct.* 74:46-57, 2006.

Burke et al., "A Cell Free System to Study Reassembly of the Nuclear Envelope at the End of Mitosis," *Cell* 44:639-652, 1986.

Campbell, "Nuclear Transfer in Farm Animal Species," *Sem. Cell Develop. Biol.* 10:245-252, 1999.

Cibelli et al., "Bovine Chimeric Offspring Produced by Transgenic Embryonic Stem Cells Generated From Somatic Cell Nuclear Transfer Embryos," *Theriogenology* 49:236, 1998.

Cibelli et al., "Cloned Transgenic Calves Produced from Nonquiescent Fetal Fibroblasts," *Science* 280:1256-1258, 1998.

Clark et al., "Gene Targeting in Livestock: A Preview," *Transgenic Res.* 9:263-275, 2000.

Clark et al., "A Future for Transgenic Livestock," *Nature Rev. Genet.* 4:825-833, 2003.

Co et al., "Generation of Transgenic Mice and Germline Transmission of a Mammalian Artificial Chromosome Introduced into Embryos by Pronuclear Microinjection," *Chromosome Res.* 8:183-191, 2000.

Collas et al., "Lipophilic Organizing Structures of Sperm Nuclei Target Membrane Vesicle Binding and Are Incorporated Into the Nuclear Envelope," *Dev. Biol.* 169:123-135, 1995.

Collas, "Sequential PKC- and Cdc2-Mediated Phosphorylation Events Elicit Zebrafish Nuclear Envelope Disassembly," *J. Cell Sci.* 112:977-987, 1999.

Collas et al., "The A-Kinase Anchoring Protein, AKAP95, is a Multivalent Protein with a Key Role in Chromatin Condensation at Mitosis," *J. Cell Biol.* 147:1167-1179, 1999.

Cubizolles et al., "pEg7, A New Xenopus Protein Required for Mitotic Chromosome Condensation in Egg Extracts," *J. Cell Biol.* 143:1437-1446, 1998.

Dai et al., "Targeted Disruption of the α1,3-Galactosyltransferase Gene in Cloned Pigs," *Nature Biotechnol.* 20:251-255, 2002.

Denning et al., "Deletion of the α(1,3)Galactosyl Transferase (*GGTA1*) Gene and the Prion Protein (*PrP*) Gene in Sheep," *Nature Biotechnol.* 19:559-562, 2001.

Denning et al., "Gene Targeting in Primary Fetal Fibroblasts from Sheep and Pig," *Cloning Stem Cells* 3:221-231, 2001.

Echelard et al., "Toward a New Cash Cow: Cloned Cattle Engineered to Carry an Artificial Chromosome Encoding Human Immunoglobulin Genes are a Significant Leap Toward the Production of Safer and More Potent Therapeutic Antibodies," *Nature Biotechnol.* 20:881-882, 2002.

Ehrenstein et al., "Targeted Gene Disruption Reveals a Role for Natural Secretory IgM in the Maturation of the Primary Immune Response," *Proc. Natl. Acad. Sci. U.S.A.* 95:10089-10093, 1998.

Erlandsson et al., "Mice with an Inactivated Joining Chain Locus have Perturbed IgM Secretion," *Eur. J. Immunol.* 28:2355-2365, 1998.

Eyestone et al., "Nuclear Transfer from Somatic Cells: Applications in Farm Animal Species," *J. Reproduct. Fertility* 54:489-497, 1999.

Farrugia et al., "Intravenous Immunoglobulin: Regulatory Perspectives on Use and Supply," *Trans. Med.* 11:63-74, 2001.

Fishwild et al., "High-Avidity Human IgGk Monoclonal Antibodies from a Novel Strain of Minilocus Transgenic Mice," *Nature Biotechnol.* 14:845-851, 1996.

Goldman et al., "Enhanced Human Cell Engraftment in Mice Deficient in RAG2 and the Common Cytokine Receptor Gamma Chain," *Br. J. Haematol.* 103:335-342, 1998.

Greiner et al., "SCID Mouse Models of Human Stem Cell Engraftment," *Stem Cell* 16:166-177, 1998.

Griffiths et al., "Current Concepts of PLP and Its Role in the Nervous Sytem," *Microscopy Res. Tech.* 41:344-358, 1998.

Grimes et al., "Engineering Mammalian Chromosomes," *Human Mol. Genet.* 7:1635-1640, 1998.

Guidos et al., "Development of CD4+CD8+ Thymocytes in RAG-Deficient Mice Through a T Cell Receptor β Chain-Independent Pathway," *J. Exp. Med.* 181:1187-1195, 1995.

Hamers-Casterman et al., "Naturally Occurring Antibodies Devoid of Light Chains," *Nature* 363:446-448, 1993.

Hyun et al., "Production of Nuclear Transfer-Derived Piglets Using Porcine Fetal Fibroblasts Transfected with the Enhanced Green Fluorescent Protein," *Biol. Reproduct.* 69:1060-1068, 2003.

Ishida et al., "Production of a Diverse Repertoire of Human Antibodies in Genetically Engineered Mice," *Microbiol. Immunol.* 42:143-150, 1998.

Ishida et al., "Production of Human Monoclonal and Polyclonal Antibodies in Transchromo Animals," *Clon. Stem Cells* 4:91-102, 2002.

Jonak et al., "Manipulation of Human B Cells to Confer Immortality," *Hum. Antibodies Hybridomonas* 3:177-185, 1992.

Joziasse et al., "Bovine Alpha 1→3-Galactosyltransferase: Isolation and Characterization of a cDNA Clone. Identification of Homologous Sequences in Human Genomic DNA," *J. Biol. Chem.* 264:14290-14297, 1989.

Joziasse et al., "Characterization of an α1→3-Galactosyltransferase Homologue on Human Chromosome 12 that is organized as a Processed Pseudogene," *J. Biol. Chem.* 266:6991-6998, 1991.

Joziasse et al., "Xenotransplantation: The Importance of the Galα1,3Gal Epitope in Hyperacute Vascular Rejection," *Biochim. Biophys. Acta* 1455:403-418, 1999.

Kaushik et al., "Novel Insight Into Antibody Diversification from Cattle," *Vet. Immunol. Immunopathol.* 87:347-350, 2002.

Keefer et al., "Generation of Dwarf Goat (*Capra hircus*) Clones Following Nuclear Transfer with Transfected and Nontransfected Fetal Fibroblasts and In Vitro-Matured Oocytes," *Biol. Reproduct.* 64:849-856, 2001.

Kitamura et al., "A B Cell-Deficient Mouse by Targeted Disruption of the Membrane Exon of the Immunoglobulin Mu Chain Gene," *Nature* 350:423-426, 1991.

Knight et al., "Genetic Engineering of Bovine lg. Construction and Characterization of Hapten-Binding Bovine/Murine Chimeric IgE, IgA, IgG1, IgG2, and IgG3 Molecules," *J. Immunol.* 140:3654-3659, 1988.

Kuroiwa et al., "Manipulation of Human Minichromosomes to Carry Greater Than Megabase-Sized Chromosome Inserts," *Nature Biotechnol.* 18:1086-1090, 2000.

Kuroiwa et al., "Cloned Transchromosomic Calves Producing Human Immunoglobulin," *Nature Biotechnol.* 20:889-894, 2002.

Lai et al., "Production of α1,3-Galactosyltransferase Knockout Pigs by Nuclear Transfer Cloning," *Science* 295:1089-1092, 2002.

Lai et al., "Creating Genetically Modified Pigs by Using Nuclear Transfer," *Reproduct. Biol. Endocrinol.* 82:1-6, 2003.

Langford et al., "Production of Pigs Transgenic Human Regulators of Complement Activation Using YAC Technology," *Transplant. Proceed.* 28:862-863, 1996.

Lansford et al., "Ig Heavy Chain Class Switching in Rag-Deficient Mice," *Int. Immunol.* 10:325-332, 1998.

Leno et al., "Initiation of DNA Replication in Nuclei from Quiescent Cells Requires Permeabilization of the Nuclear Membrane," *J. Cell Biol.* 127:5-14, 1994.

Leonard et al., "Role of the Common Cytokine Receptor Gamma Chain in Cytokine Signaling and Lymphoid Development," *Immunol. Rev.* 148:97-114, 1995.

Lohka et al., "Formation In Vitro of Sperm Pronuclei and Mitotic Chromosomes Induced by Amphibian Ooplasmic Components," *Science* 220:719-721, 1983.

Lohka et al., "Induction of Nuclear Envelope Breakdown, Chromosome Condensation and Spindle Formation in Cell-Free Extracts," *J. Cell Biol.* 101:518-523, 1985.

Lonberg et al., "Human Antibodies from Transgenic Mice," *Intern. Rev. Immunol.* 13:65-93, 1995.

Loupart et al., "Differential Stability of a Human Mini-Chromosome in Mouse Cell Lines," *Chromosoma* 107:255-259, 1998.

Lucier et al., "Multiple Sites of Vλ Diversification in Cattle," *J. Immunol.* 161:5438-5444, 1998.

Martin et al., "Engraftment of Human Lymphocytes and Thyroid Tissue into Scid and Rag2-Deficient Mice: Absent Progression of Lymphocytic Infiltration," *J. Clin. Endocrinol. Metab.* 79:716-723, 1994.

Martinez Diaz et al., "Effect of Fusion/Activation Protocol on In Vitro Development of Porcine Nuclear Transfer Embryos Constructed with Foreign Gene Transfected Fetal Fibroblasts," *J. Vet. Med. Sci.* 65:989-994, 2003.

Mazurier et al., "A Novel Immunodeficient Mouse Model—Rag2 x Common Cytokine Receptor Gamma Chain Double Mutants—Requiring Exogenous Cytokine Administration for Human Hematopoietic Stem Cell Engraftment," *J. Interferon Cytokine Res.* 19:533-541, 1999.

Mendez et al., "Functional Transplant of Megabase Human Immunoglobulin Loci Recapitulates Human Antibody Response in Mice," *Nature Genet.* 15:146-156, 1997.

Miake-Lye et al., "Induction of Early Mitotic Events in a Cell-Free System," *Cell* 41:165-175, 1985.

Mocikat, "Improving the Expression of Chimeric Antibodies Following Homologous Recombination in Hybridoma Cells," *J. Immunol. Methods* 225:185-189, 1999.

Moens et al., "Defects in Heart and Lung Development in Compound Heterozygotes for Two Different Targeted Mutations at the N-Myc Locus," *Development* 119:485-499, 1993.

Muramoto et al., "Heritable Disorder Resembling Neuronal Storage Disease in Mice Expressing Prion Protein with Deletion of an Alpha Helix," *Nature Med.* 3:750-755, 1997.

Newport, "Nuclear Reconstitution In Vitro: Stages of Assembly Around Protein-Free DNA," *Cell* 48:205-217, 1987.

Niemann et al., "Transgenic Livestock: Premises and Promises," *Animal Reproduct. Sci.* 60-61:277-293, 2000.

Niemann et al., "Transgenic Farm Animals: Present and Future," *Rev. Schi. Tech. Off. Int. Spiz* 24:285-298, 2005.

Park et al., "Developmental Potential of Porcine Nuclear Transfer Embyros Derived from Transgenic Fetal Fibroblasts Infected with the Gene for the Green Fluorescent Protein: Comparison of Different Fusion/Activation Conditions," *Biol. Reproduct.* 65:1681-1685, 2001.

Parng et al., "Gene Conversion Contributes to Ig Light Chain Diversity in Cattle," *J. Immunol.* 157:5478-5486, 1996.

Pennisi et al., "Clones: A Hard Act to Follow," *Science* 288:1722-1727, 2000.

Polejaeva et al., "New Advances in Somatic Cell Nuclear Transfer: Application in Transgenesis," *Theriogenology* 53:117-126, 2000.

Prather et al., "Development of the Techniques for Nuclear Transfer in Pigs," *Theriogenology* 51:487-198, 1999.

Prather et al., "Nuclear Remodeling and Reprogramming in Transgenic Pig Production," *Exp. Biol. Med* 229:1120-1126, 2004.

Prelle et al., "Pluripotent Stem Cells—Models of Embryonic Development, Tool for Gene Targeting, and Basis of Cell Therapy," *Anat. Histol. Embryol.* 31:169-186, 2002.

Raeber et al., "Ectopic Expression of Prion Protein (PrP) in T Lymphocytes or Hepatocytes of PrP Knockout Mice is Insufficient to Sustain Prion Replication," *Proc. Natl. Acad. Sci. U.S.A.* 96:3987-3992, 1999.

Ramsoondar et al., "Production of α1,3-Galactosyltransferase-Knockout Cloned Pigs Expressing Human α1,2-Fucosylosyltransferase," *Biol. Reproduct.* 69:437-445, 2003.

Richt et al., "Production of Cattle Lacking Prion Protein," *Nature Biotechnol.* 25:132-138, 2007.

Rideout et al., "Nuclear Cloning and Epigenetic Reprogramming of the Genome," *Science* 293:1093-1098, 2001.

Sandrin et al., "Recent Advances in Xenotransplantation," *Curr. Opin. Immunol.* 11:527-531, 1999.

Schnieke et al., "Human Factor IX Transgenic Sheep Produced by Transfer of Nuclei From Transfected Fetal Fibroblasts," *Science* 278:2130-2133, 1997.

Shen et al., "Human Mini-Chromosomes in Mouse Embryonal Stem Cells," *Hum. Mol. Genet.* 6:1375-1382, 1997.

Srikumaran et at., "Bovine X Mouse Hybridomas that Secrete Bovine Immunoglobulin G1," *Science* 220:522-524, 1983.

Steen et al., "A-Kinase Anchoring Protein (AKAP)95 Recruits Human Chromosome-Associated Protein (hCAP)-D2/Eg7 for Chromosome Condensation in Mitotic Extract," *J. Cell Biol.* 149:531-536, 2000.

Steen et al., "Recruitment of Protein Phosphatase 1 to the Nuclear Envelope by A-Kinase Anchoring Protein AKAP149 is a Pre-Requisite for Nuclear Lamina Assembly," *J. Cell Biol.* 150:1251-1261, 2000.

Stiehm et al., "Appropriate Therapeutic Use of Immunoglobulin," *Trans. Med. Rev.* 10:203-221, 1996.

Sun et al., "Expressed Swine $V_H$ Genes Belong to a Small $V_H$ Gene Family Homologous to Human $V_H III$," *J. Immumnol.* 153:5618-5627, 1994.

Suprynowicz et al., "A Fractionated Cell-Free System for Analysis of Prophase Nuclear Disassembly," *J. Cell Biol.* 103:2073-2081, 1986.

Tomizuka et al., "Functional Expression and Germline Transmission of a Human Chromosome Fragment in Chimaeric Mice," *Nature Genet.* 16:133-143, 1997.

Tomizuka et al., "Double Trans-Chromosomic Mice: Maintenance of Two Individual Human Chromosome Fragments Containing Ig Heavy and Kappa Loci and Expression of Fully Human Antibodies," *Proc. Natl. Acad. Sci. U.S.A.* 97:722-727, 2000.

Watanabe et al., "A Novel Method for the Production of Transgenic Cloned Pigs: Electroporation-Mediated Gene Transfer to Non-cultured Cells and Subsequent Selection with Puromycin," *Biol. Reproduct.* 72:309-315, 2005.

Weissman, "Molecular Biology of Transmissible Spongiform Encephalopathies," *FEBS Lett.* 389:3-11, 1996.

Wheeler et al., "Transgenic Technology and Applications in Swine," *Theriogenology* 56:1345-1369, 2001.

Wilson et al., "A Trypsin-Sensitive Receptor On Membrane Vesicles Is Required For Nuclear Envelope Formation In Vitro," *J. Cell Biol.* 107:57-68, 1988.

Yahata et al., "Reconstitution of Immune Systems in RAG2 $^{-/-}$ Mice by Transfer with Interleukin-12-Induced Splenic Hematopoietic Progenitor Cells," *Immunol. Lett.* 62:165-170, 1998.

Yang, "Application of Xenogeneic Stem Cells for Induction of Transplantation Tolerance; Present State and Future Directions," *Springer Semin. Immunol.* 26:187-200, 2004.

Zhao et al., "Artiodactyl IgD: The Missing Link," *J. Immunol.* 169:4408-4416, 2002.

Zuelke, "Transgenic Modification of Cows Milk for Value-Added Processing," *Reproduct. Fertility Develop.* 10:671-676, 1998.

\* cited by examiner

FIG. 3D

SEQ ID NO:47
ggtaccgaaaggcggccctgaacattctgcagtgagggagccgcactgagaaagctgcttcatcgccgggagggagccagc
cagctacgattgtgagcacgctcacagtgcacacggcatgtgcacggtctcagcttaaccaccttgaaggagtaactcattaaag
agcgtacgaatgcattgataaaatgcacctgagacaaattaatttcttaaacatcgactttgaaaatgaatataagtgagcagttgat
aggctctgaatgaaataccttccaacaggtgctgagaaccgccaggagcagggaacggactccccgtggagccccagaagg
agccagccctgatgatacctcggccctgggccctcctcacgctgggagagagccagctcctgttgttcatgcctggcctgtggtt
ctttgtcgtcatggccctcaaacaagcccacaggtcctggcctgagtccctcggcctgcgtgcagccgccccctcccctgctgg
aggcaccctgcctgccgtggagcccctcacccaacgttcccccgcctgatgggttgggccgcaaaggacaccgtttaaccaga
actgccttccaggagcctactgctgggaggcggccttctctgggaccaggtccactccactcccttggatagtcactgtcaggcc
cctggtggccccacaagaggcgtcctgggaagccccagtctccttccagcccctgaaattgcctccctggagagccagatcac
cctcacccagctccctcccctggccccagggtctcctctcccatcccaccgcccaccctaccctggcgttgccgtcacagctaa
cctgacctccctgggttcgagcgtgccgccgcccctgtcggccccacctggaccccgcagcctatctctgagggctaatgc
ccctgtccctgccccgctgccagctgccccctctttccaggcctttcctccgtgcctctccagtcctgcacctccctgcagcttca
cctgagacttccttcaccctccaggcaccgtcttctggcctgcaggtgaggtctcgcgctccctcagggcacgatgtggctgca
cacacaccggccctcctcccgagtccctcctgcacacaccacgcgcacccgaggttgacaagccctgccgtggttgggattcc
gggaatggcggcagagaggggcggggtgtccttggggctggtggcagggtcctcatggatgcacacagcggccccggctc
aggccaccttgggaaaccagtcctgggatctgcaactcggccatgttcctgcatctggaccagccccaagacaccaccccggc
gtggcgccactggcctgggaggagacacatgtccctttcccatcagcaatgggttcagcactaggatatgcagcacacaggag
tgtggcttgggggtaaaaaaaccttcacgaggaagcggtttcacaaaataaagta

FIG. 3E

SEQ ID NO: 48 tctagacccaccagcctcagttgaggttaaatggacccaaagcatctcaacaatttgcccaagtcaagccagctcaatgggttcc
cttctgttcacccagtctcagcccaccatggtaacccagcataccccggttaagcccaggctagcccagcccagctgagcccag
ctcagctcagttcagcccagttcaatccagatcagcccaatccaggccagctcatcgagctcagttcagctcagctcaaccctctc
agcccagctcacctgctcagccaagctaagcccagttcagcccagctcagcttaacccagctcacccactctgcccagctcagc
ccagcccctgctcaactcagcccagcacagcccaacttggctcagctcagcttagcccagctcagcccagcttacccactccgcc
cagctcaaacagcccaggtcagcccaacctagctcagttcagcccagctcagcccagcccagctcagcccagctcacccactc
tgcccagctcaacacagcccagctcaacccagctcagctcagttcagcccagctcacccactctgcccagctcaggccagctc
aacccagcccagcccagctcactcattctgccaagctcagcccagctcaaccaggctcagctcagctcagctcagccctgctga
ccnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnnnnnnnnnnnnnnnnnnnnnnnnnnnnnnnnnnnnnnnnnnnnnnnnnnnnnnnnnnnnn
nnnnnnnnnnnnnnnnnnngctcagctcagcccagctcagcccagcccagcccagctcacacacttggcccacctcagccact
ccattcagctcagcccagctcaacccagctcagctcagctcaacctagctcagccaagctaacccactccacccagctcagccc
agctcgcccactctgcccagctcaacccagctcagctcagcccagcccagyccagcccagctcacccactccatccagccca
gcccagcccagctgagcccagctcaactcagcctaacccagctcagcccagcctaacccagctcagcccagcccaaccagct
agctgagcccagctcagtgcagctcaacccagctcagctcagctagcccagcccagctcaacctggctcaacccggctcagc
ccagctcacctgctgtaggtggcctgaaccgcgaacacagacatgaaagcccagtggttctgacgagaaagggtcagatcctg
gaccatggccacggctaaaggccctggtctgtggacactgcccagctgggctcatccctcccagcctcttcccgcttctcctcct
gggagcccgctcgccccttcccctggtgcctgacacctccatcccgacaccaggcccagctggcccttctcccagctgtcagtc
accactaccctccactctgggtgaaaagcttgttggagactttagcttccctagagcatctcacaggctgagacacacttgccacc
ctcagagagaggccctgtctctgctgagcaggcagcgctgcttctctgggagaggagagcctgggcacacgtccctgggtcct
ggcctcctgggcacgtgccatgggcctgagatcccgccccgagtctaaaagagtcctggtgactaactgctctctggcaaatgt
cctcattaaaaaccacaggaaatgcatcttatctgaacctgctcccaattctgtctttatcacaaagttctgctgagaaagaggatac
tctctagcacagagaccatctgaaccccaaagctgcattgaacacctaagtgtggacgcaggaagtggtccctgtgggtgtgaa
gcaccccggcatcgcaggcagtaggtaaagacagattcccttttcaagtagaaacaaaaacaactcatacaaacatccctgggc
agtgagtctggctgcaccggctcctggtccctggcatgtcccctgggctctctgacctgggcggattcctccgaatcccttcgctg
tgttaactcgtgacctgcctactggcctgggggcagaggccaggcccacacgtccccaggtgtgggcagtcccaggagaccc
cccagccttggcgagcctggggactcagagcagagactgtccctccagacggtcccaggccccgctgactgccgccccacc
gggcatcctctcaatcccccagctagtagtgtagcagagtaactcacgacgaatgcccccgtttcacccaagtctgtcctgagat
gggtacc

FIG. 3G

SEQ ID NO: 60

```
  1  atgagattcc ctgctcagct cctggggctc ctcctgctct gggtcccagg
 51  atccagtggg gatgttgtgc tgacccagac tcccctctcc ctgtctatca
101  tccctggaga gacggtctcc atctcctgca gtctactca gagtctgaaa
151  tatagtgatg gaaaaaccta tttgtactgg cttcaacata aaccaggcca
201  atcaccacag cttttgatct atgctgtttc cagccgttac actggggtcc
251  cagacaggtt cactggcagt gggtcagaaa cagatttcac acttacgatc
301  aacagtgtgc aggctgagga tgttggagtc tattactgtc ttcaaacaac
351  atatgtccca aatactttcg gccaaggaac caaggtagag atcaaaaggt
401  ctgatgctga gccatccgtc ttcctcttca accatctga tgagcagctg
451  aagaccggaa ctgtctctgt cgtgtgcttg gtgaatgatt tctaccccaa
501  agatatcaat gtcaagtgga agtggatgg ggttactcag agcagcagca
551  acttccaaaa cagtttcaca gaccaggaca gcaagaaaag cacctacagc
601  ctcagcagca tcctgacact gcccagctca gagtaccaaa gccatgacgc
651  ctatacgtgt gaggtcagcc acaagagcct gactaccacc ctcgtcaaga
701  gcttcagtaa gaacgagtgt tag
```

| Fetus | Clone | IgH | Ig λ |
|-------|-------|-----|------|
| 5968 | B4-2 | Pos | Pos |
| 5983 | B2-13 | Neg | Neg |
| 6032 | B4-8 | Pos | Pos |
| 6045 | B2-22 | Pos | Pos |
| 5846 | B4-8 | Neg | Neg |
| 5996 | B4-2 | Pos | Neg |

Unspliced genomic fragment
Spliced transcript

FIG. 11A

SEQ ID NO: 49

5'
GGGAAGGAAGTCCTGTGCGACCANCCAACGGCGACGCTGCTCGTATCCGACG
GGGAATTCTCACAGGAGACGAGGGGGAAAAGGGTTGGGGCGGATGCACTCC
CTGACGAGACGGTGACCAGGGTTCCNTGGCCCCAGNNGTCAAA 3'

FIG. 11B

SEQ ID NOs: 50 and 51

V-D-J region           |→ constant mu region

Subject: 5'
tttgactactggggccagggaaccctggtcaccgtctcctcagggagtgcatccgcccca
------nn----------n------------------------------------------
Query Subject:
acccttttccccctcgtctcctgtgagaattccccgtcggatacgagcagcgtggccgtt
-------------------------------------------------------------
Query Subject: 5'
ggctgcctcgcacaggacttccttcccgactccatcactttctcctg 3'
--n---g-------------------- Cmu1 primer

FIG. 12A

SEQ ID NOs: 52 and 53

```
     10              19              28              37              46              55
5' GGA GGC TTG GTC AAG CCT GGA GGG TCC CTG AGA CTC TCC TGT GCA GCC TCT GGA
    G   G   L   V   K   P   G   G   S   L   R   L   S   C   A   A   S   G 64              73              82              91             100             109
   TTC ACC TTC AGT GAC TAC TAC ATG AGC TGG ATC CGC CAG GCT CCA GGG AAG GGG
    F   T   F   S   D   Y   Y   M   S   W   I   R   Q   A   P   G   K   G 118             127             136             145             154             163
   CTG GAG TGG GTT TCA TAC ATT AGT AGT AGT GGT AGT ACC ATA TAC TAC GCA GAC
    L   E   W   V   S   Y   I   S   S   S   G   S   T   I   Y   Y   A   D
                                    VH3-11
   172             181             190             199             208             217
   TCT GTG AAG GGC CGA TTC ACC ATC TCC AGG GAC AAC GCC AAG AAC TCA CTG TAT
    S   V   K   G   R   F   T   I   S   R   D   N   A   K   N   S   L   Y 226             235             244             253             262             271
   CTG CAA ATG AAC AGC CTG AGA GCC GAG GAC ACG GCT GTG TAT TAC TGT GCG AGA
    L   Q   M   N   S   L   R   A   E   D   T   A   V   Y   Y   C   A   R 280             289             298             307             316             325
   ATA ACT GGG GAT GCT TTT GAT ATC TGG GGC CAA GGG ACA ATG GTC ACC GTC TCT
    I   T   G   D   A   F   D   I   W   G   Q   G   T   M   V   T   V   S
    D7-27                              JH3
   334             343             352             361             370             379
   TCA GGG AGT GCA TCC GCC CCA ACC CTT TTC CCC CTC GTC TCC TGT GAG AAT TCC
    S   G   S   A   S   A   P   T   L   F   P   L   V   S   C   E   N   S
                                                       Cµ
   388
   CCG TCG GAT ACG AGC 3'
    P   S   D   T   S
```

FIG. 12B

SEQ ID NOs: 54 and 55

```
5' GTG GAG TCT GGG GGA GGC TTG GTA CAG CCT GGG AGG TCC CTG AGA CTC TCC TGT
   V   E   S   G   G   G   L   V   Q   P   G   R   S   L   R   L   S   C

GCA GCG TCA GGA TTC ACC TTC AGG AAC TTT GGC ATG CAC TGG GTC CGC CAG GCT
 A   A   S   G   F   T   F   R   N   F   G   M   H   W   V   R   Q   A
                        VH3-33

CCA GGC AAG GGG CTG GAG TGG GTG ACA GTT ATA TGG TAT GAC GGA AGT AAT CAA
 P   G   K   G   L   E   W   V   T   V   I   W   Y   D   G   S   N   Q

TAC TAT ATA GAC TCC GTG AAG GGC CGA TTC ACC ATC TCC AGA GAC AAT TCC AAG
 Y   Y   I   D   S   V   K   G   R   F   T   I   S   R   D   N   S   K

AAC ATG TTG TAT CTG CAA ATG AAC AGC CTG AGA GCC GAG GAT ACG GCT GTG TAT
 N   M   L   Y   L   Q   M   N   S   L   R   A   E   D   T   A   V   Y

TAC TGT GCC AGA GAT CGC AAT GGC CTG AAG TAC TTC GAT TTC TGG GGC CGT GGC
 Y   C   A   R   D   R   N   G   L   K   Y   F   D   F   W   G   R   G
                    D6-39 ?  N addition          JH2

ACC CTG GTC ACT GTC TCA TCA GGG AGT GCA TCC GCC CCA ACC CTT TTC CCC CTC
 T   L   V   T   V   S   S   G   S   A   S   A   P   T   L   F   P   L

GTC TCC TGT GAG AAT TCC CCG TCG GAT ACG AGC 3'
 V   S   C   E   N   S   P   S   D   T   S
                Cμ
```

FIG. 20

SEQ ID NOs: 56 and 57

5' ACC CTC ACT CTC CAC TGT GCA GGG TCC TGG GCC CAG TCT GTG CTG ACT CAG CCA
    T   L   T   L   H   C   A   G   S   W   A   Q   S   V   L   T   Q   P

CCC TCA GCG TCT GGG ACC CCC GGG CAG AGG GTC ACC ATC TCT TGT TCT GGA AGC
 P   S   A   S   G   T   P   G   Q   R   V   T   I   S   C   S   G   S

AGC TCC AAC ATC GGA AGT AAT TAT GTA TAC TGG TAC CAG CAG CTC CCA GGA ACG
 S   S   N   I   G   S   N   Y   V   Y   W   Y   Q   Q   L   P   G   T

GCC CCC AAA CTC CTC ATC TAT AGG AAT AAT CAG CGG CCC TCA GGG GTC CCT GAC    V1-17
 A   P   K   L   L   I   Y   R   N   N   Q   R   P   S   G   V   P   D

CGA TTC TCT GGC TCC AAG TCT GGC ACC TCA GCC TCC CTG GCC ATC AGT GGG CTC
 R   F   S   G   S   K   S   G   T   S   A   S   L   A   I   S   G   L

CGG TCC GAG GAT GAG GCT GAT TAT TAC TGT GCA GCA TGG GAT GAC AGC CTG AGT
 R   S   E   D   E   A   D   Y   Y   C   A   A   W   D   D   S   L   S

GGT CTT TTC GGC GGA GGG ACC AAG CTG ACC GTC CTA GGT CAG CCC AAG GCT GCC
 G   L   F   G   G   G   T   K   L   T   V   L   G   Q   P   K   A   A
                            JL3

CCC TCG GTC ACT CTG TTC CCA CCC TCC TCT GAG GAG CTT CAA GCC AAC AAG GCC
 P   S   V   T   L   F   P   P   S   S   E   E   L   Q   A   N   K   A
                                              Cλ

ACA CTG GTG 3'
 T   L   V

FIG. 21

SEQ ID NOs: 58 and 59

5' AGT TGG ACC CCT CTC TGG CTC ACT CTC TTC ACT CTT TGC ATA GGT TCT
   S   W   T   P   L   W   L   T   L   F   T   L   C   I   G   S

GTG GTT TCT TCT GAG CTG ACT CAG GAC CCT GCT GTG TCT GTG GCC TTG GGA CAG
 V   V   S   S   E   L   T   Q   D   P   A   V   S   V   A   L   G   Q

ACA GTC AGG ATC ACA TGC CAA GGA GAC AGC CTC AGA AGC TAT TAT GCA AGC TGG
 T   V   R   I   T   C   Q   G   D   S   L   R   S   Y   Y   A   S   W

TAC CAG CAG AAG CCA GGA CAG GCC CCT GTA CTT GTC ATC TAT GGT AAA AAC AAC  V2-13
 Y   Q   Q   K   P   G   Q   A   P   V   L   V   I   Y   G   K   N   N

CGG CCC TCA GGG ATC CCA GAC CGA TTC TCT GGC TCC AGC TCA GGA AAC ACA GCT
 R   P   S   G   I   P   D   R   F   S   G   S   S   S   G   N   T   A

TCC TTG ACC ATC ACT GGG GCT CAG GCG GAA GAT GAG GCT GAC TAT TAC TGT AAC
 S   L   T   I   T   G   A   Q   A   E   D   E   A   D   Y   Y   C   N

TCC CGG GAC AGC AGT GGT AAC CAT CTG GTA TTC GGC GGA GGG ACC AAG CTG ACC  JL2
 S   R   D   S   S   G   N   H   L   V   F   G   G   G   T   K   L   T

GTC CTA GGT CAG CCC AAG GCT GCC CCC TCG GTC ACT CTG TTC CCA CCC TCC TCT
 V   L   G   Q   P   K   A   A   P   S   V   T   L   F   P   P   S   S

GAG GAG CTT CAA GCC AAC AAG GCC ACA CTG GTG 3'
 E   E   L   Q   A   N   K   A   T   L   V     Cλ

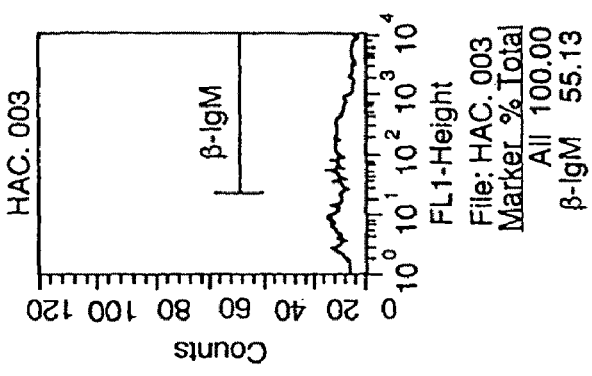
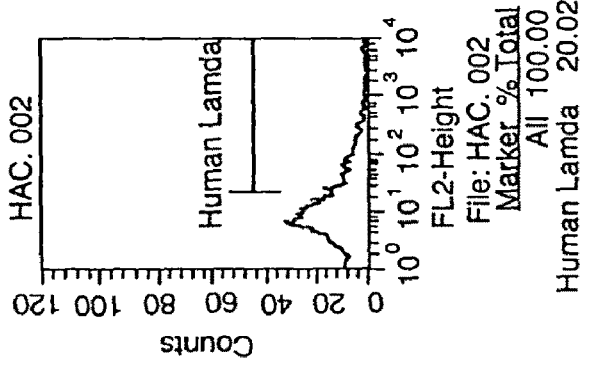
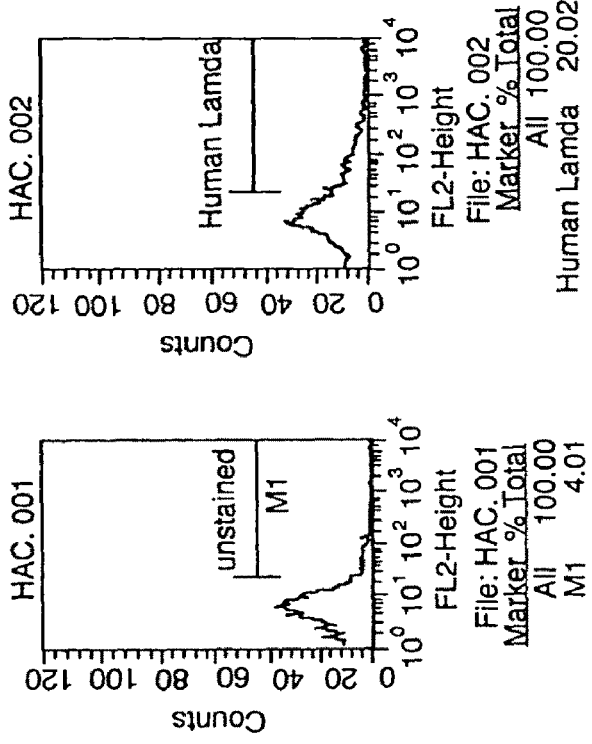
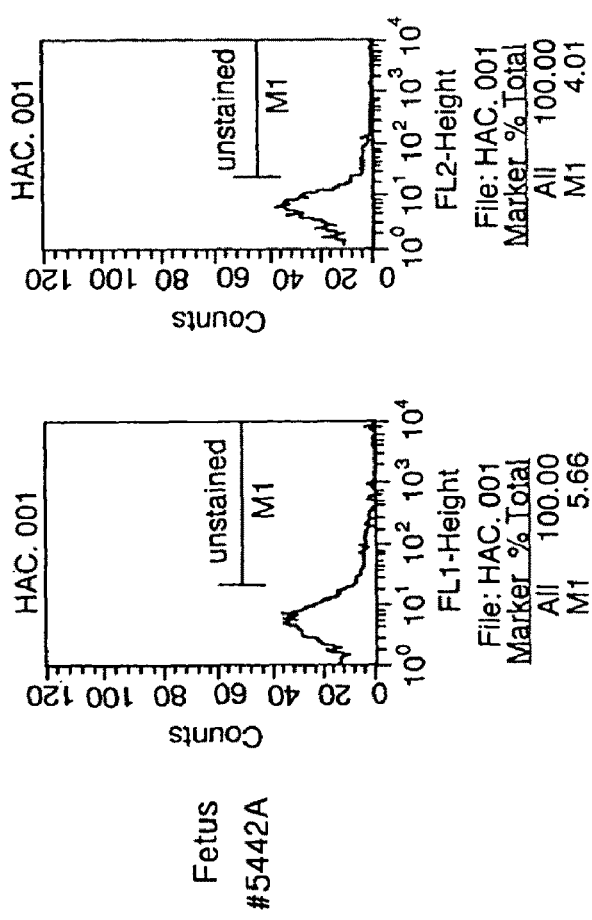

Figure 27

NT, ET and pregnancies: Delta HAC regenerated fibroblasts

| Cell line ID | Total NTs in culture | No of Blast (%) | No of Blast Tranferred | No Recips | Pregnancy status 40 d | 60 d | 90 d | 120 d | 150 d | 180 d | 210 d |
|---|---|---|---|---|---|---|---|---|---|---|---|
| D5968 | 174 | 24 (25) | 27 | 17 | 3 | 3 | 3 | 2 | 2 | 2 | 2 |
| D6045 | 215 | 10 (7) | 8 | 4 | 1 | 1 | 1 | 1 | 1 | 1 | |
| D6045 | 122 | 20 (23) | 12 | 9 | 1 | 0 | 0 | 0 | 0 | 0 | |
| D6032 | 161 | 12 (15) | 14 | 7 | 3 | 3 | 3 | 2 | 2 | 2 | |
| D6032 | 155 | 15 (11) | 11 | 11 | 3 | 0 | 0 | 0 | 0 | 0 | |
| D6032 | 195 | 20 (14) | 16 | 10 | 1 | 1 | 1 | 1 | | | |
| D6032 | 250 | 17 (12) | 12 | 5 | 2 | 2 | 2 | 2 | | | |
| D6032 | 150 | 11 (9) | 10 | 5 | 3 | 1 | 1 | 0 | | | |
| D6032 | 135 | 22 (23) | 22 | 11 | 2 | 1 | 1 | 1 | | | |
| D5968 | 140 | 35 (56) | 25 | 15 | 2 | 2 | 1 | | | | |
| D5968 | 150 | 20 (24) | 26 | 13 | 2 | 2 | 1 | | | | |
| D6045 | 170 | 46 (39) | 32 | 16 | 4 | | | | | | |
| D6045 | 20 | 7 (13) | 1 | 1 | 0 | | | | | | |
| D6045 SLOT | 105 | 9 (12) | 3 | 2 | 1 | | | | | | |
| D6045 | 78 | 8 (15) | 2 | 1 | 0 | | | | | | |
| D6045 SLOT | 125 | 12 (13) | 7 | 5 | 0 | | | | | | |
| D6045 | 47 | 6 (18) | 5 | 3 | 2 | | | | | | |
| D6045 SLOT | 112 | 3 (4) | 3 | 2 | 2 | | | | | | |
| D6045 | 120 | 28 (33) | 18 | 9 | | | | | | | |
| D6045 SLOT | 100 | 11 (16) | 2 | 1 | | | | | | | |
| D6045 | 72 | 15 (27) | 16 | 8 | | | | | | | |
| D6045 SLOT | 91 | 0 | 2 | 1 | | | | | | | |
| D6045 | 92 | 16 (23) | 10 | 5 | | | | | | | |
| D6045 SLOT | 104 | 16 (22) | 10 | 5 | | | | | | | |
| D5968 | 125 | 24 (27) | 8 | 4 | | | | | | | |
| D5968 SLOT | 65 | 10 (22) | 8 | 4 | | | | | | | |
| D5968 | 120 | 28 (33) | 14 | 7 | | | | | | | |
| D5968 SLOT | 95 | 13 (19) | 6 | 3 | | | | | | | |
| D5968 | 92 | 17 (25) | 20 | 10 | | | | | | | |
| D5968 SLOT | 93 | 14 (22) | 12 | 6 | | | | | | | |
| C | 13 | 1 (11) | 1 | 3 | | | | | | | |
| SLOT | 63 | 9 (12) | 8 | 3 | | | | | | | |
| C | 105 | 4 (5) | 4 | 3 | | | | | | | |
| SLOT | 100 | 1 (1) | 1 | 3 | | | | | | | |
| C | 90 | 10 (16) | 10 | 6 | | | | | | | |
| SLOT | 110 | 13 (17) | 13 | 6 | | | | | | | |
| C | 90 | 10 (16) | 10 | 1 | | | | | | | |
| SLOT | 83 | 5 (9) | 5 | 1 | | | | | | | |
| C | 105 | 20 (27) | 20 | 9 | | | | | | | |
| SLOT | 72 | 7 (13) | 7 | 2 | | | | | | | |
| C | 88 | 7 (11) | 7 | 4 | | | | | | | |
| SLOT | 93 | 9 (14) | 9 | 4 | | | | | | | |
| C | 65 | 20 (33) | 20 | 10 | | | | | | | |
| SLOT | 77 | 4 (7) | 4 | 2 | | | | | | | |
| | 4987 | 515 (19) | 481 | 258 | | | | | | | |

Summary

| Preg Status | No of Pregnancies |
|---|---|
| > 40 d | 9 |
| > 90 d | 2 |
| > 120 d | 4 |
| > 180 d | 3 |
| > 210 d | 3 |
| Total | 21 |

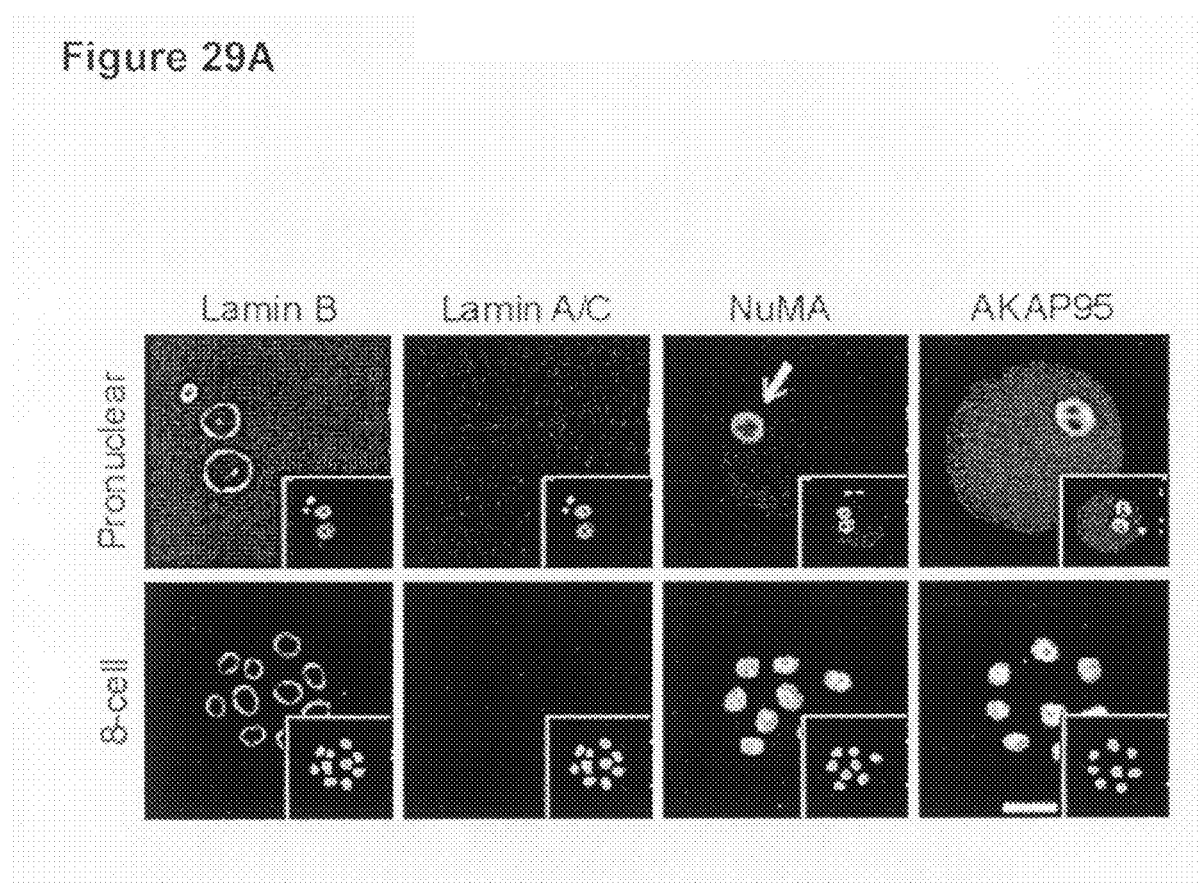

a. TC Fibroblasts    Control Fibroblasts b. Genomic PCR c. RT-PCR

Figure 38D

Igμ Sequence

```
        10              19              28              37              46              55
5' GGA GGC TTG GTC AAG CCT GGA GGG TCC CTG AGA CTC TCC TGT GCA GCC TCT GGA
    G   G   L   V   K   P   G   G   S   L   R   L   S   C   A   A   S   G 64              73              82              91              100             109
   TTC ACC TTC AGT GAC TAC TAC ATG AGC TGG ATC CGC CAG GCT CCA GGG AAG GGG
    F   T   F   S   D   Y   Y   M   S   W   I   R   Q   A   P   G   K   G 118             127             136             145             154             163
   CTG GAG TGG GTT TCA TAC ATT AGT AGT AGT GGT AGT ACC ATA TAC TAC GCA GAC
    L   E   W   V   S   Y   I   S   S   S   G   S   T   I   Y   Y   A   D
                                        VH3-11
        172             181             190             199             208             217
   TCT GTG AAG GGC CGA TTC ACC ATC TCC AGG GAC AAC GCC AAG AAC TCA CTG TAT
    S   V   K   G   R   F   T   I   S   R   D   N   A   K   N   S   L   Y 226             235             244             253             262             271
   CTG CAA ATG AAC AGC CTG AGA GCC GAG GAC ACG GCT GTG TAT TAC TGT GCG AGA
    L   Q   M   N   S   L   R   A   E   D   T   A   V   Y   Y   C   A   R 280             289             298             307             316             325
   ATA ACT GGG GAT GCT TTT GAT ATC TGG GGC CAA GGG ACA ATG GTC ACC GTC TCT
    I   Y   G   D   A   F   D   I   W   G   Q   G   T   M   V   T   V   S
    D7-27                                       JH3
        334             343             352             361             370             379
   TGA GGG AGT GCA TCC GCC CCA ACC CTT TTC CCC CTC GTC TCC TGT GAG AAT TCC
    S   G   S   A   S   A   P   T   L   F   P   L   V   S   C   E   N   S
                                                    Cμ
        388
   CCG TCG GAT ACG AGC 3'
    P   S   D   T   S
```

Igλ Sequence

```
        10              19              28              37              46              55
5' ACC CTC CTC ACT CAC TGT GCA GGG TCC TGG GCC CAG TCT GTG CTG ACT CAG CCA
    T   L   L   T   H   C   A   G   S   W   A   Q   S   V   L   T   Q   P 64              73              82              91              100             109
   CCC TCA GCG TCT GGG ACC CCC GGG CAG AGG GTC ACC ATC TCT TGT TCT GGA AGC
    P   S   A   S   G   T   P   G   Q   R   V   T   I   S   C   S   G   S 118             127             136             145             154             163
   AGC TCC AAC ATC GGA AGT AAT TAT GTA TAC TGG TAC CAG CAG CTC CCA GGA ACG
    S   S   N   I   G   S   N   Y   V   Y   W   Y   Q   Q   L   P   G   T
                                        V1-17
        172             181             190             199             208             217
   GCC CCC AAA CTC CTC ATC TAT AGG AAT AAT CAG CGG CCC TCA GGG GTC CCT GAC
    A   P   K   L   L   I   Y   R   N   N   Q   R   P   S   G   V   P   D 226             235             244             253             262             271
   CGA TTC TCT GGC TCC AAG TCT GGC ACC TCA GCC TCC CTG GCC ATC AGT GGG CTC
    R   F   S   G   S   K   S   G   T   S   A   S   L   A   I   S   G   L 280             289             298             307             316             325
   CGG TCC GAG GAT GAG GCT GAT TAT TAC TGT GCA GCA TGG GAT GAC AGC CTG AGT
    R   S   E   D   E   A   D   Y   Y   C   A   A   W   D   D   S   L   S 334             343             352             361             370             379
   GGT CTT TTC GGC GGA GGG ACC AAG CTG ACC GTC CTA GGT CAG CCC AAG GCT GCC
    G   L   F   G   G   G   T   K   L   T   V   L   G   Q   P   K   A   A
                JL3
        388             397             406             415             424             433
   CCC TCG GTC ACT CTG TTC CCA CCC TCC TCT GAG GAG CTT CAA GCC AAC AAG GCC
    P   S   V   T   L   F   P   P   S   S   E   E   L   Q   A   N   K   A
                                                    Cλ
   442
```

A  Transchromosomic Calves

B  Genomic PCR

C  FISH Labeling with Human Cot I DNA

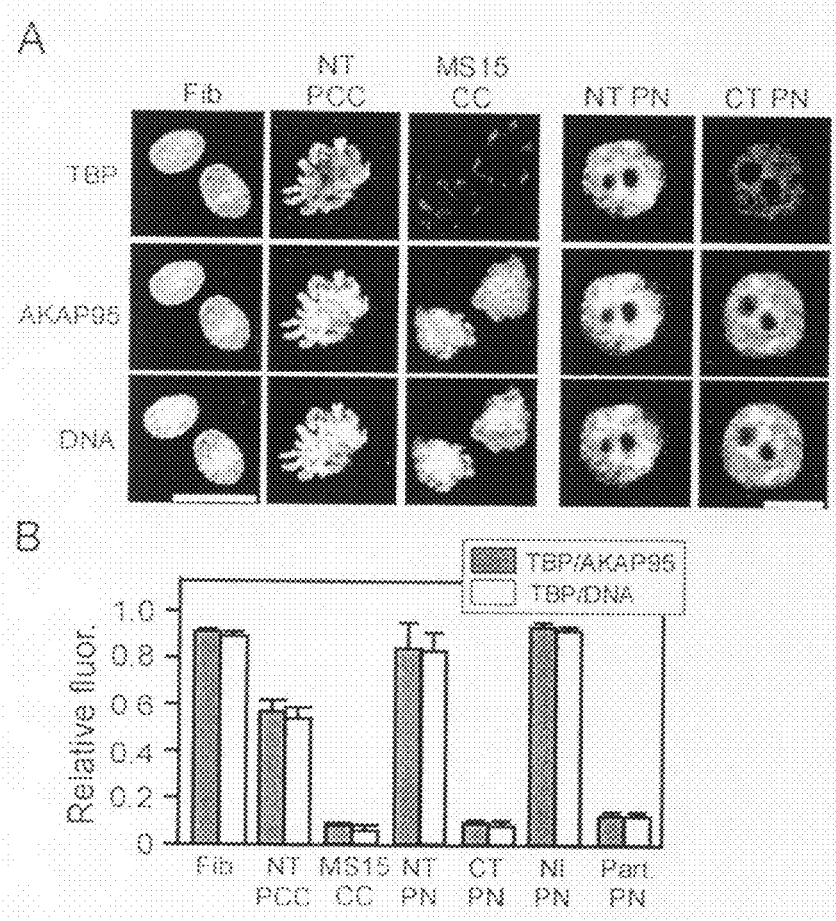

| Cell line | No of screened clone | Primers F7 x R7 | Primers F10 x R10 | Frequency |
|---|---|---|---|---|
| Holstein | 94 | 51 | 51 | >50 % |
| Holstein x Jersey | 141 | 75 | 75 | >50 % |

Fig. 44C

SEQUENCE LISTING

<160> NUMBER OF SEQ ID NOS: 94

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
agtgagataa gcagtggatg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
cttgtgctac tcccatcact                                                    20

<210> SEQ ID NO 3
<211> LENGTH: 22
<212> TYPE: DNA
<213> ORGANISM: Artificial Sequence
<220> FEATURE:
<223> OTHER INFORMATION: Synthetic Primer

<400> SEQUENCE: 3
ggagaccacc aaaccctcca aa                                                 22

<210> SEQ ID NO 4
<211> LENGTH: 23
<212> TYPE: DNA
<213> ORGANISM: Artificial Sequence
<220> FEATURE:
<223> OTHER INFORMATION: Synthetic Primer

<400> SEQUENCE: 4
gagagttgca gaagggtyg act                                                 23

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
accacctatg acagcgtgac                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gtggcagcaa gtagacatcg                                                    20

<210> SEQ ID NO 7
<211> LENGTH: 22

-continued

```
<212> TYPE: DNA
<213> ORGANISM: Artificial Sequence
<220> FEATURE:
<223> OTHER INFORMATION: Synthetic Primer

<400> SEQUENCE: 7
gtcatcatct ctgccccttc tg                                              22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
aacaacttct tgatgtcatc at                                              22

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
ccctcctctt tgtgctgtca                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
caccgtgctc tcatcggatg                                                 20

<210> SEQ ID NO 11
<211> LENGTH: 23
<212> TYPE: DNA
<213> ORGANISM: Artificial Sequence
<220> FEATURE:
<223> OTHER INFORMATION: Synthetic Primer

<400> SEQUENCE: 11
caggtgcagc tggtggagtc tgg                                             23

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
caggagaaag tgatggagtc                                                 20

<210> SEQ ID NO 13
<211> LENGTH: 22
<212> TYPE: DNA
<213> ORGANISM: Artificial Sequence
<220> FEATURE:
<223> OTHER INFORMATION: Synthetic Primer

<400> SEQUENCE: 13
```

```
ggagaccacc aaaccctcca aa                                              22
```

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14

```
gtggcagcaa gtagacatcg                                                 20
```

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15

```
caggagaaag tgatggagtc                                                 20
```

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16

```
aggcagccaa cggccacgct                                                 20
```

<210> SEQ ID NO 17
<211> LENGTH: 23
<212> TYPE: DNA
<213> ORGANISM: Artificial Sequence
<220> FEATURE:
<223> OTHER INFORMATION: Synthetic Primer

<400> SEQUENCE: 17

```
caggtgcagc tggtggagtc tgg                                             23
```

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18

```
agtgagataa gcagtggatg                                                 20
```

<210> SEQ ID NO 19
<211> LENGTH: 20
<212> TYPE: DNA
<213> ORGANISM: Artificial Sequence
<220> FEATURE:
<223> OTHER INFORMATION: Synthetic Primer

<400> SEQUENCE: 19

```
cttgtgctac tcccatcact                                                 20
```

<210> SEQ ID NO 20
<211> LENGTH: 22
<212> TYPE: DNA
<213> ORGANISM: Artificial Sequence

```
<220> FEATURE:
<223> OTHER INFORMATION: Synthetic Primer

<400> SEQUENCE: 20
ggagaccacc aaaccctcca aa                                        22

<210> SEQ ID NO 21
<211> LENGTH: 23
<212> TYPE: DNA
<213> ORGANISM: Artificial Sequence
<220> FEATURE:
<223> OTHER INFORMATION: Synthetic Primer

<400> SEQUENCE: 21
gagagttgca gaaggggtyg act                                       23

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
ggagaccacc aaaccctcca aa                                        22

<210> SEQ ID NO 23
<211> LENGTH: 22
<212> TYPE: DNA
<213> ORGANISM: Artificial Sequence
<220> FEATURE:
<223> OTHER INFORMATION: Synthetic Primer

<400> SEQUENCE: 23
gagagttgca gaaggggtga ct                                        22

<210> SEQ ID NO 24
<211> LENGTH: 23
<212> TYPE: DNA
<213> ORGANISM: Artificial Sequence
<220> FEATURE:
<223> OTHER INFORMATION: Synthetic Primer

<400> SEQUENCE: 24
caggtgcagc tggtggagtc tgg                                       23

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
caggagaaag tgatggagtc                                           20

<210> SEQ ID NO 26
<211> LENGTH: 22
<212> TYPE: DNA
<213> ORGANISM: Artificial Sequence
<220> FEATURE:
<223> OTHER INFORMATION: Synthetic Primer

<400> SEQUENCE: 26
gtcatcatct ctgcccccttc tg                                       22
```

<210> SEQ ID NO 27
<211> LENGTH: 22
<212> TYPE: DNA
<213> ORGANISM: Artificial Sequence
<220> FEATURE:
<223> OTHER INFORMATION: Synthetic Primer

<400> SEQUENCE: 27
aacaacttct tgatgtcatc at                                      22

<210> SEQ ID NO 28
<211> LENGTH: 29
<212> TYPE: DNA
<213> ORGANISM: Artificial Sequence
<220> FEATURE:
<223> OTHER INFORMATION: Synthetic Primer

<400> SEQUENCE: 28
gggaattcgg gtagaagttc actgatcag                               29

<210> SEQ ID NO 29
<211> LENGTH: 28
<212> TYPE: DNA
<213> ORGANISM: Artificial Sequence
<220> FEATURE:
<223> OTHER INFORMATION: Synthetic Primer

<400> SEQUENCE: 29
gggaattcgg gtagaagtca cttatgag                                28

<210> SEQ ID NO 30
<211> LENGTH: 28
<212> TYPE: DNA
<213> ORGANISM: Artificial Sequence
<220> FEATURE:
<223> OTHER INFORMATION: Synthetic Primer

<400> SEQUENCE: 30
gggaattcgg gtagaagtca cttacgag                                28

<210> SEQ ID NO 31
<211> LENGTH: 29
<212> TYPE: DNA
<213> ORGANISM: Artificial Sequence
<220> FEATURE:
<223> OTHER INFORMATION: Synthetic Primer

<400> SEQUENCE: 31
cccccaagct trcckgstyy cctctcctc                               29

<210> SEQ ID NO 32
<211> LENGTH: 29
<212> TYPE: DNA
<213> ORGANISM: Artificial Sequence
<220> FEATURE:
<223> OTHER INFORMATION: Synthetic Primer

<400> SEQUENCE: 32
cccccaagct tgcctggacc cctctctgg                               29

<210> SEQ ID NO 33
<211> LENGTH: 32
<212> TYPE: DNA
<213> ORGANISM: Artificial Sequence
<220> FEATURE:
<223> OTHER INFORMATION: Synthetic Primer

<400> SEQUENCE: 33
atcggcaaag cttggacccc tctctggctc ac					32

<210> SEQ ID NO 34
<211> LENGTH: 29
<212> TYPE: DNA
<213> ORGANISM: Artificial Sequence
<220> FEATURE:
<223> OTHER INFORMATION: Synthetic Primer

<400> SEQUENCE: 34
cccccaagct tctcggcgtc cttgcttac					29

<210> SEQ ID NO 35
<211> LENGTH: 29
<212> TYPE: DNA
<213> ORGANISM: Artificial Sequence
<220> FEATURE:
<223> OTHER INFORMATION: Synthetic Primer

<400> SEQUENCE: 35
gggaattcgg gtagaagttc actgatcag					29

<210> SEQ ID NO 36
<211> LENGTH: 28
<212> TYPE: DNA
<213> ORGANISM: Artificial Sequence
<220> FEATURE:
<223> OTHER INFORMATION: Synthetic Primer

<400> SEQUENCE: 36
gggaattcgg gtagaagtca cttatgag					28

<210> SEQ ID NO 37
<211> LENGTH: 28
<212> TYPE: DNA
<213> ORGANISM: Artificial Sequence
<220> FEATURE:
<223> OTHER INFORMATION: Synthetic Primer

<400> SEQUENCE: 37
gggaattcgg gtagaagtca cttacgag					28

<210> SEQ ID NO 38
<211> LENGTH: 29
<212> TYPE: DNA
<213> ORGANISM: Artificial Sequence
<220> FEATURE:
<223> OTHER INFORMATION: Synthetic Primer

<400> SEQUENCE: 38
cccccaagct trcckgstyy cctctcctc					29

<210> SEQ ID NO 39
<211> LENGTH: 28
<212> TYPE: DNA
<213> ORGANISM: Artificial Sequence
<220> FEATURE:
<223> OTHER INFORMATION: Synthetic Primer

<400> SEQUENCE: 39
gggaattcgg gtagaagtca ctgatcag					28

<210> SEQ ID NO 40

```
<211> LENGTH: 28
<212> TYPE: DNA
<213> ORGANISM: Artificial Sequence
<220> FEATURE:
<223> OTHER INFORMATION: Synthetic Primer

<400> SEQUENCE: 40
gggaattcgg gtagaagtca cttatgag                                        28

<210> SEQ ID NO 41
<211> LENGTH: 28
<212> TYPE: DNA
<213> ORGANISM: Artificial Sequence
<220> FEATURE:
<223> OTHER INFORMATION: Synthetic Primer

<400> SEQUENCE: 41
gggaattcgg gtagaagtca cttacgag                                        28

<210> SEQ ID NO 42
<211> LENGTH: 30
<212> TYPE: DNA
<213> ORGANISM: Artificial Sequence
<220> FEATURE:
<223> OTHER INFORMATION: Synthetic Primer

<400> SEQUENCE: 42
cttgaagacg aaagggcctc gtgatacgcc                                      30

<210> SEQ ID NO 43
<211> LENGTH: 30
<212> TYPE: DNA
<213> ORGANISM: Artificial Sequence
<220> FEATURE:
<223> OTHER INFORMATION: Synthetic Primer

<400> SEQUENCE: 43
ctgagacttc ctttcaccct ccaggcaccg                                      30

<210> SEQ ID NO 44
<211> LENGTH: 31
<212> TYPE: DNA
<213> ORGANISM: Artificial Sequence
<220> FEATURE:
<223> OTHER INFORMATION: Synthetic Primer

<400> SEQUENCE: 44
cgatgaatgc cccatttcac ccaagtctgt c                                    31

<210> SEQ ID NO 45
<211> LENGTH: 23
<212> TYPE: DNA
<213> ORGANISM: Artificial Sequence
<220> FEATURE:
<223> OTHER INFORMATION: Synthetic Primer

<400> SEQUENCE: 45
ctgagccaag cagtggcccc gag                                             23

<210> SEQ ID NO 46
<211> LENGTH: 26
<212> TYPE: DNA
<213> ORGANISM: Artificial Sequence
<220> FEATURE:
<223> OTHER INFORMATION: Synthetic Primer

<400> SEQUENCE: 46
```

```
gggctgagac tgggtgaaca gaaggg                                         26

<210> SEQ ID NO 47
<211> LENGTH: 1479
<212> TYPE: DNA
<213> ORGANISM: Bovine

<400> SEQUENCE: 47
ggtaccgaaa ggcggccctg aacattctgc agtgagggag ccgcactgag aaagctgctt     60
catcgccggg agggagccag ccagctacga ttgtgagcac gctcacagtg cacacggcat    120
gtgcacggtc tcagcttaac caccttgaag gagtaactca ttaaagagcg tacgaatgca    180
ttgataaaat gcacctgaga caaattaatt tcttaaacat cgactttgaa aatgaatata    240
agtgagcagt tgataggctc tgaatgaaat accttccaac aggtgctgag aaccgccagg    300
agcagggaac ggactcccg tggagcccca aaggagcca gccctgatga tacctcggcc     360
ctgggccctc ctcacgctgg gagagagcca gctcctgttg ttcatgcctg gcctgtggtt    420
ctttgtcgtc atggccctca aacaagccca caggtcctgg cctgagtccc tcggcctgcg    480
tgcagccgcc ccctcccctg ctggaggcac cctgcctgcc gtggagcccc tcacccaacg    540
ttcccccgcc tgatgggttg ggccgcaaag acaccgtttt aaccagaact gccttccagg    600
agcctactgc tgggaggcgg ccttctctgg gaccaggtcc actccactcc cttggatagt    660
cactgtcagg cccctggtgg ccccacaaga ggcgtcctgg gaagcccag tctccttcca    720 gcccctgaaa ttgcctccct ggagagccag atcaccctca cccagctccc tccctggcc     780 cccagggtct cctctcccat cccaccgccc accctaccct ggcgttgccg tcacagctaa    840
cctgacctcc ctgggttcga gcgtgccgcc gcccctgtcg gccccacct ggaccccgc     900 agcctatctc tgagggctaa tgccctgtc cctgccccg ctgccagctg ccccctcttt     960
ccaggccttt cctccgtgcc tctccagtcc tgcacctccc tgcagcttca cctgagactt   1020
cctttcaccc tccaggcacc gtcttctggc ctgcaggtga ggtctcgcgc tccctcaggg   1080
cacgatgtgg ctgcacacac accggccctc ctcccgagtc cctcctgcac acaccacgcg   1140
cacccgaggt tgacaagccc tgccgtggtt gggattccgg gaatggcggc agagagggc    1200 ggggtgtcct tggggctggt ggcagggtcc tcatggatgc acacagcggc cccggctcag   1260
gccaccttgg gaaaccagtc ctgggatctg caactcggcc atgttcctgc atctggacca   1320
gccccaagac accaccccgg cgtggcgcca ctggcctggg aggagacaca tgtcccttc    1380 ccatcagcaa tgggttcagc actaggatat gcagcacaca ggagtgtggc ttgggggtaa   1440
aaaaaccttc acgaggaagc ggtttcacaa aataaagta                           1479

<210> SEQ ID NO 48
<211> LENGTH: 3120
<212> TYPE: DNA
<213> ORGANISM: Bovine
<220> FEATURE:
<221> NAME/KEY: misc_feature
<222> LOCATION: (1)...(3120)
<223> OTHER INFORMATION: n=a, t, c, g or no nucleotide

<400> SEQUENCE: 48
tctagaccca ccagcctcag ttgaggttaa atggacccaa agcatctcaa caatttgccc     60
aagtcaagcc agctcaatgg gttcccttct gttcacccag tctcagccca ccatggtaac    120
ccagcatacc ccggttaagc ccaggctagc ccagcccagc tgagcccagc tcagctcagt    180
```

| | |
|---|---:|
| tcagcccagt tcaatccaga tcagcccaat ccaggccagc tcatcgagct cagttcagct | 240 |
| cagctcaacc ctctcagccc agctcacctg ctcagccaag ctaagcccag ttcagcccag | 300 |
| ctcagcttaa cccagctcac ccactctgcc cagctcagcc cagccctgct caactcagcc | 360 |
| cagcacagcc caacttggct cagctcagct tagcccagct cagcccagct tacccactcc | 420 |
| gcccagctca aacagcccag gtcagcccaa cctagctcag ttcagcccag ctcagcccag | 480 |
| cccagctcag cccagctcac ccactctgcc cagctcaaca cagcccagct caacccagct | 540 |
| cagctcagtt cagcccagct cacccactct gcccagctca ggccagctca acccagccca | 600 |
| gcccagctca ctcattctgc caagctcagc ccagctcaac caggctcagc tcagctcagc | 660 |
| tcagccctgc tgaccnnnnn nnnnnnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnnnnnn nnnnnnnnnn nnnnnnnnnn nnnnnnnnnn nnnnnnnnnn nnnnnnnnnn | 840 |
| nnnnnnnnnn nnnnnnnnnn nnnnnnnnnn nnnnnnnnnn nnnnnnnnnn nnnnnnnnnn | 900 |
| nnnnnnnnnn nnnnnnnnnn nnnnnnnnnn nnnnnnnnnn nnnnnnnnnn nnnnnnnnnn | 960 |
| nnnnnnnnnn nnnnnnnnnn nnnnnnnnnn nnnnnnnnnn nnnnnnnnnn nnnnnnnnnn | 1020 |
| nnnnnnnnnn nnnnnnnnnn nnnnnnnnnn nnnnnnnnnn nnnnnnnnnn nnnnnnnnnn | 1080 |
| nnnnnnnnnn nnnnnnnnnn nnnnnnnnnn nnnnnnnnnn nnnnnnnnnn nnnnnnnnnn | 1140 |
| nnnnnnnnnn nnnnnnnnnn nnnnnnnnnn nnnnnnnnnn nnnnnnnnnn nnnnnnnnnn | 1200 |
| nnnnnnnnnn nnnnnnnnnn nnnnnnnnnn nnnnnnnnnn nnnnnnnnnn nnnnnnnnnn | 1260 |
| nnnnnnnnnn nnnnnnnnnn nnnnnnnnnn nnnnnnnnnn nnnnnnnnnn nnnnnnnnnn | 1320 |
| nnnnnnnnnn nnnnnnnnnn nnnnnnnnnn nnnnnnnnnn nnnnnnnnnn nnnnnnnnnn | 1380 |
| nnnnnnnnnn nnnnnnnnnn nnnnnnnnnn nnnnnnnnnn nnnnnnnnnn nnnnnnnnnn | 1440 |
| nnnnnnnnnn nnnnnnnnnn nnnnnnnnnn nnnnnnnnnn nnnnnnnnnn nnnnnnnnnn | 1500 |
| nnnnnnnnnn nnnnnnnnnn nnnnnnnnnn nnnnnnnnnn nnnnnnnnnn nnnnnnnnnn | 1560 |
| nnnnnnnnnn nnnnnnnnnn nnnnnnnnnn nnnnnnnnnn nnnnnnnnnn nnnnnnnnnn | 1620 |
| nnnnngctca gctcagccca gctcagccca gcccagccca gctcacacac ttggcccacc | 1680 |
| tcagccactc cattcagctc agcccagctc aacccagctc agctcagctc aacctagctc | 1740 |
| agccaagcta acccactcca cccagctcag cccagctcgc ccactctgcc cagctcaacc | 1800 |
| cagctcagct cagcccagcc cagyccagcc cagctcaccc actccatcca gcccagccca | 1860 |
| gcccagctga gcccagctca actcagccta acccagctca gcccagccta acccagctca | 1920 |
| gcccagccca accagctagc tgagcccagc tcagtgcagc tcaacccagc tcagctcagc | 1980 |
| tagcccagcc cagctcaacc tggctcaacc cggctcagcc cagctcacct gctgtaggtg | 2040 |
| gcctgaaccg cgaacacaga catgaaagcc cagtggttct gacgagaaag ggtcagatcc | 2100 |
| tggaccatgg ccacggctaa aggccctggt ctgtggacac tgcccagctg ggctcatccc | 2160 |
| tcccagcctc ttcccgcttc tcctcctggg agcccgctcg ccccttcccc tggtgcctga | 2220 |
| cacctccatc ccgacaccag gcccagctgg cccttctccc agctgtcagt caccactacc | 2280 |
| ctccactctg ggtgaaaagc ttgttggaga ctttagcttc cctagagcat ctcacaggct | 2340 |
| gagacacact tgccaccctc agagagaggc cctgtctctg ctgagcaggc agcgctgctt | 2400 |
| ctctgggaga ggagagcctg ggcacacgtc cctgggtcct ggcctcctgg gcacgtgcca | 2460 |
| tgggcctgag atcccgcccc gagtctaaaa gagtcctggt gactaactgc tctctggcaa | 2520 |
| atgtcctcat taaaaaccac aggaaatgca tcttatctga acctgctccc aattctgtct | 2580 |

| | |
|---|---|
| ttatcacaaa gttctgctga gaaagaggat actctctagc acagagacca tctgaacccc | 2640 |
| aaagctgcat tgaacaccta agtgtggacg caggaagtgg tccctgtggg tgtgaagcac | 2700 |
| cccggcatcg caggcagtag gtaaagacag attccctttc aagtagaaac aaaaacaact | 2760 |
| catacaaaca tccctgggca gtgagtctgg ctgcaccggc tcctggtccc tggcatgtcc | 2820 |
| cctgggctct ctgacctggg cggattcctc cgaatcccct cgctgtgtta actcgtgacc | 2880 |
| tgcctactgg cctgggggca gaggccaggc ccacacgtcc ccaggtgtgg gcagtcccag | 2940 |
| gagaccccc agccttggcg agcctgggga ctcagagcag agactgtccc tccagacggt | 3000 |
| cccaggcccc gctgactgcc gccccaccgg gcatcctctc aatcccccag ctagtagtgt | 3060 |
| agcagagtaa ctcacgacga atgccccgt ttcacccaag tctgtcctga gatgggtacc | 3120 |

```
<210> SEQ ID NO 49
<211> LENGTH: 146
<212> TYPE: DNA
<213> ORGANISM: Bovine
<220> FEATURE:
<221> NAME/KEY: misc_feature
<222> LOCATION: (1)...(146)
<223> OTHER INFORMATION: n=a,t,c, or g

<400> SEQUENCE: 49
```

| | |
|---|---|
| gggaaggaag tcctgtgcga ccanccaacg gccacgctgc tcgtatccga cggggaattc | 60 |
| tcacaggaga cgaggggaa aagggttggg gcggatgcac tccctgagga gacggtgacc | 120 |
| agggttccnt ggccccagnn gtcaaa | 146 |

```
<210> SEQ ID NO 50
<211> LENGTH: 167
<212> TYPE: DNA
<213> ORGANISM: Bovine

<400> SEQUENCE: 50
```

| | |
|---|---|
| tttgactact ggggccaggg aaccctggtc accgtctcct cagggagtgc atccgcccca | 60 |
| acccttttcc ccctcgtctc ctgtgagaat tccccgtcgg atacgagcag cgtggccgtt | 120 |
| ggctgcctcg cacaggactt ccttcccgac tccatcactt tctcctg | 167 |

```
<210> SEQ ID NO 51
<211> LENGTH: 147
<212> TYPE: DNA
<213> ORGANISM: Bovine
<220> FEATURE:
<221> NAME/KEY: misc_feature
<222> LOCATION: (1)...(147)
<223> OTHER INFORMATION: n=a, t, c, or g

<400> SEQUENCE: 51
```

| | |
|---|---|
| tttgacnnct ggggccangg aaccctggtc accgtctcct cagggagtgc atccgcccca | 60 |
| acccttttcc ccctcgtctc ctgtgagaat tccccgtcgg atacgagcag cgtggccgtt | 120 |
| ggntgcgtcg cacaggactt ccttccc | 147 |

```
<210> SEQ ID NO 52
<211> LENGTH: 393
<212> TYPE: DNA
<213> ORGANISM: Bovine

<400> SEQUENCE: 52
```

| | |
|---|---|
| ggaggcttgg tcaagcctgg agggtccctg agactctcct gtgcagcctc tggattcacc | 60 |

```
ttcagtgact actacatgag ctggatccgc caggctccag ggaagggggct ggagtgggtt    120 tcatacatta gtagtagtgg tagtaccata tactacgcag actctgtgaa gggccgattc    180
accatctcca gggacaacgc caagaactca ctgtatctgc aaatgaacag cctgagagcc    240
gaggacacgg ctgtgtatta ctgtgcgaga taactgggg atgcttttga tatctggggc    300
caagggacaa tggtcaccgt ctcttcaggg agtgcatccg ccccaaccct tttccccctc    360
gtctcctgtg agaattcccc gtcggatacg agc                                 393
```

<210> SEQ ID NO 53
<211> LENGTH: 131
<212> TYPE: PRT
<213> ORGANISM: Bovine

<400> SEQUENCE: 53

```
Gly Gly Leu Val Lys Pro Gly Gly Ser Leu Arg Leu Ser Cys Ala Ala
1               5                   10                  15

Ser Gly Phe Thr Phe Ser Asp Tyr Tyr Met Ser Trp Ile Arg Gln Ala
            20                  25                  30

Pro Gly Lys Gly Leu Glu Trp Val Ser Tyr Ile Ser Ser Ser Gly Ser
        35                  40                  45

Thr Ile Tyr Tyr Ala Asp Ser Val Lys Gly Arg Phe Thr Ile Ser Arg
    50                  55                  60

Asp Asn Ala Lys Asn Ser Leu Tyr Leu Gln Met Asn Ser Leu Arg Ala
65                  70                  75                  80

Glu Asp Thr Ala Val Tyr Tyr Cys Ala Arg Ile Thr Gly Asp Ala Phe
                85                  90                  95

Asp Ile Trp Gly Gln Gly Thr Met Val Thr Val Ser Ser Gly Ser Ala
            100                 105                 110

Ser Ala Pro Thr Leu Phe Pro Leu Val Ser Cys Glu Asn Ser Pro Ser
        115                 120                 125

Asp Thr Ser
    130
```

<210> SEQ ID NO 54
<211> LENGTH: 411
<212> TYPE: DNA
<213> ORGANISM: Bovine

<400> SEQUENCE: 54

```
gtggagtctg ggggaggctt ggtacagcct ggggaggtccc tgagactctc ctgtgcagcg    60
tcaggattca ccttcaggaa ctttggcatg cactgggtcc gccaggctcc aggcaagggg   120
ctggagtggg tgacagttat atggtatgac ggaagtaatc aatactatat agactccgtg   180
aagggccgat tcaccatctc cagagacaat tccaagaaca tgttgtatct gcaaatgaac   240
agcctgagag ccgaggatac ggctgtgtat tactgtgcga gatcgcaa tggcctgaag   300 tacttcgatc tctggggccg tggcaccctg gtcactgtct catcagggag tgcatccgcc   360
ccaacccttt tccccctcgt ctcctgtgag aattccccgt cggatacgag c            411
```

<210> SEQ ID NO 55
<211> LENGTH: 137
<212> TYPE: PRT
<213> ORGANISM: Bovine

<400> SEQUENCE: 55

```
Val Glu Ser Gly Gly Gly Leu Val Gln Pro Gly Arg Ser Leu Arg Leu
1               5                   10                  15
```

-continued

```
Ser Cys Ala Ala Ser Gly Phe Thr Phe Arg Asn Phe Gly Met His Trp
            20                  25                  30
Val Arg Gln Ala Pro Gly Lys Gly Leu Glu Trp Val Thr Val Ile Trp
        35                  40                  45
Tyr Asp Gly Ser Asn Gln Tyr Tyr Ile Asp Ser Val Lys Gly Arg Phe
    50                  55                  60
Thr Ile Ser Arg Asp Asn Ser Lys Asn Met Leu Tyr Leu Gln Met Asn
65                  70                  75                  80
Ser Leu Arg Ala Glu Asp Thr Ala Val Tyr Tyr Cys Ala Arg Asp Arg
                85                  90                  95
Asn Gly Leu Lys Tyr Phe Asp Leu Trp Gly Arg Gly Thr Leu Val Thr
            100                 105                 110
Val Ser Ser Gly Ser Ala Ser Ala Pro Thr Leu Phe Pro Leu Val Ser
        115                 120                 125
Cys Glu Asn Ser Pro Ser Asp Thr Ser
    130                 135
```

<210> SEQ ID NO 56
<211> LENGTH: 441
<212> TYPE: DNA
<213> ORGANISM: Bovine

<400> SEQUENCE: 56

```
accctcctca ctcactgtgc agggtcctgg gcccagtctg tgctgactca gccaccctca    60
gcgtctggga cccccgggca gagggtcacc atctcttgtt ctggaagcag ctccaacatc   120
ggaagtaatt atgtatactg gtaccagcag ctcccaggaa cggcccccaa actcctcatc   180
tataggaata atcagcggcc ctcaggggtc cctgaccgat tctctggctc caagtctggc   240
acctcagcct ccctggccat cagtgggctc cggtccgagg atgaggctga ttattactgt   300
gcagcatggg atgacagcct gagtggtctt ttcggcggag ggaccaagct gaccgtccta   360
ggtcagccca aggctgcccc ctcggtcact ctgttcccac cctcctctga ggagcttcaa   420
gccaacaagg ccacactggt g                                             441
```

<210> SEQ ID NO 57
<211> LENGTH: 147
<212> TYPE: PRT
<213> ORGANISM: Bovine

<400> SEQUENCE: 57

```
Thr Leu Leu Thr His Cys Ala Gly Ser Trp Ala Gln Ser Val Leu Thr
1               5                   10                  15
Gln Pro Pro Ser Ala Ser Gly Thr Pro Gly Gln Arg Val Thr Ile Ser
            20                  25                  30
Cys Ser Gly Ser Ser Ser Asn Ile Gly Ser Asn Tyr Val Tyr Trp Tyr
        35                  40                  45
Gln Gln Leu Pro Gly Thr Ala Pro Lys Leu Leu Ile Tyr Arg Asn Asn
    50                  55                  60
Gln Arg Pro Ser Gly Val Pro Asp Arg Phe Ser Gly Ser Lys Ser Gly
65                  70                  75                  80
Thr Ser Ala Ser Leu Ala Ile Ser Gly Leu Arg Ser Glu Asp Glu Ala
                85                  90                  95
Asp Tyr Tyr Cys Ala Ala Trp Asp Asp Ser Leu Ser Gly Leu Phe Gly
            100                 105                 110
Gly Gly Thr Lys Leu Thr Val Leu Gly Gln Pro Lys Ala Ala Pro Ser
```

-continued

```
                  115                 120                 125
Val Thr Leu Phe Pro Pro Ser Ser Glu Glu Leu Gln Ala Asn Lys Ala
    130                 135                 140

Thr Leu Val
145
```

<210> SEQ ID NO 58
<211> LENGTH: 459
<212> TYPE: DNA
<213> ORGANISM: Bovine

<400> SEQUENCE: 58

```
agttggaccc ctctctggct cactctcttc actctttgca taggttctgt ggtttcttct    60
gagctgactc aggaccctgc tgtgtctgtg gccttgggac agacagtcag gatcacatgc   120
caaggagaca gcctcagaag ctattatgca agctggtacc agcagaagcc aggacaagcc   180
cctgtacttg tcatctatgg taaaaacaac cggccctcag ggatcccaga ccgattctct   240
ggctccagct caggaaacac agcttccttg accatcactg gggctcaggc ggaggatgag   300
gctgactatt actgtaactc ccgggacagc agtggtaacc atgtggtatt cggcggaggg   360
accaagctga ccgtcctagg tcagcccaag ctgcccccct cggtcactct gttcccaccc   420
tcctctgagg agcttcaagc caacaaggcc acactggtg                          459
```

<210> SEQ ID NO 59
<211> LENGTH: 153
<212> TYPE: PRT
<213> ORGANISM: Bovine

<400> SEQUENCE: 59

```
Ser Trp Thr Pro Leu Trp Leu Thr Leu Phe Thr Leu Cys Ile Gly Ser
  1               5                  10                  15
Val Val Ser Ser Glu Leu Thr Gln Asp Pro Ala Val Ser Val Ala Leu
             20                  25                  30
Gly Gln Thr Val Arg Ile Thr Cys Gln Gly Asp Ser Leu Arg Ser Tyr
         35                  40                  45
Tyr Ala Ser Trp Tyr Gln Gln Lys Pro Gly Gln Ala Pro Val Leu Val
     50                  55                  60
Ile Tyr Gly Lys Asn Asn Arg Pro Ser Gly Ile Pro Asp Arg Phe Ser
 65                  70                  75                  80
Gly Ser Ser Ser Gly Asn Thr Ala Ser Leu Thr Ile Thr Gly Ala Gln
                 85                  90                  95
Ala Glu Asp Glu Ala Asp Tyr Tyr Cys Asn Ser Arg Asp Ser Ser Gly
            100                 105                 110
Asn His Val Val Phe Gly Gly Gly Thr Lys Leu Thr Val Leu Gly Gln
        115                 120                 125
Pro Lys Ala Ala Pro Ser Val Thr Leu Phe Pro Pro Ser Ser Glu Glu
    130                 135                 140
Leu Gln Ala Asn Lys Ala Thr Leu Val
145                 150
```

<210> SEQ ID NO 60
<211> LENGTH: 723
<212> TYPE: DNA
<213> ORGANISM: Bovine

<400> SEQUENCE: 60

```
atgagattcc ctgctcagct cctggggctc ctcctgctct gggtcccagg atccagtggg    60
```

-continued

```
gatgttgtgc tgacccagac tcccctctcc ctgtctatca tccctggaga gacggtctcc    120
atctcctgca agtctactca gagtctgaaa tatagtgatg aaaaaccta tttgtactgg     180 cttcaacata aaccaggcca atcaccacag cttttgatct atgctgtttc cagccgttac    240
actggggtcc cagacaggtt cactggcagt gggtcagaaa cagatttcac acttacgatc    300
aacagtgtgc aggctgagga tgttggagtc tattactgtc ttcaaacaac atatgtccca    360
aatactttcg gccaaggaac caaggtagag atcaaaaggt ctgatgctga gccatccgtc    420
ttcctcttca aaccatctga tgagcagctg aagaccggaa ctgtctctgt cgtgtgcttg    480
gtgaatgatt tctaccccaa agatatcaat gtcaagtgga agtggatggg ggttactcag    540
agcagcagca acttccaaaa cagtttcaca gaccaggaca gcaagaaaag cacctacagc    600
ctcagcagca tcctgacact gcccagctca gagtaccaaa gccatgacgc ctatacgtgt    660
gaggtcagcc acaagagcct gactaccacc ctcgtcaaga gcttcagtaa gaacgagtgt    720
tag                                                                 723
```

<210> SEQ ID NO 61
<211> LENGTH: 20
<212> TYPE: DNA
<213> ORGANISM: Artificial Sequence
<220> FEATURE:
<223> OTHER INFORMATION: Synthetic Primer

<400> SEQUENCE: 61

```
gatgatgtct ccaggatgcc                                                20
```

<210> SEQ ID NO 62
<211> LENGTH: 21
<212> TYPE: DNA
<213> ORGANISM: Artificial Sequence
<220> FEATURE:
<223> OTHER INFORMATION: Synthetic Primer

<400> SEQUENCE: 62

```
gacaagctta atatccgcag g                                              21
```

<210> SEQ ID NO 63
<211> LENGTH: 30
<212> TYPE: DNA
<213> ORGANISM: Artificial Sequence
<220> FEATURE:
<223> OTHER INFORMATION: Synthetic Primer

<400> SEQUENCE: 63

```
aagaagagaa aggtagaaga ccccaaggac                                     30
```

<210> SEQ ID NO 64
<211> LENGTH: 28
<212> TYPE: DNA
<213> ORGANISM: Artificial Sequence
<220> FEATURE:
<223> OTHER INFORMATION: Synthetic Primer

<400> SEQUENCE: 64

```
cctgggtata gacaggtggg tattgtgc                                       28
```

<210> SEQ ID NO 65
<211> LENGTH: 40
<212> TYPE: DNA
<213> ORGANISM: Artificial Sequence
<220> FEATURE:

```
<223> OTHER INFORMATION: Synthetic Primer

<400> SEQUENCE: 65
ggggtctaga gcagacacta cactgatggg cccttggtcc                              40

<210> SEQ ID NO 66
<211> LENGTH: 36
<212> TYPE: DNA
<213> ORGANISM: Artificial Sequence
<220> FEATURE:
<223> OTHER INFORMATION: Synthetic Primer

<400> SEQUENCE: 66
ggggaagctt cgtgtccctg gtcctgtctg acacag                                  36

<210> SEQ ID NO 67
<211> LENGTH: 34
<212> TYPE: DNA
<213> ORGANISM: Artificial Sequence
<220> FEATURE:
<223> OTHER INFORMATION: Synthetic Primer

<400> SEQUENCE: 67
ggggctcgag gtcggcgaag gatgggggga ggtg                                    34

<210> SEQ ID NO 68
<211> LENGTH: 35
<212> TYPE: DNA
<213> ORGANISM: Artificial Sequence
<220> FEATURE:
<223> OTHER INFORMATION: Synthetic Primer

<400> SEQUENCE: 68 gggggggtacc gctgggctga gctgggcaga gtggg                                  35

<210> SEQ ID NO 69
<211> LENGTH: 20
<212> TYPE: DNA
<213> ORGANISM: Artificial Sequence
<220> FEATURE:
<223> OTHER INFORMATION: Synthetic Primer

<400> SEQUENCE: 69
tggtcactcc aagtgagtcg                                                    20

<210> SEQ ID NO 70
<211> LENGTH: 21
<212> TYPE: DNA
<213> ORGANISM: Artificial Sequence
<220> FEATURE:
<223> OTHER INFORMATION: Synthetic Primer

<400> SEQUENCE: 70
tggagtgaaa tcaggtgaag g                                                  21

<210> SEQ ID NO 71
<211> LENGTH: 29
<212> TYPE: DNA
<213> ORGANISM: Artificial Sequence
<220> FEATURE:
<223> OTHER INFORMATION: Synthetic Primer

<400> SEQUENCE: 71
ccacaaagga aaagctgca ctgctatac                                           29
```

<210> SEQ ID NO 72
<211> LENGTH: 28
<212> TYPE: DNA
<213> ORGANISM: Artificial Sequence
<220> FEATURE:
<223> OTHER INFORMATION: Synthetic Primer

<400> SEQUENCE: 72
tgtgggatca ggaggtcaga tagacatc                                    28

<210> SEQ ID NO 73
<211> LENGTH: 28
<212> TYPE: DNA
<213> ORGANISM: Artificial Sequence
<220> FEATURE:
<223> OTHER INFORMATION: Synthetic Primer

<400> SEQUENCE: 73
tttggtcctg tagtttgcta acacaccc                                    28

<210> SEQ ID NO 74
<211> LENGTH: 26
<212> TYPE: DNA
<213> ORGANISM: Artificial Sequence
<220> FEATURE:
<223> OTHER INFORMATION: Synthetic Primer

<400> SEQUENCE: 74
ggatcagtgc ctatcactcc aggttg                                      26

<210> SEQ ID NO 75
<211> LENGTH: 33
<212> TYPE: DNA
<213> ORGANISM: Homo sapiens

<400> SEQUENCE: 75
tactgtgcaa gagatgagaa tgcttttgat gtc                              33

<210> SEQ ID NO 76
<211> LENGTH: 51
<212> TYPE: DNA
<213> ORGANISM: Homo sapiens

<400> SEQUENCE: 76
attactgtgc gaagaacaaa atagcagcag ctggtacgat ctttgactac t           51

<210> SEQ ID NO 77
<211> LENGTH: 49
<212> TYPE: DNA
<213> ORGANISM: Homo sapiens

<400> SEQUENCE: 77
actgtaccac agatctgata gcagtggctg gtactgggta cttccagca             49

<210> SEQ ID NO 78
<211> LENGTH: 46
<212> TYPE: DNA
<213> ORGANISM: Homo sapiens

<400> SEQUENCE: 78
tactgtgcga gtcgtagtac cagctgctat gatgcttttg atgtct                46

<210> SEQ ID NO 79
<211> LENGTH: 45
<212> TYPE: DNA

```
<213> ORGANISM: Homo sapiens

<400> SEQUENCE: 79
ttactgtgcg agttttgggt ggtggtcaca tttagactac tgggg            45

<210> SEQ ID NO 80
<211> LENGTH: 48
<212> TYPE: DNA
<213> ORGANISM: Homo sapiens

<400> SEQUENCE: 80
actgtgcgag acatgaaaaa cttcggggag ttataatcta ctggggcc         48

<210> SEQ ID NO 81
<211> LENGTH: 46
<212> TYPE: DNA
<213> ORGANISM: Homo sapiens

<400> SEQUENCE: 81
ttactgtgcg aggggatgg cagcagctgg taccgactac tggggc            46

<210> SEQ ID NO 82
<211> LENGTH: 56
<212> TYPE: DNA
<213> ORGANISM: Homo sapiens

<400> SEQUENCE: 82
actgtgcgag agattgtagt agtaccagct gccaagatcg taagtggtac ttcgat    56

<210> SEQ ID NO 83
<211> LENGTH: 43
<212> TYPE: DNA
<213> ORGANISM: Homo sapiens

<400> SEQUENCE: 83
ttactgtgcg agatgggttt ttgatcccca gtttgactac tgg              43

<210> SEQ ID NO 84
<211> LENGTH: 43
<212> TYPE: DNA
<213> ORGANISM: Homo sapiens

<400> SEQUENCE: 84
tcactgtgcg agaattttac tggggatgat gcttttgatg tct              43

<210> SEQ ID NO 85
<211> LENGTH: 27
<212> TYPE: DNA
<213> ORGANISM: Homo sapiens

<400> SEQUENCE: 85
agcctgagtg gtctttcgg cggaggg                                 27

<210> SEQ ID NO 86
<211> LENGTH: 30
<212> TYPE: DNA
<213> ORGANISM: Homo sapiens

<400> SEQUENCE: 86
cagtggtaac catctggtat tcggcggagg                             30

<210> SEQ ID NO 87
<211> LENGTH: 28
```

```
<212> TYPE: DNA
<213> ORGANISM: Homo sapiens

<400> SEQUENCE: 87
cagcctgagt gctgtcttcg gaactggg                                          28

<210> SEQ ID NO 88
<211> LENGTH: 27
<212> TYPE: DNA
<213> ORGANISM: Homo sapiens

<400> SEQUENCE: 88
agcaacttcg tgtagttcgg cggagag                                           27

<210> SEQ ID NO 89
<211> LENGTH: 26
<212> TYPE: DNA
<213> ORGANISM: Homo sapiens

<400> SEQUENCE: 89
ggtagtagca cttctcggcg gaggga                                            26

<210> SEQ ID NO 90
<211> LENGTH: 29
<212> TYPE: DNA
<213> ORGANISM: Homo sapiens

<400> SEQUENCE: 90
cagtggtaac cattatgtct tcggaactg                                         29

<210> SEQ ID NO 91
<211> LENGTH: 28
<212> TYPE: DNA
<213> ORGANISM: Homo sapiens

<400> SEQUENCE: 91
gacagcagca cttatgtctt cggaactg                                          28

<210> SEQ ID NO 92
<211> LENGTH: 31
<212> TYPE: DNA
<213> ORGANISM: Homo sapiens

<400> SEQUENCE: 92
ggcagcaaca atttcgatgt cttcggaact g                                      31

<210> SEQ ID NO 93
<211> LENGTH: 26
<212> TYPE: DNA
<213> ORGANISM: Homo sapiens

<400> SEQUENCE: 93
agcagcagca ctcgtttcgg cggagg                                            26

<210> SEQ ID NO 94
<211> LENGTH: 23
<212> TYPE: DNA
<213> ORGANISM: Homo sapiens

<400> SEQUENCE: 94
agcagcagca ctcggaactg gga                                               23
```

TRANSGENIC BOVINE HAVING REDUCED PRION PROTEIN ACTIVITY AND USES THEREOF

CROSS-REFERENCE TO RELATED APPLICATIONS

This application is a continuation of Ser. No. 10/705,519, filed Nov. 10, 2003 which claims the benefit of U.S. Provisional Application Nos. 60/425,056 (filed Nov. 8, 2002) and 60/506,901 (filed Sep. 26, 2003), each of which is hereby incorporated by reference.

BACKGROUND OF THE INVENTION

In general, the invention features cloned transgenic ungulates (e.g., bovines) in which prion protein (PrP) activity is reduced by one or more genetically engineered mutations. Because such transgenic bovines with reduced prion protein activity should be resistant to prion-related diseases such as bovine spongiform encephalopy (BSE, also known as mad cow disease), they are a safer and preferred source for agricultural and pharmaceutical products, such as human therapeutic antibodies.

Since the first case of BSE was discovered in the United Kingdom in 1986, this infectious disease has spread to other parts of the world, such as Japan. The threat of this disease has a great impact on the agricultural and pharmaceutical fields and has limited the use of cattle in these industries. Based on over a decade of research, prion protein has been identified as a substantial cause of this infectious disease. Animals having reduced prion protein activity are desirable because of their expected resistance to prion protein-related infection.

So far, transgenic mice having reduced prion protein activity have been created using conventional gene targeting strategies in homologous recombination-proficient murine embryonic stem (ES) cells. However, ES cells from ungulates such as cattle have been difficult to isolate, culture, and genetically modify.

In the generation of prion knockout sheep, fetal fibroblasts were transfected with a promoterless knockout (KO) vector because the prion protein gene is very actively expressed in fetal fibroblasts (Denning et al., Nature Biotech., 19:559-562, 2001). By using this type of knockout vector, homologously targeted clones can be selected using an appropriate drug, such as G418 or puromycin, because the promoterless drug-resistant gene (e.g., a neomycin or puromycin-resistant gene) in the knockout vector can be expressed only when it is integrated into an actively expressed gene loci. However, only one live lamb was produced by nuclear transfer of these hemizygously targeted ovine fibroblasts, and then the lamb died about 12 days after birth. Unlike murine ES cells with an unlimited life-span, somatic fibroblasts have a limited life-span, which has made somatic gene targeting difficult because of the length of time required to culture the cells under stringent drug selection to select the desired knockout cells. Furthermore, in general, the frequency of homologous recombination in somatic fibroblasts is about 10-100 fold lower than in murine ES cells. These limitations pertaining to somatic fibroblasts in addition to the low success rate of traditional nuclear transfer methods have made it difficult to produce viable livestock with a desired site-specific mutation.

Reduction of prion protein activity by gene targeting has been attempted in cattle. To our knowledge, successful generation of transgenic bovines with a mutation at the prion locus has not been reported, probably because of a lack of appropriate knockout vectors and/or nuclear transfer methods. Thus, improved knockout vectors are needed to mutate the prion locus in ungulate cells (e.g., bovine cells) with high efficiency. Additionally, improved methods for generating transgenic ungulates (e.g., bovines) from these genetically modified donor cells are desirable.

SUMMARY OF THE INVENTION

The present invention features the design of knockout vectors with which very high frequency hemizygous and homozygous targeted integration (so-called homologous recombination) can be accomplished at the prion locus in ungulates (e.g., bovines) in donor cells such as fetal somatic fibroblasts. The invention also features methods for producing live calves having a hemizygous or homozygous mutation at the prion locus using genetically modified donor cells in any of the nuclear transfer methods described herein. These cattle are useful for producing pharmaceutical and agricultural products, such as therapeutic human antibodies for human use.

The method of the present invention is achieved using several technologies, such as (i) prion gene knockout cells described herein, (ii) mammalian cloning methods such as nuclear transfer or chromatin transfer described in PCT Publication No. WO02/051997, and (iii) introduction of a human artificial chromosome (HAC) such as delta HAC into an ungulate (PCT Publication No. WO02/70648; Kuroiwa et al., Nature Biotechnol. 20:889-894, 2002). The prion knockout ungulate cell is used as source of donor genetic material in a mammalian cloning method, resulting in prion knockout (hemi or homo) offspring.

Prion knockout ungulates may also have other useful features, such as production of human antibody. Such ungulates can be generated using a combination of the above technologies. For example, a prion knockout and human antibody-producing bovine can be generated by crossbreeding of a prion knockout ungulate and a human antibody-producing ungulate as described in PC Publication No. WO02/70648. Sequential manipulation of fetal fibroblast cells can also be used to generate such an ungulate, with or without breeding ungulates. Sequential manipulation of bovine fetal fibroblasts includes repeating the following steps: (i) genetic manipulation of an ungulate (e.g., a bovine) fibroblast cell, (ii) mammalian cloning using this cell, (iii) generation of a fetus, and (iv) isolation of a genetically-modified fetal fibroblast cell. For example, a prion knockout fibroblast cell can be sequentially manipulated to retain a HAC and to inactivate endogenous Ig genes.

The resulting monoclonal or polyclonal xenogenous antibodies have a variety of uses; for example, they may be used as ingredients in prophylactic or therapeutic compositions for infection of pathogenic microorganisms such as bacteria or viruses.

Transgenic Ungulates and Ungulate Cells

In one aspect, the invention provides an ungulate (e.g., bovine) or ungulate cell (e.g., bovine cell) having a non-naturally occurring mutation (e.g., a mutation after the initial ATC codon, such as a mutation that is within 10, 20, 50, or 100 nucleotides of this codon) in one or both alleles of an endogenous prion nucleic acid. Preferably, the mutation reduces or substantially eliminates the expression of functional prion protein. In preferred embodiments, expression of functional or total prion protein is decreased by at least 10, 20, 40, 60, 80, 90, 95, or 100%. The mutation may be hemizygous or homozygous. In some embodiments, the mutation includes an insertion of a positive selection marker (e.g., an antibiotic resistance gene) into the prion nucleic acid. Preferably, the positive selection marker is operably linked to a xenogenous promoter. For ungulates or ungulate cells with an antibiotic resistance gene inserted into both alleles of a prion nucleic acid, each allele may contain the same or a different antibiotic resistance gene. In a preferred embodiment, a negative selection marker (e.g., DT-A or Tk) is operably linked to a xenogenous promoter and is present in a vector used to mutate an endogenous prion allele. The mutation may or may not include the deletion of one or more nucleotides (e.g., contiguous nucleotides) in the prion nucleic acid.

In preferred embodiments of the above aspect, the ungulate (e.g., bovine) or ungulate cell (e.g., bovine cell) has one or more transgenes and expresses an mRNA or protein (e.g., antibody) encoded by the transgene(s). Preferred ungulates contain naturally arranged segments of human chromosomes (e.g., human chromosomal fragments) or artificial chromosomes that comprise artificially engineered human chromosome fragments (i.e., the fragments may be rearranged relative to the human genome). In some embodiments, the xenogenous nucleic acid is contained within a chromosome fragment. The nucleic acid may be integrated into a chromosome of the ungulate or maintained in the ungulate cell independently from the host chromosome. In various embodiments, the nucleic acid is contained in a chromosome fragment, such as a ΔHAC or a ΔΔHAC. In other embodiments, the xenogenous antibody is an antibody from another genus, such as a human antibody.

Preferred ungulates and ungulate cells have one or more nucleic acids having a xenogenous antibody gene locus (e.g., a nucleic acid encoding all or part of a xenogenous immunoglobulin (Ig) gene that undergoes rearrangement and expresses at least one xenogenous Ig molecule) in one or more B-cells. Preferably, the nucleic acid has unrearranged antibody light chain nucleic acid segments in which all of the nucleic acid segments encoding a V gene segment are separated from all of the nucleic acid segments encoding a J gene segment by one or more nucleotides. Other preferred nucleic acids have unrearranged antibody heavy chain nucleic acid segments in which either (i) all of the nucleic acid segments encoding a V gene segment are separated from all of the nucleic acid segments encoding a D gene segment by one or more nucleotides and/or (ii) all of the nucleic acid segments encoding a D gene segment are separated from all of the nucleic acid segments encoding a J gene segment by one or more nucleotides. Other preferred ungulates have one or more nucleic acids encoding all or part of a rearranged xenogenous immunoglobulin (Ig) gene that expresses at least one xenogenous Ig molecule.

In other preferred embodiments, the light chain and/or heavy chain of the xenogenous antibodies is encoded by a human nucleic acid. In preferred embodiments, the heavy chain is any class of heavy chain, such as μ, γ, δ, ε, or α, and the light chain is a lambda or kappa light chain. In other preferred embodiments, the nucleic acid encoding the xenogenous immunoglobulin chain or antibody is in its unrearranged form. In other preferred embodiments, more than one class of xenogenous antibody is produced by the ungulate. In various embodiments, more than one different xenogenous Ig or antibody is produced by the ungulate. The xenogenous antibody may be a polyclonal or monoclonal antibody.

In various embodiments of the above aspect, the ungulate (e.g., bovine) or ungulate cell (e.g., bovine cell) has a mutation that reduces the expression of an endogenous antibody. Preferably, the mutation reduces the expression of functional IgM heavy chain or substantially eliminates the expression of functional IgM heavy chain. In other preferred embodiments, the mutation reduces the expression of functional Ig light chain or substantially eliminates the expression of functional Ig light chain. In yet other preferred embodiments, the mutation reduces the expression of functional IgM heavy chain and functional Ig light chain, or the mutation substantially eliminates the expression of functional IgM heavy chain and functional Ig light chain. Preferably, the ungulate also has a mutation in one or both alleles of an endogenous nucleic acid encoding alpha-(1,3)-galactosyltransferase and/or J chain. In other preferred embodiments, the ungulate has a nucleic acid encoding an exogenous J chain, such as a human J chain. Preferably, the mutation reduces or eliminates the expression of the endogenous alpha-(1,3)-galactosyltransferase enzyme, galactosyl(α1,3)galactose epitope, and/or J chain. Preferably, the ungulate produces human IgA or IgM molecules containing human J chain. Preferred ungulate cells (e.g., bovine cells) include, somatic cells, such as fetal fibroblasts or B-cells.

The invention also features hybridomas that produce xenogenous (e.g., human) antibodies. In one such aspect, the invention provides a hybridoma formed from the fusion of a B-cell of the invention with a myeloma cell. Preferably, the antibody is reactive with an antigen of interest.

Methods for Producing Transgenic Ungulate Cells

The invention also features methods for generating ungulate cells (e.g., bovine cells) with a mutation in one or both alleles of a prion nucleic acid. These cells may be used as donor cells for the generation of transgenic ungulates (e.g., bovine prion knockout ungulates). Preferably, the mutation leads to a decrease in the amount of functional prion protein and/or a decreased incidence of prion related infections or diseases, such as BSE.

Accordingly, in one such aspect the invention features a method for producing a transgenic ungulate (e.g., bovine). This method involves introducing a first prion gene-targeting vector into an ungulate cell under conditions that allow homologous recombination between the first vector and a first allele of an endogenous prion nucleic acid in the cell, thereby introducing a hemizygous mutation in the cell. Preferably, the first vector includes a first region of homology having substantial sequence identity to a first region of an endogenous prion nucleic acid of the cell, a positive selection marker, and a second region of homology having substantial sequence identity to a second region of the prion nucleic acid. In a preferred embodiment, one region of homology is at least 1, 2, 3, 4, 5, 6, or 8 kilobases longer than the other region of homology. Preferably, the method also includes re-introducing the first vector into the cell under conditions that allow homologous recombination between the first vector and a second allele of an endogenous prion nucleic acid in the cell, thereby introducing a homozygous mutation in the cell. In other embodiments, the method also includes introducing a second prion gene targeting vector that has a different antibiotic resistance gene than the first vector into the cell under conditions that allow homologous recombination between the second vector and a second allele of an endogenous prion nucleic acid in the cell, thereby introducing a homozygous mutation in the cell. Preferably, the first and/or second vector is introduced into the cell in the presence of 1 mM of spermidine. Preferred cells include bovine fetal fibroblasts.

In various embodiments of the invention, the nucleic acid used to mutate an endogenous prion nucleic acid (e.g., a knockout cassette which includes a promoter operably linked to a nucleic acid encoding a selectable marker and operably linked to a nucleic acid having substantial sequence identity to a prion nucleic acid) is not contained in a viral vector, such as an adenoviral vector or an adeno-associated viral vector. For example, the nucleic acid may be contained in a plasmid or artificial chromosome that is inserted into an ungulate cell, using a standard method such as transfection or lipofection that does not involve viral infection of the cell. In yet another embodiment, the nucleic acid used to mutate an endogenous prion nucleic acid (e.g., a knockout cassette which includes a promoter operably linked to a nucleic acid encoding a selectable marker and operably linked to a nucleic acid having substantial sequence identity to a prion nucleic acid) is contained in a viral vector, such as an adenoviral vector or an adeno-associated viral vector. According to this embodiment, a virus containing the viral vector is used to infect an ungulate cell, resulting in the insertion of a portion or the entire viral vector into the ungulate cell.

Methods for Producing Transgenic Ungulates

The invention also provides methods for producing transgenic ungulates with one or more mutations in endogenous prion nucleic acids. One such method involves inserting a cell of any of the above aspects of the invention, a chromatin mass from the cell, or a nucleus from the cell into an oocyte. The cell has a first mutation in an endogenous prion nucleic acid. The oocyte or an embryo formed from the oocyte is transferred into the uterus of a host ungulate under conditions that allow the oocyte or the embryo to develop into a fetus. Preferably, the fetus develops into a viable offspring.

In preferred embodiments, the first mutation is introduced into the cell by inserting a nucleic acid comprising a cassette that includes a promoter operably linked to a nucleic acid encoding a selectable marker and operably linked to one or more nucleic acids having substantial sequence identity to an endogenous prion nucleic acid, whereby the cassette is integrated into one endogenous allele of a prion nucleic acid. In other preferred embodiments, the mutation is introduced in the cell by inserting into the cell a nucleic acid comprising a first cassette that includes a first promoter operably linked to a nucleic acid encoding a first selectable marker and operably linked to a first nucleic acid having substantial sequence identity to a endogenous prion nucleic acid, whereby the first cassette is integrated into a first endogenous allele of a prion nucleic acid producing a first transgenic cell. Into the first transgenic cell is inserted a nucleic acid that includes a second cassette that includes a second promoter operably linked to a nucleic acid encoding a second selectable marker and operably linked to a second nucleic acid having substantial sequence identity to a prion nucleic acid. The second selectable marker differs from the first selectable marker, and the second cassette is integrated into a second endogenous allele of a prion nucleic acid producing a second transgenic cell.

In still other preferred embodiments, a cell is isolated from the embryo, the fetus, or an offspring produced from the fetus, and another mutation is introduced into a prion nucleic acid or another nucleic acid (e.g., an antibody heavy or light chain nucleic acid) of the cell. A second round of nuclear transfer is then performed using the resulting cell, a chromatin mass from the cell, or a nucleus from the cell to produce a transgenic ungulate with two or more mutations. The mutations are in the same or different alleles of a gene or are in different genes. The cell used in the first or optional second round of nuclear transfer encodes a xenogenous antibody. In particular embodiments, the cell includes one or more nucleic acids encoding all or part of a xenogenous Ig gene that is capable of undergoing rearrangement and expressing one or more xenogenous Ig molecules in B-cells. In preferred embodiments, the cell that is mutated is a fibroblast (e.g., a fetal fibroblast). Preferably, the endogenous gene that is mutated is operably linked to an endogenous promoter that is not active in a fibroblast. In other preferred embodiments, the endogenous promoter operably linked to the endogenous gene that is mutated is less than 80, 70, 60, 50, 40, 30, 20, 10% as active as an endogenous promoter operably linked to a endogenous housekeeping gene such as GAPDH. Promoter activity may be measured using any standard assay, such as assays that measure the level of mRNA or protein encoded by the gene (see, for example, Ausubel et al., Current Protocols in Molecular Biology, volume 2, p. 11.13.1-11.13.3, John Wiley & Sons, 1995). This method for generating a transgenic ungulate has the advantage of allowing a gene that is not expressed in the donor cell (i.e., the cell that is the source of the genetic material used for nuclear transfer) to be mutated.

Preferably, the cell used in the production of the transgenic ungulate has a mutation in one or both alleles of an endogenous nucleic acid encoding alpha-(1,3)-galactosyltransferase and/or J chain. In other preferred embodiments, the cell has a nucleic acid encoding an exogenous J chain, such as a human J chain, or a nucleic acid encoding a xenogenous antibody. Preferably, the xenogenous nucleic acid encodes all or part of a xenogenous Ig gene, and the gene is capable of undergoing rearrangement and expressing more than one xenogenous Ig molecule in B-cells. In other preferred embodiments, the antibody is a polyclonal antibody. In yet other preferred embodiments, the immunoglobulin chain or antibody is expressed in serum and/or milk.

We have previously disclosed a variety of improved methods for cloning mammals (e.g., ungulates such as bovines) that may be used to clone mammals with one or more mutations in a prion nucleic acid (see, e.g., U.S. Patent Publication No. 2002-0046722 A1 and PCT Publication No. WO02/051997). In some of these methods, a permeabilized cell is incubated with a reprogramming media (e.g., a cell extract) to allow the addition or removal of factors from the cell, and then the plasma membrane of the permeabilized cell is resealed to enclose the desired factors and restore the membrane integrity of the cell. Some of these methods also involve the condensation of a donor nucleus (e.g., an isolated nucleus or a nucleus within a donor cell) into a chromatin mass to allow the release of nuclear components such as transcription factors that may promote the transcription of genes that are undesirable for the development of the nuclear transplant embryo into a viable offspring. If desired, the steps of any of these methods may be repeated one or more times or different reprogramming methods may be performed sequentially to increase the extent of reprogramming, resulting in greater viability of the cloned fetuses.

One method for generating a transgenic ungulate (e.g., bovine) involves incubating a permeabilized cell of any the above aspects of the invention (e.g., a cell that has one or more mutations in an endogenous prion nucleic acid) with a reprogramming media (e.g., a cell extract) under conditions that allow the removal of a factor (e.g., a nuclear or cytoplasmic component such as a transcription factor) from a nucleus, chromatin mass, or chromosome of the permeabilized cell or the addition of a factor to the nucleus, chromatin mass, or chromosome, thereby forming a reprogrammed cell. The reprogrammed cell is inserted into an enucleated oocyte, and the resulting oocyte or an embryo formed from the oocyte is transferred into the uterus of a host ungulate under conditions that allow the oocyte or embryo to develop into a fetus. In preferred embodiments, the permeabilized cell is contacted with one or more of the following under conditions that allow formation of a chromatin mass: a mitotic extract in the presence or absence of an anti-NuMA antibody, a detergent and/or salt solution, or a protein kinase solution. In yet another preferred embodiment, the permeabilized cell is incubated with an interphase reprogramming media (e.g., an interphase cell extract). In still another preferred embodiment, the nucleus in the permeabilized cell remains membrane-bounded, and the chromosomes in the nucleus do not condense during incubation with this interphase reprogramming media. In certain embodiments, incubating the permeabilized cell in the reprogramming media does not cause DNA replication or only causes DNA replication in less than 50, 40, 30, 20, 10, or 5% of the cells. In other embodiments, incubating the permeabilized cell in the reprogramming media causes DNA replication in at least 60, 70, 80, 90, 95, or 100% of the cells. In various embodiments, the permeabilized cell is formed by incubating an intact cell with a protease such as trypsin, a detergent, such as digitonin, or a bacterial toxin, such as Streptolysin O. In a preferred embodiment, the reprogrammed cell is not incubated under conditions that allow the membrane of the reprogrammed cell to reseal prior to insertion into the oocyte. In yet another embodiment, the reprogrammed cell is incubated under conditions that allow the membrane of the reprogrammed cell to reseal prior to insertion into the oocyte. In other preferred embodiments, the reconstituted oocyte or the resulting embryo expresses lamin A, lamin C, or NuMA protein at a level that is less than 5-fold greater than the corresponding level expressed by a control oocyte or a control embryo with the same number of cells and from the same species.

In another aspect, the invention provides another method for generating a transgenic ungulate (e.g., bovine). This method involves (a) incubating a donor nucleus from a cell of the invention (e.g., a nucleus that has one or more mutations in an endogenous prion nucleic acid) under conditions that allow formation of a chromatin mass without causing DNA replication, (b) inserting the chromatin mass into an enucleated oocyte, thereby forming a nuclear transfer oocyte and (c) transferring the nuclear transfer oocyte or an embryo formed from the nuclear transfer oocyte into the uterus of a host ungulate under conditions that allow the nuclear transfer oocyte or embryo to develop into a fetus. In a preferred embodiment, the donor nucleus is incubated with a reprogramming media (e.g., a cell extract) under conditions that allow nuclear or cytoplasmic components such as transcription factors, repressor proteins, or chromatin remodeling proteins to be added to, or removed from, the nucleus or resulting chromatin mass. Preferably, the donor nucleus is contacted with one or more of the following under conditions that allow formation of a chromatin mass: a mitotic extract in the presence or absence of an anti-NuMA antibody, a detergent and/or salt solution, or a protein kinase solution. In other preferred embodiments, the reconstituted oocyte or the resulting embryo expresses lamin A, lamin C, or NuMA protein at a level that is less than 5-fold greater than the corresponding level expressed by a control oocyte or a control embryo with the same number of cells and from the same species. Preferably, the nucleus has fewer than four sets of homologous chromosomes (i.e., has fewer than two pairs of complete chromatids).

Preferred Methods for Generating Chimeric Ungulates

Other preferred ungulates are chimeric ungulates produced using cells from two or more embryos. For example, cells from a nuclear transfer embryo (e.g., an embryo formed by inserting a cell, nucleus, or chromatin mass into an enucleated oocyte) can be combined with cells from an in vitro fertilized, naturally-occurring, or parthenogenetically-activated embryo. Preferably, the majority of the cells and their progeny from the nuclear transfer embryo are incorporated into fetal tissue of the resulting chimeric embryo. At least some of the cells and their progeny from the second embryo are preferably incorporated into placental tissue and promote the viability of the resulting chimeric embryo. In preferred embodiments, the nuclear transfer embryo has a mutation in an endogenous prion nucleic acid and has a nucleic acid encoding a xenogenous antibody.

Accordingly, in one such aspect, the invention provides a method of producing a transgenic ungulate by inserting a cell, nucleus, or chromatin mass of the invention (e.g., a cell, nucleus, or chromatin mass having a mutation in an endogenous prion nucleic acid and optionally having one or more nucleic acids encoding a xenogenous antibody) into an oocyte, thereby forming a first embryo. One or more cells from the first embryo are contacted with one or more cells from a second embryo, thereby forming a third embryo. The second embryo is an in vitro fertilized embryo, naturally-occurring embryo, or parthenogenetically-activated embryo. The third embryo is transferred into the uterus of a host ungulate under conditions that allow the third embryo to develop into a fetus.

In another related aspect, the invention provides yet another method of generating a transgenic ungulate (e.g., a bovine). This method involves incubating a permeabilized cell of the invention (e.g., a cell having a mutation in an endogenous prion nucleic acid and optionally having one or more nucleic acids encoding a xenogenous antibody) in a reprogramming media (e.g., cell extract) under conditions that allow the removal of a factor from a nucleus, chromatin mass, or chromosome of the permeabilized cell or the addition of a factor from the reprogramming media to the nucleus, chromatin mass, or chromosome, thereby forming a reprogrammed cell. The reprogrammed cell is inserted into an enucleated oocyte, thereby forming a first embryo. One or more cells from the first embryo are contacted with one or more cells from an in vitro fertilized, naturally-occurring, or parthenogenetically-activated second embryo, forming a third embryo. The third embryo is transferred into the uterus of a host ungulate under conditions that allow the third embryo to develop into a fetus.

In a preferred embodiment, the permeabilized cell is incubated with a reprogramming media (e.g., a cell extract) under conditions that allow nuclear or cytoplasmic components such as transcription factors to be added to, or removed from, the nucleus or resulting chromatin mass. In other preferred embodiments, the permeabilized cell is contacted with one or more of the following under conditions that allow formation of a chromatin mass: a mitotic extract in the presence or absence of an anti-NuMA antibody, a detergent and/or salt solution, or a protein kinase solution. In yet another preferred embodiment, the permeabilized cell is incubated with an interphase reprogramming media (e.g., an interphase cell extract). In still another preferred embodiment, the nucleus in the permeabilized cell remains membrane-bounded, and the chromosomes in the nucleus do not condense during incubation with this interphase reprogramming media. In some embodiments, incubating the permeabilized cell in the reprogramming media does not cause DNA replication or only causes DNA replication in less than 50, 40, 30, 20, 10, or 5% of the cells. In other embodiments, incubating the permeabilized cell in the reprogramming media causes DNA replication in at least 60, 70, 80, 90, 95, or 100% of the cells. In various embodiments, the permeabilized cell is formed by incubating an intact cell with a protease such as trypsin, a detergent, such as digitonin, or a bacterial toxin, such as Streptolysin O. In a preferred embodiment, the reprogrammed cell is not incubated under conditions that allow the membrane of the reprogrammed cell to reseal prior to insertion into the oocyte. In yet another embodiment, the reprogrammed cell is incubated under conditions that allow the membrane of the reprogrammed cell to reseal prior to insertion into the oocyte.

In still other embodiments, the ungulate is generated by contacting a donor nucleus from a cell of the invention (e.g., a nucleus having a mutation in an endogenous prion nucleic acid and optionally having one or more nucleic acids encoding a xenogenous antibody) with a reprogramming media (e.g., cell extract) under conditions that allow formation of a chromatin mass, and inserting the chromatin mass into an enucleated oocyte, thereby forming a first embryo. One or more cells from the first embryo are contacted with one or more cells from an in vitro fertilized, naturally-occurring, or parthenogenetically activated second embryo, forming a third embryo. The third embryo is transferred into the uterus of a host ungulate under conditions that allow the third embryo to develop into a fetus. In a preferred embodiment, the chromatin mass is formed by contacting a donor nucleus that has less than four sets of homologous chromosomes with a reprogramming media under conditions that allow formation of a chromatin mass without causing DNA replication. Preferably, the donor nucleus is contacted with one or more of the following under conditions that allow formation of a chromatin mass: a mitotic extract in the presence or absence of an anti-NuMA antibody, a detergent and/or salt solution, or a protein kinase solution.

In preferred embodiments of any of the above aspects involving ungulates produced using cells from two embryos, at least one of the first embryo and the second embryo is a compaction embryo. In another embodiment, the first embryo and the second embryo are at different cell-stages. The first embryo and the donor cell used to produce the second embryo can be from the same species or from different genuses or species. Preferably, at least 10, 20, 30, 40, 50, 60, 70, 80, 90, 95, or 100% cells in the trophectoderm or placental tissue of the fetus are derived from the second embryo, or at least 30, 40, 50, 60, 70, 80, 90, 95, or 100% cells in the inner cell mass or fetal tissue of the fetus are derived from the first embryo. In other preferred embodiments, the first embryo or the third embryo expresses lamin A, lamin C, or NuMA protein at a level that is less than 5-fold greater than the corresponding level expressed by a control embryo with the same number of cells and from the same species.

In other preferred embodiments of any of the above aspects involving ungulates produced using cells from two embryos, part or all of the zona pellucida of the first embryo or second embryo is removed before the cells from each embryo are contacted. In one embodiment, the cells from the first and second embryos are contacted by being placed adjacent to each other in solution or on a solid support. In another embodiment, standard techniques are used to inject cells from the first embryo into the second embryo. The cells can be injected into any region of the second embryo, such as the periphery of the embryo between the zona pellucida and the embryo itself. Naturally occurring embryos include embryos that are surgically or nonsurgically removed from a pregnant ungulate (e.g., a bovine) using standard methods. In vitro fertilized embryos include intra-cytoplasmic sperm injection embryos generated using standard methods. It is also contemplated that cells from more than two embryos (e.g., cells from three, four, five, six, or more embryos) can be combined to form a chimeric embryo for generation of a cloned ungulate.

Preferred Embodiments for Generating Ungulates

In preferred embodiments of any of the above aspects, the reprogramming media (e.g., a cell extract) is modified by the enrichment or depletion of a factor, such as a DNA methyltransferase, histone deacetylase, histone, protamine, nuclear lamin, transcription factor, activator, or repressor. In other preferred embodiments, the level of expression of NuMA or AKAP95 protein in the oocyte or chimeric embryo is at least 2-, 5-, 10-, or 20-fold greater in the nucleus than in the cytoplasm. In yet other embodiments, at least 30, 40, 50, 60, 70, 80, 90, or 100% of the AKAP95 protein in the oocyte or chimeric embryo is extracted with a solution of 0.1% Triton X-100, 1 mg/ml DNase I, and either 100 mM or 300 mM NaCl. Preferably, the chromatin mass is purified from the reprogramming media (e.g., extract) prior to insertion into the enucleated oocyte. In another preferred embodiment, inserting the chromatin mass into the enucleated oocyte involves contacting the chromatin mass and the oocyte with a fusigenic compound under conditions that allow the chromatin mass to enter the ooctye. In yet another preferred embodiment, the fetus develops into a viable offspring. Preferably, at least 1, 3, 5, 10, 20, 30, 40, 50, 60, 70, 80, or 90% of the nuclear transfer oocytes or embryos develop into viable offspring. In this method, the oocyte containing the chromatin mass or reprogrammed cell may be cultured under conditions that allow cell division and one of the resulting cells may be recloned one or more times. The donor nucleus, donor chromatin mass, or donor cell and the oocyte used in the method may be from the same species, or they may be from different species or genuses. Desirably, the donor cell or resulting transgenic ungulate expresses at least 10, 20, 40, 60, 80, 90, 95, or 100% less functional or total protein than a corresponding, naturally-occurring cell or ungulate. The oocyte may be fertilized or unfertilized. Preferably the donor nucleus, chromatin mass, or permeabilized cell is from a $G_1$ or $G_0$ phase cell. In addition, the genomic DNA of the cloned embryo, fetus, or ungulate is preferably substantially identical to that of the donor cell. It is also contemplated that the chromatin mass or reprogrammed cell may be inserted into an embryo for the production of a chimeric embryo, fetus, or ungulate containing a mixture of cells with DNA substantially identical to that of the chromatin mass or reprogrammed cell and cells with DNA substantially identical to that of the naturally-occurring cells in the embryo. It is also contemplated that a nucleated oocyte may be used in the methods of the invention.

The reprogramming media used in any of the aspects of the invention may or may not contain exogenous nucleotides. In other preferred embodiments, a chromatin mass in a reprogramming media or formed in a permeabilized cell is contacted with a vector having a nucleic acid encoding a gene of interest under conditions that allow random integration or homologous recombination between the nucleic acid in the vector and the corresponding nucleic acid in the genome of the chromatin mass, resulting in the alteration of the genome of the chromatin mass. Due to the lack of an intact plasma membrane and the lack of a nuclear membrane, a chromatin mass in a permeabilized cell or in solution may be easier to genetically modify than a naturally-occurring cell. Examples of cells that may be used to generate reprogramming extracts include embryonic stem cells and adult stem cells from brain, blood, bone marrow, pancreas, liver, skin, or any other organ or tissue. Other exemplary reprogramming cell extracts include oocyte extracts (e.g., bovine or sea urchin oocyte extracts) and male germ cell extracts (e.g., spermatogonia, spermatocyte, spermatid, or sperm extracts from vertebrates, invertebrates, or mammals such as bovine). The donor or permeabilized cell can be non-immortalized or naturally, spontaneously, or genetically immortalized. The donor cell, permeabilized cell, recipient cell, or cytoplast can be from a source of any age, such as an embryo, fetus, youth, or adult mammal (e.g., ungulate). Cells from younger sources may have acquired fewer spontaneous mutations and may have a longer lifespan after insertion into an oocyte.

Methods for Breeding Ungulates

In preferred embodiments of any of the above methods for generating ungulates or ungulate cells, an ungulate of the invention is mated with another ungulate (e.g., an ungulate with a mutation in an antibody heavy or light chain nucleic acid or an ungulate with a nucleic acid encoding a xenogenous antibody) to produce a fetus or live offspring with two or more genetic modifications. Preferably, one or more cells are isolated from the fetus or offspring, and one or more additional genetic modifications are introduced into the isolated cell(s).

Methods for Producing Antibodies

The invention also provides method for producing antibodies using an ungulate of the invention that expresses xenogenous antibodies (e.g., human antibodies). One such method involves administering one or more antigens of interest to an ungulate of the invention having nucleic acid encoding a xenogenous antibody gene locus. The nucleic acid segments in the gene locus undergo rearrangement resulting in the production of antibodies specific for the antigen. Antibodies are recovered from the ungulate. The antibodies may be monoclonal or polyclonal and are preferably reactive with an antigen of interest. Preferably, the antibodies are recovered from the serum or milk of the ungulate.

In a related aspect, the invention provides another method for producing antibodies that involves recovering xenogenous antibodies from an ungulate of the invention having nucleic acid encoding a xenogenous antibody gene locus. The nucleic acid segments in the gene locus undergo rearrangement resulting in the production of xenogenous antibodies. The antibodies may be monoclonal or polyclonal and are preferably reactive with an antigen of interest. Preferably, the antibodies are recovered from the serum or milk of the ungulate.

Nucleic Acids

The invention also provides nucleic acids (e.g., vectors) that are useful for mutating a prion gene in ungulates (e.g., bovines). One such nucleic acid has a cassette which includes, in 5' to 3' order, a first region of homology having substantial sequence identity to a first region of an endogenous prion nucleic acid of an ungulate cell, a positive selection marker, and a second region of homology having substantial sequence identity to a second region of the prion nucleic acid. In one embodiment, the first region of homology (e.g., a region of less than 3, 2, 1.5, or 1 kilobases) is shorter than the second region of homology (e.g., a region of at least 7, 8, 9, or 10 kilobases), and the cassette is capable of integrating into an endogenous prion nucleic acid of the cell. In another embodiment, the first region of homology is longer than the second region of homology. Preferably, the first and/or second region of homology is isogenic to the corresponding region of an endogenous prion nucleic acid in a cell to be mutated.

In a related aspect, the invention provides a nucleic acid that has a cassette which includes a first region of homology having substantial sequence identity to a first region of an endogenous prion nucleic acid of an ungulate cell, a positive selection marker, a second region of homology having substantial sequence identity to a second region of the prion nucleic acid, and a negative selection marker (e.g., DT-A or Tk) in the opposite orientation as the positive selection marker (e.g., a negative selection marker for which the promoter is linked to the end of the shorter region of homology). The cassette is capable of integrating into an endogenous prion nucleic acid of the cell. Desirably, one region of homology is at least 7, 8, 9, or 10 kilobases in length, and the other region of homology is less than 3, 2, 1.5, or 1 kilobases in length. In some embodiments, part or all of the negative selection marker is within the shorter region of homology. Preferably, the first and/or second region of homology is isogenic to the corresponding region of an endogenous prion nucleic acid in a cell to be mutated.

In another aspect, the invention provides a composition that includes a nucleic acid of the invention and spermidine (e.g., 0.1 to 10 mM spermidine).

Preferred Embodiments of Above Aspects

Preferably, the ungulate antiserum or milk has polyclonal human immunoglobulins. Preferably, the antiserum or milk is from a bovine, ovine, porcine, or caprine. In another preferred embodiment, the Igs are directed against a desired antigen. In preferred embodiments, the antiserum is used as intravenous immunoglobulin (IVIG) for the treatment or prevention of disease in humans. In another preferred embodiment, an antigen of interest is administered to the ungulate, and Igs directed against the antigen are produced by the ungulate. Preferably, the nucleic acid segments in the xenogenous immunoglobulin gene locus rearrange, and xenogenous antibodies reactive with the antigen of interest are produced. Preferably, the antiserum and/or milk contains at least 2, 5, 10, 20, or 50 fold more xenogenous antibody than endogenous antibody, or contains no endogenous antibody. If desired, hybridomas and monoclonal antibodies can be produced using xenogenous B-cells derived from the above-described transgenic ungulates (for example, transgenic bovines). It is also contemplated that xenogenous antibodies (e.g., human antibodies) isolated from ungulates may be subsequently chemically modified so that they are covalently linked to a toxin, therapeutically active compound, enzyme, cytokine, radiolabel, fluorescent label, or affinity tag. If desired, the fluorescent or radiolabel may be used for imaging of the antibody in vitro or in vivo.

Preferably, the mutation in a prion nucleic acid decreases the generation of the infectious form of prion protein. In preferred embodiments, the amount of the infectious form of prion protein produced by the ungulate is less than 80, 70, 60, 50, 40, 30, 20, 10, or 5% of that produced by a control ungulate without the mutation. Preferably, no infections prion protein is produced.

In preferred embodiments, the mutation is the insertion of part or all of a prion nucleic acid (e.g., the coding region) from another animal (e.g., a different ungulate species or breed). Preferably, this xenogenous prion nucleic acid replaces part or all of an endogenous prion nucleic acid. In preferred embodiments, the xenogenous prion nucleic acid is from a species or breed with increased resistance to a prion infection, such as sheep that are resistant to scrapie. Preferably, the percentage of ungulates with the mutation that have a prion infection is less than 80, 70, 60, 50, 40, 30, 20, 10, or 5% of the percentage of control ungulates without the mutation that have a prion infection.

Preferred Ungulates and Donor Cells

Ungulates include members of the orders Perissodactyla and Artiodactyla, such as any member of the genus *Bos*. Other preferred ungulates include sheep, big-horn sheep, goats, buffalos, antelopes, oxen, horses, donkeys, mule, deer, elk, caribou, water buffalo, camels, llama, alpaca, pigs, and elephants.

Preferred donor cells include differentiated cells such as epithelial cells, neural cells, epidermal cells, keratinocytes, hematopoietic cells, melanocytes, chondrocytes, B-lymphocytes, T-lymphocytes, erythrocytes, macrophages, monocytes, fibroblasts, and muscle cells; and undifferentiated cells such as embryonic cells (e.g., stem cells and embryonic germ cells). In another preferred embodiment, the cell is from the female reproductive system, such as a mammary gland, ovarian cumulus, granulosa, or oviductal cell. Other preferred cells include fetal cells and placental cells. Preferred cells also include those from any organ, such as the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, and uterus. Preferably, the donor cell, donor nucleus, donor chromatine mass, or reconstituted oocyte is not tetraploid.

In yet another preferred embodiment, the nucleus, permeabilized cell, or chromosomes are from a transgenic cell or ungulate or contain a mutation not found in the donor cell or not found in a naturally-occurring cell. Preferred transgenic donor nuclei and donor cells encode proteins that confer improved resistance to disease or parasites in the cloned ungulate. Alternatively, the donor nuclei or donor cells may be engineered so that the cloned ungulate produces a recombinant product, such as the production of a human protein in the urine, blood, or milk of a bovine. For example, proteins may be expressed in the urine of cattle by inserting a polynucleotide sequence encoding a human protein under the control of an uroplakin promoter. Therapeutic proteins that may be produced in the milk of cloned bovines include human clotting factors such as any of factors I to XIII (Voet and Voet, Biochemistry, John Wiley & Sons, New York, 1990). These heterologous proteins may be expressed under the control of a prolactin promoter or any other promoter suitable for expression in the milk of a bovine. Recombinant proteins from these or other tissues or fluids may be purified using standard purification methods (see, for example, Ausubel et al., supra).

Definitions

As used herein, by "artificial chromosome" is meant a mammalian chromosome or fragment thereof which has an artificial modification such as the addition of a selectable marker, the addition of a cloning site, the deletion of one or more nucleotides, the substitution of one or more nucleotides, and the like. By "human artificial chromosome" or "HAC" is meant an artificial chromosome generated from one or more human chromosome(s). An artificial chromosome can be maintained in the host cell independently from the endogenous chromosomes of the host cell. In this case, the HAC can stably replicate and segregate along side endogenous chromosomes. Alternatively, it may be translocated to, or inserted into, an endogenous chromosome of the host cell. Two or more artificial chromosomes can be introduced to the host cell simultaneously or sequentially. For example, artificial chromosomes derived from human chromosome #14 (comprising the Ig heavy chain gene), human chromosome #2 (comprising the Ig kappa chain gene), and human chromosome #22 (comprising the Ig lambda chain gene) can be introduced. Alternatively, an artificial chromosome(s) comprising both a xenogenous Ig heavy chain gene and Ig light chain gene, such as ΔHAC or ΔΔHAC, may be introduced. Preferably, the heavy chain loci and the light chain loci are on different chromosome arms (i.e., on different side of the centromere). In still other preferred embodiments, the total size of the HAC is less than or equal to approximately 10, 9, 8, or 7 megabases.

By "a nucleic acid in its pre-arranged or unrearranged form" is meant a nucleic acid that has not undergone V(D)J recombination. In preferred embodiments, all of the nucleic acid segments encoding a V gene segment of an antibody light chain are separated from all of the nucleic acid segments encoding a J gene segment by one or more nucleotides. Preferably, all of the nucleic acid segments encoding a V gene segment of an antibody heavy chain are separated from all of the nucleic acid segments encoding a D gene segment by one or more nucleotides, and/or all of the nucleic acid segments encoding a D gene segment of an antibody heavy chain are separated from all of the nucleic acid segments encoding a J gene segment by one or more nucleotides. Preferably, a nucleic acid in its unrearranged form is substantially human. In other preferred embodiments, the nucleic acid is at least 70, 80, 90, 95, or 99% identical to the corresponding region of a naturally-occurring nucleic acid from a human.

By "reducing the quantity and/or activity of endogenous antibody" is meant reducing the amount of endogenous, functional antibodies produced by a B-cell or a population of B-cells, as described, for example, in U.S. Ser. No. 10/441, 503, filed May 19, 2003. This reduction in the amount of endogenous antibodies may be due to a decrease in the amount of endogenous antibodies produced per B-cell, a decrease in the number of functional endogenous B-cells, or a combination thereof. Preferably, the amount of an endogenous antibody secreted by a B-cell or expressed on the surface of a B-cell expressing or secreting endogenous antibody is reduced by at least 25, 50, 75, 90, or 95%. In another preferred embodiment, the number of endogenous B-cells in a sample from the recipient mammal, such as a blood sample, is reduced by at least 25, 50, 75, 90, or 95%.

By "bifunctional antibody" is meant an antibody that includes an antibody or a fragment of an antibody covalently linked to a different antibody or a different fragment of an antibody. In one preferred embodiment, both antibodies or fragments bind to different epitopes expressed on the same antigen. Other preferred bifunctional antibodies bind to two different antigens, such as to both an antibody light chain and an antibody heavy chain. Standard molecular biology techniques such as those described herein may be used to operably link two nucleic acids so that the fusion nucleic acid encodes a bifunctional antibody.

By "fragment" is meant a polypeptide having a region of consecutive amino acids that is identical to the corresponding region of an antibody of the invention but is less than the full-length sequence. The fragment has the ability to bind the same antigen as the corresponding antibody based on standard assays, such as those described herein. Preferably, the binding of the fragment to the antigen is at least 20, 40, 60, 80, or 90% of that of the corresponding antibody.

By "purified" is meant separated from other components that naturally accompany it. Typically, a factor is substantially pure when it is at least 50%, by weight, free from proteins, antibodies, and naturally-occurring organic molecules with which it is naturally associated. Preferably, the factor is at least 75%, more preferably, at least 90%, and most preferably, at least 99%, by weight, pure. A substantially pure factor may be obtained by chemical synthesis, separation of the factor from natural sources, or production of the factor in a recombinant host cell that does not naturally produce the factor. Proteins, vesicles, and organelles may be purified by one skilled in the art using standard techniques such as those described by Ausubel et al. (supra). The factor is preferably at least 2, 5, or 10 times as pure as the starting material, as measured using polyacrylamide gel electrophoresis, column chromatography, optical density, HPLC analysis, or western blot analysis (Ausubel et al., supra). Preferred methods of purification include immunoprecipitation, column chromatography such as immunoaffinity chromatography, magnetic bead immunoaffinity purification, and panning with a plate-bound antibody.

By "chromatin mass" is meant more than one chromosome not enclosed by a membrane. Preferably, the chromatin mass contains all of the chromosomes of a cell. An artificially induced chromatin mass containing condensed chromosomes may be formed by exposure of a nucleus to a mitotic reprogramming media (e.g., a mitotic extract) as described herein. Alternatively, an artificially induced chromatin mass containing decondensed or partially condensed chromosomes may be generated by exposure of a nucleus to one of the following, as described herein: a mitotic extract containing an anti-NuMA antibody, a detergent and/or salt solution, or a protein kinase solution. A chromatin mass may contain discrete chromosomes that are not physically touching each other or may contain two or more chromosomes that are in physical contact.

If desired, the level of chromosome condensation may be determined using standard methods by measuring the intensity of staining with the DNA stain, DAPI. As chromosomes condense, this staining intensity increases. Thus, the staining intensity of the chromosomes may be compared to the staining intensity for decondensed chromosomes in interphase (designated 0% condensed) and maximally condensed chromosomes in mitosis (designated 100% condensed). Based on this comparison, the percent of maximal condensation may be determined. Preferred condensed chromatin masses are at least 50, 60, 70, 80, 90, or 100% condensed. Preferred decondensed or partially condensed chromatin masses are less than 50, 40, 30, 20, or 10% condensed.

By "nucleus" is meant a membrane-bounded organelle containing most or all of the DNA of a cell. The DNA is packaged into chromosomes in a decondensed form. Preferably, the membrane encapsulating the DNA includes one or two lipid bilayers or has nucleoporins.

By "nucleus that has less than four sets of homologous chromosomes" is meant a nucleus that has a DNA content of less than 4n, where "n" is the number of chromosomes found in the normal haploid chromosome set of a mammal of a particular genus or species. Such a nucleus does not have four copies of each gene or genetic locus. Preferably, the nucleus is diploid and thus has two sets of homologous chromosomes but has less than two complete pairs of chromatids.

By "pronucleus" is meant a haploid nucleus resulting from meiosis or a nuclear transfer pronucleus. The female pronucleus is the nucleus of the oocyte or ovum before fusion with the male pronucleus. The male pronucleus is the sperm nucleus after it has entered the oocyte or ovum at fertilization but before fusion with the female pronucleus. A nuclear transfer pronucleus is a pronucleus (e.g., a diploid pronucleus) that forms after introduction of a donor cell, nucleus, or chromatin mass into an oocyte. The nuclear transfer pronucleus has less than four sets of homologous chromosomes.

By "donor cell" is meant a cell from which a nucleus or chromatin mass is derived, or a permeabilized cell.

By "permeabilization" is meant the formation of pores in the plasma membrane or the partial or complete removal of the plasma membrane.

By "reprogramming media" is meant a solution that allows the removal of a factor from a cell, nucleus, chromatin mass, or chromosome or the addition of a factor from the solution to the cell, nucleus, chromatin mass, or chromosome. Preferably, the addition or removal of a factor increases or decreases the level of expression of an mRNA or protein in the donor cell, chromatin mass, or nucleus or in a cell containing the reprogrammed chromatin mass or nucleus. In another embodiment, incubating a permeabilized cell, chromatin mass, or nucleus in the reprogramming media alters a phenotype of the permeabilized cell or a cell containing the reprogrammed chromatin mass or nucleus relative to the phenotype of the donor cell. In yet another embodiment, incubating a permeabilized cell, chromatin mass, or nucleus in the reprogramming media causes the permeabilized cell or a cell containing the reprogrammed chromatin mass or nucleus to gain or lose an activity relative to the donor cell.

Exemplary reprogramming media include solutions, such as buffers, that do not contain biological molecules such as proteins or nucleic acids. Such solutions are useful for the removal of one or more factors from a nucleus, chromatin mass, or chromosome. Other preferred reprogramming medias are extracts, such as cellular extracts from cell nuclei, cell cytoplasm, or a combination thereof. Exemplary cell extracts include extracts from oocytes (e.g., mammalian, vertebrate, or invertebrate oocytes), male germ cells (mammalian, vertebrate, or invertebrate germ cells such as spermatogonia, spermatocyte, spermatid, or sperm), and stem cells (e.g., adult or embryonic stem cells). Yet other reprogramming media are solutions or extracts to which one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) have been added, or extracts from which one or more factors have been removed. Still other reprogramming media include solutions of detergent (e.g., 0.01% to 0.1%, 0.1% to 0.5%, or 0.5% to 2% ionic or non-ionic detergent such as one or more of the following detergents: SDS, Triton X-100, Triton X-114, CHAPS, Na-deoxycholate, n-octyl glucoside, Nonidet P40, IGEPAL, Tween 20, Tween 40, or Tween 80), salt (e.g., ~0.1, 0.15, 0.25, 0.5, 0.75, 1, 1.5, or 2 M NaCl or KCl), polyamine (e.g., ~1 µM, 10 µM, 100 µM, 1 mM or 10 mM spermine, spermidine, protamine, or poly-L-lysine), a protein kinase (e.g., cyclin-dependent kinase 1, protein kinase C, protein kinase A, MAP kinase, calcium/calmodulin-dependent kinase, CK1 casein kinase, or CK2 casein kinase), and/or a phosphatase inhibitor (e.g., ~10 µM, 100 µM, 1 mM, 10 mM, 50 mM, 100 mM of one or more of the following inhibitors: Na-orthovanadate, Na-pyrophosphate, Na-fluoride, NIPP1, inhibitor 2, PNUTS, SDS22, AKAP149, or ocadaic acid). In some embodiments, the reprogramming medium contains an anti-NuMA antibody. If desired, multiple reprogramming media may be used simultaneously or sequentially to reprogram a donor cell, nucleus, or chromatin mass.

By "interphase reprogramming media" is meant a media (e.g., an interphase cell extract) that induces chromatin decondensation and nuclear envelope formation.

By "mitotic reprogramming media" is meant a media (e.g., a mitotic cell extract) that induces chromatin condensation and nuclear envelope breakdown.

By "reprogrammed cell" is meant a cell that has been exposed to a reprogramming media. Preferably, at least 1, 5, 10, 15, 20, 25, 50, 75, 100, 150, 200, 300, or more mRNA or protein molecules are expressed in the reprogrammed cell that are not expressed in the donor or permeabilized cell. In another preferred embodiment, the number of mRNA or protein molecules that are expressed in the reprogrammed cell, but not expressed in the donor or permeabilized cell, is between 1 and 5, 5 and 10, 10 and 25, 25 and 50, 50 and 75, 75 and 100, 100 and 150, 150 and 200, or 200 and 300, inclusive. Preferably, at least 1, 5, 10, 15, 20, 25, 50, 75, 100, 150, 200, 300, or more mRNA or protein molecules are expressed in the donor or permeabilized cell that are not expressed in the reprogrammed cell. In yet another preferred embodiment, the number of mRNA or protein molecules that are expressed in the donor or permeabilized cell, but not expressed in the reprogrammed cell, is between 1 and 5, 5 and 10, 10 and 25, 25 and 50, 50 and 75, 75 and 100, 100 and 150, 150 and 200, or 200 and 300, inclusive. In still another preferred embodiment, these mRNA or protein molecules are expressed in both the donor cell (i.e., the donor or permeabilized starting cell) and the reprogrammed cell, but the expression levels in these cells differ by at least 2, 5, 10, or 20-fold, as measured using standard assays (see, for example, Ausubel et al, supra).

By "addition of a factor" is meant the binding of a factor to chromatin, a chromosome, or a component of the nuclear envelope, such as the nuclear membrane or nuclear matrix. Alternatively, the factor is imported into the nucleus so that it is bounded or encapsulated by the nuclear envelope. Preferably, the amount of factor that is bound to a chromosome or located in the nucleus increases by at least 25, 50, 75, 100, 200, or 500%.

By "removal of a factor" is meant the dissociation of a factor from chromatin, a chromosome, or a component of the nuclear envelope, such as the nuclear membrane or nuclear matrix. Alternatively, the factor is exported out of the nucleus so that it is no longer bounded or encapsulated by the nuclear envelope. Preferably, the amount of factor that is bound to a chromosome or located in the nucleus decreases by at least 25, 50, 75, 100, 200, or 500%.

By "enrichment or depletion of a factor" is meant the addition or removal of a naturally-occurring or recombinant factor by at least 20, 40, 60, 80, or 100% of the amount of the factor originally present in an reprogramming media (e.g., a cell extract). Alternatively, a naturally-occurring or recombinant factor that is not naturally present in the reprogramming media may be added. Preferred factors include proteins such as DNA methyltransferases, histone deacetylases, histones, protamines, nuclear lamins, transcription factors, activators, and repressors; membrane vesicles, and organelles. In one preferred embodiment, the factor is purified prior to being added to the reprogramming media, as described below. Alternatively, one of the purification methods described below may be used to remove an undesired factor from the reprogramming media.

By "recloned" is meant used in a second round of cloning. In particular, a cell from an embryo, fetus, or adult generated from the methods of the invention may be incubated in a mitotic reprogramming media (e.g., a mitotic cell extract) to form a chromatin mass for insertion into an enucleated oocyte, as described above. Alternatively, the cell may be permeabilized, incubated in a reprogramming media, and inserted into an enucleated oocyte, as described above. Performing two or more rounds of cloning may result in additional reprogramming of the donor chromatin mass or donor cell, thereby increasing the chance of generating a viable offspring after the last round of cloning.

By "viable offspring" is meant a mammal that survives ex utero. Preferably, the mammal is alive for at least one second, one minute, one hour, one day, one week, one month, six months, or one year from the time it exits the maternal host. The mammal does not require the circulatory system of an in utero environment for survival.

By "nuclear transfer oocyte" or "nuclear transplant oocyte" is meant an oocyte in which a donor cell, nucleus, or chromatin mass is inserted or fused. An embryo formed from the oocyte is referred to as a "nuclear transfer" or "nuclear transplant" embryo.

By "embryo" or "embryonic" is meant a developing cell mass that has not implanted into the uterine membrane of a maternal host. Hence, the term "embryo" may refer to a fertilized oocyte; an oocyte containing a donor chromatin mass, nucleus, or reprogrammed cell; a pre-blastocyst stage developing cell mass; or any other developing cell mass that is at a stage of development prior to implantation into the uterine membrane of a maternal host and prior to formation of a genital ridge. An embryo may represent multiple stages of cell development. For example, a one cell embryo can be referred to as a zygote; a solid spherical mass of cells resulting from a cleaved embryo can be referred to as a morula, and an embryo having a blastocoel can be referred to as a blastocyst. An "embryonic cell" is a cell isolated from or contained in an embryo.

By "cells derived from an embryo" is meant cells that result from the cell division of cells in the embryo.

By "chimeric embryo" is meant an embryo formed from cells from two or more embryos. The resulting fetus or offspring can have cells that are derived from only one of the initial embryos or cells derived from more than one of the initial embryos. If desired, the percentage of cells from each embryo that are incorporated into the placental tissue and into the fetal tissue can be determined using standard FISH analysis or analysis of a membrane dye added to one embryo.

By "chimeric ungulate" is meant an ungulate formed from cells from two or more embryos. The ungulate can have cells that are derived from only one of the initial embryos or cells derived from more than one of the initial embryos. If desired, the percentage of cells from each embryo that are incorporated into the placental tissue and into the fetal tissue can be determined using standard FISH analysis or analysis of a membrane dye added to one embryo.

By "precompaction embryo" is meant an embryo prior to compaction. A precompaction embryo expresses essentially no E-cadherin on the surface of its blastomereres. Preferred precompaction embryos express at least 3, 5, 10, 20, 30, or 40-fold less E-cadherin than a fully compacted embryo of the same species, or express no E-adherin.

By "compaction embryo" is meant an embryo undergoing compaction or following compaction. The blastomeres of a compaction embryo express E-cadherin on their surface. This E-cadherin expression can be measuring using standard methods with an anti-E-cadherin antibody. E-cadherin increases the adherence between blastomeres. Preferred compaction embryos include embryos in which the compaction process is completed. Other preferred compaction embryos express at least 3, 5, 10, 20, 30, or 40-fold more E-cadherin than a precompaction embryo of the same species.

By "fetus" is meant a developing cell mass that has implanted into the uterine membrane of a maternal host. A fetus may have defining features such as a genital ridge that is easily identified by a person of ordinary skill in the art. A "fetal cell" is any cell isolated from or contained in a fetus.

By "parthenogenesis" or "parthenogenetic activation" is meant development of an oocyte or ovum without fusion of its nucleus with a male pronucleus to form a zygote. For example, an oocyte can be induced to divide without fertilization.

By "zona pellucida" is meant a translucent, elastic, non-cellular layer surrounding the oocyte or ovum of many mammals.

By "trophectoderm" is meant the outermost layer of cells surrounding the blastocoel during the blastocyst stage of mammalian embryonic development. Trophectoderm gives rise to most or all of the placental tissue upon further development.

By "inner cell mass" is meant the cells surrounded by the trophectoderm. The inner cell mass cells give rise to most of the fetal tissues upon further development.

By "mRNA or protein specific for one cell type" is meant an mRNA or protein that is expressed in one cell type at a level that is at least 10, 20, 50, 75, or 100 fold greater than the expression level in all other cell types. Preferably, the mRNA or protein is only expressed in one cell type.

By "mutation" is meant an alteration in a naturally-occurring or reference nucleic acid sequence, such as an insertion, deletion, frameshift mutation, silent mutation, nonsense mutation, or missense mutation. Preferably, the amino acid sequence encoded by the nucleic acid sequence has at least one amino acid alteration from a naturally-occurring sequence. Examples of recombinant DNA techniques for altering the genomic sequence of a cell, embryo, fetus, or mammal include inserting a DNA sequence from another organism (e.g., a human) into the genome, deleting one or more DNA sequences, and introducing one or more base mutations (e.g., site-directed or random mutations) into a target DNA sequence. Examples of methods for producing these modifications include retroviral insertion, artificial chromosome techniques, gene insertion, random insertion with tissue specific promoters, homologous recombination, gene targeting, transposable elements, and any other method for introducing foreign DNA. All of these techniques are well known to those skilled in the art of molecular biology (see, for example, Ausubel et al., supra). Chromatin masses, chromosomes, and nuclei from transgenic cells containing modified DNA or donor transgenic cells may be used in the methods of the invention.

By "immortalized" is meant capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2-, 5-, 10-, or 20-fold more cell divisions than the control cell. More preferably, the immortalized cell is capable of undergoing an unlimited number of cell divisions. Immortalized cells include cells that naturally acquire a mutation in vivo or in vitro that alters their normal growth-regulating process. Still other preferred immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al., Immunol. Lett. 65:153-159, 1999; Knight et al., Proc. Nat. Acad. Sci. USA 85:3130-3134, 1988; Shammah et al., J. Immunol. Methods 160-19-25, 1993; Gustafsson and Hinkula, Hum. Antibodies Hybridomas 5:98-104, 1994; Kataoka et al., Differentiation 62:201-211, 1997; Chatelut et al., Scand. J. Immunol. 48:659-666, 1998). Cells can also be genetically modified to express the telomerase gene (Roques et al., Cancer Res. 61:8405-8507, 2001).

By "non-immortalized" is meant not immortalized as described above.

By "fusigenic compound" is meant a compound that increases the probability that a chromatin mass or nucleus is inserted into a recipient cell when located adjacent to the cell. For example, the fusigenic compound may increase the affinity of a chromatin mass or a nucleus for the plasma membrane of a cell. The fusigenic compound may also promote the joining of the nuclear membrane of a nucleus with the plasma membrane of a cell.

By "substantially identical" is meant having a sequence that is at least 60, 70, 80, 90, or 100% identical to that of another sequence. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

Advantages

The present invention provides a number of advantages related to the production of transgenic ungulates (e.g., bovines) with a mutation in one or both alleles of the prion gene. For example, the prion knockout vector, cell culture method, and transfection method described herein inactivated the prion gene in bovine cells at a surprisingly high frequency. The large number of correctly targeted donor cells in combination with the improved nuclear transfer methods of the invention (e.g., chromatin transfer and SLOT) greatly facilitate the generation of cloned transgenic ungulates (e.g., bovines) with reduced or no expression of prion protein. These resulting transgenic ungulates are desirable sources of agricultural products (e.g., meat) and pharmaceutical products (e.g., human therapeutic antibodies encoded by one or more xenogenous nucleic acids in the transgenic ungulates).

Other features and advantages of the invention will be apparent from the following detailed description and from the claims.

BRIEF DESCRIPTION OF THE DRAWINGS

The application file contains drawings executed in color (FIGS. 31, 34A-34C, 36A, 36B, 42A-42D, 45A, 46D, 47A, 47C, 48, 49B, 50A-50D, and 51C-51E). Copies of this patent or patent application with color drawings will be provided by the Office upon request and payment of the necessary fee.

In FIGS. 1A and 1B, "Homo" denotes homozygous; "Hemi" denotes hemizygous; "H" denotes heavy chain; "L" denotes light chain; "HAC" denotes human artificial chromosome; "HAC 1" denotes either HAC; and "HAC2" denotes a second HAC.

FIG. 3D depicts the polynucleotide sequence of the 1.5 kb region of the genomic bovine mu heavy chain locus that was used as the first region of homology in the mu knockout construct (SEQ ID NO: 47).

FIG. 3E depicts the polynucleotide sequence of the 3.1 kb region of the genomic bovine mu heavy chain locus that was used as the second region of homology in the mu knockout construct (SEQ ID NO: 48). In this sequence, each "n" represents any nucleotide or no nucleotide. The region of consecutive "n" nucleotides represents an approximately 0.9 to 1.0 kb region for which the polynucleotide sequence has not been determined.

FIG. 3G depicts the polynucleotide sequence of a bovine kappa light chain cDNA (SEQ ID NO: 60). All or part of this sequence may be used in a kappa light chain knockout construct. Additionally, this kappa light chain may be used to isolate a genomic kappa light chain sequence for use in a kappa light chain knockout construct.

FIG. 11A is the polynucleotide sequence of a rearranged human heavy chain transcript from ΔHAC fetus #5996 (SEQ ID NO: 49).

FIG. 11B is a sequence alignment of a region of this sequence ("Query") with a human anti-pneumococcal antibody ("Sbjct") (SEQ ID NOs: 50 and 51, respectively). For the query sequence from ΔHAC fetus #5996, only those nucleotides that differ from the corresponding nucleotides of the human anti-pneumococcal antibody sequence are shown.

FIGS. 12A-12B depict two additional polynucleotide sequences (SEQ ID NOs: 52 and 54) and their deduced amino acid sequences (SEQ ID NOs: 53 and 55, respectively) of rearranged human heavy chain transcripts from ΔHAC fetus #5996.

FIG. 20 depicts the polynucleotide sequence and the corresponded deduced amino acid sequence of a rearranged human light chain transcript from ΔΔHAC fetus #5442A (SEQ ID NOs: 56 and 57, respectively).

FIG. 21 depicts another polynucleotide sequence and the corresponding deduced amino acid sequence of a rearranged human light chain transcript from ΔΔHAC fetus #5442A (SEQ ID NOs: 58 and 59, respectively).

FIGS. 22A-22H are graphs of a FACS analysis of expression of human lambda light chain and bovine heavy chain proteins by ΔΔΔΔHAC fetuses #5442A (FIGS. 22A-22D) and 5442B (FIGS. 22E-22H). Lymphocytes from the spleens of these fetuses were reacted with a phycoerytherin labeled anti-human lambda antibody (FIGS. 22C and 22D), a FITC labeled anti-bovine IgM antibody (FIGS. 22D and 22H), or no antibody (FIGS. 22A, 22B, (22E, and 22F) and then analyzed on a FASCalibur cell sorter. The percent of cells that were labeled with one of the antibodies is displayed beneath each histogram.

FIG. 27 is a table listing pregnancy rates for HAC carrying embryos.

FIGS. 28A-28J are photographs of FACS analysis of peripheral blood lymphocytes from either experimental fetuses injected with an anti-bovine IgM antibody (das6) to inhibit B-cell development or control fetuses. FIGS. 28A-28E are photograph of the FACS analysis performed using an anti-bovine IgM antibody to detect IgM molecules expressed on the surface of B-cells. As illustrated in FIG. 28A and FIG. 28B, approximately 19.82 to 26.61% of the peripheral blood lymphocytes from the control fetuses expressed IgM. In contrast, 7.78, 11.80, or 3.95% of the peripheral blood lymphocytes from the three fetuses injected with the anti-bovine IgM antibody expressed IgM (FIGS. 28C-28E, respectively). FIGS. 28F-28J are photographs of the FACS analysis performed using an anti-bovine light chain antibody (das10) to detect antibody light chain molecules expressed on the surface of B-cells. As illustrated in FIG. 28F and FIG. 28G, approximately 12.43 to 29.47% of the peripheral blood lymphocytes from the control fetuses expressed antibody light chain molecules. In contrast, 2.54, 13.77, or 3.99% of the peripheral blood lymphocytes from the three fetuses injected with the anti-bovine IgM antibody expressed antibody light chain molecules (FIGS. 28H-28J, respectively).

FIGS. 29A-29B illustrate the immunodetection of nuclear envelope and nuclear matrix proteins in bovine preimplantation embryos. FIG. 29A is a picture of in vitro-fertilized bovine embryos at the pronuclear and 8-cell stage examined using the same antibodies. Arrows in FIG. 29A to anti-NuMA and anti-AKAP95 labeling in the female pronucleus of pronuclear stage embryos. Insets in FIG. 29A are pictures of DNA labeled with 0.1 μg/ml Hoechst 33342 (bars, 20 μm). FIG. 29B is the immunoblotting analysis of bovine fibroblasts (upper rows) and pronuclear stage embryos (lower rows). Molecular weight markers are shown in kDa on the right of FIG. 29B.

FIG. 36A shows the analysis of lamins A/C and B. FIG. 36B shows the analysis of AKAP95 and NuMA. Lamins A/C (green label) only appear in nuclear transplant and nuclear injection pronuclei (bars, 30 µm).

FIGS. 38A-38D illustrate the analysis of Tc fetuses. G418 selection of regenerated Tc fibroblast line and control non-transgenic fibroblasts (FIG. 38A). Genomic PCR of IgH and Igl loci in Tc fetuses and controls. The three fetuses, #5968 (lane 1), #6032 (lane 2) and #6045 (lane 3) were derived from ΔHAC fibroblasts, fetus #5580 (lane 4) was from ΔΔHAC fibroblasts. As a control, a non-transgenic fetus (lane N) was recovered and evaluated (FIG. 38B). In all Tc fetuses and a positive control human liver DNA sample (lane P), both human IgH and Igl loci were detected by PCR, but not in the negative control (lane N). Rearranged and expressed human Igµ and Igλ transcripts amplified by RT-PCR from negative control non-transgenic bovine spleen (lane N), from brain (lane 1), liver (lane 2) and spleen (lane 3) of cloned Tc fetus and positive control human spleen (lane P) (FIG. 38C). A representative nucleotide and deduced amino acid sequence of human Igµ and Igλ transcripts amplified by RT-PCR from a cloned Tc fetus recovered at 91 days (FIG. 38D). RT-PCR was carried out as described (Kuroiwa et al., *Nature Biotech* 18:1086-1090, 2000). For human Igµ transcripts, VH1/5BACK, VH3BACK, and VH4BACK were used as a 5' primers and Cµ-2 was used as a 3' primer. For human Igλ transcripts, Vλ1LEA1, Vλ2MIX and Vλ3MIX were used as 5' primers, and CλMIX was used as a 3' primer. The amplified cDNAs were subcloned using a TA cloning kit (Invitrogen) and sequenced using a DNA autosequencer (ABI3700 system).

Bars, 10 μm. FIG. 41C is a bar graph of the mean±SD immunofluorescence intensity of lamins A/C and B and NuMA in CHX- and ActD-treated NT embryos relative to untreated (−) NT embryos (100% fluorescence; n=30 embryos/group in three replicates). FIG. 41D is a bar graph of the intranuclear association of AKAP95 in pronuclei of NT embryos. PN stage parthenotes (Part.) and NT embryos (NT), and donor fibroblasts (Fib) were extracted with 0.1% Triton X-100/1 mg/ml DNAse I/300 mM NaCl prior to fixation. Lamin B and AKAP95 were examined by immunofluorescence, and DNA was stained with Hoechst 33342. Data are shown as mean±SD fluorescence labeling intensity of lamin B, DNA, and AKAP95 relative to fluorescence in non-extracted parthenogenetic or NT embryos, or in somatic cells (100% fluorescence; n~30 embryos/group in three replicates). Bars, 10 μm.

FIGS. 43A-43B illustrate the in vitro donor nucleus disassembly and alteration of TBP localization in reconstituted pronuclei by CT. Dynamics of TBP during NT and CT was followed by immunofluorescence analysis of donor fibroblasts (Fib), condensed chromatin at the PCC stage (NT PCC), donor chromosomes condensed in mitotic extract (MS15 CC), NT pronuclei (NT PN), and CT pronuclei (CT PN) are compared in FIG. 43B. DNA was labeled with Hoechst 33342. Bars, 20 μm. TBP/AKAP95 and TBP/DNA fluorescence intensity ratios at stages shown in FIG. 43A and in parthenogenetic pronuclei (Part. PN) (FIG. 43B). Mean±SD fluorescence intensity in 10-13 embryos per group is shown.

FIG. 44C is a table listing the frequency of homologous recombination at the prion protein locus by using the prion protein knockout vector of the present invention in different bovine fibroblast cell lines.

FIG. 46A shows the immunofluorescence distribution of lamin B, lamin A/C, and TBP in bovine fibroblasts and IVP pronuclear (PN) and 8-16-cell stage bovine embryos. Insets, DNA labeled with Hoechst 33342. Bars, (left) 10 μm, (right) 50 μm. FIG. 46B is a picture of an immunoblot of lamin B, lamin A/C, and TBP in fetal fibroblasts and pronuclear embryos. FIG. 46C is a picture of immunofluorescence analysis of lamin B, lamin A/C, and TBP at the PCC and pronuclear (NT-PN) stages in NT embryos. Bars, 10 μm. FIG. 46D is a bar graph of the immunolabeling intensity of indicated proteins in male (MPN) and female (FPN) pronuclei of IVP embryos and in pronuclei of NT embryos (NT-PN). Data are expressed as mean±SD ratio of antibody fluorescence over Hoechst 33342 (DNA) fluorescence. Over 20 embryos per marker were analyzed in 3-5 replicates in (A, C, D).

FIG. 47A is a bar graph of the immunolabeling intensity (mean±SD) of TBP and DNA (Hoechst 33342) in pronuclear IVP and NT embryos and in fibroblasts after in situ extraction with 1% Triton X-100/1 mg/ml DNAse I/300 mM NaCl. Labeling intensity is expressed relative to that of non-extracted embryos (n=30 embryos or cells per group). FIG. 47B is a photograph illustrating expression of markers in NT embryos activated as (b) described herein, or (b') in the presence of 10 μg/ml CHX or (b'') 5 μg/ml ActD (n=30 embryos/group in 2-3 replicates). Insets, DNA. Bar, 10 μm. FIG. 47C is a bar graph of the ratio (mean±SD) of immunolabeling intensity of indicated proteins over Hoechst 33342 (DNA) fluorescence in embryos activated as in FIG. 47B (n=15-20 embryos/treatment/marker).

FIG. 49A demonstrates that the mitotic extract does not elicit apoptosis. Intact bovine fibroblasts (lane 1), fibroblasts induced into apoptosis with 5 μg/ml nocodazole for 20 hours (lane 2), or SLO-permeabilized fibroblasts exposed to mitotic (lane 3) or interphase (lane 4) extract for one hour were immunoblotted using anti-PARP antibodies (upper panel). DNA degradation was evaluated by gel electrophoresis in 0.8% agarose and staining with ethidium bromide (lower panel). FIG. 49B is a picture of the immunofluorescence analysis of lamin B, lamins A/C, TBP, and AKAP95 after a 45-minute incubation of permeabilized fibroblasts in mitotic extract with (+ATP) or without (−ATP) an ATP-regenerating system. Bars, 10 μm. Over 1,000 cells analyzed in 4 replicates displayed consistent labeling as shown. FIG. 49C is a picture of the immunoblotting analysis interphase fibroblasts (lane 1), fibroblasts synchronized at mitosis with 1 μg/ml nocodazole (lane 2), chromatin isolated from permeabilized fibroblasts exposed to mitotic extract with or without the ATP-regenerating system (lanes 3, 4) or to interphase extract (lane 5), and whole permeabilized fibroblasts exposed to mitotic extract (lane 6). Blots were probed using antibodies to indicated proteins. Histone H4 was used as a protein loading control in the gel.

FIG. 50A illustrates chromatin morphology (arrow) within 30 minutes of introduction into an oocyte by SLOT or NT as indicated. Dotted line delineates the oocyte cytoplast. Panels on the right show enlargements of donor chromatin in a SLOT and NT embryo. Bar, 20 µm. FIG. 50B illustrates the distribution of lamin B, lamin A/C, and TBP in pronuclear (upper two panels) and 8-16-cell stage (lower two panels) embryos produced by NT or SLOT. Bars, 20 µM (n=20-30 embryos/marker in 3 replicates). FIG. 50C is a bar graph of the ratio (mean±SD) of immunolabeling intensity over Hoechst 33342 (DNA) fluorescence intensity for indicated protein in pronuclei of NT or SLOT embryos (n~20 embryos/marker in 3 replicates). FIG. 50D is a bar graph of the immunolabeling intensity (mean±SD) of TBP and DNA (Hoechst 33342) in pronuclear NT and SLOT embryos after extraction with 0.1% Triton X-100/1 mg/ml DNAse I/300 mM NaCl, relative to that in non-extracted embryos (n=15 embryos/group in 2 replicates).

FIG. 51A is a bar graph of the rates of in vivo development of NT and SLOT clones. Pregnancy rates were assessed by ultrasonography at indicated days of gestation. Percentages of calves born and of live calves at 24 hour post-partum are also shown. Twelve SLOT and 23 NT calves were born from 59 and 211 embryos transfers, respectively, over eight weeks. P values were produced by Fisher's Exact Tests. FIG. 51B is a picture of SLOT clones (Simintal×Angus cross identical females) at 5-6 weeks of age. FIG. 51C is a graph of the scores of individual SLOT and NT calves and placentas within 24 hours of birth. FIG. 51D is a graph of the birth weights of individual SLOT and NT clones. In FIGS. 51C and 51D within SLOT (dots) or NT (squares) clones, one color represents calf score, placenta score, and birth weight for the same individual. FIG. 51E is the box plot analysis of calf scores, placenta scores, and birth weights of SLOT and NT clones.

DETAILED DESCRIPTION

Figure 1A:
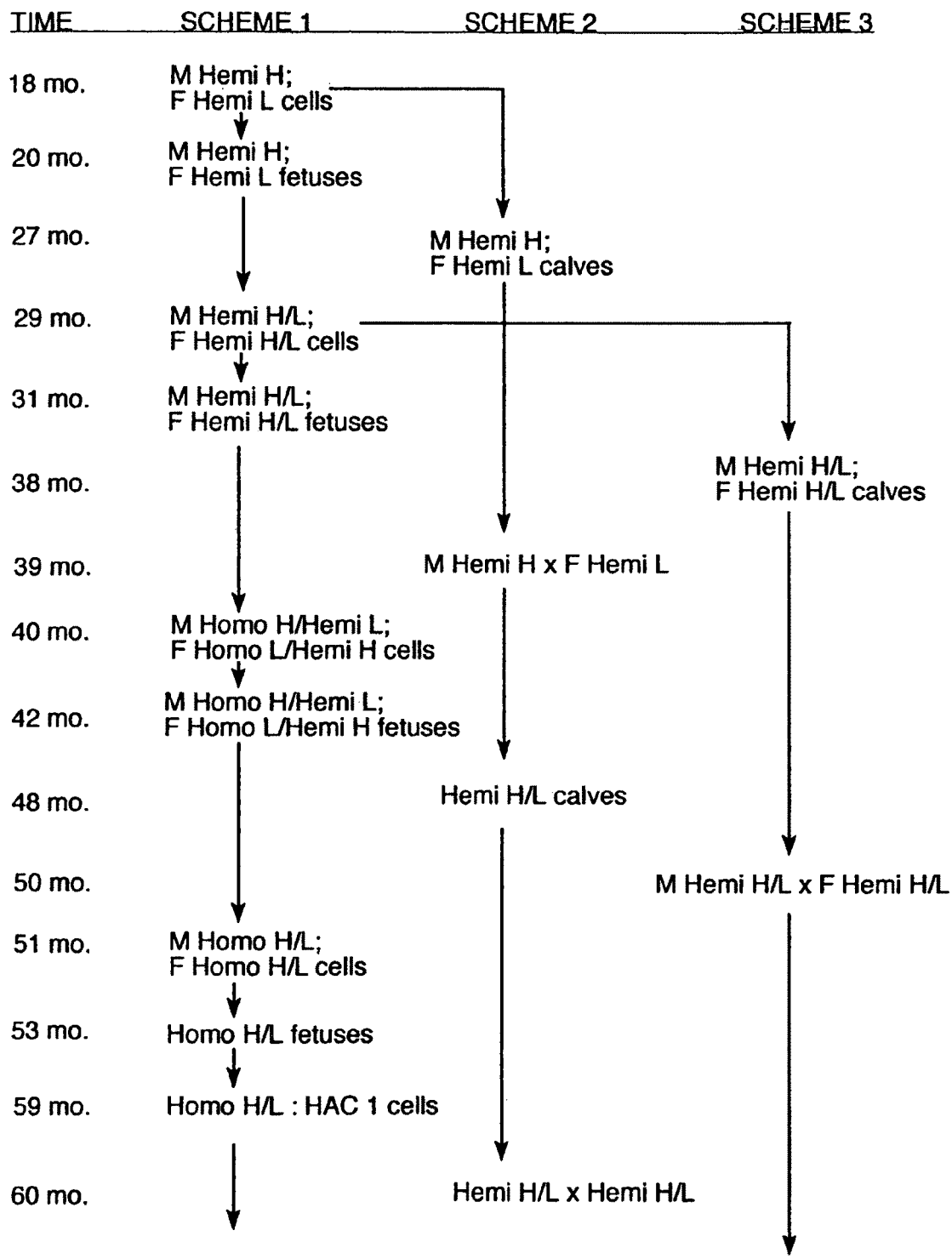
FIG. 1A depicts an overview of the procedures used to produce a cow that contains an Ig knockout and human artificial chromosome. The time line in FIG. 1A is based on an estimated 18 months to prepare the Ig knockout vector and generate knockout cells, 2 months to generate fetuses from the knockout cells, 9 months to perform subsequent knock-outs, 9 months of gestation for calves to be born, 12 months before embryos can be produced from calves, and 6 months to perform the HAC transfers.
Figure 1A:
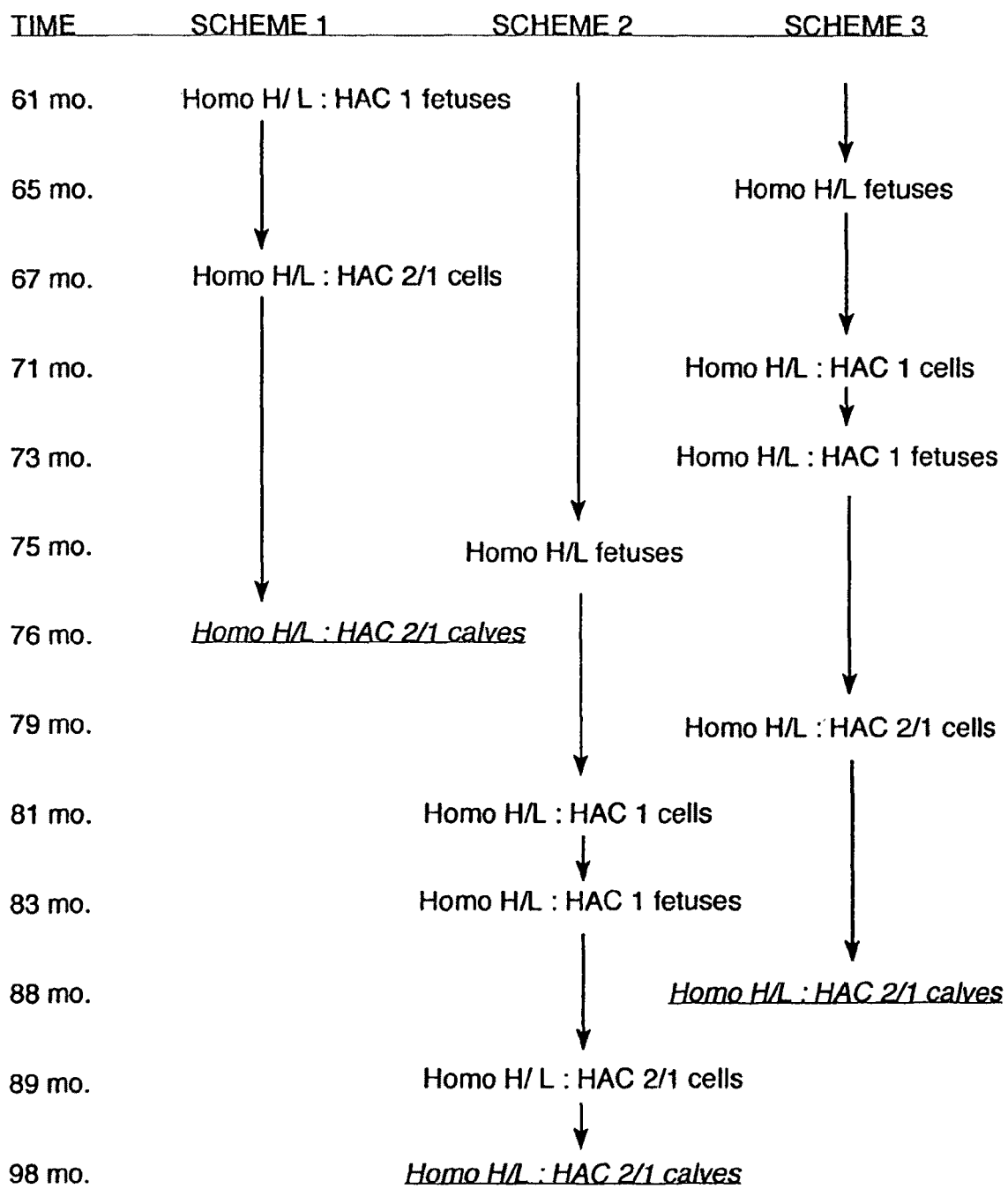
Figure 1B:
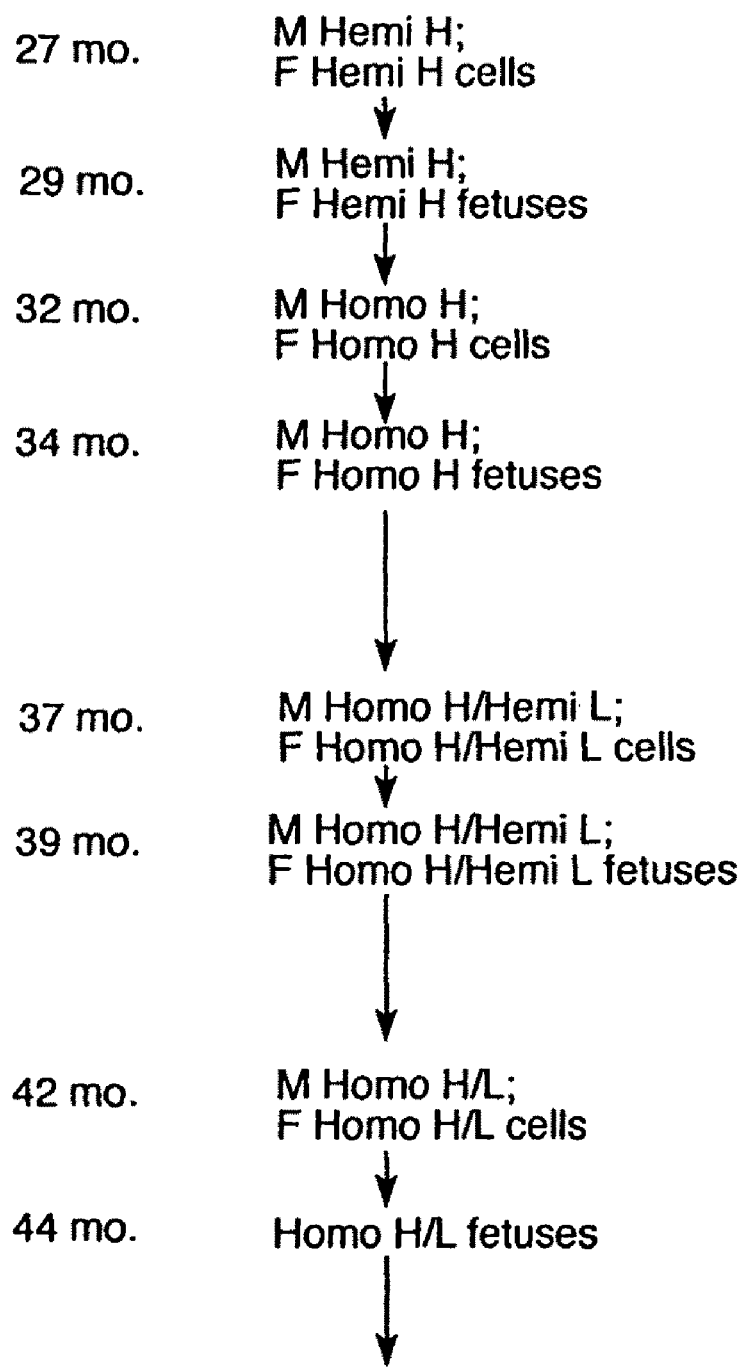
FIG. 1B depicts an overview of the methods used to produce a cow that contains a mutation in an endogenous Ig gene and contains ΔHAC or ΔΔHAC. For the time line in FIG. 1B, it is estimated that 250 colonies are screened per week for a total of 3,000 colonies in 3 months to isolate male and female knockout cells. It is assumed that one or more knockout colonies are produced per 1,500 colonies. Homozygous knockout ungulates may be produced by (1) introducing a second Ig mutation in an isolated knockout cell before nuclear transfer, (2) introducing a second Ig mutation in a cell obtained from a embryo, fetus (e.g., fetus at ~60 gestation days), or offspring produced from a first round of nuclear transfer and using the resulting homozygous cell as the donor cell in a second round of nuclear transfer, or (3) mating hemizygous ungulates.
Figure 1B:
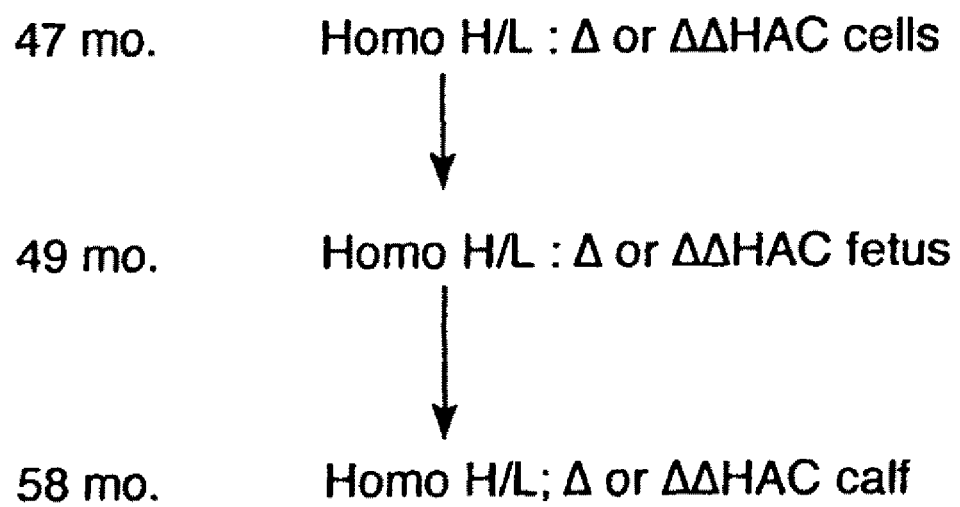

The present invention is based in part on the surprisingly high frequency of inactivation of the bovine prion locus using the methods described herein. The large number of correctly targeted prion knockout cells greatly facilitates the generation of prion knockout ungulates (e.g., bovines). Additionally, the invention provides improved methods for increasing the efficiency of nuclear transfer to further simplify the production of prion knockout ungulates. These resulting transgenic ungulates are desirable sources of agricultural products (e.g., meat) and pharmaceutical products (e.g., human therapeutic antibodies encoded by one or more xenogenous nucleic acids in the transgenic ungulates).

The knockout vector used to inactivate the prion locus in donor bovine cells was based in part on the sequence of the bovine prion protein gene locus deposited in Genbank (AJ298878). The source of the genomic sequence of the prion protein gene used for construction of the knockout vector matches that of strain of fibroblasts that were genetically modified. In particular, the Holstein genomic sequence of prion protein gene was used for construction of the knockout vector for efficient targeting in Holstein-derived fibroblasts. The knockout vector contained two regions of homology to the prion locus that are contiguous in the prion locus and was designed to insert a transcriptional termination (STOP) sequence together with a drug-resistant gene flanked by two loxp sites into the prion locus. An alternative strategy involves using two noncontiguous regions of homology in the knockout vector to delete the region of the endogenous prion protein gene between the two regions of homology. To reduce the activity of prion protein, the STOP sequence was inserted just behind its initial ATG codon in exon 3. For efficient homologous recombination at the locus, one region of homology was longer than the other region of homology. In particular, the length of the 3' region was 8.3 kb, which is much longer than that of the 1.1 kb 5' region of homology. To concentrate homologous recombinants, a negative selection marker, such as DT-A gene, was attached to the short 5' region of homology in an opposite direction relative to the prion protein gene. The knockout vector was linearlized before transfection by an appropriate restriction enzyme so that the basal plasmid vector, such as pUC of pBluescript, could be attached to the end of the negative selection marker. Furthermore, to enhance homologous recombination, the linearized knockout vector was treated with HBS (Hepes buffered saline) containing 1 mM spermidine before addition to fibroblasts.

Polyamine and any other compound can be added to the targeting vector to facilitate the efficiency of homologous recombination. A preferable concentration of polyamine is 0.1 to 10 mM; most preferably, the concentration is 1 mM. Polyamine may be selected from, e.g., spermidine, spermine, cadaverine, and putrescine. A preferred polyamine is spermidine. The other compound may be selected from compounds that can and form an ionic bond to the phosphate residue of DNA, such as poly-L-lysine or poly-L-arginine.

Further homologous recombination efficiency can be facilitated by placing the negative selection marker so that it is not exposed on the terminus of the linearized targeting vector. Preferably, the 5' and 3' termini of the functional unit of the negative selection marker are located at least 1 Kb, preferably at least 2 Kb, away from the 5' and 3' termini of the linearized targeting vector, respectively. Generally, homologous genomic sequence is located on the 5' and 3' side of the negative selection marker, resulting in a sufficient distance of the negative selection marker from the termini of the linearized targeting vector. In the linearized targeting vector, the other side of the negative selection markers can be designed to retain at least 1 Kb, preferably at least 2 Kb extra sequence. For example, the pUC vector sequence in the targeting vector can be used as this extra sequence.

In one particular method, a Holstein-derived knockout vector was electroporated into Holstein fetal fibroblasts, and hemizygously targeted clones were obtained at a surprisingly high frequency of more than 50%. The large number of correctly targeted clones should be sufficient to efficiently produce healthy fetuses and calves. To produce homozygously targeted fetuses and calves, hemizygous knockout fibroblasts isolated from hemizygous targeted fetuses can be electroporated with the same knockout vector or a knockout vector with a different antibiotic resistance gene to mutate the remaining allele of the prion locus. Alternatively, homozygous knockout calves can be produced by mating male and female hemizygous knockout cattle.

Methods for Producing Ungulates that Express Xenogenous Antibodies

Homozygous prion protein knockout bovines producing human antibodies (prion protein KO/hAb bovine) can be generated by introduction of human immunoglobulin loci into bovine fibroblasts with a homozygous prion protein knockout genotype, e.g., as described in WO02/70648 and Kuroiwa et al. Nature Biotechnol. 20; 889-894, 2002. Suitable approaches include, for example, the insertion of a human artificial chromosome (HAC) containing both heavy and light chain immunoglobulin genes into an ungulate or the insertion of human B-cells or B-cell precursors into an ungulate during its fetal stage or after it is born (e.g., an immune deficient or immune suppressed ungulate) (see, for example, PCT Publication Nos. WO01/35735 and WO02/074938).

Standard methods can be used to introduce a desired nucleic acid that contains genes (preferably, entire gene loci) for producing antibodies of a particular species (e.g., a human) into a donor cell for use in generating a transgenic ungulate that expresses xenogenous antibodies. Preferably, human artificial chromosomes are used, such as those disclosed in PCT Publication Nos. WO97/07671 and WO00/10383. These human artificial chromosomes also are described in issued Japanese patent JP 30300092. Each of these publications is incorporated by reference in their entirety herein. Also, the construction of artificial human chromosomes or transgenes that contain and express human immunoglobulin genes is disclosed in Shen et al., Hum. Mol. Genet. 6:1375-1382 (1997); Kuroiwa et al., Nature Biotechnol. 18:1086-1090 (2000); Loupert et al., Chromosome 107: 255-259 (1998); PCT Publication Nos. WO00/10383, WO98/24893, WO96/33735, WO97/13852, WO98/24884, and WO97/07671; and U.S. Pat. Nos. 5,877,397, 5,874,299, 5,814,318, 5,789,650, 5,770,429, 5,661,016, 5,633,425, 5,625,126, 5,569,825, and 5,545,806, each of which is incorporated by reference in its entirety herein. Human artificial chromosomes may also be utilized to introduce xenogenous antibody genes into wild-type animal cells; this is accomplished using the methods described above. Introduction of artificial chromosome into animal cells, especially fetal fibroblast cells can be performed by microcell fusion as described herein.

In an alternative to the use of human artificial chromosome, nucleic acid encoding immunoglobulin genes may be integrated into the chromosome using a YAC vector, BAC vector, or cosmid vector. Vectors comprising xenogenous Ig genes (described, e.g., in PCT Publication Nos. WO98/24893, WO96/33735, WO97/13852, and WO98/24884, and U.S. Pat. Nos. 5,849,992 and 5,827,690) can be introduced to fetal fibroblasts cells using known methods, such as electroporation, lipofection, fusion with a yeast spheroplast comprising a YAC vector, and the like. Further, vectors comprising xenogenous Ig genes can be targeted to the endogenous Ig gene loci of the fetal fibroblast cells, resulting in the simultaneous introduction of the xenogenous Ig gene and the disruption of the endogenous Ig gene.

Integration of a nucleic acid encoding a xenogenous immunoglobulin gene may also be carried out as described in the patents by Lonberg et al. (supra). In the "knockin" construct used for the insertion of xenogenous immunoglobulin genes into a chromosome of a host ungulate, one or more immunoglobulin genes and an antibiotic resistance gene may be operably-linked to a promoter which is active in the cell type transfected with the construct. For example, a constitutively active, inducible, or tissue specific promoter may be used to activate transcription of the integrated antibiotic resistance gene, allowing transfected cells to be selected based on their resulting antibiotic resistance. Alternatively, a knockin construct in which the knockin cassette containing the Ig gene(s) and the antibiotic resistance gene is not operably-linked to a promoter may be used. In this case, cells in which the knockin cassette integrates downstream of an endogenous promoter may be selected based on the resulting expression of the antibiotic resistance marker under the control of the endogenous promoter. These selected cells may be used in the nuclear transfer procedures described herein to generate a transgenic ungulate containing a xenogenous immunoglobulin gene integrated into a host chromosome.

Using similar methodologies, it is possible to produce and insert artificial chromosomes containing genes for expression of Ig of different species such as dog, cat, other ungulates, non-human primates among other species. As discussed above, and as known in the art, immunoglobulin genes of different species are well known to exhibit substantial sequence homology across different species.

Once it has been determined that the inserted artificial chromosome, for example, a human artificial chromosome, has been stably introduced into a cell line, e.g., a bovine fetal fibroblast, it is utilized as a donor for nuclear transfer. This may be determined by PCR methods. The resulting transgenic calves comprise a stably introduced nucleic acid, such as a human artificial chromosome. After calves have been obtained which include the stably incorporated nucleic acid (for example, human artificial chromosome), the animals are tested to determine whether they express human Ig genes in response to immunization and affinity maturation.

Methods for Reducing Production of Endogenous Antibodies in Ungulates that Also Express Xenogenous Antibodies Modifications of the overall procedure described above may also be performed. For example, to reduce the amount of endogenous antibody expressed by the resulting transgenic ungulate, one or more endogenous Ig genes may be inactivated in the donor cell before or after insertion of the xenogenous nucleic acid. Further, an animal retaining xenogenous Ig genes may be mated with an animal in which an endogenous Ig gene is inactivated. An exemplary scheme for the sequential manipulation of donor cells (e.g., bovine fibroblasts) is described below.

First, generation of homozygous prion protein knockout fetal fibroblasts are generated. Then, hemizygous bovine immunoglobulin heavy chain (BIgH) knockout fibroblasts are generated by gene targeting, and fetuses are producing using nuclear transfer (e.g., SLOT or chromatin transfer). Homozygous BIgH knockout fibroblasts are produced by second gene targeting, and then fetuses are produced using nuclear transfer. Hemizygous bovine immunoglobulin light chain (BIgL) knockout fibroblasts are produced by gene targeting, followed by production of fetuses by nuclear transfer. Homozygous BIgL knockout fibroblasts are generated through second gene targeting, and fetuses are produced by nuclear transfer. Then, human immunoglobulin gene loci are introduced into the above sequential knockout fibroblasts having a homozygous prion protein/BIgH/BIgL knockout genotype, and fetuses and calves are produced by means of nuclear transfer.

Exemplary Methods for Generating Ungulates of the Invention

Preferred methods for generating an ungulate having a mutation in an endogenous prion nucleic acid and optionally having one or more nucleic acids encoding a xenogenous antibody involve remodeling the donor genetic material before it is inserted into a recipient oocyte to form the transgenic ungulate. Remodeling refers to any morphological change that improves development of the resulting nuclear transplant oocyte over that derived from either transferring whole cells or intact nuclei into a recipient oocyte. Reprogramming is achieved by incubating a donor nucleus that has a mutation in an endogenous prion nucleic acid and optionally has one or more nucleic acids encoding a xenogenous antibody in a reprogramming media (e.g., a mitotic extract, detergent and/or salt solution, or protein kinase solution)

resulting in nuclear envelope dissolution and possibly chromatin condensation. This nuclear envelope breakdown and chromatin condensation allows the release of transcription regulatory proteins that were attached to the chromosomes and that would otherwise promote the transcription of genes undesirable for oocyte, embryo, or fetus development. Additional regulatory proteins may be removed by purifying the chromatin mass prior to transferring it into a recipient oocyte. Alternatively, specific regulatory proteins that are released from the chromosomes may be immunodepleted or otherwise removed from the reprogrammed media (e.g., a cell extract) to prevent them from re-binding the chromosomes. After nuclear transfer, new proteins from the oocyte cytoplasm may be bound to the chromosomes during decondensation of the chromatin and nuclear envelope formation in the oocyte. These proteins promote the transcription of genes that allow the oocyte to develop into a viable offspring.

Another cloning method that can be used to produce the transgenic ungulate involves reprogramming a permeabilized cell (i.e., a cell having a mutation in an endogenous prion nucleic acid and optionally having one or more nucleic acids encoding a xenogenous antibody) by incubating it in a reprogramming media (e.g., a cell extract) to allow the addition or removal of factors from the cell. The plasma membrane of the permeabilized cell is preferably resealed to enclose the desired factors and restore the membrane integrity of the cell. The reprogrammed cell is then transferred into a recipient ooctye for the production of a cloned mammal. This cloning method has been used to produce fetuses without a xenogenous immunoglobulin nucleic acid that have survived past day 60. Preliminary results indicate that fetal survival between day 40 and day 60 is higher for fetuses formed using this method (7/10; 70%) than for conventional nuclear transfer fetuses (8/16; 50%). Similar results are expected for fetuses having a mutation in an endogenous prion nucleic acid and/or having one or more nucleic acids encoding a xenogenous antibody In alternative methods, chimeric embryos in which the majority of the placental tissue is from one genetic source and the majority of the fetal tissue is from another genetic source are generated. These chimeric embryos may have fewer placental abnormalities and thus may have an increased survival rate. In one such method, cells from an in vitro fertilized or naturally-occurring embryo are contacted with cells from an embryo that has a mutation in an endogenous prion nucleic acid and optionally has one or more nucleic acids encoding a xenogenous antibody and that is produced using traditional nuclear transfer methods or any of the other cloning methods described herein. For example, cells from an in vitro fertilized embryo can be injected into the periphery of a nuclear transfer embryo (e.g., between the zona pellucida and the embryo itself). This method was used to produce chimeric embryos without xenogenous antibody genes that had a 67% survival rate at day 40 compared to a 25% survival rate for control nuclear transfer embryos. Similar results are expected using cells from nuclear transfer embryos having a mutation in an endogenous prion nucleic acid and/or having one or more nucleic acids encoding a xenogenous antibody. In an alternative method, cells from a precompaction, in vitro fertilized or naturally-occurring embryo are incubated with cells from a precompaction nuclear transfer embryo under conditions that allow cells from each embryo to reorganize to produce a single chimeric embryo (Wells and Powell, Cloning 2:9-22, 2000). In both methods, the cells from the in vitro fertilized or naturally-occurring embryo are preferentially incorporated into the placenta, and the cells from the nuclear transfer method are preferentially incorporated into the fetal tissue.

STATE OF THE ART PRIOR TO PRESENT INVENTION

While human Ig has been expressed in mice, it was unpredictable whether human Ig will be fractionally rearranged and expressed in bovines, or other ungulates, because of differences in antibody gene structure, antibody production mechanism, and B-cell friction. In particular, unlike mice, cattle and sheep differ from humans in their immunophysiology (Lucier et al., J. Immunol. 161:5438, 1998; Parng et al., J. Immunol. 157:5478, 1996; and Butler, Rev. Sci. Tech. 17:43, 2000). For example, antibody gene diversification in bovines and ovines relies much more on gene conversion than gene rearrangement as in humans and mice. Also, the primary location of B-cells in humans and mice is in the bone marrow, whereas in bovines and ovines B-cells are located in the illeal Peyer's patch. Consequently, it would have been difficult, if not impossible, prior to the present invention, to predict whether immunoglobulin rearrangement and diversification of a human immunoglobulin loci would take place within the bovine (or other ungulate) B-cell lineage. In addition, it would also have been unpredictable whether a bovine would be able to survive, i.e., elicit its normal immune functions, in the absence of its endogenous Ig or with interference from human antibodies. For example, it was not certain if bovine B-cells expressing human Ig would correctly migrate to the illeal Peyer's Patch in bovines because this does not happen in humans. Also, it is not clear if human Fc receptor function, which mediates complement activation, induction of cytokine release, and antigen removal, would be normal in a bovine system. It was unpredictable whether such ungulates would survive because it is uncertain whether human Igs will be functionally expressed, or expressed in sufficient amounts to provide for adequate immune responses. Also, it was uncertain whether human chromosomes would be stably maintained in transgenic ungulates.

While the approaches to be utilized in the invention have been described above, the techniques that are utilized are described in greater detail below. These examples are provided to illustrate the invention, and should not be construed as limiting. In particular, while these examples focus on transgenic bovines, the methods described may be used to produce and test any transgenic ungulate.

EXAMPLE 1

Transgenic Ungulates Having Reduced Prion Protein Activity

Bovine fibroblast cell clones in which both alleles of the PrP locus are mutated were generated by sequential homologous recombination. The DNA construct for generating the PrP homozygous knockout cells was used to prevent transcription of functional, full-length PrP mRNA by inserting both a neomycin or puromycin-resistance gene (neo or puro, described in Example 3) and a transcription termination cassette (STOP) in exon 3 just behind its initial ATG codon. Thus, the resulting immature PrP transcripts lack the functional coding domain. The DNA construct containing neo gene (i.e., the PrPKOneo vector) was firstly electroporated into bovine fibroblast cell lines, and then neomycin-resistant colonies were isolated. Based on PCR analysis, homologous recombination in the exon 3 occurred in some colonies. Thus, bovine fibroblast cell lines in which one allele of PrP locus is mutated were generated. From the hemizygously mutated (hemi-PrPKO) fibroblasts, three fetuses in which one allele of PrP locus is mutated were generated and the hemi-PrPKO fibroblast cell lines were reestablished. Then another DNA construct containing puro gene (i.e., the PrPKOpuro vector) was secondly electroporated into the hemi-PrPKO fibroblasts, and then puromycin-resistant colonies were isolated. Based on PCR analysis, homologous recombination in the exon 3 of the remaining allele occurred in some clones at a frequency of ~5%. In this way, bovine fibroblast clones in which both alleles of PrP locus are mutated (homo-PrPKO) were generated.

From the homozygously mutated (homo-PrPKO) fibroblasts, ten fetuses in which both alleles of PrP locus are mutated were generated and the homo-PrPKO fibroblast cell lines were reestablished. In these homo-PrP KO fibroblasts, the complete absence of PrP expression was confirmed by RT-PCR analysis. The homo-PrPKO fibroblasts can be also generated by a combination of the same one knockout vector and a higher concentration of antibiotic to select for homozygous knockout cells. By using nuclear transfer, homo-PrPKO calves will be generated from the homo-PrPKO fibroblasts.

These methods are described further below.

Construction of a Prion Protein Knockout Vector

Figure 44A:
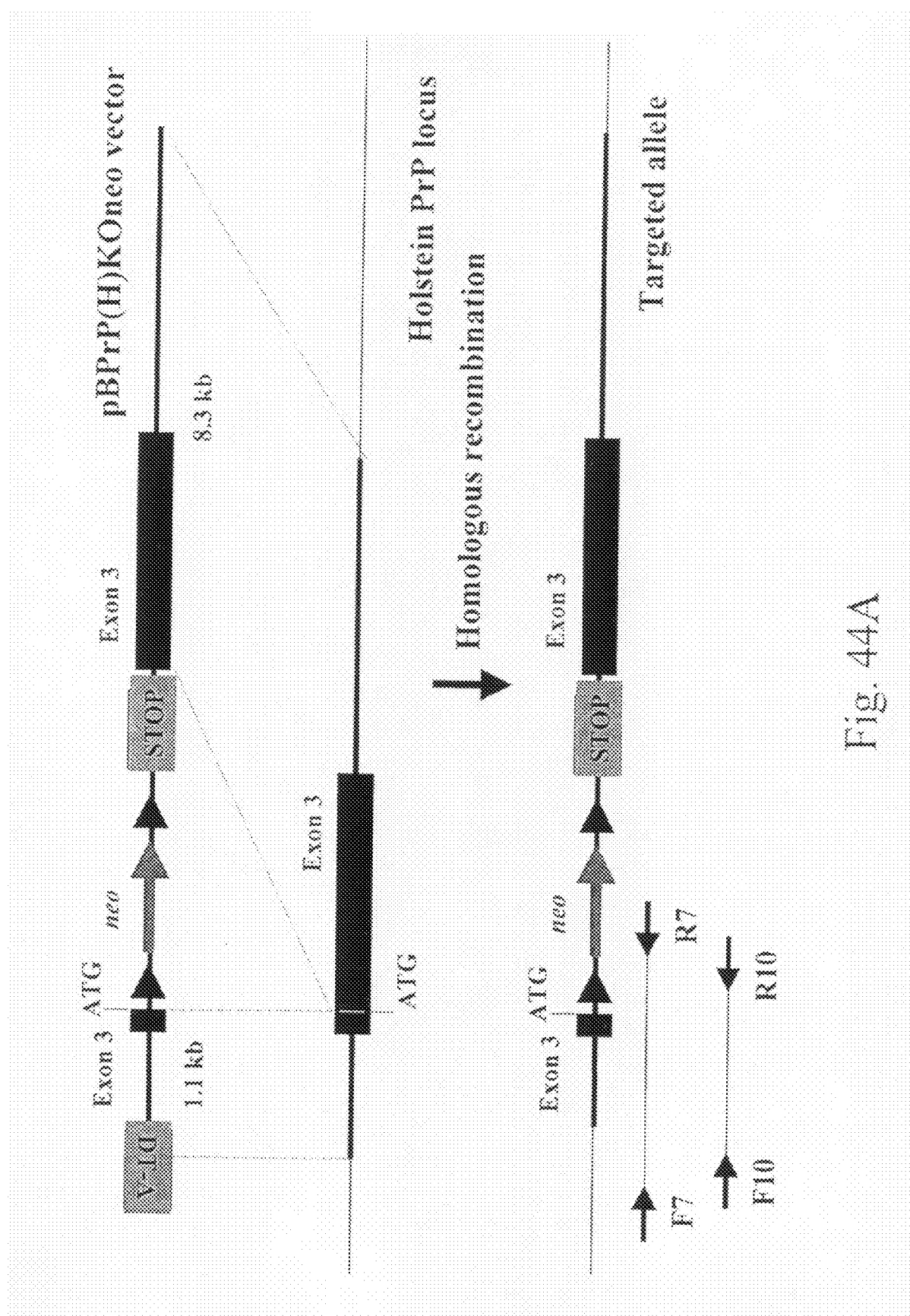
FIG. 44A is a schematic illustration of a prion protein knockout vector of the invention containing a neomycin-resistant gene (pBPrP(H)KOneo vector). This scheme illustrates how to identify the correctly targeted clones.
Figure 44B:
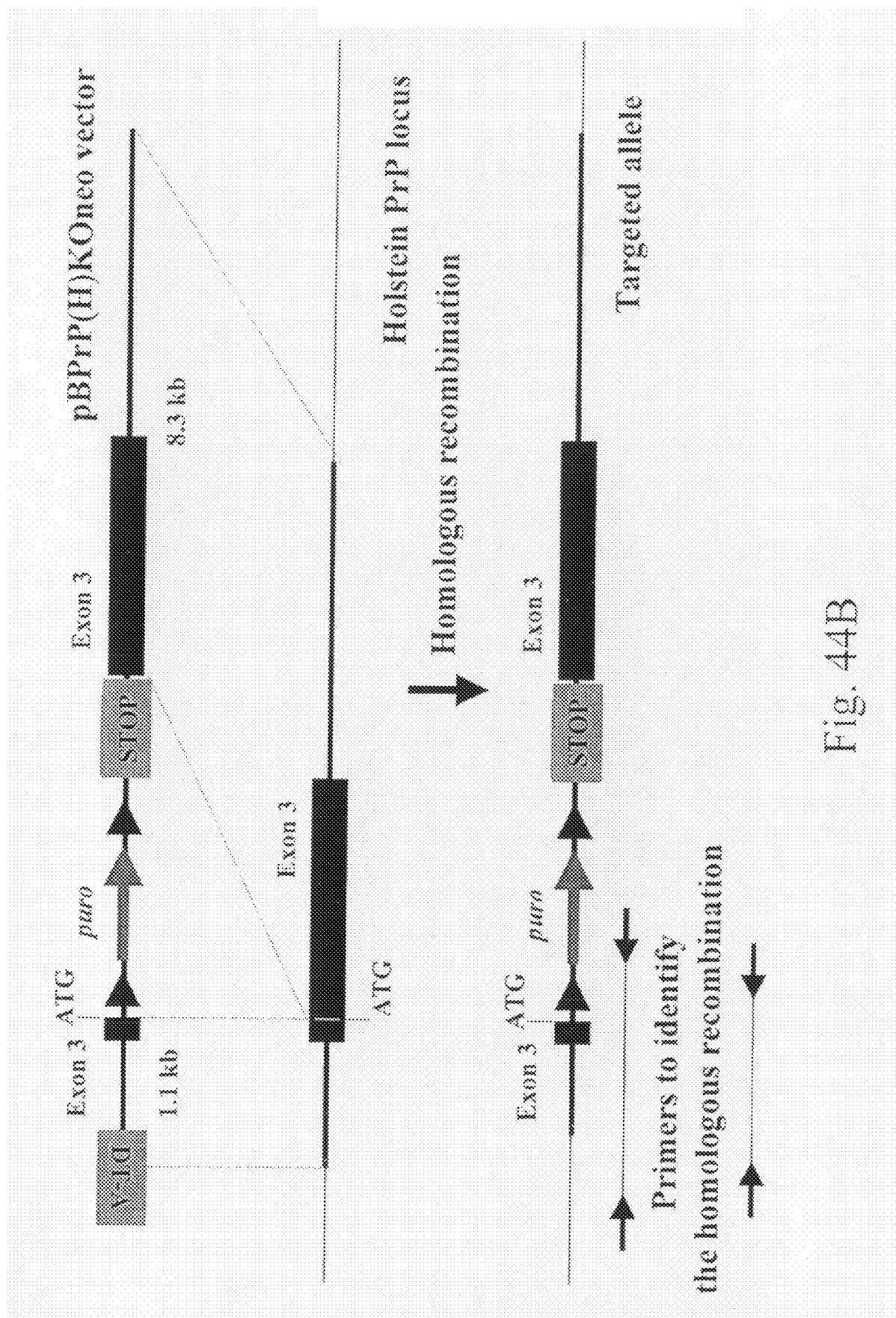
FIG. 44B is a schematic illustration of a prion protein knockout vector of the invention containing a puromycin-resistant gene (pBPrP(H)KOpuro vector) and a method for identifying the correctly targeted clones.

The prion protein knockout vector was generated as follows (FIG. 44A). To isolate genomic DNA around exon 3 of the prion protein gene, a DNA probe was PCR amplified using the following primer pair 5'-CCA CAT AGG CAG TTG GAT CC-3' (SEQ ID NO: 69) and 5'-ATA AGA GGC CTG CTC ATG GC-3' (SEQ ID NO: 70). Using this probe, a bovine (Holstein) genomic k phage library was screened, and four positive λ phage clones were identified. One clone out of the four clones was analyzed further by restriction mapping. The 8.3 kb BamHI genomic fragment (3' homologous arm) containing exon 3 and the 1.2 kb BamHI-BglII fragment were subcloned into pBluescript II SK(−), and then neo and STOP cassettes were inserted at the Bam HIH site, which is just behind its initial ATG codon. The BglII site was converted to blunt ends, and a NotI-linker was inserted at this site. A diphtheria toxin gene (DT-A, Gibco) was then added to the newly created NotI site. DT-A was inserted in the reverse orientation relative to the neomycin-resistance gene in the targeting cassette to kill cells in which the targeting cassette was randomly integrated in the genome (pBPrP(H)KOneo vector). A similar knockout vector containing a puro gene was also constructed (pBPrP(H)KOpuro vector; FIG. 44B). These prion protein knockout vectors can be linearlized using the SrfI restriction enzyme (TOYOBO) so that the pBluescript II SK(−) can be attached to the DT-A gene.

Transfection/Knockout Procedures

Transfection of fetal male Holstein fibroblasts cell lines was performed using a standard electroporation protocol as follows. The medium used to culture the bovine fetal fibroblasts contained 500 ml Alpha MEM (Gibco, 12561-049), 50 ml fetal calf serum (Hy-Clone #ABL13080), 5 ml penicillin-streptomycin (Sigma), and 1 ml 2-mercaptoethanol (Gibco/BRL #21985-023). On the day prior to transfection, cells were seeded on a T175 tissue culture flask with a confluency of 80-100%, as determined by microscopic examination. On the day of transfection, about $10^7$ bovine fibroblasts cells were trypsinized and washed once with alpha-MEM medium. After resuspension of the cells in 800 μl of alpha-MEM, 30 μg of the pBprion protein(H)KOneo vector which was already dissolved in HBS (Hepes buffer saline) containing 1 mM spermidine, was added to the cell suspension and mixed well by pipetting. The cell-DNA suspension was transferred into an electroporation cuvette and electroporated at 550 V and 50 μF. After that, the electroporated cells were plated onto sixty 24-well plates with the alpha-MEM medium supplemented with the serum. After a 48 hour-culture, the medium was replaced with medium containing 500 μg/ml of G418, and the cells were cultured for 2-3 weeks to select neomycin resistant cells. After selection, all colonies that reached close to 100% confluency were picked and divided in replica plates (24-well plates). Cells in one plate were used for genomic DNA extraction, and cells in the other plate were used for nuclear transfer. Genomic DNA was extracted from the colonies to screen for the desired homologous recombination events by PCR. Typically, about 100 G418-colonies were analyzed.

Screening for Targeted Integrations

As described above, the genomic DNA was extracted from each 24-well independently using the PUREGENE DNA isolation Kit (Gentra Systems) according to the manufacturer's protocol. Each genomic DNA sample was resuspended in 20 μl of 10 mM Tris-Cl (pH 8.0) and 1 mM EDTA (EDTA). Screening by PCR was performed using the following primer pair F7 (5'-TGT CAA AGA GAC ACT CCT CAT TTG TCT TCC-3', SEQ ID NO: 71) and R7 (5'-TCA TAG CCG AAT AGC CTC TCC ACC C-3', SEQ ID NO: 72). The sequence of one primer is located in the knockout vector, and the sequence of the other primer is located just outside of the integrated vector in the targeted endogenous locus (FIG. 44A). Therefore, the expected PCR product should be detected only when the knockout vector is integrated into the targeted locus by homologous recombination. The PCR reaction mixtures contained 17.9 μl water, 3 μl of 10×LA PCR buffer II ($Mg^{2+}$ plus), 4.8 μl of dNTP mixture, 10 pmol forward primer, 10 pmol of reverse primer, 2 μl of genomic DNA, and 0.3 μl of LA Taq. Thirty cycles of PCR were performed by incubating the reaction mixtures at the following conditions: 85° C. for three minutes, 94° C. for one minute, 98° C. for 10 seconds, and 68° C. for 5 minutes. After PCR, the reaction mixtures were analyzed by electrophoresis. PCR products of the expected size were generated from approximately 50% of 94 screened neomycin-resistant clones (FIG. 44B). These positive clones were also confirmed by PCR-amplification another primer pair F10 using (5'-TGA AGA TGT CCC AGT GCT GGG GAT-3', SEQ ID NO: 73) and R10 (5'-GAG TTA GGG GCG GGA CTA TGG TTG C-3', SEQ ID NO: 74), giving PCR products of the expected size of 2.7 kb. The high frequency of homologous recombination of more than 50% was reproduced in another fibroblast cell line, female F1 (Holstein× Jersey) cell line (FIG. 44C). Thus, bovine fibroblast cell lines in which one allele of the prion locus is mutated by the knockout vector were successfully generated, irrespective of the initial cell line used.

Chromatin Transfer

The hemizygous prion knockout cells or the nuclei from these cells can be used in any of the nuclear transfer methods described herein to generate a hemizygous prion knockout ungulate (e.g., a knockout bovine calf). If desired, cells from a knockout fetus or live ungulate can be used as described below to generate homozygous prion knockout cells. In one particular method, fibroblasts (e.g., bovine primary fetal fibroblasts) were synchronized in mitosis with 1 μg/ml nocodazole for 18 hours, harvested by mitotic shake-off, and washed twice in phosphate buffered saline and once in cell lysis buffer (20 mM Hepes, pH 8.2, 5 mM $MgCl_2$, 10 mM EDTA, 1 mM DTT and protease inhibitors). Sedimented cells were resuspended in one volume of ice-cold cell lysis buffer, allowed to swell on ice for one hour, and Dounce-homogenized using a tight-fitting glass pestle. The lysate was centrifuged at 15,000×g for 15 minutes at 4° C., and the supernatant (mitotic extract) was aliquoted, frozen in liquid nitrogen, and stored at −80° C. Fresh or frozen extracts were used.

In vitro-matured oocytes were enucleated at 20 hpm. Transfected bovine fetal fibroblasts from selected colonies were washed in $Ca^{2+}/Mg^{2+}$-free Hank's Balanced Salt Solution (HBSS) and permeabilized by incubation of cells in suspension with 31.2 U Streptolysin O (SLO; Sigma) in 100 μl HBSS for 30 minutes in an approximately 37° C. water bath. Permeabilization was assessed by uptake of the membrane impermeant DNA stain, propidium iodide (0.1 μg/ml). Permeabilized fibroblasts were sedimented, washed, and incubated in 40 μl mitotic extract containing an ATP-generating system (1 mM ATP, 10 mM creatine phosphate, and 25 μg/ml creatine kinase) for 30-45 minutes at approximately 37° C. Aliquots were labeled with 0.1 μg/ml Hoechst 33342 to monitor chromatin condensation. At the end of incubation, the reaction mixture was diluted with 500 μl Alpha MEM/ 10% fetal bovine serum (Hyclone). Cells were fused to enucleated oocytes; oocytes were activated at 28 hpm, and embryos cultured to the blastocyst stage in vitro. Two embryos were transferred per recipient female. Pregnancies were monitored by ultrasonography, and C-sections were performed on recipients to recover fetuses for cell line production.

Second Transfection/Knockout Procedures

Transfection of the hemi-PrPKO fetal fibroblasts cell lines where the first KO vector is already integrated into "allele A" was performed as follows. The medium used to culture the bovine fetal fibroblasts contained 500 ml Alpha MEM (Gibco, 12561-049), 50 ml fetal calf serum-(Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a confluency of 80-100%, as determined by microscopic examination. On the day of transfection, about $10^7$ bovine fibroblasts cells were trypsinized and washed once with alpha-MEM medium. After resuspension of the cells in 800 μl of alpha-MEM, 30 μg of the KO vector {pBPrP(H)KOpuro vector} which was already dissolved in HBS (Hepes buffer saline) containing 1 mM spermidine was added to the cell suspension and mixed well by pipetting. The cell-DNA suspension was transferred into an electroporation cuvette and electroporated at 550 V and 50 μF. After that, the electroporated cells were plated onto thirty 48-well plates with the alpha-MEM medium supplemented with the serum. After a 48 hour-culture, the medium was replaced with medium containing 1 μg/ml of puromycin, and the cells were cultured for 2-3 weeks to select puromycin resistant cells. After selection, all colonies which reached close to 100% confluency were picked up and divided to replica plates (24-well and 48-well plates); one was for genomic DNA extraction, the other for nuclear transfer. Genomic DNA was extracted from the colonies to screen for the desired homologous recombination events by PCR.

Screening for Homozygously Targeted Integrations

As described above, the genomic DNA was extracted from each 24-well independently using the PUREGENE DNA isolation Kit (Gentra Systems) according to the manufacturer's protocol. Each genomic DNA sample was resuspended in 20 μl of 10 mM Tris-Cl (pH8.0) and 1 mM EDTA (EDTA). Screening by PCR was performed using the following primer pair F14; 5'-TTG CTC CAC CTT CCG TCT TCT GTC-3' (SEQ ID NO: 3) and R14; 5'-GTT GGC GCC TAC CGG TGG ATG TG-3' (SEQ ID NO: 4). The sequence of one primer is located in the KO vector, and the sequence of the other primer is located just outside of the integrated vector in the targeted endogenous locus (FIG. 1). Therefore, the expected PCR product should be detected only when the KO vector is integrated into the targeted locus by homologous recombination. The PCR reaction mixtures contained 17.9 μl water, 3 μl of 10×LA PCR buffer II ($Mg^{2+}$ plus), 4.8 μl of dNTP mixture, 10 pmol forward primer, 10 pmol of reverse primer, 2 μl of genomic DNA, and 0.3 μl of LA Taq. Thirty cycles of PCR were performed by incubating the reaction mixtures at the following conditions: 85° C. for three minutes, 94° C. for one minute, 98° C. for 10 seconds, and 68° C. for 5 minutes. After PCR, the reaction mixtures were analyzed by electrophoresis. As a result of screening of 332 clones, 15 clones (#26, 86, 113, 116, 118, 173, 177, 213, 235, 250, 251, 266, 285, 318, 330) showed the expected PCR products, confirmed by sequencing the PCR product. Based on the polymorphic sequence, it turned out that the KO vector was integrated into "allele B" of the exon 3 of PrP locus in all the clones. The eight clones were subjected to nuclear transfer to generate fetuses and three fetuses (#1395, 1468, 1476) from #285 and seven fetuses (#1439-1, 1439-2, 1487, 3583, 3632, 3682-1, 368-2-2, 4961) from #113 proved to be homozygous PrP KO where the puroKO vector and the neoKO vector are integrated into "allele B" and "allele A," respectively. Thus, ten bovine fibroblast cell lines in which both alleles of the PrP locus are mutated by the KO vectors were successfully generated.

Table 1 summarizes the data pertaining to pregnancies following chromatin transfer using homozygous PrP KO clones derived from hemizygous PrP KO cell lines.

TABLE 1

| Cell line ID | No of recipients pregnancy checked | Pregnancy at 40 d (%) | Pregnancy at 90 d (%) |
|---|---|---|---|
| 1395 | 50 | 28 (56) | 17 (34) |
| 4661 | 23 | 13 (56) | 5 (22) |
| 1439 | 12 | 6 (50) | 4 (33) |
| 1487-1 | 14 | 10 (71) | 1 (7) |
| Control 6594 | 18 | 10 (56) | 8 (44) |

Verification of Absence of PrP Expression in the Homo-PrP Fetuses

From some fetuses, fibroblasts were established and total RNA was extracted by using RNeasy Mini kit (QIAGEN). One microliter of total RNA was subjected to first-strand cDNA synthesis (SuperScript First-Strand Synthesis System for RT-PCR; Invitrogen), followed by RT-PCR. The RT-PCR was carried out as below. The primers used were 5'-AAG AAG CGA CCA AAA CCT GG-3' and 5'-GTA ACG GTG CAT GTT TTC ACG-3'. The PCR reaction mixtures contained 32.5 μl water, 5 μl of 10×Ex Taq buffer (TAKARA), 8 μl of dNTP mixture, 10 pmol forward primer, 10 pmol of reverse primer, 2 μl of the first-strand cDNA, and 0.5 μl of Ex Taq (TAKARA). Thirty five cycles of PCR were performed by incubating the reaction mixtures at the following conditions: 85° C. for three minutes, 94° C. for one minute, 98° C. for 10 seconds, 62° C. for 30 seconds and 72° C. for 1 minute. After PCR, the reaction mixtures were analyzed by electrophoresis. Whereas the clear PCR products were detected in both wild-type and hemi-PrP KO cells, there were no positive PCR products in any of the ten homo-PrP KO cell lines. This result verifies the complete absence of PrP expression in the homo-PrP KO cell lines.

EXAMPLE 2

Introduction and Rearrangement of HAC

Summary of Procedures for Insertion of HACs

For the generation of ungulates (e.g., bovines) that have a mutation in one or both alleles of the prion gene and that express xenogenous antibody, standard methods may be used to insert a nucleic acid encoding a xenogenous antibody (e.g., a HAC) into a cell. For example, a HAC can be inserted before or after one or both alleles of the prion gene are inactivated. If desired, one or more endogenous antibody genes may also be mutated in the cell. The cell is then used in standard nuclear transfer procedures to produce the desired transgenic ungulate, as described in more detail below.

Essentially, male and female bovine fetal fibroblast cell lines containing human artificial chromosome sequences (e.g., #14fg., #2fg., and #22fg.) are obtained and selected and used to produce cloned calves from these lines.

For example, HACs derived from human chromosome #14 ("#14fg," comprising the Ig heavy chain gene), human chromosome #2 ("#2fg," comprising the Ig kappa chain gene) and human chromosome #22 ("#22fg," comprising the Ig lambda chain gene) can be introduced simultaneously or successively.

The transmission of these chromosome fragments is tested by mating a male #14fg. animal to female #2fg. and #22fg. animals and evaluating offspring. If transmission is successful then the two lines are mated to produce a line containing all three chromosome fragments.

Also, #14fg., #2fg., and #22fg. chromosome fragments may be inserted into fetal cells (e.g., transgenic Homo H/L fetal cells) and used to generate cloned calves or cross transgenic HAC calves with other transgenic calves (e.g., Homo H/L calves). Alternatively, other HACs, such as ΔHAC or ΔΔHAC, may be introduced as described below or introduced using any other chromosome transfer method.

Rationale

Germline transmission of HACs should be useful for introducing the HACs into the animals (e.g., Ig knockout animals) and in propagating animals in production herds. The concern in propagation of HACs through the germline is incomplete pairing of chromosomal material during meiosis. However, germline transmission has been successful in mice as shown by Tomizuka et al. (Proc. Natl. Acad. Sci. USA, 97:722, 2000).

The strategy outlined in FIG. 1A consists of inserting #14fg. into a male line of cells and #2fg. and #22fg. each into female cell lines. Calves retaining a HAC are produced and germline transmission can be tested both through females and males. Part of the resulting offspring (~25%) should contain both heavy and light chain HACs. Further crossing should result in a line of calves containing all three chromosomal fragments. These animals are optionally used for crossing with transgenic animals (e.g., Homo H/L animals), produced from fetal cells as previously described.

Experimental Design

Cells are obtained from the original screening of cell lines. These may be Holstein or different lines than those used above. This allows crossing while maintaining as much genetic variation in the herd as possible. Introduction of HACs into cell lines and selection of positive cell lines is then effected. Selected cell lines are used for nuclear transfer and calves are produced. Starting at 12 months of age semen and eggs are collected, fertilized, and transferred into recipient animals. Cell samples are taken for DNA marker analysis and karyotyping. Beginning at birth, blood samples are taken and analyzed for the presence of human Ig proteins.

As indicated above, HACs are also optionally transferred into Homo H/L cell lines using the procedures developed in the above experiments.

The following examples are additionally provided as further exemplification of the invention.

Exemplary Procedures for Insertion of RACs

Additional experiments were carried out to demonstrate that xenogenous (e.g., human) immunoglobulin heavy chain (mu) and lambda light chain may be produced by a bovine host, either alone or in combination. In addition, these experiments demonstrated that the human immunoglobulin chains were rearranged and that polyclonal sera was obtained. In these procedures, immunoglobulin-expressing genes were introduced into bovine fibroblasts using human artificial chromosomes. The fibroblasts were then utilized for nuclear transfer, and fetuses were obtained and analyzed for antibody production. These procedures and results are described in more detail below. Similar results are expected from fibroblasts that are isolated from a fetus with a mutation in one or both alleles of the prion gene and that are used in the methods described below for the introduction of a HAC. Alternatively, a HAC can be introduced into a cell, and then a mutation can be introduced (i) into the prion gene of the cell with the HAC or (ii) into the prion gene of a cell from a cloned fetus generated using the cell with the HAC.

HAC Constructs

The human artificial chromosomes (HACs) were constructed using a previously described chromosome-cloning system (Kuroiwa et al., Nature Biotech. 18: 1086-1090, 2000). Briefly, for the construction of ΔHAC, the previously reported human chromosome 22 fragment (hChr22) containing a loxp sequence integrated at the HCF2 locus was truncated at the AP000344 locus by telomere-directed chromosomal truncation (Kuroiwa et al., Nucleic Acid Res., 26: 3447-3448, 1998). Next, cell hybrids were formed by fusing the DT40 cell clone containing the above hChr22 fragment (hCF22) truncated at the AP000344 locus with a DT40 cell clone (denoted "R clone") containing the stable and germline-transmittable human minichromosome SC20 vector. The SC20 vector was generated by inserting a loxp sequence at the RNR2 locus of the S20 fragment. The SC20 fragment is a naturally-occurring fragment derived from human chromosome 14 that includes the entire region of the human Ig heavy chain gene (Tomizuka et al., Proc. Natl. Acad. Sci. USA 97:722, 2000). The resulting DT40 cell hybrids contained both hChr fragments. The DT40 hybrids were transfected with a Cre recombinase-expression vector to induce Cre/loxP-mediated chromosomal translocation between hCF22 and the SC20 vector. The stable transfectants were analyzed using nested PCR to confirm the cloning of the 2.5 megabase hChr22 region, defined by the HCF2 and AP000344 loci, into the loxP-cloning site in the SC20 vector. The PCR-positive cells that were expected to contain ΔHAC were then isolated by FACS sorting based on the fluorescence of the encoded green fluorescent protein. Fluorescent in situ hybridization (FISH) analysis of the sorted cells was also used to confirm the presence of ΔHAC, which contains the 2.5 megabase hChr22 insert.

Similarly, ΔΔHAC was also constructed using this chromosome-cloning system. The hChr22 fragment was truncated at the AP000344 locus, and then the loxP sequence was integrated into the AP000553 locus by homologous recombination in DT40 cells. The resulting cells were then fused with the R clone containing the SC20 minichromosome vector. The cell hybrids were transfection with a Cre-expression vector to allow Cre/loxP-mediated chromosomal translocation. The generation of ΔΔHAC, which contains the 1.5 megabase hChr22 insert, defined by the AP000553 and AP000344 loci, was confirmed by PCR and FISH analyses.

The functionality of ΔHAC and ΔΔHAC in vivo was assessed by the generation of chimeric mice containing these HACs. These HACs were individually introduced into mouse embryonic stem (ES) cells, which were then used for the generation of chimeric mice using standard procedures (Japanese patent number 2001-142371; filed May 11, 2000). The resulting mice had a high degree of chimerism (85-100% of coat color), demonstrating a high level of pluripotency of the ES cells containing these HACs and the mitotic stability of these HACs in vivo. Furthermore, ΔHAC was transmitted through the germline of the ΔHAC chimeric mouse to the next offspring, demonstrating the meiotic stability of this HAC.

Chicken DT40 cells retaining these HACs have been deposited under the Budapest treaty on May 9, 2001 in the International Patent Organism Depository, National Institute of Advanced Industrial Science and Technology, Tsukuba Central 6, 1-1, Higashi 1-Chome Tsukuba-shi, Ibaraki-ken, 305-8566 Japan. The depository numbers are as follows: ΔHAC (FERM BP-7582), ΔΔHAC (FERM BP-7581), and SC20 fragment (FERM BP-7583). Chicken DT40 cells retaining these HACs have also been deposited in the Food Industry Research and Development Institute (FIRDI) in Taiwan. The depository numbers and dates are as follows: ΔHAC (CCRC 960144; Nov. 9, 2001), ΔΔHAC (CCRC 960145; Nov. 9, 2001), and SC20 fragment (the cell line was deposited under the name SC20 (D); CCRC 960099; Aug. 18, 1999).

The 2.5 megabase (Mb) hChr22 insert in ΔHAC is composed of the following BAC contigs, which are listed by their GenBank accession number: AC002470, AC002472, AP000550, AP000551, AP000552, AP000556, AP000557, AP000558, AP000553, AP000554, AP000555, D86995, D87019, D87012, D88268, D86993, D87004, D87022, D88271, D88269, D87000, D86996, D86989, D88270, D87003, D87018, D87016, D86999, D87010, D87009, D87011, D87013, D87014, D86991, D87002, D87006, D86994, D87007, D87015, D86998, D87021, D87024, D87020, D87023, D87017, AP000360, AP00361, AP000362, AC000029, AC000102, U07000, AP000343, and AP000344. The 1.5 Mb hChr22 insert in ΔΔHAC is composed of the following BAC contigs: AP000553, AP000554, AP000555, D86995, D87019, D87012, D88268, D86993, D87004, D87022, D88271, D88269, D87000, D86996, D86989, D88270, D87003, D87018, D87016, D86999, D87010, D87009, D87011, D87013, D87014, D86991, D87002, D87006, D86994, D87007, D87015, D86998, D87021, D87024, D87020, D87023, D87017, AP000360, AP00361, AP000362, AC000029, AC000102, U07000, AP000343, and AP000344 (Dunham et al, Nature 402:489-499, 1999).

Generation of Bovine Fetal Fibroblasts

To generate bovine fetal fibroblasts, day 45 to 60 fetuses were collected from disease-tested Holstein or Jersey cows housed at Trans Ova (Iowa), in which the pedigree of the male and female parents were documented for three consecutive generations. The collected fetuses were shipped on wet ice to Hematech's Worcester Molecular Biology Division for the generation of primary fetal fibroblasts. Following arrival, the fetuses were transferred to a non-tissue culture grade, 100 mm plastic petri dish in a tissue culture hood. Using sterile forceps and scissors, the extraembryonic membrane and umbilical cord were removed from the fetus. After transferring the fetus to a new plastic petri dish, the head, limbs and internal organs were removed. The eviscerated fetus was transferred to a third petri dish containing approximately 10 ml of fetus rinse solution composed of: 125 ml 1× Dulbecco's-PBS (D-PBS) with $Ca^{2+}$ and Mg 2+(Gibco-BRL, cat#. 14040); 0.5 ml Tylosine Tartrate (8 mg/ml, Sigma, cat#. T-3397); 2 ml Penicillin-Streptomycin (Sigma, cat#. P-3539); and 1 ml Fungizone (Gibco-BRL, cat#. 15295-017) (mixed and filtered through a 0.2 μm nylon filter unit [Nalgene, cat#. 150-0020).

Each fetus was washed an additional three times with the fetus rinse solution to remove traces of blood, transferred to a 50 ml conical tissue culture tube, and finely minced into small pieces with a sterile scalpel. The tissue pieces were washed once with 1×D-PBS without $Ca^{2+}$ and $Mg^{2+}$ (Gibco-BRL, cat#. 14190). After the tissue pieces settled to the bottom of the tube, the supernatant was removed and replaced with approximately 30 ml of cell dissociation buffer (Gibco-BRL, cat#. 13151-014). The tube was inverted several times to allow mixing and incubated at 38.5° C./5% $CO_2$ for 20 minutes in a tissue culture incubator. Following settling of the tissue to the bottom of the tube, the supernatant is removed and replaced with an equivalent volume of fresh cell dissociation buffer. The tissue and cell dissociation buffer mixture was transferred to a sterile, 75 ml glass trypsinizing flask (Wheaton Science Products, cat#. 355393) containing a 24 mm, round-ended, spin bar. The flask was transferred to a 38.5° C./5% $CO_2$ tissue culture incubator, positioned on a magnetic stir plate, and stirred at a sufficient speed to allow efficient mixing for approximately 20 minutes. The flask was transferred to a tissue culture hood; the tissue pieces allowed to settle, followed by removal of the supernatant and harvesting of the dissociated cells by centrifugation at 1,200 rpm for five minutes. The cell pellet was re-suspended in a small volume of complete fibroblast culture media composed of: 440 ml alpha MEM (BioWhittaker, cat# 12-169F); 50 ml irradiated fetal bovine serum; 5 ml GLUTAMAX-I supplement (Gibco-BRL, cat# 25050-061); 5 ml Penicillin-Streptomycin (Sigma, cat# P-3539); 1.4 ml 2-mercaptoethanol (Gibco-BRL, cat# 21985-023) (all components except the fetal bovine serum were mixed were filtered through 0.2 μm nylon filter unit [Nalgene, cat# 151-4020]), and stored on ice. The dissociation process was repeated three additional times with an additional 30 ml of cell dissociation solution during each step. Cells were pooled; washed in complete fibroblast media; passed sequentially through 23 and 26 gauge needles, and finally through a 70 μm cell strainer (B-D Falcon, cat# 352350) to generate a single cell suspension. Cell density and viability were determined by counting in a hemacytometer in the presence of trypan blue (0.4% solution, Sigma, cat#. T-8154).

Primary fibroblasts were expanded at 38.5° C./5% $CO_2$ in complete fibroblast media at a cell density of 1×10⁶ viable cells per T75 cm² tissue culture flask. After 3 days of culture or before the cells reached confluency, the fibroblasts were harvested by rinsing the flask once with 1×D-PBS (without $Ca^{2+}$ and $Mg^{2+}$) and incubating with 10 ml of cell dissociation buffer for 5 to 10 minutes at room temperature. Detachment of cells was visually monitored using an inverted microscope. At this step, care was taken to ensure that cell clumps were disaggregated by trituration. After washing and quantitation, the dissociated fibroblasts were ready for use in gene targeting experiments. These cells could also be cryopreserved for long-term storage.

Introduction of RACs into Bovine Fetal Fibroblasts

ΔHAC and ΔΔHAC were transferred from the DT40 cell hybrids to Chinese hamster ovary (CHO) cells using microcell-mediated chromosome transfer (MMCT) (Kuroiwa et al. Nature Biotech. 18: 1086-1090, 2000). The CHO clone containing ΔHAC ("D15 clone") was cultured in F12 (Gibco) medium supplemented with 10% FBS (Gibco), 1 mg/ml G418, and 0.2 mg/ml hygromycin B at 37° C. and 5% $CO_2$. The D15 clone was expanded into twelve T25 flasks. When the confluency reached 80-90%, colcemid (Sigma) was added to the medium at a final concentration of 0.1 μg/ml. After three days, the medium was exchanged with DMEM (Gibco) supplemented with 10 μg/ml of cytochalacin B (Sigma). The flasks were centrifuged for 60 minutes at 8,000 rpm to collect microcells. The microcells were purified through 8-, 5-, and 3-μm filters (Costar) and then resuspended in DMEM medium. The microcells were used for fusion with bovine fibroblasts as described below.

Bovine fetal fibroblasts were cultured in α-MEM (Gibco) medium supplemented with 10% FBS (Gibco) at 37° C. and 5% $CO_2$. The fibroblasts were expanded in a T175 flask. When the confluency reached 70-80%, the cells were detached from the flask with 0.05% trypsin. The fibroblast cells were washed twice with DMEM medium and then overlayed on the microcell suspension. After the microcell-fibroblast suspension was centrifuged for five minutes at 1,500 rpm, PEG1500 (Roche) was added to the pellet according to the manufacturer's protocol to enable fusion of the microcells with the bovine fibroblasts. After fusion, the fused cells were plated into six 24-well plates and cultured in α-MEM medium supplemented with 10% FBS for 24 hours. The medium was then exchanged with medium containing 0.7 mg/ml of G418. After growth in the presence of the G418 antibiotic for about two weeks, the G418 resistant, fused cells were selected. These G418-resistant clones were used for nuclear transfer, as described below.

Similarly, ΔΔHAC from the CHO clone C13 was transferred into bovine fetal fibroblasts by means of MMCT. The selected G418-resistant clones were used for nuclear transfer.

Nuclear Transfer, Activation, and Embryo Culture

The nuclear transfer procedure was carried out essentially as described earlier (Cibelli et al., Science 1998: 280:1256-1258). In vitro matured oocytes were enucleated about 18-20 hours post maturation (hpm) and chromosome removal was confirmed by bisBenzimide (Hoechst 33342, Sigma) labeling under UV light. These cytoplast-donor cell couplets were fused, by using single electrical pulse of 2.4 kV/cm for 20 μsec (Electrocell manipulator 200, Genetronics, San Diego, Calif.). After 3-4 hrs, a random sub-set of 25% of the total transferred couplets was removed, and the fusion was confirmed by bisBenzimide labeling of the transferred nucleus. At 30 hpm reconstructed oocytes and controls were activated with calcium ionophore (5 μM) for 4 minutes (Cal Biochem, San Diego, Calif.) and 10 μg Cycloheximide and 2.5 μg Cytochalasin D (Sigma) in ACM culture medium for 6 hours as described earlier (Lin et al., Mol. Reprod. Dev. 1998: 49:298-307; Presicce et al., Mol. Reprod. Dev. 1994:38:380-385). After activation eggs were washed in HEPES buffered hamster embryo culture medium (HECM-Hepes) five times and placed in culture in 4-well tissue culture plates containing irradiated mouse fetal fibroblasts and 0.5 ml of embryo culture medium covered with 0.2 ml of embryo tested mineral oil (Sigma). Twenty five to 50 embryos were placed in each well and incubated at 38.5° C. in a 5% CO₂ in air atmosphere. On day four 10% FCS was added to the culture medium.

Embryo Transfer

Day 7 and 8 nuclear transfer blastocysts were transferred into day 6 and 7 synchronized recipient heifers, respectively. Recipient animals were synchronized using a single injection of Lutalyse (Pharmacia & Upjohn, Kalamazoo, Mich.) followed by estrus detection. The recipients were examined on day 30 and day 60 after embryo transfer by ultrasonography for the presence of conceptus and thereafter every 30 days by rectal palpation until 270 days. The retention of a HAC in these bovine fetuses is summarized in Table 2 and is described in greater detail in the sections below.

TABLE 2

Summary of HAC retention in bovine fetuses

| HAC | Cell Clone | Recip/Fetus No. | NT Date | Recovery Date | Fetal Age | HAC Retention H | L |
|---|---|---|---|---|---|---|---|
| ΔΔ | 4-12 | 5580 | 2/14 | 4/13 | 58 | + | + |
| ΔΔ | 2-14 | 5848 | 2/15 | 4/13 | 57 | − | − |
| ΔΔ | 4-12 | 5868A | 2/14 | 6/13 | 119 | + | + |
| ΔΔ | 4-12 | 5868B | 2/14 | 6/13 | 119 | + | + |
| ΔΔ | 4-12 | 5542A | 2/14 | 5/16 | 91 | + | + |
| ΔΔ | 4-12 | 5542B | 2/14 | 5/16 | 91 | + | + |
| ΔΔ | 4-12 | 5174 | 2/14 | 5/16 | 91 (abnormal) | nd | nd |
| ΔΔ | 4-12 | 6097 | 2/14 | Remains | 160 (7/24) | nd | nd |
| Δ | 4-8 | 6032 | 1/31 | 3/30 | 58 | + | + |
| Δ | 2-13 | 5983 | 2/2 | 3/30 | 56 | − | − |

TABLE 2-continued

Summary of HAC retention in bovine fetuses

| HAC | Cell Clone | Recip/Fetus No. | NT Date | Recovery Date | Fetal Age | HAC Retention H | L |
|---|---|---|---|---|---|---|---|
| Δ | 4-2 | 5968 | 2/2 | 3/30 | 56 | + | + |
| Δ | 2-22 | 6045 | 2/2 | 3/30 | 56 | + | + |
| Δ | 4-8 | 5846 | 1/31 | 4/20 | 79 | − | − |
| Δ | 2-13 | 6053 | 2/2 | 4/27 | 84 | + | − |
| Δ | 4-2 | 5996 | 2/1 | 4/20 | 77 | + | − |

Introduction of a HAC Containing a Fragment of Chromosome #14

The SC20 fragment, a human chromosome #14 fragment ("hchr.14fg," containing the Ig heavy chain gene), was introduced into fetal fibroblast cells in substantially the same manner as described above. Any other standard chromosome transfer method may also be used to insert this HAC or another HAC containing a human Ig gene into donor cells. The resulting donor cells may be used in standard nuclear transfer techniques, such as those described above, to generate transgenic ungulates with the HAC.

The pregnancy status of the 28 recipients to whom cloned embryos were transferred from cells containing the hchr.14fg was checked by ultrasonography. The results are summarized in Table 3.

If desired, a cell from the resulting HAC fetus or HAC offspring can be used in a second round of nuclear transfer to generate additional cloned offspring. Cells from the initial HAC fetus or HAC offspring may also be frozen to form a cell line to be used as a source of donor cells for the generation of additional HAC ungulates.

TABLE 3

Pregnancy at 40 days using donor cells containing hchr.14fg

| Clone ID | No of recips transferred | Pregnancy at 40 days (%) |
|---|---|---|
| 2-1 | 8 | 3 (38) |
| 4-2 | 10 | 0 (0) |
| 4-1 | 5 | 0 (0) |
| 4-1 | 3 | 1 (33) |
| 2-1 | 2 | 1 (50) |
| Total | 28 | 5 (18) |

The pregnancy rates were lower than anticipated. This is believed to be attributable to extremely abnormally hot weather during embryo transfer.

As illustrated in FIG. 27, pregnancy rates for HAC carrying embryos appear to be equivalent to non-transgenic cloned pregnancies. One recipient carrying a ΔΔHAC calf gave birth recently to a live healthy calf. Others will be born over the next several months.

Demonstration of Rearrangement and Expression of Human Heavy Chain Locus in a ΔHAC Bovine Fetus Cloned ΔHAC-transgenic bovine fetuses were removed at various gestational days and analyzed for the presence, rearrangement, and expression of the human immunoglobulin loci. Analysis of genomic DNA and cDNA obtained by RT-PCR from spleen and nonlymphoid tissues (liver and brain) of one of these fetuses indicated the presence, rearrangement, and expression of the ΔHAC.

Presence of Human Heavy and/or Light Chain in ΔHAC Fetuses

To determine whether the human heavy and light chains were retained in ΔHAC fetuses, liver DNA was isolated from ΔHAC fetuses and analyzed by PCR for the presence of genomic DNA encoding human heavy and light chains.

For the detection of genomic heavy chain DNA, the following primers were used: VH3-F 5'-AGT GAG ATA AGC AGT GGA TG-3' (SEQ ID NO: 1) and VH3-R 5'-CTT GTG CTA CTC CCA TCA CT-3' (SEQ ID NO: 2). The primers used for detection of lambda light chain DNA were IgL-F 5'-GGA GAC CAC CAA ACC CTC CAA A-3' (SEQ ID NO: 3) and IgL-R 5'-GAG AGT TGC AGA AGG GGT YGA CT-3' (SEQ ID NO: 4). The PCR reaction mixtures contained 18.9 μl water, 3 μl of 10×Ex Taq buffer, 4.8 μl of dNTP mixture, 10 pmol forward primer and 10 μmol of reverse primer, 1 μl of genomic DNA, and 0.3 μl of Ex Taq. Thirty-eight cycles of PCR were performed by incubating the reaction mixtures at the following conditions: 85° C. for three minutes, 94° C. for one minute, 98° C. for 10 seconds, 56° C. for 30 seconds, and 72° C. for 30 seconds.

Figure 5:
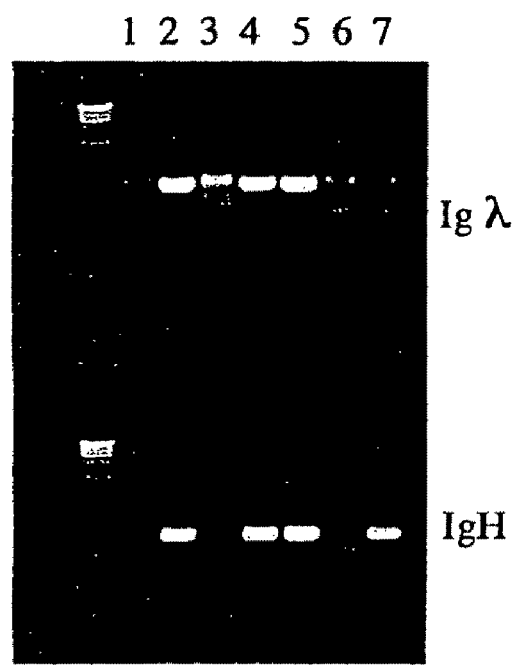
FIG. 5 is a photograph of an agarose gel showing the presence of genomic DNA encoding human heavy and light chains in ΔHAC fetuses: lane 1, bovine genomic DNA (negative); lane 2, fetus 5968 genomic DNA at 56 days; lane 3, fetus 5983 genomic DNA at 56 days; lane 4, fetus 6032 genomic DNA at 58 days; lane 5, fetus 6045 genomic DNA at 56 days; lane 6, fetus 5846 genomic DNA at 79 days; and lane 7, fetus 5996 genomic DNA at 77 days.

As shown in FIG. 5, fetuses #5968, 6032 and 6045 each contained both human heavy chain (μ) and light chain (λ) loci. Fetus #5996 contained only the human heavy chain locus. Fetus #5983 did not contain the human heavy chain and may not have contained the human light chain. Fetus #5846 did not contain either human sequence. Thus, fetuses #5983 and 5846 may not have retained the HAC. These results suggested that ΔHAC can be stably retained up to gestational day 58 in bovines.

Presence of Human Cmu Exons in ΔHAC Fetus #5996

Primers specific for a mRNA transcript including portions of Cmu 3 and Cmu 4 were used to determine whether ΔHAC was present and expressing transcripts encoding the constant region of the human mu locus of fetus #5996.

Figure 7:
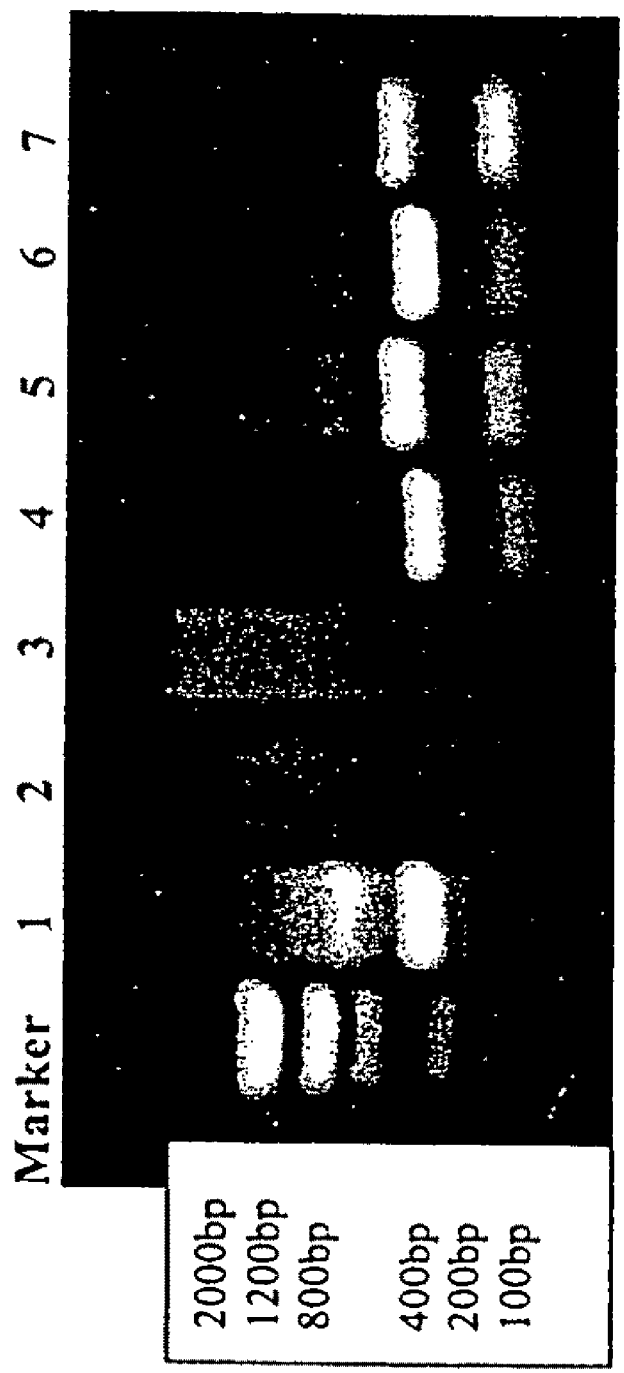
FIG. 7 is a photograph of an agarose gel showing the rearrangement of endogenous bovine heavy chain in ΔHAC fetus #5996: lane 1, GAPDH primers in bovine liver cDNA; lane 2, bovine rearranged Cmu heavy chain in bovine brain cDNA from fetus 5996; lane 3, bovine rearranged Cmu heavy chain in bovine liver cDNA from fetus 5996; lane 4, GAPDH primers in bovine spleen cDNA from fetus 5996; lane 5, bovine rearranged Cmu heavy chain in bovine spleen cDNA from fetus 5996; lane 6, GAPDH primers in bovine brain cDNA from fetus 5996; and lane 7, bovine rearranged Cmu heavy chain positive control.

For this RT-PCR analysis of the genomic constant region of the human mu heavy chain, primers "CH3-F1" (5'-acc acc tat gac agc gtg α-3', SEQ ID NO: 5) and "CH4-R2" (5'-gtg gca gca agt aga cat cg-3', SEQ ID NO: 6) were used to generate a RT-PCR product of 350 base pairs. This PCR amplification was performed by an initial denaturing incubation at 95° C. for five minutes. Then, 35 cycles of denaturation, annealing, and amplification were performed by incubation at 95° C. for one minute, 59° C. for one minute, and 72° C. for two minutes. Then, the reaction mixtures were incubated at 72° C. for 10 minutes. Rearranged bovine heavy chain was detected using primers 17L and P9, as described below (FIG. 7). As an internal control, levels of GAPDH RNA was detected using primers "GAPDH forward" (5'-gtc atc atc tct gcc cot tct g-3', SEQ ID NO: 7) and "GAPDH reverse" (5'-aac aac ttc ttg atg tca tca t-3', SEQ ID NO: 8). For this amplification of GAPDH RNA, samples were incubated at 95° C. for five minutes, followed by 35 cycles of incubation at 95° C. for one minute, 55° C. for one minute, and 72° C. for two minutes. Then, the mixtures were incubated at 72° C. for seven minutes.

Figure 6:
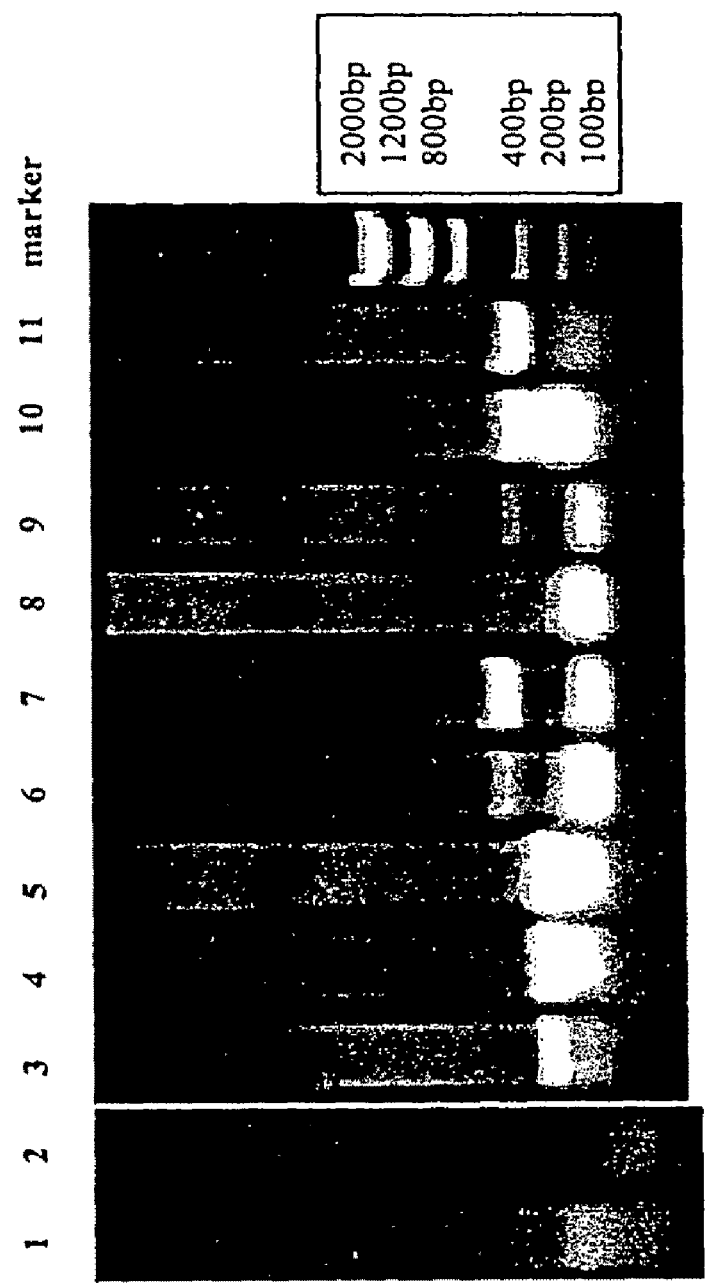
FIG. 6 is a photograph of an agarose gel showing the expression of human Cmu exons 3 and 4 in a ΔHAC fetus at 77 gestational days (fetus #5996): lane 1, human mu constant region in bovine liver cDNA from fetus 5996; lane 2, human mu constant region in bovine brain cDNA from fetus 5996; lane 3, human mu constant region in bovine spleen cDNA from fetus 5996; lane 4, human mu constant region in human spleen cDNA; lane 5, human mu constant region in mouse spleen cDNA with HAC; lane 6, bovine rearranged Cmu heavy chain in bovine spleen cDNA from fetus 5996; lane 7, bovine rearranged Cmu heavy chain in human spleen cDNA; lane 8, bovine rearranged Cmu heavy chain in mouse spleen cDNA with HAC; lane 9, GAPDH primers in bovine spleen cDNA from fetus 5996; lane 10, GAPDH primers in bovine liver cDNA; and lane 11, GAPDH primers in mouse spleen cDNA with HAC.

This analysis showed that RT-PCR analysis of the spleen of fetus #5996 produced a band (lane 3) matching the amplification products generated using control human spleen cDNA (lane 4) and cDNA obtained from a ΔHAC chimeric mouse (lane 5) (FIG. 6). No such band was detected in nonlymphoid tissues: bovine liver (lane 1) or bovine brain (lane 2). The capacity of these tissues to support RT-PCR was shown by the successful amplification of the housekeeping gene, GADPH, in both liver (lane 10 of FIG. 6) and brain (lane 6 of FIG. 7).

Rearrangement of Bovine Heavy Chain Locus by 77 Gestational Days

The ΔHAC fetus #5996 was tested to determine whether it had undergone the developmental processes necessary for the expression and activation of the recombination system required for immunoglobulin heavy chain locus rearrangement. For this analysis, standard RT-PCR analysis was performed to detect the presence of mRNA transcripts encoding mu-VH rearrangements. RNA isolated from the spleen, liver, and brain of fetus #5996 was analyzed by RT-PCR using primers "17L" (5'-ccc tcc tct ttg tgc tgt ca-3', SEQ ID NO: 9) and "P9" (5'-cac cgt gct ctc atc gga tg-3', SEQ ID NO: 10). The PCR reaction mixtures were incubated at 95° C. for 3 minutes, and then 35 cycles of denaturation, annealing, and amplification were performed using the following conditions: 95° C. for one minute, 58° C. for one minute, and 72° C. for two minutes. The reaction mixture was then incubated at 72° C. for 10 minutes.

Lane 5 of FIG. 7 shows that a product of the size expected for amplification of a rearranged bovine heavy chain (450 base pairs) was obtained. This product migrated to a position equivalent to that of a control bovine Cmu heavy chain cDNA known to contain sequences corresponding to rearranged bovine heavy chain transcripts (lane 7). As expected, the rearranged heavy chain was expressed in the spleen (lane 5), but absent from the brain (lane 2) and liver (lane 3) at this point in development.

Rearrangement and Expression of the Human Heavy Chain Locus in the ΔHAC Fetus #5996

The rearrangement and expression of the human heavy chain locus was demonstrated by the amplification of a segment of DNA including portions of Cmu and VH regions. Primers specific for RNA transcripts including portions of Cmu (Cmu1) and VH (VH3-30) were used to determine if RNA transcripts containing rearranged human Cmu-VDJ sequences were present (FIG. 8).

For this RT-PCR analysis, primers "Cmu1" (5'-cag gtg cag ctg gtg gag tct gg-3', SEQ ID NO: 11) and "VH3-30" (5'-cag gag aaa gtg atg gag ta-3', SEQ ID NO: 12) were used to produce a RT-PCR product of 450 base pairs. This RT-PCR was performed by incubating reaction mixtures at 950 for 3 minutes, followed by 40 cycles of incubation at 95° for 30 minutes, 69° for 30 minutes, and 72° for 45 minutes, and one cycle of incubation at 72° for 10 minutes. This RT-PCR product was then reamplified with the same primers by one cycle of incubation at 95° C. for three minute, 40 cycles of incubation at 95° C. for one minute, 59° C. for one minute, 72° C. for one minute, and one cycle of incubation at 72° C. for 10 minutes. As an internal control, RT-PCR amplification of GAPDH was performed as described above.

Figure 8:
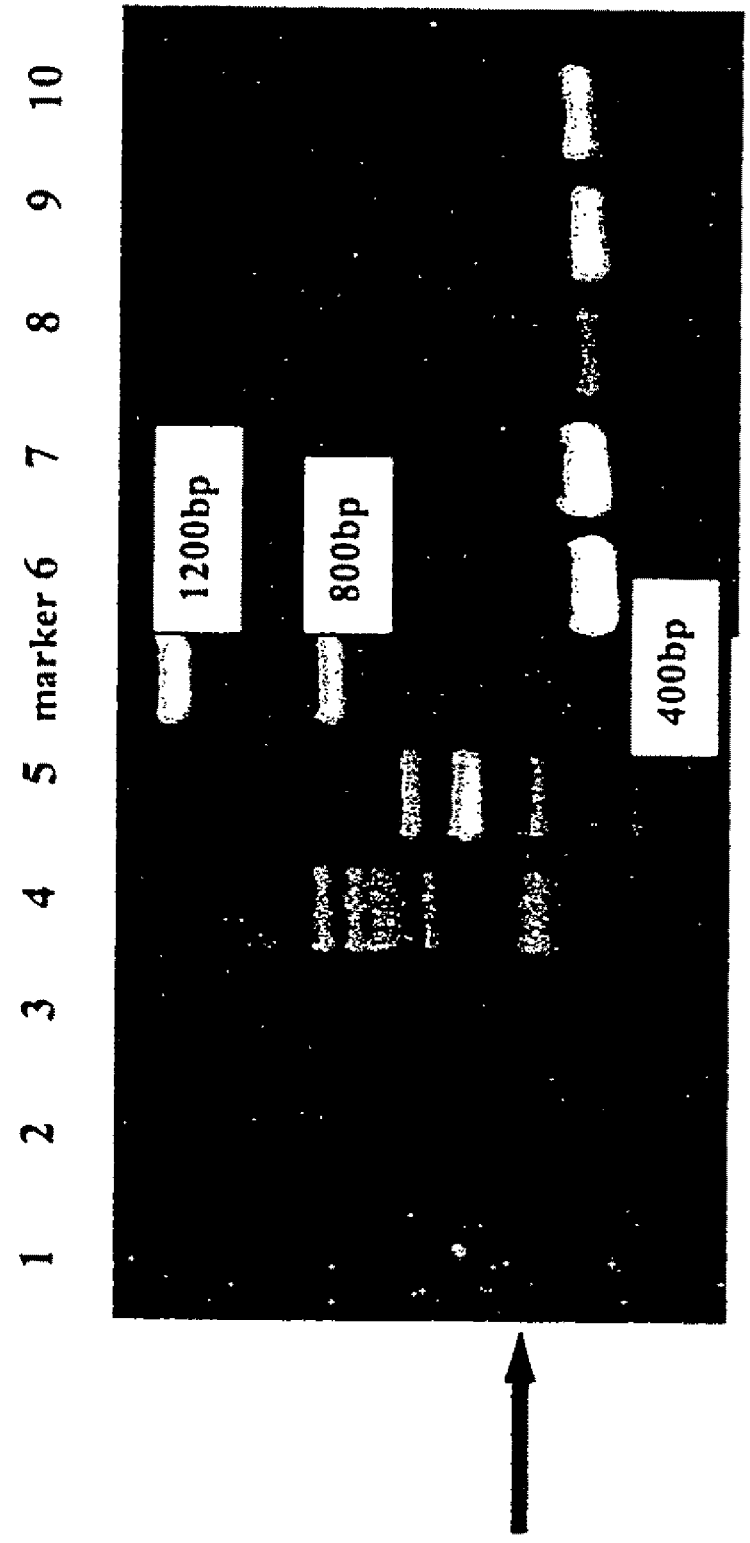
FIG. 8 is a photograph of an agarose gel showing the expression of rearranged human heavy chain in ΔHAC fetus #5996: lane 1, human rearranged Cmu heavy chain in mouse spleen cDNA with HAC (positive control); lane 2, human rearranged Cmu heavy chain in bovine liver cDNA from fetus; lane 3, human rearranged Cmu heavy chain in bovine brain cDNA from fetus 5996; lane 4, human rearranged Cmu heavy chain in human spleen cDNA (positive control); lane 5, human rearranged Cmu heavy chain in bovine spleen cDNA from fetus 5996; lane 6, GAPDH primers in bovine spleen cDNA from fetus 5996; lane 7, GAPDH primers in mouse spleen cDNA with HAC; lane 8, GAPDH primers in bovine brain cDNA from fetus 5996; lane 9, GAPDH primers in bovine liver cDNA from fetus 5996; and lane 10, GAPDH primers positive control.

The gel in FIG. 8 shows that RT-PCR analysis of the spleen from fetus #5996 produced a band (lane 5) matching the amplification products generated using human spleen cDNA (lane 4) or ΔHAC chimeric mouse spleen cDNA (lane 1). No such band was detected in bovine liver (lane 2) or bovine brain (lane 3). As a positive control, amplification of GADPH RNA (lanes 8 and 9) showed the capacity of these tissues to support RT-PCR.

Rearrangement and expression of the human heavy chain region in fetus #5996 was also demonstrated by RT-PCR analysis using primers CH3-F3 (5'-GGA GAC CAC CAA ACC CTC CAA A-3'; SEQ ID NO: 13) and CH4-R2 (5'-GTG GCA GCA AGT AGA CAT CG-3'; SEQ ID NO: 14). These PCR reaction mixtures contained 18.9 μl water, 3 μl of 10×Ex Taq buffer, 4.8 μl of dNTP mixture, 10 pmol forward primer, 10 pmol of reverse primer, 1 μl of cDNA, and 0.3 μl of Ex Taq. Forty PCR cycles were performed by incubating the reaction mixtures under the following conditions: 85° C. for three minutes, 94° C. for one minute, 98° C. for 10 seconds, 60° C. for 30 seconds, and 72° C. for 30 seconds.

Figure 9:
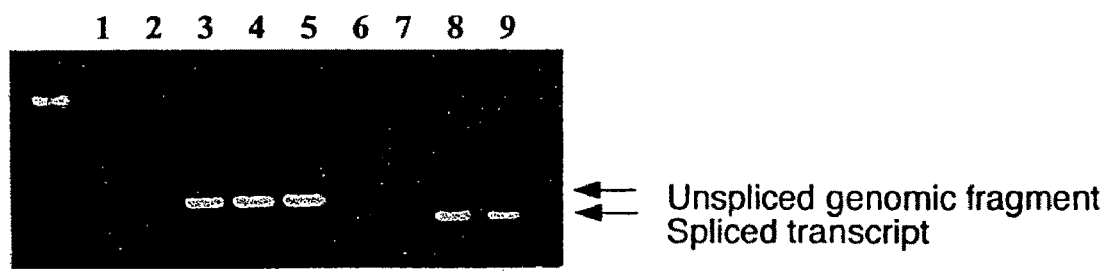
FIG. 9 is a photograph of an agarose gel showing the expression of the spliced constant region from the human heavy chain locus in ΔHAC fetus #5996: lane 1, mouse spleen (negative control); lane 2, bovine spleen (negative control); lane 3, fetus 5996 brain; lane 4, fetus 5996 liver; lane 5, fetus 5996 liver; lane 6, fetus 5996 spleen; lane 7, fetus 5996 spleen; lane 8, ΔHAC-chimeric mouse spleen (positive control); and lane 9, human spleen (positive control).

As shown in lanes 6 and 7 of FIG. 9, an amplified sequence from the spleen of fetus #5996 was the same size as the spliced constant region fragments from the two positive controls: a sample from a human spleen (lane 8) and a ΔHAC chimeric mouse spleen (lane 9). As expected, the negative controls from a normal mouse spleen and a bovine spleen did not contain an amplified sequence (lanes 1 and 2). Samples from the liver and brain of fetus #5996 did not contain an amplified spliced sequence of the same size as the spliced human mu heavy chain constant region fragments but did contain a amplified sequence of an unspliced genomic fragment derived from genomic DNA contaminating the RNA sample (lanes 3, 4, and 5).

VDJ Rearrangement of the Human Heavy Chain Locus in a ΔHAC Fetus

RT-PCR analysis was also performed to further demonstrate VDJ rearrangement in the heavy chain locus in ΔHAC fetus #5996. Nested RT-PCR was performed using primer Cmu-1 (5'-CAGGAGAAAGTGATGGAGTC-3'; SEQ ID NO: 15) for the first reaction, primer Cmu-2 (5'-AGG CAG CCA ACG GCC ACG CT-3'; SEQ ID NO: 16) for the second reaction, and primer VH3-30.3 (5'-CAG GTG CAG CTG GTG GAG TCT GG-3'; SEQ ID NO: 17) for both reactions. The RT-PCR reaction mixtures contained 18.9 μl water, 3 μl of 10×Ex Taq buffer, 4.8 μl of dNTP mixture, 10 pmol forward primer, 10 pmol of reverse primer, 1 μl of cDNA, and 0.3 μl of Ex Taq. The RT-PCR was performed using 38 cycles under the following conditions for the first reaction: 85° C. for three minutes, 94° C. for one minute, 98° C. for 10 seconds, 65° C. for 30 seconds, and 72° C. for 30 seconds. For the second reaction, 38 cycles were performed under the following conditions: 85° C. for three minutes, 94° C. for one minute, 98° C. for 10 seconds, 65° C. for 30 seconds, and 72° C. for 30 seconds using primers VH3-30.3 and Cmu-2 (5'-AGG CAG CCA ACG GCC ACG CT-3'; SEQ ID NO: 16).

Figure 10:
FIG. 10 is a photograph of an agarose gel showing the expression of rearranged human heavy chain in ΔHAC fetus #5996: lane 1, mouse spleen (negative control); lane 2, bovine spleen (negative control); lane 3, fetus 5996 brain; lane 4, fetus 5996 liver; lane 5, fetus 5996 liver; lane 6, fetus 5996 spleen; lane 7, fetus 5996 spleen; lane 8, ΔHAC-chimeric mouse spleen (positive control); and lane 9, human spleen (positive control).

As shown in lanes 6 and 7 of FIG. 10, RT-PCR analysis of the spleen of fetus #5996 produced a heavy chain band of the same size as the positive controls in lanes 8 and 9. Samples from the liver and brain of fetus #5996 contained some contaminating rearranged DNA (lanes 3 and 5). The negative controls in lanes 1 and 2 produced bands of the incorrect size.

Verification of ΔHAC Rearrangement by Sequencing

The cDNA obtained by reverse transcription of RNA from the spleen of the ΔHAC fetus #5996 was amplified with primers specific for rearranged human mu and run on an agarose gel. The band produced by amplification with the Cmu1-VH3-30 primer pair was excised from the gel. The amplified cDNA was recovered from the band and cloned. DNA from a resulting clone that was PCR-positive for rearranged human mu was purified and sequenced (FIG. 11A).

The sequence from this ΔHAC fetus is greater than 95% homologous to over 20 known human heavy chain sequences. For example, the mu chain of a human anti-pneumococcal antibody is 97% homologous to a region of this sequence (FIG. 11B).

Additional sequences from rearranged human heavy chains were also obtained by RT-PCR analysis of the spleen of fetus #5996 using primers Cmu-1 and VH3-30.3, followed by reamplification using primers Cmu-2 and VH3-30.3. The RT-PCR products were purified using CHROMA SPIN column (CLONETECH) and cloned into the pCR2.1 TA-cloning vector (Invitrogen) according to manufacturer's protocol. The Dye Terminator sequence reaction (ABI Applied System) was performed in a 10 μl volume reaction mixture composed of BigDye Terminator reaction mixture (3 μl), template plasmid (200 ng), and the Cmu-2 primer (1.6 pmol). The sequencing reaction was performed using a ABI 3700 sequencer. For this analysis, twenty-five cycles were conducted under the following conditions: 96° C. for one minute, 96° C. for 10 seconds, 55° C. for five seconds, and 60° C. for four minutes.

At least two rearranged human heavy chain transcripts were identified, which were VH3-11/D7-27/JH3/Cμ and VH3-33/D6-19/JH2/Cμ (FIGS. 12A and 12B). These results demonstrate that VDJ rearrangement of the human mu heavy chain locus occurs in the ΔHAC in the spleen of fetus #5996. The identification of more than one rearranged heavy chain sequence from the same fetus also demonstrates the ability of ΔHAC fetuses to generate diverse human immunoglobulin sequences.

Rearrangement and Expression of Human Heavy and Light Chain Loci in ΔΔHAC Fetus

Cloned fetuses derived from bovine fetal fibroblasts transchromosomal for the ΔΔHAC were removed from recipient cows at various gestational days. The fetuses were analyzed for the presence and rearrangement of the HAC-borne human immunoglobulin heavy and lambda light chain loci. Studies of genomic DNA from these tissues indicated the presence of the human immunoglobulin heavy and light chains in some of the fetuses. Examination of cDNA derived from the spleens of these fetuses indicated rearrangement and expression of the immunoglobulin heavy and light chain loci in some of these fetuses. FACS analysis also demonstrated the expression of human lambda light chain protein on the surface of splenic lymphocytes in two of the fetuses.

Presence of Human Heavy and Light Chain Loci in ΔΔHAC Fetuses

To determine whether ΔΔHAC fetuses retained the human heavy and light chain loci, PCR analysis was performed on genomic DNA from the liver of 58 day fetus #5580, 57 day fetus #5848, and 91 day fetuses #5442A and 5442B. The PCR primers used for detection of the heavy chain loci were VH3-F (5'-AGT GAG ATA AGC AGT GGA TG-3'; SEQ ID NO: 18) and VH3-R (5'-CTT GTG CTA CTC CCA TCA CT-3'; SEQ ID NO: 19), and the primers used for the detection of the light chain were IgL-F (5'-GGA GAC CAC CAA ACC CTC CAA A-3'; SEQ ID NO: 20) and IgL-R (5'-GAG AGT TGC AGA AGG GGT YGA CT-3'; SEQ ID NO: 21). The PCR reaction mixtures contained 18.9 μl water, 3 ul of 10×Ex Taq buffer, 4.8 μl of dNTP mixture, 10 pmol forward primer, 10 pmol of reverse primer, 1 μl of genomic DNA, and 0.3 ul of Ex Taq. Thirty-eight PCR cycles were performed as follows: 85° C. for three minutes, 94° C. for one minute, 98° C. for 10 seconds, 56° C. for 30 seconds, and 72° C. for 30 seconds (FIGS. 13 and 14).

Figure 13:
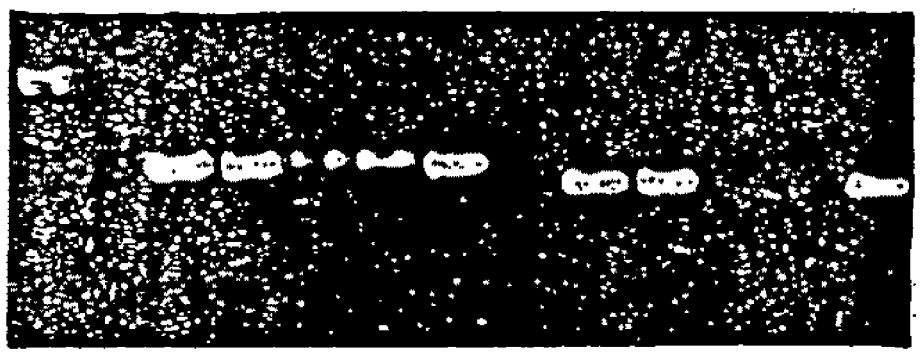
FIG. 13 is a photograph of an agarose gel demonstrating that ΔΔHAC fetus #5580 contains both human heavy and light chain immunoglobulin loci: lane 1, bovine genomic DNA (negative control); lane 2, fetus 5580 genomic DNA (Igλ); lane 3, fetus 5580 genomic DNA (Igλ); lane 4, fetus 5848 genomic DNA (Igλ); lane 5, fetus 5848 genomic DNA (Igλ); lane 6, positive control (human genomic DNA); lane 7, bovine genomic DNA (negative control); lane 8, fetus 5580 genomic DNA (IgH); lane 9, fetus 5580 genomic DNA (IgH); lane 10, fetus 5848 genomic DNA (IgH); lane 11, fetus 5848 genomic DNA (IgH); and lane 12, positive control (human genomic DNA).
Figure 14:
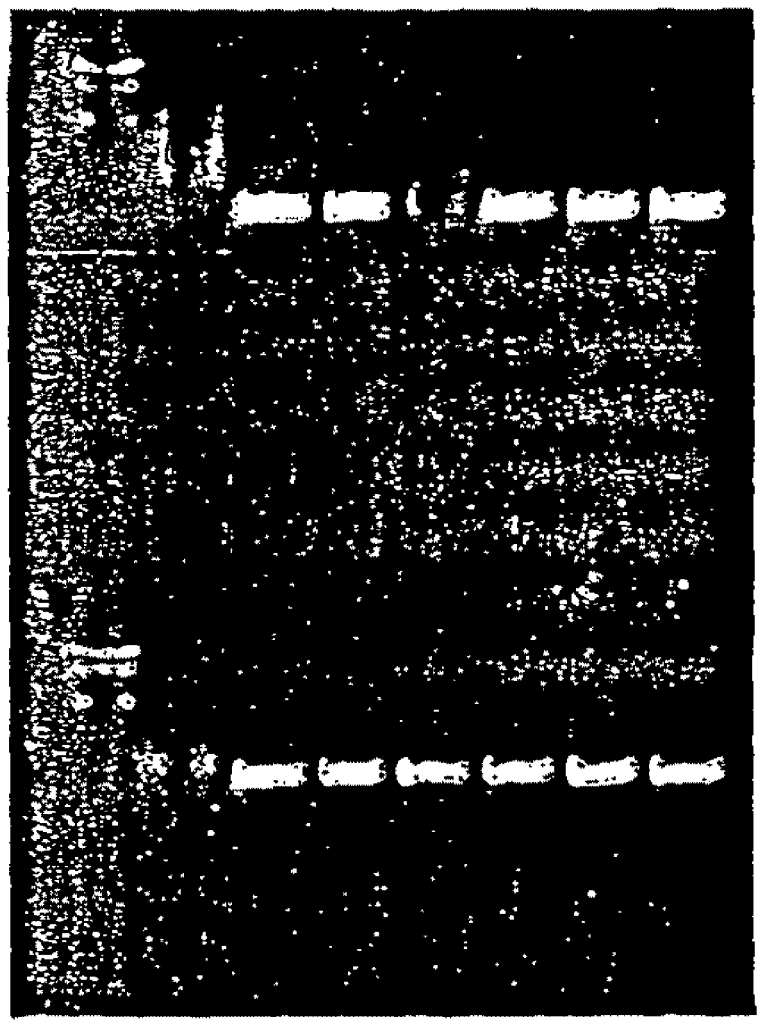
FIG. 14 is a photograph of an agarose gel demonstrating that ΔΔHAC fetuses #5442A and 5442B contain both human heavy and light chain loci: lane 1, bovine genomic DNA (negative control); lane 2, fetus 5442A genomic DNA (91 day); lane 3, fetus 5442A genomic DNA (91 day); lane 4, fetus 5442B genomic DNA (91 day); lane 5, fetus 5442B genomic DNA (91 day); lane 6, fetus 5968 genomic DNA (56 day; positive control); and lane 7, human genomic DNA (positive control).

As illustrated in FIGS. 13 and 14, positive control 58 day fetus #5580 contained both human heavy and light chain immunoglobulin loci. Additionally, the 91 day fetuses #5442A and 5442B also contained both heavy and light chain loci (FIG. 14). In contrast, fetus #5848 did not contain either human loci and may not have contained ΔΔHAC. These results suggested that ΔΔHAC can be stably retained up to gestational day 91 in bovine.

Rearrangement and Expression of Human Heavy Chain Locus in ΔΔHAC Fetus #5442A

RT-PCR was used to detect expression of rearranged human heavy chain RNA transcripts in ΔΔHAC fetus #5542A. The RT-PCR primers used were CH3-F3 (5'-GGA GAC CAC CAA ACC CTC CAA A-3'; SEQ ID NO: 22) and CH4-R2 (5'-GAG AGT TGC AGA AGG GGT GAC T-3'; SEQ ID NO: 23). The RT-PCR reaction mixtures contained 18.9 μl water, 3 μl of 10×Ex Taq buffer, 4.8 μl of dNTP mixture, 10 pmol forward primer, 10 pmol of reverse primer, 1 μl of cDNA, and 0.3 μl of Ex Taq. Forty cycles of RT-PCR cycles were performed as follows: 85° C. for three minutes, 94° C. for one minute, 98° C. for 10 seconds, 60° C. for 30 seconds, and 72° C. for 30 seconds.

Figure 15:
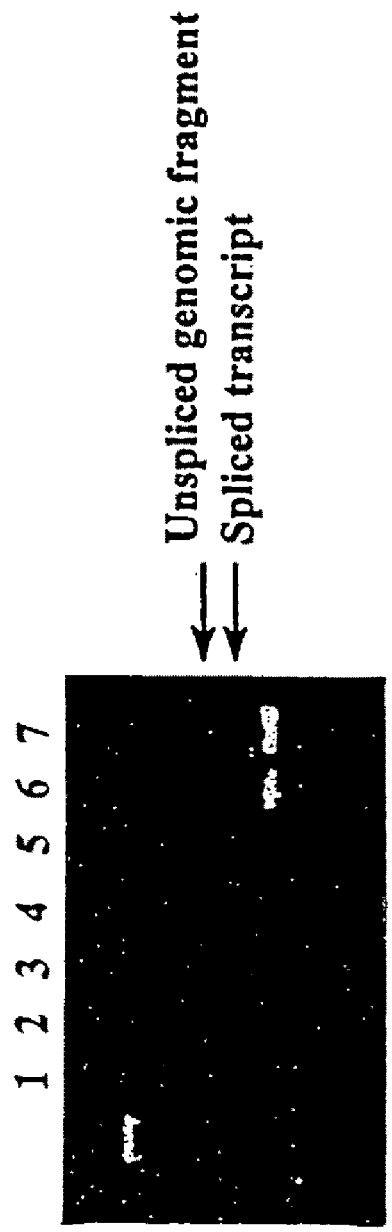
FIG. 15 is a photograph of an agarose gel showing the expression of the spliced mu constant region from the human heavy chain locus in ΔΔHAC fetus #5542A: lane 1, bovine spleen (negative control); lane 2, fetus 5442A brain; lane 3, fetus 5442A liver; lane 4, fetus 5442A spleen; lane 5, fetus 5442A spleen; lane 6, fetus 5996 spleen (positive control); and lane 7, ΔHAC-chimeric mouse spleen (positive control).

Lanes 4 and 5 of FIG. 15 contained amplified spliced mu heavy chain constant region sequences from the spleen of fetus #5442A that are similar in size to that of the positive control samples. These results indicate that fetus #5442A expressed a rearranged mu heavy chain transcript in its spleen. Faint bands were also seen in the region of the unspliced genomic sequence, which are amplified from genomic DNA contaminated in the RNA sample. Control samples from the liver and brain of fetus #5442A did not produce a band of the size expected for an amplified rearranged heavy chain sequence.

Rearrangement and Expression of Human Heavy Chain Locus in ΔΔHAC Fetus #5868A

RT-PCR was used to detect expression of rearranged human heavy chain RNA transcripts in the spleen of a ΔΔHAC fetus at 119 gestational days (fetus #5868A). The primers used for this analysis were VH30-3 (5'-cag gtg cag ctg gtg gag tct gg-3'; SEQ ID NO: 24) and CM-1 (5'-cag gag aaa gtg atg gag ta-3'; SEQ ID NO: 25). Additionally, primers "GAPDH up" (5'-gtc atc atc tct gcc cct tct g-3'; SEQ ID NO: 26) and "GAPDH down" (5'-aac aac ttc ttg atg tca tca t-3'; SEQ ID NO: 27) were used to amplify GAPDH control transcripts. For this PCR analysis, the reaction mixture was incubated at 95° C. for five minutes and then multiple cycles of denaturation, annealing, and amplification were performed by incubation at 95° C. for one minute, 58° C. for one minute, and 72° C. for two minutes. Then, the mixture was incubated at 72° C. for 10 minutes.

Figure 16:
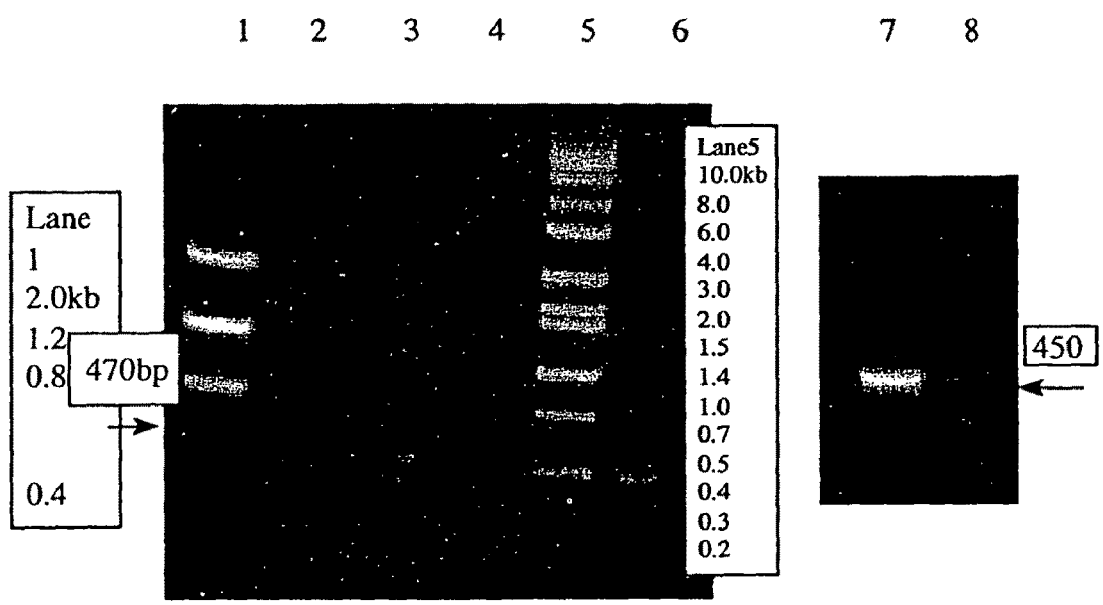
FIG. 16 is a photograph of an agarose gel showing the rearrangement and expression of human heavy chain locus in ΔΔHAC fetus #5868A: lane 1, low mass ladder (2.0 kb, 1.2 kb, 0.8 kb, 0.4 kb, 0.2 kb, and 0.1 kb); lane 2, normal bovine spleen cDNA negative; lane 3, ΔΔHAC 5868A spleen; lane 4, empty; lane 5, Hi Lo (10.0 kb, 8.0 kb, 6.0 kb, 4.0 kb, 3.0 kb, 2.0 kb, 1.5 kb, 1.4 kb, 1.0 kb, 0.7 kb, 0.5 kb, 0.4 kb, 0.3 kb, and 0.2 kb); lane 6, Tc mouse HAC spleen cDNA positive; lane 7, GAPDH product from 5868A spleen cDNA; and lane 8, GAPDH product from normal bovine cDNA.

Lane 3 of FIG. 16 contains the RT-PCR product produced from this analysis of ΔΔHAC fetus# 5868A. This RT-PCR product was the size expected for the amplification of a rearranged human heavy chain (470 base pairs) and migrated to the same position in the gel as the control cDNA known to contain sequences corresponding to rearranged human heavy chain transcripts. As controls, both ΔΔHAC fetus# 5868A fetal spleen cDNA and normal bovine cDNA samples generated a product when amplified with GAPDH primers, demonstrating the capacity of the cDNA to support amplification (lanes 7 and 8).

Rearrangement and Expression of Human Lambda Locus in ΔΔHAC Fetuses #5442A and 5442B Primers specific for amplification of a transcript including portions of human lambda were used to detect RNA transcripts from a rearranged human lambda light chain locus.

Figure 17:
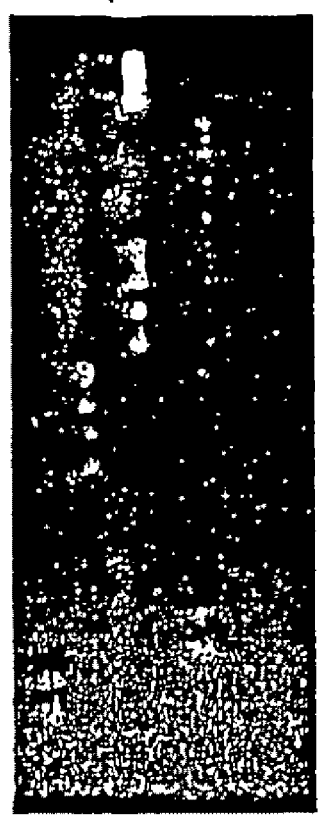
FIG. 17 is a photograph of an agarose gel showing rearrangement and expression of the human Ig lambda locus in ΔΔHAC fetuses #5442A and 5442B: lane 1, bovine spleen (negative control); lane 2, fetus 5442A brain; lane 3, fetus 5442B brain; lane 4, fetus 5442A liver; lane 5, fetus 5442B liver; lane 6, fetus 5442A spleen; lane 7, fetus 5442A spleen; lane 8, fetus 5442B spleen; lane 9, fetus 5442B spleen; and lane 10, ΔHAC-chimeric mouse spleen (positive control).

For the RT-PCR analysis shown in FIG. 17, an equimolar mixture of primers Cλ1 (5'-GGG AAT TCG GGT AGA AGT TCA CTG ATC AG-3'; SEQ ID NO: 28), Cλ2-3 (5'-GGG AAT TCG GGT AGA AGT CAC TTA TGA G-3'; SEQ ID NO: 29), and Cλ7 (5'-GGG AAT TCG GGT AGA AGT CAC TTA CGA G-3'; SEQ ID NO: 30) was used with primer Vλ1 LEA1 (5'-CCC AAG CTT RCC KGS TYY CCT CTC CTC-3'; SEQ ID NO: 31). The RT-PCR reaction mixtures contained 18.9 μl water, 3 μl of 10×Ex Taq buffer, 4.8 μl of dNTP mixture, 10 pmol forward primer, 10 pmol of reverse primer, 1 μl of cDNA and 0.3 μl of Ex Taq. The RT-PCR conditions were as follows: 40 cycles of 85° C. for three minutes, 94° C. for one minute, 98° C. for 10 seconds, 60° C. for 30 seconds, and 72° C. for one minute.

Figure 18:
FIG. 18 is a photograph of an agarose gel showing rearrangement and expression of the human Ig lambda locus in ΔΔHAC fetus #5442A: lane 1, bovine spleen (negative control); lane 2, fetus 5442A brain; lane 3, fetus 5442A liver; lane 4, fetus 5442A spleen; lane 5, fetus 5442A spleen; and lane 6, ΔHAC-chimeric mouse spleen (positive control).

As shown in FIG. 18, this RT-PCR analysis was also performed using an equimolar mixture of primers Vλ3LEA1 (5'-CCC CCA AGC TTG CCT GGA CCC CTC TCT GG-3'; SEQ ID NO: 32), Vλ3JLEAD (5'-ATC GGC AAA GCT TGG ACC CCT CTC TGG CTC AC-3'; SEQ ID NO: 33), VλBACK4 (5'-CCC CCA AGC TTC TCG GCG TCC TTG CTT AC-3'; SEQ ID NO: 34) and an equimolar mixture of primers Cλ1 (5'-GGG AAT TCG GGT AGA AGT TCA CTG ATC AG-3'; SEQ ID NO: 35) Cλ2-3 (5'-GGG AAT TCG GGT AGA AGT CAC TTA TGA G-3'; SEQ ID NO: 36) and Cλ7 (5'-GGG AAT TCG GGT AGA AGT CAC TTA CGA G-3'; SEQ ID NO: 37). The RT-PCR reaction conditions were the same as those described above for FIG. 7.

Lanes 6 and 7 of FIG. 17 and lanes 4 and 5 of FIG. 18 contained RT-PCR products from the spleen of fetus #5442A that are similar in size to the positive control bands, indicating the presence of rearranged light chain RNA transcripts in this fetus. The spleen sample from fetus #5442B produced very weak bands (that are not visible in the picture) of the appropriate size. This RT-PCR product indicates that fetus #5442B also expressed a rearranged light chain immunoglobulin transcript in its spleen. As expected, samples from the brain of fetuses #5442A and 5442B did not express human rearranged lambda light chain transcripts.

Rearrangement and Expression of Human Lambda Locus in ΔΔHAC Fetus #5868A

RNA transcripts from a rearranged human lambda light chain locus were also detected in ΔΔHAC fetus# 5868A. For this analysis, primers specific for amplification of a transcript including portions of human lambda were used to detect ΔΔHAC-encoded expression of transcripts encoding portions of a rearranged human lambda locus. Primer VL1 LEA1 (5'-ccc cca agc ttR ccK gSt Yyc ctc tcc ta-3'; SEQ ID NO: 38) and an equimolar mixture of primers CL1 (5'-ggg aat tcg ggt aga agt cac tga tca g-3'; SEQ ID NO: 39), CL2-3 (5'-ggg aat tcg ggt aga agt cac tta tga g-3'; SEQ ID NO: 40), and CL7 (5'-ggg aat tcg ggt aga agt cac tta cga g-3'; SEQ ID NO: 41) were used for this analysis. For this RT-PCR reaction, the reaction mixtures were incubated at 95° C. for 5 minutes and then multiple cycles of denaturation, annealing, and amplification were performed by incubation at 95° C. for one minute, 60° C. for one minute, and 72° C. for two minutes. Then, the mixtures were incubated at 72° C. for 10 minutes.

Figure 19:
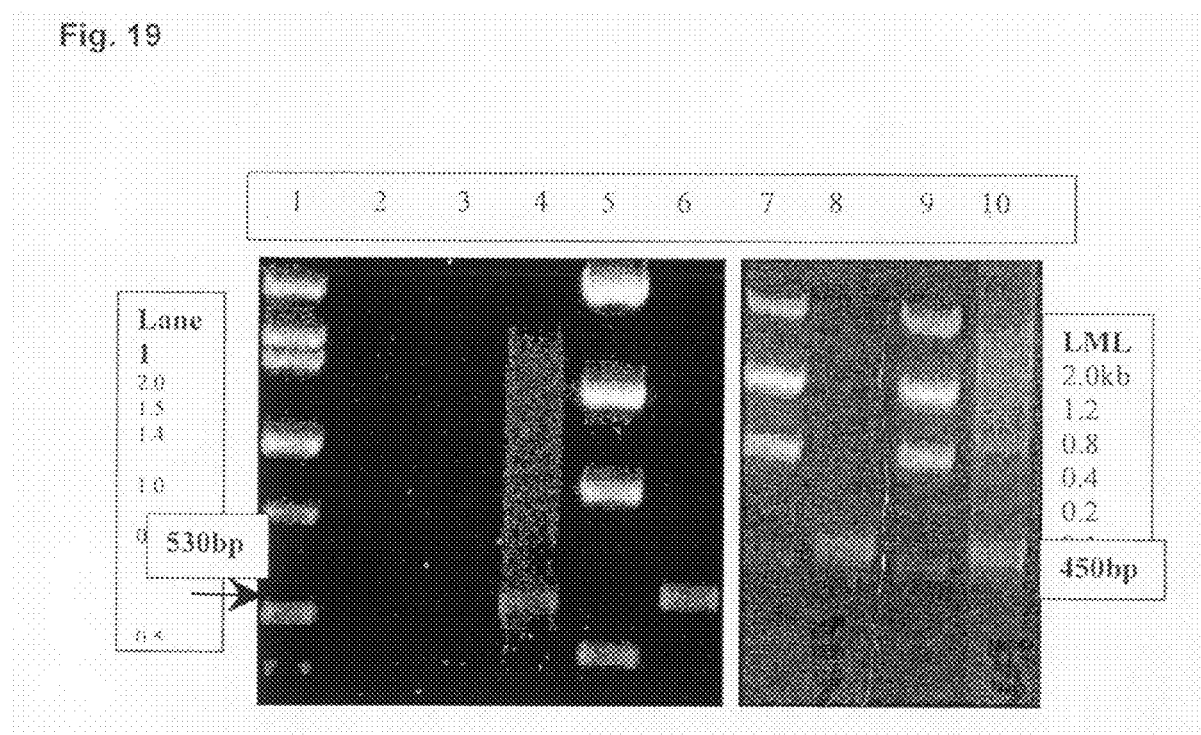
FIG. 19 is a photograph of an agarose gel showing rearrangement and expression of the human Ig lambda locus in ΔΔHAC fetus #5868A: lane 1, Hi-Lo (2.0 kb, 1.5 kb, 1.4 kb, 1.0 kb, 0.7 kb, and 0.5 kb); lane 2, ΔΔHAC 5868A fetal brain cDNA; lane 3, ΔΔHAC 5868A fetal liver cDNA; lane 4, ΔΔHAC 5868A fetal spleen cDNA; lane 5, low mass ladder (2.0 kb, 1.2 kb, 0.8 kb, 0.4 kb, and 0.2 kb); lane 6, Tc mouse HAC spleen cDNA positive control (530 bp); lane 7, low mass ladder (2.0 kb, 1.2 kb, 0.8 kb, 0.4 kb, and 0.2 kb); lane 8, GAPDH ΔΔHAC 5868A brain cDNA; lane 9, low mass ladder (2.0 kb, 1.2 kb, 0.8 kb, 0.4 kb, and 0.2 kb); and lane 10, GAPDH ΔΔHAC 5868A liver cDNA.

This analysis demonstrated that spleen cDNA from ΔΔHAC #5868A (lane 4 of FIG. 19) produced a RT-PCR product of the same size as the TC mouse spleen cDNA (lane 6) positive control. No such RT-PCR product was detected using either brain or liver cDNA from ΔΔHAC #5868A (lanes 2 and 3, respectively). The capacity of each of these tissues to support RT-PCR was shown by successful amplification of the housekeeping gene, GAPDH using primers "GAPDH up" and "GAPDH down" (lanes 8 and 10).

Verification of ΔΔHAC Rearrangement by Sequencing

RT-PCR analysis was performed on a spleen sample from fetus #5442A using an equimolar mixture of primers Cλ1, Cλ2-3, and Cλ7 with primer Vλ1LEA1, or an equimolar mixture of primers Vλ3LEA1, Vλ3JLEAD, and VλBACK4 and an equimolar mixture of primers Cλ1, Cλ2-3, and Cλ7. The PCR products were purified using a CHROMA SPIN column (Clontech) and cloned into the pCR2.1 TA-cloning vector (Invitrogen), according to manufacturer's protocol. The Dye Terminator sequence reaction (ABI Applied System) was carried out using the Cλ1, Cλ2-3, and Cλ7 primers in an equimolar mixture. Twenty-five cycles were performed at 96° C. for one minute, 96° C. for 10 seconds, 55° C. for five seconds, and 60° C. for four minutes. The 10 μl reaction mixture contained BigDye Terminator reaction mixture (3 μl), template plasmid (200 ng), and the Cλ1, Cλ2-3, and Cλ7 primers (1.6 pmol). The reaction mixture was analyzed using a ABI 3700 sequencer.

At least two rearranged human lambda light chain transcripts were identified (V1-17/JL3/Cλ and V2-13/JL2/Cλ). These results demonstrate that VJ rearrangement of human lambda light chain genes occurs in the ΔΔHAC in the spleen of fetus #5442A (FIGS. 20 and 21).

Figures 22E, 22F, 22G, 22H:
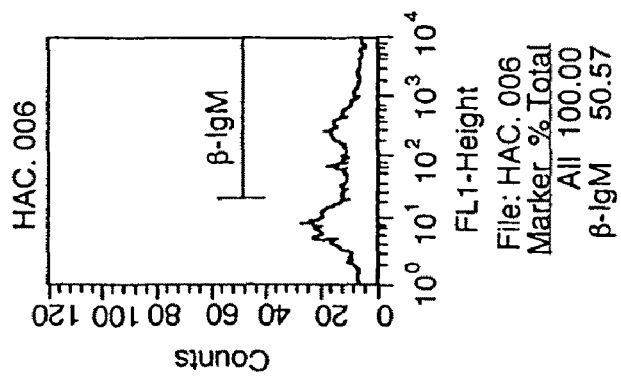

FACS Analysis of Expression of Human Lambda Light Chain and Bovine Heavy Chain in ΔΔHAC Fetus #5442A and 5442B Splenic lymphocytes from ΔΔHAC Fetus #5442A and 5442B were analyzed for the expression of human lambda light chain and bovine heavy chain proteins. These cells were reacted with a phycoerytherin labeled anti-human lambda antibody (FIGS. 22C and 22D), a FITC labeled anti-bovine IgM antibody (FIGS. 22D and 22H), or no antibody (FIGS. 22A, 22B, 22E, and 22F) for 20 minutes at 4° C. Cells were then washed twice with PBS plus 2% FCS and analyzed on a FASCalibur cell sorter. The percent of cells reacting with the antibody was calculated using the non antibody controls to electronically set the gates. These percentages are displayed beneath each histogram. Fetus # 5442A (FIGS. 22A-22D) and fetus #5442B (FIGS. 22E-22H) expressed both human lambda light chain protein and bovine heavy chain protein.

Expression of Human Antibody Protein in HAC Calves

Figure 37:
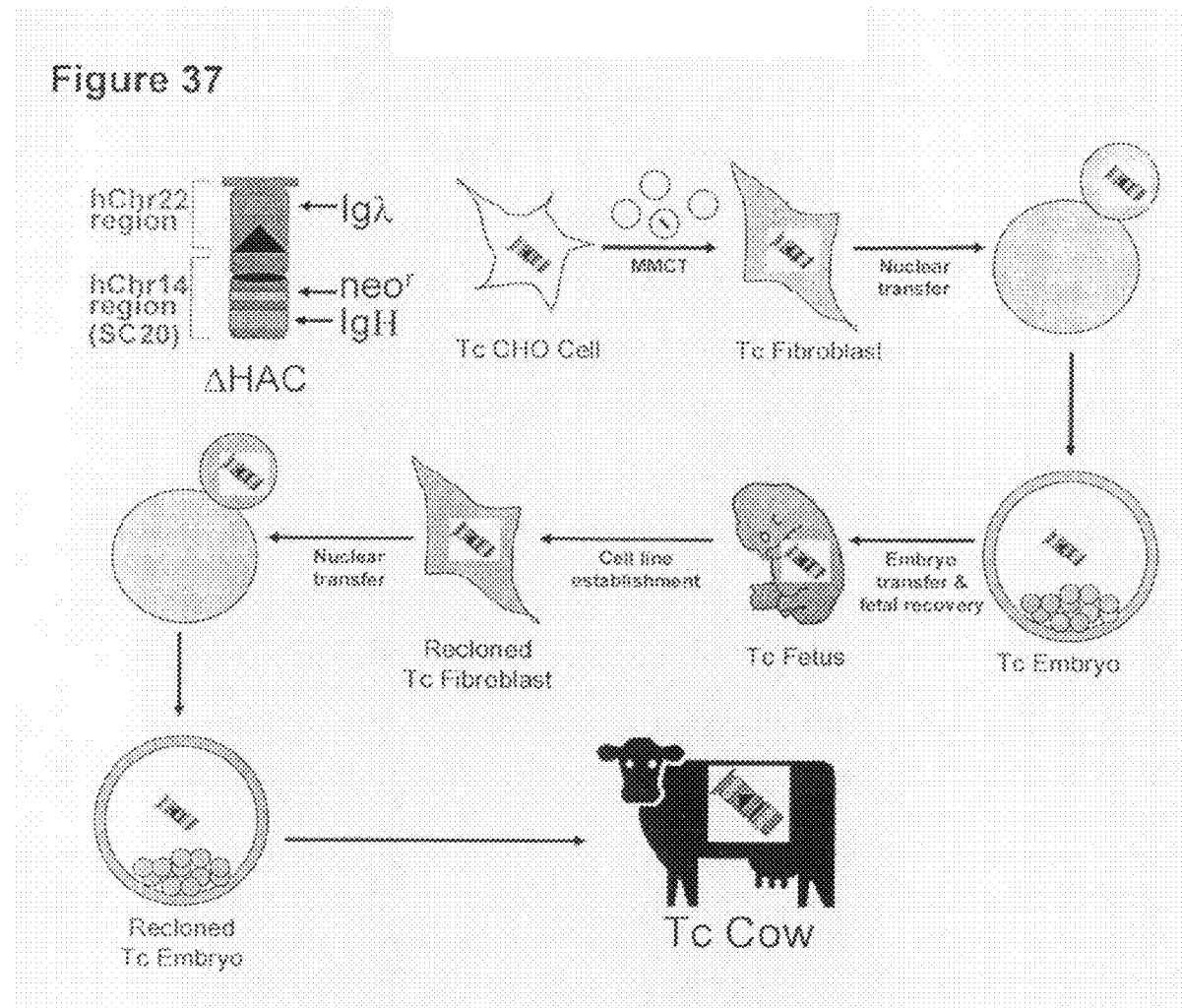
FIG. 37 is a schematic illustration of a procedure for production of cloned Tc calves. Construction of HAC is shown with hChr22 and hChr14 regions containing Igk and IgH genes and the position of the neo selection marker. From a CHO clone, the HAC was transferred into fetal bovine fibroblasts by means of a MMCT technique. Tc fibroblasts were fused with an enucleated oocyte for nuclear transfer. The reconstituted Tc embryos were cultured in vitro to the blastocyst stage then implanted into recipient cows. Around 60 days of gestation Tc fetuses were recovered; fibroblast cell lines were reestablished, evaluated and used for further nuclear transfer. Recloned Tc embryos were transferred to recipients to produce Tc calves.

As described above, a novel procedure was developed for producing transchromosomic (Tc) calves (FIG. 37). This method overcame the limitations due to the limited life span of only about 35 population doublings for primary bove fibroblasts and the requirement for a large DNA insert to be introduced and maintained in the donor cells. In particular, a human artificial chromosome (HAC) vector was used to introduce both the entire unrearranged human Ig heavy (IgH) and lambda light chain (Igλ) loci into bovine primary fibroblasts. Selected fibroblast clones were rejuvenated and expanded by producing cloned fetuses. Cloned fetal cells were selected and recloned to produce four healthy, Tc calves that functionally rearranged both heavy and light chain human Ig loci and produced human polyclonal antibodies. These results demonstrate the feasibility of using HAC vectors for production of transgenic livestock. More importantly, Tc cattle containing human Ig genes may be used to produce novel human polyclonal therapeutics with applications ranging from the prevention of antibiotic resistant infections to combating bioterrorism. This method is described in more detail below.

HACs were introduced into bovine fetal fibroblasts from CHO clones using the MMCT technique described herein. The fibroblasts were placed under selection for the neo gene marker on the HAC vector with G418 (700 μg/ml) until colonies began to appear. Complete antibiotic selection and DNA-based screening was avoided at this step to minimize cell divisions prior to nuclear transfer. Colonies were picked on the basis of growth and morphology and nuclear transfer was carried out as previously described (Lucier et al., J. Immunol. 161:5438-5444, 1998). Because the cells were only useful for nuclear transfer for a few days, final selection was done after rejuvenation and expansion of cells by production of cloned fetuses.

Figure 38A:
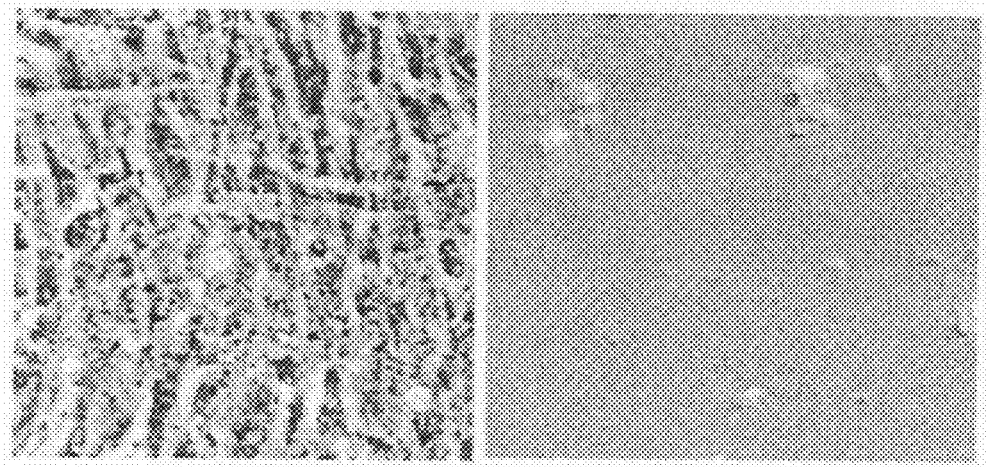
Figure 38B:
Figure 38C:
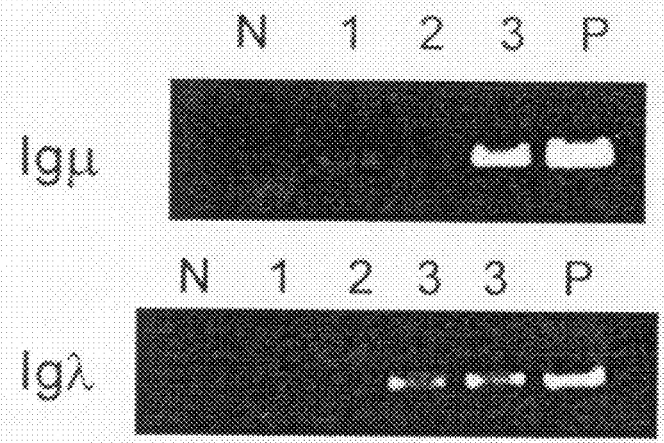

Development to the blastocyst stage ranged from 17 to 21% and pregnancy at 40 days ranged from 22 to 50% with no differences among cell lines. At 56 to 58-days, four ΔHAC and two ΔΔHAC fetuses were recovered and fibroblast cell lines were regenerated and cryopreserved for further analysis and nuclear transfer. Retention of the HACs in the fibroblast lines derived from the fetuses collected at 56 to 58-days and seven additional fetuses collected between 77 and 119-days was evaluated by G418-resistance (FIG. 38A) and genomic PCR of IgH and Igλ loci (FIG. 38B). Nine of 13 fetuses were resistant to G418 and eight of them showed the presence of both human IgH and Igλ loci. Three ΔHAC (#5968, #6032 and #6045) and one ΔΔHAC (#5580) positive 56 to 58-day fetuses were used for recloning and production of offspring. Five positive 77 to 119-day fetuses were evaluated for expression and rearrangement of the human Ig loci by RT-PCR analysis, followed by sequencing of the amplified products. Human IgH and Igλ genes were expressed (FIG. 38C) in all fetuses and showed evidence of proper V(D)J recombination (FIG. 38D).

Figure 39A:
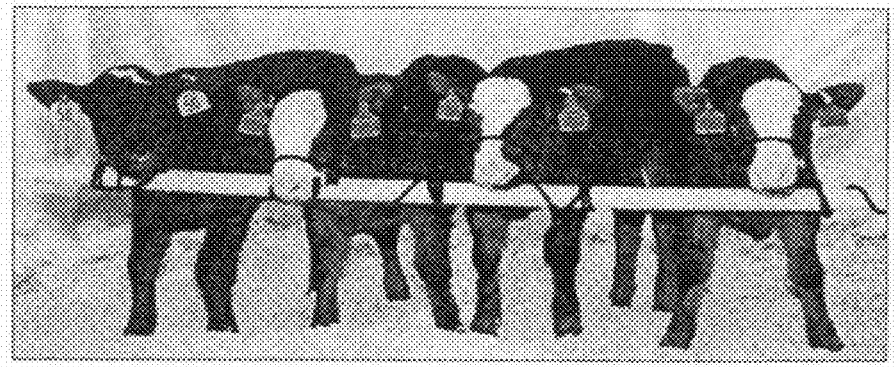
FIGS. 39A-39C are photographs illustrating the analysis of cloned Tc calves. Four cloned Tc calves; male calf (#50) from cell line #6045 and female calves (#1064, #1065, #1066) from cell line #5968 (FIG. 39A). Genomic PCR of IgH and Igλ loci from PBLs from cloned Tc calves and controls; calf #1064 (lane 1), #1065 (lane 2), #1066 (lane 3), #50 (lane 4), #1067 (lane 5) and #1068 (lane 6) (FIG. 39B). In all the Tc calves and positive control human liver DNA (lane P) both human IgH and Igλ loci were detected by genomic PCR, but not in a negative control, non-transgenic calf (lane N). FISH analysis in metaphase chromosome spreads in a cell showing a single signal and a cell showing a double signal (FIG. 39C). Arrows indicate location of HACs amongst surrounding bovine chromosomes. HAC painting was done using digoxigenin labeled human COT-1 DNA as a probe and detected with an anti-digoxigenin-rhodamine.
Figure 39B:
Figure 39C:
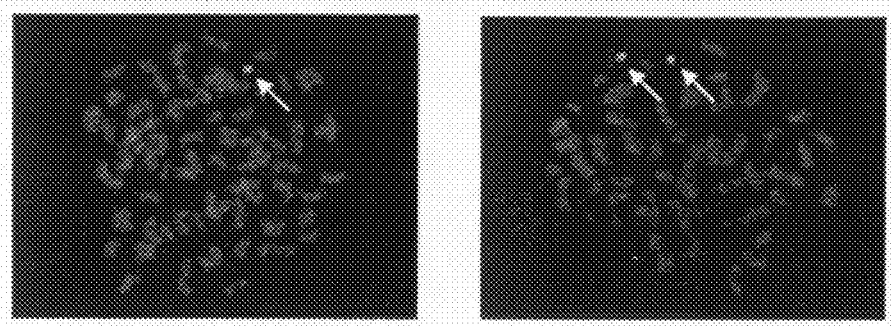

Recloned ΔHAC cell lines produced one male (from cell line #6045) and 5 female (from cell lines #5968 and #6032) calves from 37 recipients (16%, FIG. 39A). The two calves derived from cell line #6032 died within 48 hours after birth. One calf was born from non-regenerated ΔΔHAC cells. All five live calves were healthy and phenotypically normal. Retention of the HAC was confirmed in all the calves by G418 selection, genomic PCR and fluorescent in situ hybridization (FISH) analyses (FIGS. 39B and 39C). Results of FISH analysis indicated that the HAC was retained as an independent chromosome and the proportion of cells retaining the HAC was 78 to 100%. No obvious differences were observed in retention rates between peripheral blood lymphocytes (PBLs, 91%) and fibroblasts (87%). Donor cell line #6045 may have had a higher retention rate than donor cell line #5968 (97% and 86%, respectively). Interestingly, retention rate in the Tc bovine may be higher than we previously observed in mouse. To determine whether the human Ig loci were rearranged and expressed in calves as well as in fetuses, we performed RT-PCR analysis on PBLs. We observed the expression of both human IgH and Igλ genes in the PBLs and the diversity of the human IgH and Igλ repertoire was determined by sequence analysis (Table 4). A representative set of the sequences showed a wide utilization of $V_H$/Vλ, $D_H$ and $J_H$/Jλ segments distributed over the loci. In the Igλ transcripts, the frequent utilization of V segments from $V_H1$ and $V_H3$ was observed, which is similar to the usage of $V_H$ segments in human. Addition of non-germline nucleotides (N-addition), as well as nucleotide deletion, was also observed in both IgH and Igλ transcripts. This produced a high degree of diversification in the third complementarity determining regions (CDR3s) of both heavy and light chains. Furthermore, human Ig protein was detected at levels ranging from 13 to 258 ng/ml (Ig expression is typically very low to undetectable in newborn calves) in blood samples collected prior to colostrum feeding in five of the seven calves as determined by solid phase ELISA. These data indicate that the HAC transfer can be accomplished efficiently in primary cells using a recloning strategy and that human Ig genes carried by the HAC can be properly processed and expressed with a high degree of diversity in Tc calves.

The results of this study demonstrate that a combination of chromosome-cloning, chromosome transfer and somatic cell recloning technologies can be used to produce healthy calves retaining a HAC vector carrying Mb-sized genomic transgenes. Furthermore, these technologies were used to demonstrate the transfer and retention of the entire loci for both the human IgH and Igλ genes in cattle. Interestingly, both loci were demonstrated to have undergone proper processing and express functionally rearranged human immunoglobulin genes in a species with substantially different immunophysiology than either the human or mouse. This HAC system may be useful for the expression of a variety of complex human proteins (e.g., hemoglobin) or large collections of proteins for pharmaceutical applications. For example, the Tc calves produced in this study, which retain both the human IgH and Igλ loci, are useful for production of human polyclonal antibodies. Human polyclonal antibodies are currently only available from human blood or plasma donors. Consequently, there are limitations in supply and application of human polyclonal products. Tc cows may be hyperimmunized to produce large quantities of novel polyclonal therapeutics for treatment of a wide variety of human diseases.

TABLE 4

Repertoire analysis of human immunoglobulin heavy and lambda chain transcripts in cloned Tc calves

HUMAN μ NUCLEOTIDE SEQUENCES

| VH | N | DH | N | JH |
|---|---|---|---|---|
| 6-1<br>TACTGTGCA----- | 0 | DS-24<br>AGAGATG | 3<br>AGA | JH3<br>-ATGCTTTTGATGTC |
| 3-33<br>ATTACTGTGCGA---- | 8<br>AGAACAAA | D6-13<br>ATAGCAGCAGCTGGTAC | 3<br>GAT | JH4<br>----CTTTGACTACT |
| 3-15<br>ACTGTACCACAGA | 4<br>TCTG | D6-19<br>ATAGCAGTGGCTGGTAC | 4<br>TGGG | JH1<br>------TACTTCCAGCA |
| 3-66<br>TACTGTGCGAG | 2<br>TC | D2-2<br>GTAGTACCAGCTGCTAT | 0 | JH3<br>GATGCTTTTGATGTCT |
| 3-21<br>TTACTGTGCGAG--- | 6<br>TTTTGG | D2-21<br>GTGGTGGT | 8<br>CACATTTA | JH4<br>--------GACTACTGGGG |
| 4-39<br>ACTGTGCGAGACA | 8<br>TGAAAAAC | D3-10<br>TTCGGGGAGTTAT | 3<br>AAT | JH4<br>---------CTACTGGGGCC |
| 1-69<br>TTACTGTGCGAG--- | 7<br>GGGGATG | D6-13<br>GCAGCAGCTGGTAC | 1<br>C | JH4<br>-------GACTACTGGGGC |
| 1-8<br>ACTGTGCGAGAG- | 0 | D2-2<br>ATTGTAGTAGTACCAGCTGC | 12<br>CAAGATCGTAAG | JH2<br>----TGGTACTTCGAT |
| 1-18<br>TTACTGTGC------ | 0 | D5-24<br>GAGATGG | 15<br>GTTTTTGATCCCCAG | JH4<br>-----TTTGACTACTGG |
| 3-20<br>TCACTGTGCGAGAA | 4<br>TTTT | D7-27<br>ACTGGGGA | 1<br>T | JH3<br>GATGCTTTTGATGTCT |

HUMAN λ NUCLEOTIDE SEQUENCES

| Vλ | | N | | Jλ | |
|---|---|---|---|---|---|
| 1-17 | AGCCTGAGTGGTC-- | 2 | (TT) | Jλ3 | --------TTCGGCGGAGGG |
| 2-13 | CAGTGGTAACCATCT | 0 | | Jλ2 | ---GGTATTCGGCGGAGG |
| 1-19 | CAGCCTGAGTGCTG- | 0 | | Jλ1 | -----TCTTCGGAACTGGG |
| 5-2 | AGCAACTTCGTGTA- | 2 | (TA) | Jλ3 | ---GTTCGGCGGAGAG |
| 1-7 | GGTAGTAGCACTT-- | 1 | (C) | J3 | --------TCGGCGGAGGGA |
| 2-13 | CAGTGGTAACCAT-- | 0 | | Jλ1 | -TATGTCTTCGGAACTG |
| 2-1 | GACAGCAGCACT--- | 0 | | Jλ1 | -TATGTCTTCGGAACTG |
| 1-2 | GGCAGCAACAATTTC | 1 | (G) | Jλ1 | --ATGTCTTCGGAACTG |
| 1-4 | AGCAGCAGCACTC-- | 2 | (GT) | Jλ3 | ------- TTCGGCGGAGG |
| 1-4 | AGCAGCAGCACTC- | 0 | | Jλ1 | ---------- GGAACTGGGA |

Human μ and λ-specific mRNAs were amplified by RT-PCR, cloned and sequenced. Nucleotide sequences of V(D)J junctions of each of 10 independent μ and λ clones are shown (SEQ ID Nos: 75-84 and SEQ ID Nos: 85-94, respectively, divided into V$_H$/Vλ, D$_H$, J$_H$/Jλ and N segments, as identified by homology to published germline sequences (Ig-BLAST).

EXAMPLE 3

Transgenic Ungulates Producing Xenogenous Antibodies that Have a Mutation in One or More Endogenous Antibodies In an ungulate that expressed xenogenous antibodies and that has a mutation in a prion gene as described in Example 2, the expression of endogenous antibodies may be optionally reduced by mutating one or more endogenous antibody genes. By increasing the number of functional xenogenous immunoglobulin heavy or light chain genes relative to the number of functional endogenous heavy or light chain genes, the percentage of B-cells expressing the desired xenogenous antibodies (e.g., human therapeutic antibodies) should increase.

To generate these transgenic ungulates, ΔHAC or ΔΔHAC transgenic ungulates may be mated with transgenic ungulates containing a mutation in one or both alleles of an endogenous immunoglobulin chain (e.g., a mu heavy chain or a lambda or kappa light chain). If desired, the resulting transgenic ungulates may be mated with (i) transgenic ungulates containing a mutation in one or both alleles of an endogenous alpha-(1,3)-galactosyltransferase, prion, and/or J chain nucleic acid or (ii) transgenic ungulates containing an exogenous J chain nucleic acid (e.g., human J chain). Alternatively, a cell (e.g., a fetal fibroblast) from a ΔHAC or ΔΔHAC transgenic fetus may be genetically modified by the mutation of one or more endogenous immunoglobulin genes. In another possible method, ΔHAC or ΔΔHAC is introduced into a cell (e.g., a fetal fibroblast) in which endogenous immunoglobulins (mu heavy and/or lambda light chains) are hemizgously or homozygously inactivated. In any of the above methods, the cells may also be genetically modified by (i) the introduction of a mutation, preferably a knockout mutation, into one or both alleles of an endogenous alpha-(1,3)-galactosyltransferase, prion, and/or J chain nucleic acid or (ii) the introduction of an exogenous J chain nucleic acid. The resulting transgenic cell may then be used in nuclear transfer procedures to generate the desired transgenic ungulates. Exemplary methods are described below.

DNA Constructs

Figure 2A:
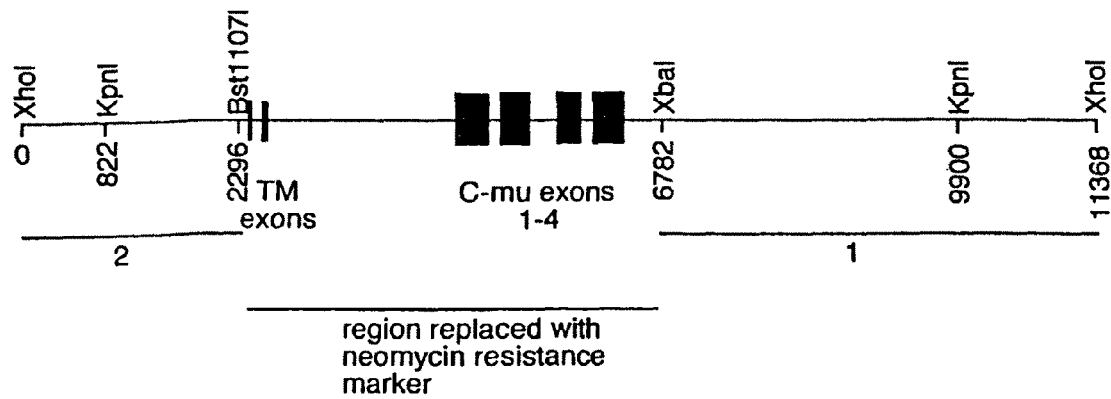
FIG. 2A contains a mu (IgM heavy chain) knockout construct according to the invention.
Figure 3A:
FIGS. 3A-3B contain schematic illustrations of constructs pSTneoB and pLoxP-STneoB. Respectively, that were used to produce the mu knockout DNA construct.
Figure 3B:
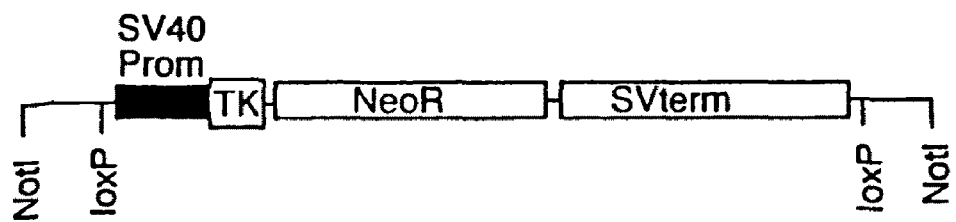

The mu heavy chain (FIG. 2A), lambda light chain, kappa light chain, alpha-(1,3)-galactosyltransferase, prion, and/or J chain knockout constructs described above may be used. Alternatively, the puromycin resistant mu heavy chain construct described below may be used (FIG. 3F). This knockout construct was designed to remove the 4 main coding exons of the bovine mu heavy chain locus but leave the transmembrane domain intact, resulting in the inactivation of the mu heavy chain locus.

The puromycin resistant construct was assembled as follows. A 4.4 kilobase XhoI fragment containing the region immediately proximal to coding exon 1 was inserted into the XhoI site of pBluescript II SK+. Plasmid pPGKPuro, which contains a puromycin resistant gene, was obtained from Dr. Peter W. Laird, Whitehead Institute, USA. A 1.7 Kb XhoI fragment containing a puromycin resistance gene was subcloned adjacent to, and downstream of, the 4.4 Kb fragment into the SalI site present in the polylinker region. This 1.7 Kb puromycin marker replaces the coding exons CH1, CH2, CH3 and CH4 of the bovine immunoglobulin heavy chain locus. An XbaI fragment containing a 4.6 Kb region of the mu locus that is downstream of these four exons in the wild-type genomic sequence was added to this construct for use as the second region of homology.

To generate the final targeting construct, a subclone of this construct was generated by cutting the three assembled fragments with NotI and MluI. The MluI restriction digestion truncates the 4.6 Kb fragment down to 1.4 Kb. The NotI site lies in the polylinker and does not cut into the subcloned DNA itself. The MluI site was filled in with a Klenow fragment to generate a blunt end, and the NotI/filled in MluI fragment was subcloned into a fresh pBluescript II SK+ vector using the NotI and SmaI sites present in the pBluescript vector. For gene targeting, the final vector is linearized with NotI.

Gene Targeting by Electroporation and Drug Selection of Transfected Fibroblasts

For electroporation, a single cell suspension of $1 \times 10^7$ bovine fetal fibroblasts (e.g., fibroblasts obtained as described in Example 2 from a ΔHAC or ΔΔHAC transgenic fetus) that had undergone a limited number of population doublings is centrifuged at 1200 rpm for five minutes and re-suspended in 0.8 ml of serum-free Alpha-MEM medium. The re-suspended cells are transferred to a 0.4 cm electroporation cuvette (Invitrogen, cat#. P460-50). Next, 30 µg of a restriction enzyme-linearized, gene targeting vector DNA is added, and the contents of the cuvette are mixed using a 1 ml pipette, followed by a two minute incubation step at room temperature. The cuvette is inserted into the shocking chamber of a Gene Pulser II electroporation system (Biorad) and then electroporated at 1000 volts and 50 µF. The cuvette is quickly transferred to a tissue culture hood and the electroporated cells are pipetted into approximately 30 ml of complete fibroblast medium. The cells are equally distributed into thirty 100 mm tissue culture dishes (Corning, cat# 431079), gently swirled to evenly distribute the cells, and incubated at 38.5° C./5% $CO_2$ for 16 to 24 hours. The media is removed by aspiration and replaced with complete fibroblast medium containing the selection drug of choice. The media is changed every two days and continued for a total time period of 7 to 14 days. During the drug selection process, representative plates are visually monitored to check for cell death and colony formation. Negative control plates are set up that contained fibroblasts that are electroporated in the absence of the gene targeting vector and should yield no colonies during the drug selection process.

Picking of Drug-Resistant Fibroblast Colonies and Expansion of Cells

Following completion of the drug selection step (usually 7 to 14 days), the drug resistant colonies are macroscopically visible and ready for transfer to 48 well tissue culture plates for expansion. To assist in the transferring process, individual colonies are circled on the bottom of the tissue culture plate using a colored marker (Sharpie). Tissue culture plates containing colonies are washed 2× with 1×D-PBS (without $Ca^{2+}$ and $Mg^{2+}$) and then 5 ml of a 1:5 dilution of the cell dissociation buffer is added per plates. Following a three to five minute room temperature incubation step, individual colonies start to detach from the bottom of the tissue culture dish. Before the colonies detached, they are individually transferred to a single well of a 48 well tissue culture plate using a P200 pipetmen and an aerosol barrier pipette tip (200 or 250 µl). Following transfer, the colony is completely dissociated by pipetting up-and-down and 1 ml of complete fibroblast medium is added. To ensure that the cells are drug resistant, drug selection is continued throughout the 48 well stage. The transferred colonies are cultured at 38.5° C./5% $CO_2$ and visually monitored using an inverted microscope. Two to seven days later, wells that are approaching confluency are washed two times with 1×D-PBS (without $Ca^{2+}$ and $Mg^{2+}$) and detached from the bottom of the well by the addition of 0.2 ml of cell dissociation buffer, followed by a five minutes room temperature incubation step. Following detachment, the cells are further dissociated by pipetting up-and-down using a P 1000 pipetmen and an aerosol pipette tip (1000 µl). Approximately 75% of the dissociated fibroblasts are transferred to an individual well of a 24 well tissue culture plate to expand further for subsequent PCR analysis and the remaining 25% is transferred to a single well of a second 24 well plate for expansion and eventually used for somatic cell nuclear transfer experiments. When cells in the plate containing 75% of the original cells expanded to near confluency, DNA is isolated from that clone for genetic analysis.

DNA Preparation

The procedure used to isolate DNA for genetic analyses is adapted from Laird et al, Nucleic Acids Research, 1991, Volume 19, No. 15. In particular, once a particular clone has attained near-confluency in one well of a 24 well plate, culture medium is aspirated from that well and the adherent cells are washed twice with PBS. The PBS is aspirated off and replaced with 0.2 ml buffer to lyse the cells and digest excess protein from the DNA to be isolated. This buffer is composed of 100 mM Tris-HCl (pH 8.5), 5 mM EDTA, 0.2% SDS, 200 mM NaCl and 100 µg/ml proteinase K. The 24 well plate is returned to the tissue culture incubator for a minimum of three hours to allow the release of the DNA and digestion of protein. The viscous product of this procedure is transferred to a 1.5 ml microcentrifuge tube and 0.2 ml of isopropanol added to precipitate the DNA. The precipitate is recovered by centrifugation, the DNA pellet is rinsed with 70% ethanol, and after air-drying the pellet is resuspended in 25-50 µl of buffer containing 10 mM Tris, pH 8, and 1 mM EDTA. This DNA is used for PCR analyses of clones.

Screening of Clones

Two different approaches are used to screen clones, both employing the polymerase chain reaction (PCR). All approaches described in this section are adaptable to the targeting of any other gene, the only difference being the sequences of the primers used for genetic analysis.

According to the first approach, two separate pairs of primers are used to independently amplify products of stable transfection. One pair of primers is used to detect the presence of the targeting vector in the genome of a clone, regardless of the site of integration. The primers are designed to anneal to DNA sequences both present in the targeting vector. The intensity of the PCR product from this PCR reaction may be correlated with the number of copies of the targeting vector that have integrated into the genome. Thus, cells containing only one copy of the targeting vector tend to result in less intense bands from the PCR reaction. The other pair of primers is designed to detect only those copies of the vector that integrated at the desired locus. In this case, one primer is designed to anneal within the targeting vector and the other is designed to anneal to sequences specific to the locus being targeted, which are not present in the targeting vector. In this case, a PCR product is only detected if the targeting vector has integrated directly next to the site not present in the targeting vector, indicating a desired targeting event. If product is detected, the clone is used for nuclear transfer.

For the neomycin resistant heavy chain knockout construct, primers Neo1 (5'-CTT GAA GAC GAA AGG GCC TCG TGA TAC GCC-3'; SEQ ID NO: 42) and IN2521 (5'-CTG AGA CTT CCT TTC ACC CTC CAG GCA CCG-3'; SEQ ID NO: 43) are used to detect the presence of the targeting vector in cells, regardless of the location of integration. Primers Neo1 and OUT3570 (5'-CGA TGA ATG CCC CAT TTC ACC CAA GTC TGT C-3'; SEQ ID NO: 44) are used to specifically amplify only those copies of the targeting construct that integrated into the mu heavy chain locus.

For these PCR reactions to analyze the integration of the neomycin resistant heavy chain knockout construct, a Qiagen PCR kit is used. The PCR reaction mixture contains 1 pmole of each primer, 5 ul of 10× reaction buffer, 10 µl of Q solution, 5 µl of DNA, and 1 µl of dNTP solution. The reaction mixture is brought to a total volume of 50 µl with $H_2O$. This PCR amplification is performed using an initial denaturing incubation at 94° C. for two minutes. Then, 30 cycles of denaturation, annealing, and amplification are performed by incubation at 94° C. for 45 seconds, 60° C. for 45 seconds, and 72° C. for two minutes. Then, the reaction mixture is incubated at 72° C. for five minutes and at 4° C. until the mixture is removed from the PCR machine.

In the alternative approach, a single primer set is used to amplify the targeted locus and the size of the PCR products is diagnostic for correct targeting. One primer is designed to anneal to a region of the locus not present in the targeting vector and the other primer is designed to anneal to a site present in the targeting vector but also present in the wild type locus. In this case, there is no detection of targeting vector that had integrated at undesirable sites in the genome. Because the region deleted by the targeting vector is different in size from the drug selection marker inserted in its place, the size of the product depended on whether the locus amplified is of wild-type genotype or of targeted genotype. Amplification of DNA from clones containing incorrect insertions or no insertions at all of the targeting vector results in a single PCR product of expected size for the wild type locus. Amplification of DNA from clones containing a correctly targeted ("knocked out") allele results in two PCR products, one representing amplification of the wild type allele and one of altered, predictable size due to the replacement of some sequence in the wild-type allele with the drug resistance marker, which is of different length from the sequence it replaced.

For the puromycin resistant heavy chain knockout construct, primers Shortend (5'-CTG AGC CAA GCA GTG GCC CCG AG-3'; SEQ ID NO: 45) and Longend (5'-GGG CTG AGA CTG GGT GAA CAG AAG GG-3'; SEQ ID NO: 46) are used. This pair of primers amplifies both the wild-type heavy chain locus and loci that have been appropriately targeted by the puromycin construct. The size difference between the two bands is approximately 0.7 Kb. The presence of the shorter band is indicative of appropriate targeting.

For this PCR reaction to analyze the integration of the puromcying resistant heavy chain knockout construct, a Promega Master Mix kit is used. The PCR reaction mixture contains 1 pmole of each primer, 2.5 µl of DNA, and 25 µl of 2× Promega Master Mix. The reaction mixture is brought to a total volume of 50 µl with $H_2O$. This PCR amplification is performed using an initial denaturing incubation at 94° C. for two minutes. Then, 30 cycles of denaturation, annealing, and amplification are performed by incubation at 94° C. for 45 seconds, 60° C. for 45 seconds, and 72° C. for two minutes. Then, the reaction mixture is incubated at 72° C. for five minutes and at 4° C. until the mixture is removed from the PCR machine.

First Round of Nuclear Transfer

Selected fibroblast cells in which an immunoglobulin gene has been inactivated may be used for nuclear transfer as described in Example 2 to generate a transgenic ungulate containing a mutation in an endogenous immunoglobulin gene and containing a HAC encoding a xenogenous immunoglobulin gene. Alternatively, nuclear transfer may be performed using standard methods to insert a nucleus or chromatin mass (i.e., one or more chromosomes not enclosed by a membrane) from a selected transgenic fibroblast into an enucleated oocyte (described, for example, in U.S. Ser. No. 60/258,151; filed Dec. 22, 2000). These methods may also be used for cells in which an endogenous alpha-(1,3)-galactosyltransferase, prion, and/or J chain nucleic acid has been mutated.

Second Round of Mutagenesis and Nuclear Transfer

If desired, a cell (e.g., a fetal fibroblast) may be obtained from a transgenic ungulate generated from the first round of nuclear transfer. Another round of gene targeting may be performed as described above to inactivate the second allele of the gene inactivated in the first round of targeting. Alternatively, another immunoglobulin (e.g., mu heavy chain, lambda light chain, kappa light chain, or J chain), alpha-(1, 3)-galactosyltransferase, or prion gene may be inactivated in this round of targeting. For this second round of targeting, either a higher concentration of antibiotic may be used or a knockout construct with a different antibiotic resistance marker may be used. Antibiotic resistance cells may be selected as described above. The selected cells may be used in a second round of nuclear transfer as described above to generate, for example, a transgenic ungulate containing two mutations in endogenous immunoglobulin genes and containing a HAC encoding a xenogenous immunoglobulin gene. Alternatively, the selected antibiotic resistant cells may first be treated to isolate G1 phase cells as described below, which are used for the second round of nuclear transfer.

To isolation of G1 cells for nuclear transfer, $5.0 \times 10^5$ cells are plated onto 100 mm tissue culture plates containing 10 ml of α-MEM+FCS, twenty four hours prior to isolation. The following day, plates are washed with PBS and the culture medium is replaced for 1-2 hours before isolation. The plates are then shaken for 30-60 seconds on a Vortex-Genie 2 (Fisher Scientific, Houston, Tex., medium speed), the medium is removed, spun at 1000 G for five minutes and the pellet is re-suspended in 250 µl of MEM+FCS. Newly divided cell doublets attached by a cytoplasmic bridge, are then selected, as these cells are in early G1. This isolation procedure is referred to as the "shake-off" method.

EXAMPLE 4

Additional Methods to Mutate Endogenous Immunoglobulin Genes

In some embodiments of the present approach, xenogenous immunoglobulin production in an ungulate with one or more mutations in a prion gene is accomplished essentially by the combined use of homologous recombination techniques, introduction of artificial chromosomes carrying entire xenogenous Ig loci, nuclear transfer, and administration of an antibody to eliminate endogenous antibody. More specifically, the process preferably involves the targeted disruption of one or both alleles of the IgM heavy chain gene, and optionally one or both alleles of the Ig light chain gene, although xenogenous antibody production can also be accomplished in animals without mutations in Ig nucleic acids. Gene knockouts may be effected by sequential homologous recombination, then another mating procedure. In a preferred embodiment, this is effected by initially effecting targeted disruption of one allele of the IgM heavy chain gene of a male or female ungulate (for example, bovine) fetal fibroblast in tissue culture using a suitable homologous recombination vector. The use of fetal fibroblasts is preferred over some other somatic cells as these cells are readily propagated and genetically manipulated in tissue culture. However, the use of fetal fibroblasts is not essential to the invention, and indeed other cell lines may be substituted therefor with equivalent results.

This process, of course, entails constructing a DNA construct having regions of homology to the targeted IgM heavy chain allele such that the construct upon integration into an IgM heavy chain allele in the ungulate genome disrupts the expression thereof. An exemplary vector for carrying out such targeted disruption of an IgM allele is described in the example that follows. In this regard, methods for constructing vectors that provide for homologous recombination at a targeted site are well known to those skilled in the art. Moreover, in the present instance, the construction of a suitable vector is within the level of skill in the art, given especially that the sequence of the bovine IgM heavy chain and Ig lambda light chain genes are known, as are the sequences of immunoglobulin genes from other ungulates (see below). In order to facilitate homologous recombination, the vectors used to effect homologous recombination and inactivation of the IgM gene, respectively, comprise portions of DNA that exhibit substantial sequence identity to the ungulate IgM heavy and Ig light chain genes. Preferably, these sequences possessing at least 98% sequence identity, more preferably, at least 99% sequence identity, and still more preferably will be isogenic with the targeted gene loci to facilitate homologous recombination and targeted deletion or inactivation.

Typically, and preferably the construct will comprise a marker gene that provides for selection of desired homologous recombinants, for example, fibroblast cells, wherein the IgM heavy chain gene and/or Ig light chain gene has been effectively disrupted. Exemplary marker genes include antibiotic resistance markers, drug resistance markers, and green fluorescent protein, among others. A preferred construct is shown in FIG. 2A and starting materials used to make this construct in FIGS. 3A and 3B. Other constructs containing two regions of homology to an endogenous immunoglobulin gene, which flank a positive selection marker (e.g., an antibiotic resistance gene) that is operably linked to a promoter, may be generated using standard molecular biology techniques and used in the methods of the present invention.

Figure 3C:
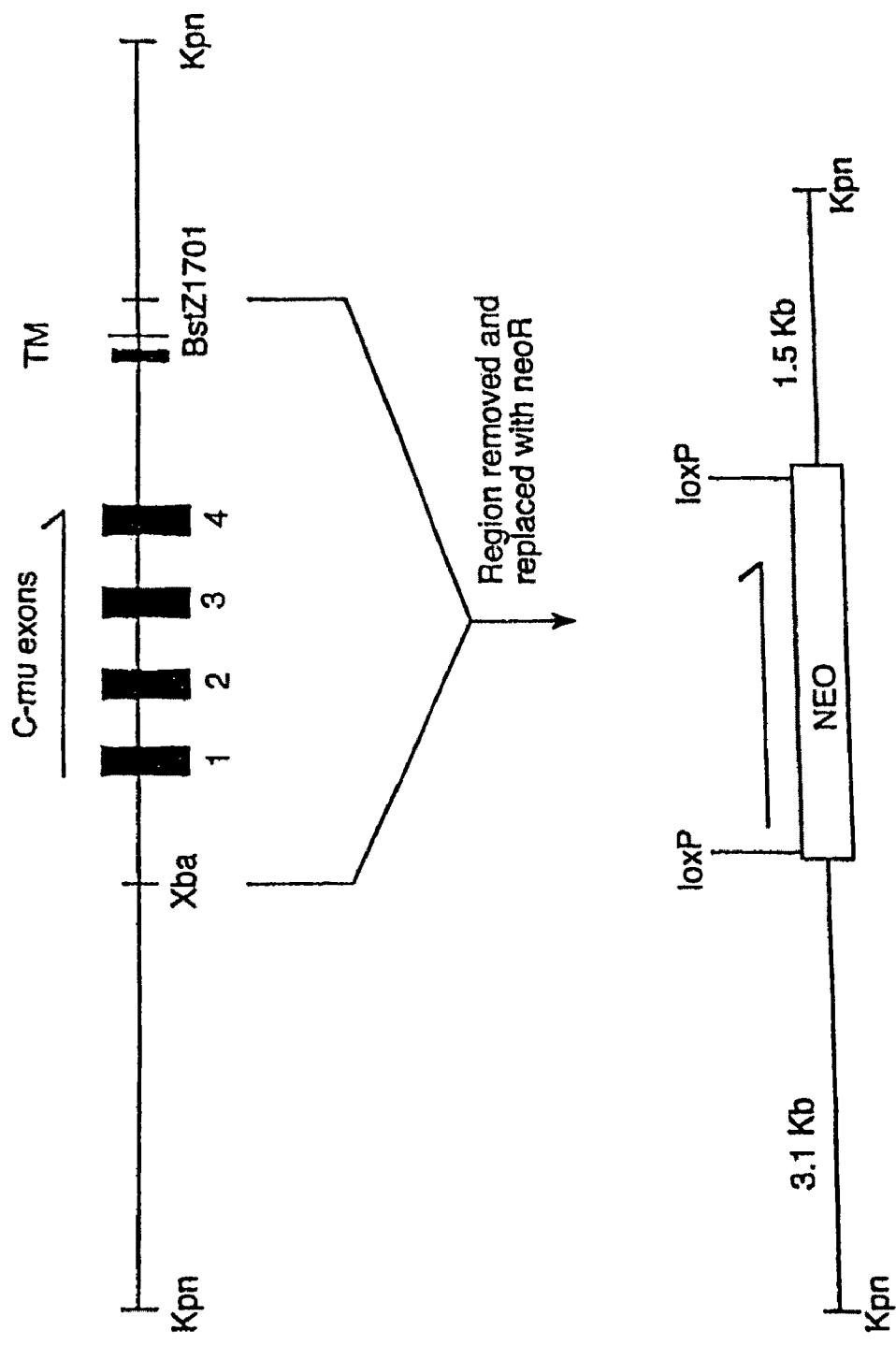
FIG. 3C depicts mu knockout DNA construct.
Figure 3F:
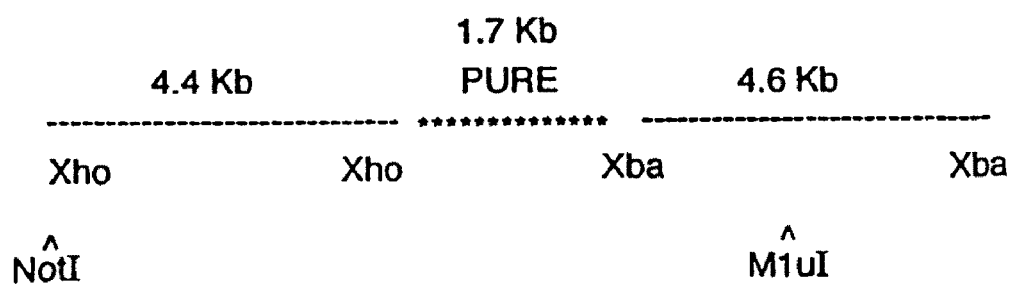
FIG. 3F depicts a puromycin resistant, bovine mu heavy chain knockout construct.
Figure 4:
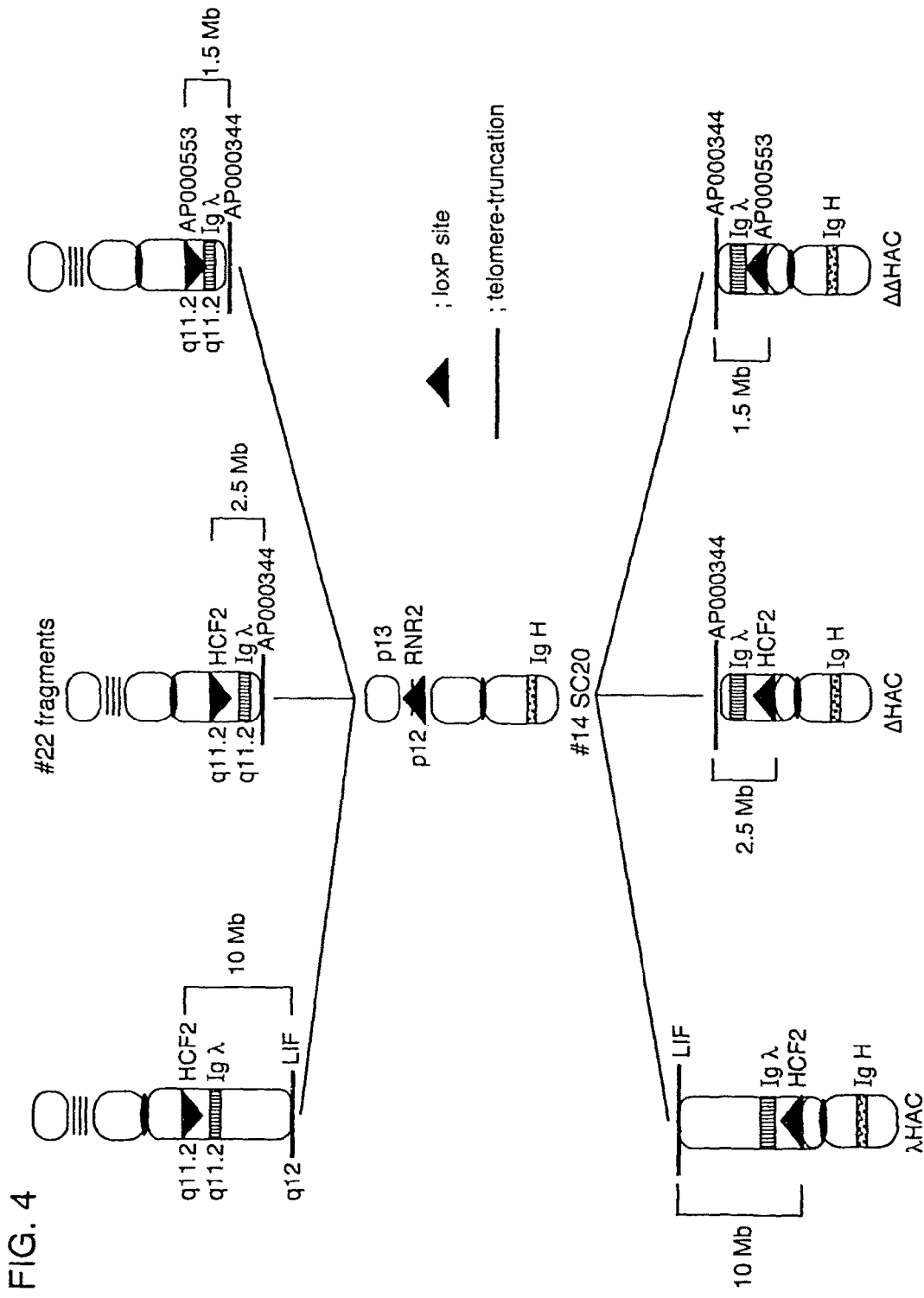
FIG. 4 is a schematic illustration of the construction of ΔHAC and ΔΔHAC.

The mu knockout construct shown in FIGS. 2A and 3C was designed to remove the exons encoding the bovine immunoglobulin heavy chain constant region, designated as "C-mu exons 1-4" and the two exons encoding the transmembrane domain, designated "TM exons".

To construct this vector, the region designated as "1", an XbaI-XhoI fragment from the genomic mu heavy chain bovine sequence, was subcloned into the commercial DNA vector, pBluescript (Stratagene, LaJolla, Calif.), previously cut with the enzymes XbaI and XhoI. Once this fragment was cloned, there was a NotI restriction enzyme recognition sequence adjacent to the XbaI site, used to insert a NotI fragment of approximately 3.5 Kb. This fragment contains a neomycin resistance marker, described further below. If desired, other mu knockout constructs may be constructed using the genomic mu heavy chain sequence from another ungulate breed, species, or genus (e.g., the mu heavy chain sequence deposited as Genbank accession number U63637 from a Swiss Bull/Holstein cross).

Once fragment "1" and the neomycin resistance marker were joined together into pBluescript, there remained a SacI site adjacent to the neomycin resistance marker. The new construct was linearized with SacI and converted to a blunt end by filling in the sticky ends left from the SacI digest, using DNA polymerase.

The fragment designated "2" was isolated as an XhoI-Bst 1071 fragment and converted to a blunt-ended fragment by filling in the sticky ends left from the XhoI and Bst 1071 enzymes, using DNA polymerase.

Once finished, the final construct contained region 2, the neomycin resistance marker and region 1, respectively.

For transfection of bovine fibroblasts, the construct was digested with the restriction enzyme, KpnI (two KpnI sites are shown in the diagram) and the DNA fragment was used for homologous recombination.

The neomycin resistance construct was assembled as follows. A construct designated "pSTneoB" (Katoh et al., Cell Struct. Funct. 12:575, 1987; Japanese Collection of Research Biologicals (JCRB) deposit number VE039) was designed to contain a neomycin resistance gene under the control of an SV40 promoter and TK enhancer upstream of the coding region. Downstream of the coding region is an SV40 terminator sequence. The neo cassette was excised from "pSTneoB" as a XhoI fragment. After the ends of the fragment were converted to blunt ends using standard molecular biology techniques, the blunt ended fragment was cloned into the EcoRV site in the vector, pBS246 (Gibco/Life Technologies). This site is flanked by loxp sites. The new construct, designated "pLoxP-STNeoR", was used to generate the mu knockout DNA construct. The desired fragment of this construct is flanked by loxp sites and NotI sites, which were originally present in the pBS246 cloning vector. The desired NotI fragment, which contains loxP-neo-loxp, was used for replacement of the immunoglobulin mu constant region exons. The SV40 promoter operably linked to the neomycin resistance gene activates the transcription of the neomycin resistance gene, allowing cells in which the desired NotI fragment has replaced the mu constant region exons to be selected based on their resulting antibiotic resistance.

After a cell line is obtained in which the IgM heavy chain allele has been effectively disrupted, it is used as a nuclear transfer donor to produce a cloned ungulate fetus (for example, a cloned bovine fetus) and eventually a fetus or animal wherein one of the IgM heavy alleles is disrupted. Thereafter, a second round of gene targeted disruption can be effected using somatic cells derived therefrom, e.g., fibroblasts, in order to produce cells in which the second IgM heavy chain allele is inactivated, using a similar vector, but containing a different selectable marker.

Preferably, concurrent to the first targeted gene disruption, a second ungulate (for example, bovine) somatic cell line is also genetically modified, which similarly may be of male or female origin. If the first cell line manipulated is male, it is preferable to modify a female cell line; vice versa if the first cell line manipulated is female, it is preferable to select a male cell line. Again, preferably, the manipulated cells comprise ungulate (for example, bovine) fetal fibroblasts.

In a preferred embodiment, the female fetal fibroblast is genetically modified so as to introduce a targeted disruption of one allele of the Ig lambda light chain gene. This method similarly is carried out using a vector having regions of homology to the ungulate (for example, bovine) Ig lambda light chain, and a selectable marker, which DNA construct is designed such that upon integration and homologous recombination with the endogenous Ig light chain results in disruption (inactivation) of the targeted Ig lambda light gene.

Once a female fibroblast cell line is selected having the desired targeted disruption, it similarly is utilized as a donor cell for nuclear transfer or the DNA from such cell line is used as a donor for nuclear transfer.

Alternatively, this cell may be subjected to a second round of homologous recombination to inactivate the second Ig lambda light chain using a similar DNA construct to that used to disrupt the first allele, but containing a different selectable marker.

Methods for effecting nuclear transfer, and particularly for the production of cloned bovines and cloned transgenic bovines have been reported and are described in U.S. Pat. No. 5,945,577. Alternatively, the nuclear transfer techniques disclosed in any one of PCT Publication Nos. WO95/16670, WO96/07732, WO97/07669, or WO97/07668 (collectively, Roslin Methods) may be used. The Roslin methods differ from the University of Massachusetts techniques in that they use quiescent rather than proliferating donor cells. All of these patents are incorporated by reference herein in their entirety. These nuclear transfer procedures will produce a transgenic cloned fetus which can be used to produce a cloned transgenic bovine offspring, for example, an offspring which comprises a targeted disruption of at least one allele of the Ig light chain gene and/or IgM gene. After such cell lines have been created, they can be utilized to produce a male and female heavy and light chain hemizygous knockout (M and F Hemi H/L) fetus and offspring. Moreover, these techniques are not limited to use for the production of transgenic bovines; the above techniques may be used for nuclear transfer of other ungulates as well.

Following nuclear transfer, production of desired animals may be affected either by mating the ungulates or by secondary gene targeting using the homologous targeting vector previously described.

As noted previously, a further object of the invention involves creating male and female heavy and light chain hemizygous knockouts wherein such hemizygous knockouts are produced using the cell lines already described. This may be affected either by mating of the offspring produced according to the above described methods, wherein an offspring which comprises a disrupted allele of the IgM heavy chain gene is mated with another offspring which comprises a disrupted allele of the Ig light chain. Alternatively, this may be affected by secondary gene targeting by manipulating a cell that is obtained from an offspring produced according to the above-described procedures. This will comprise effecting by homologous recombination targeted disruption of an allele of the IgM heavy chain gene or allele of the Ig light chain. After a cell line is produced which comprises a male and female heavy and light chain hemizygous knockout (M and F Hemi H/L) it will be used to produce a fetus or calf that comprises such a knockout. As noted, this is effected either by mating or secondary gene targeting.

Once the male and female heavy and light chain hemizygous knockouts are obtained, cells from these animals may be utilized to create homozygous knockout (Homo H/L) fetuses. Again, this is affected either by sequential gene targeting or mating. Essentially, if affected by mating, this will involve mating the male heavy and light chain hemizygous knockout with a female heavy and light chain hemizygous knockout and selection of an offspring that comprises a homozygous knockout. Alternatively, the cells from the hemizygous knockout described above may be manipulated in tissue culture, so as to knock out the other allele of the IgM or Ig light chain (lambda) gene. Secondary gene targeting may be preferred to mating as this may provide for more rapid results, especially given that the gestation period of ungulates, such as bovines, is relatively long.

During this sequential knockout and/or breeding strategy, one or both allele of the prion gene can be mutated in any donor cell produced during this process (e.g., a donor cell with or without a mutation in an endogenous Ig nucleic acid and with or without a xenogenous Ig nucleic acid). The ungulates generated using the methods described herein can thus have any number of desired mutations in a prion gene, Ig heavy chain gene, Ig light chain gene, alpha-(1,3)-galactosyltransferase gene, and/or J chain gene and can have one or more xenogenous Ig and/or J chain genes.

Knockout Procedures to Produce Transgenic Ungulates that Express Human Igs

Approaches for the production of Homo H/L fetuses or calves are summarized in FIG. 1. There are three schemes outlined therein. The first relies on successive knockouts in regenerated fetal cell lines. This approach is the technically most difficult and has the highest level of risk but as noted above potentially yields faster results than breeding approaches. The other two schemes rely on breeding animals. In the second scheme, only single knockouts of heavy and light chain genes are required in male and female cell lines, respectively. This scheme does not rely on regeneration of cell lines and is technically the simplest approach but takes the longest for completion. Scheme 3 is an intermediate between schemes 1 and 2. In all schemes only Homo H/L fetuses are generated because of potential difficulties in survival and maintenance of Homo H/L knockout calves. If necessary, passive immunotherapy can be used to increase the survival of Homo H/L knockout calves.

Experimental Design

The present invention preferably involves the production of a hemizygous male heavy chain knockout (M Hemi H) and a hemizygous female light chain knockout (F Hemi L) and the production of 40 day fetuses from these targeted deletions. The cells from the embryos are harvested, and one allele of the light locus is targeted in the M Hemi H cells and one allele of the heavy chain locus is targeted in the F Hemi L cells resulting in cells with hemizygous deletions of both the H and L loci (Hemi HL). These cells are used to derive 40 day fetuses from which fibroblasts are isolated.

The M Hemi H/L fibroblasts are targeted with the other H chain allele to create M Homo H/Hemi L, and the F Hemi H/L are targeted with the other L chain allele to create F Homo L/Hemi H. In order to create homozygous deletions, higher drug concentrations are used to drive homozygous targeting. However, it is possible that this approach may not be successful and that breeding may be necessary. An exemplary strategy that relies on cre/lox targeting of the selection cassette allows the same selective systems to be used for more than one targeted deletion. These fibroblasts are cloned and 40 day fetuses harvested and fibroblast cells isolated. The fetal cells from this cloning are targeted to produce homozygous deletions of either the H or L loci resulting in M Homo HA/L and F Homo H/L fetal fibroblasts. These fibroblasts are cloned and 40 day fetuses derived and fibroblasts isolated. The Homo H/L fetal fibroblasts are then used for incorporation of the HAC optionally by the use of breeding procedures.

Library Construction

Fetal fibroblast cells are used to construct a genomic library. Although it is reported to be significant that the targeting construct be isogenic with the cells used for cloning, it is not essential to the invention. For example, isogenic, substantially isogenic, or nonisogenic constructs may be used to produce a mutation in an endogenous immunoglobulin gene. In one possible method, Holstein cattle, which genetically contain a high level of inbreeding compared to other cattle breeds, are used. We have not detected any polymorphisms in immunoglobulin genes among different animals. This suggests that sequence homology should be high and that targeting with nonisogenic constructs should be successful.

Figure 2B:
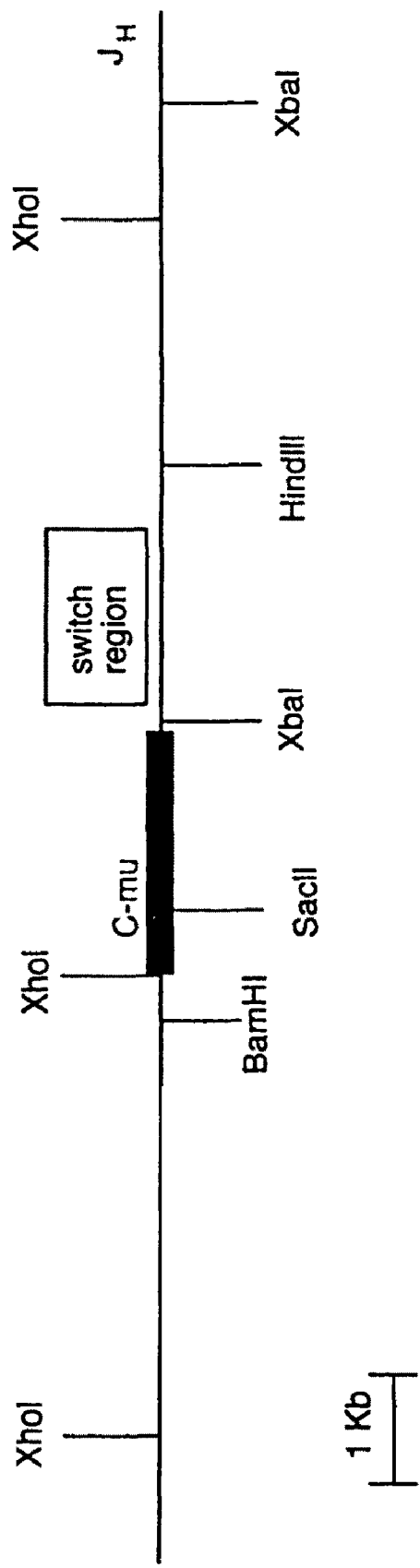
FIG. 2B is a restriction map of immunoglobulin loci from a Holstein cattle.

A library is constructed from one male cell line and one female cell line at the same time that the "clonability" testing is being conducted. It is envisioned that at the end of the process, a library will be produced and a number of different fetal cell lines will be tested and one cell line chosen as the best for cloning purposes. Genomic libraries are constructed using high molecular weight DNA isolated from the fetal fibroblast cells. DNA is size fractionated and high molecular weight DNA between 20-23 Kb is inserted into the lambda phage vector LambdaZap or LambdaFix. The inventors have had excellent success with Stratagene prepared libraries. Therefore, DNA is isolated and the size selected DNA is sent to Stratagene for library preparation. To isolate clones containing bovine heavy and light chains, radiolabeled IgM cDNA and radiolabeled light chain cDNA is used. Additionally, light chain genomic clones are isolated in case it is necessary to delete the locus. Each fetal cell library is screened for bovine heavy and light chain containing clones. It is anticipated that screening approximately $10^5$-$10^6$ plaques should lead to the isolation of clones containing either the heavy chain or light chain locus. Once isolated, both loci are subcloned into pBluescript and restriction mapped. A restriction map of these loci in Holsteins is provided in FIG. 2B (Knight et al. J. Immunol. 140: 3654-3659, 1988). Additionally, a map from the clones obtained is made and used to assemble the targeting construct.

Production of Targeting Constructs

Once the heavy and light chain genes are isolated, constructs are made. The IgM construct is made by deleting the IgM constant region membrane domain. As shown by Rajewsky and colleagues in mice, deletion of the membrane domain of IgM results in a block in B-cell development since surface IgM is a required signal for continued B-cell development (Kitamura et al., Nature 350:423-426). Thus homozygous IgM cattle lack B-cells. This should not pose a problem since in the present strategy no live births of animals lacking functional Ig are necessary. However, if necessary, passive immunotherapy may be used to improve the survival of the animals until the last step when the human Ig loci are introduced.

An exemplary targeting construct used to effect knockout of the IgM heavy chain allele is shown in FIG. 2A. For the heavy chain, the membrane IgM domain is replaced with a neomycin cassette flanked by lox P sites. The attached membrane domain is spliced together with the neo cassette such that the membrane domain has a TAG stop codon inserted immediately 5' to the lox P site ensuring that the membrane domain is inactivated. This is placed at the 5' end of the targeting construct with approximately 5-6 kilobases of 3' chromosomal DNA.

If increasing drug concentrations does not allow deletion of the second allele of either IgM heavy or light chains, the cre/lox system (reviewed in Sauer, 1998, Methods 14:381-392) is used to delete the selectable marker. As described below, the cre/lox system allows the targeted deletion of the selectable marker. All selectable markers are flanked with loxP sequences to facilitate deletion of these markers if this should be necessary.

The light chain construct contains the bovine lambda chain constant region (e.g., the lambda light chain constant region found in GenBank accession number AF396698 or any other ungulate lambda light chain constant region) and a puromycin resistance gene cassette flanked by lox P sites and will replace the bovine gene with a puromycin cassette flanked by lox P sites. Approximately 5-6 kilobases of DNA 3' to the lambda constant region gene will be replaced 3' to the puromycin resistance gene. The puromycin resistance gene will carry lox P sites at both 5' and 3' ends to allow for deletion if necessary. Due to the high degree of homology between ungulate antibody genes, the bovine lambda light chain sequence in GenBank accession number AF396698 is expected to hybridize to the genomic lambda light chain sequence from a variety of ungulates and thus may be used in standard methods to isolate various ungulate lambda light chain genomic sequences. These genomic sequences may be used in standard methods, such as those described herein, to generate knockout constructs to inactivate endogenous lambda light chains in any ungulate.

A kappa light chain knockout construct may be constructed similarly using the bovine kappa light chain sequence in FIG. 3G or any other ungulate kappa light chain sequence. This bovine kappa light chain may be used as a hybridization probe to isolate genomic kappa light chain sequences from a variety of ungulates. These genomic sequences may be used in standard methods, such as those described herein, to generate knockout constructs to inactivate endogenous kappa light chains in any ungulate.

Additional ungulate genes may be optionally mutated or inactivated. For example, the endogenous ungulate Ig J chain gene may be knocked out to prevent the potential antigenicity of the ungulate Ig J chain in the antibodies of the invention that are administered to humans. For the construction of the targeting vector, the cDNA sequence of the bovine Ig J chain region found in Genbank accession number U02301 may be used. This cDNA sequence may be used as a probe to isolate the genomic sequence of bovine Ig J chain from a BAC library such as RPC1-42 (BACPAC in Oakland, Calif.) or to isolate the genomic sequence of the J chain from any other ungulate. Additionally, the human J chain coding sequence may be introduced into the ungulates of present invention for the functional expression of human IgA and IgM molecules. The cDNA sequence of human J chain is available from GenBank accession numbers AH002836, M12759, and M12378. This sequence may be inserted into an ungulate fetal fibroblast using standard methods, such as those described herein. For example, the human J chain nucleic acid in a HAC, YAC vector, BAC vector, cosmid vector, or knockin construct may be integrated into an endogenous ungulate chromosome or maintained independently of endogenous ungulate chromosomes. The resulting transgenic ungulate cells may be used in the nuclear transfer methods described herein to generate the desired ungulates that have a mutation that reduces or eliminates the expression of functional ungulate J chain and that contain a xenogenous nucleic acid that expresses human J chain.

Additionally, the ungulate α-(1,3)-galactosyltransferase gene may be mutated to reduce or eliminate expression of the galactosyl(α1,3)galactose epitope that is produced by the α-(1,3)-galactosyltransferase enzyme. If human antibodies produced by the ungulates of the present invention are modified by this carbohydrate epitope, these glycosylated antibodies may be inactivated or eliminated, when administered as therapeutics to humans, by antibodies in the recipients that are reactive with the carbohydrate epitope. To eliminate this possible immune response to the carbohydrate epitope, the sequence of bovine alpha-(1,3)-galactosyltransferase gene may be used to design a knockout construct to inactive this gene in ungulates (Genbank accession number J04989; Joziasse et al., J. Biol. Chem. 264:14290-14297, 1989). This bovine sequence or the procine alpha-(1,3)-galactosyltransferase sequence disclosed in U.S. Pat. Nos. 6,153,428 and 5,821,117 may be used to obtain the genomic alpha-(1,3)-galactosyltransferase sequence from a variety of ungulates to generate other ungulates with reduced or eliminated expression of the galactosyl(α1,3)galactose epitope.

If desired, the ungulate prion gene may be mutated or inactivated to reduce the potential risk of an infection such as bovine spongiform encephalopathy (BSE). For the construction of the targeting vector, the genomic DNA sequence of the bovine prion gene may be used (GenBank accession number AJ298878), as described in Example 1. Alternatively, this genomic prion sequence may be used to isolate the genomic prion sequence from other ungulates. The prion gene may be inactivated using the methods described herein. Alternatively, the previously described methods for mutating the alpha-(1,3)-galactosyltransferase gene or prion gene in sheep (Denning et al., Nature Biotech., 19: 559-562, 2001) can be adapted based on the teachings described herein. For example, the improved methods that are described herein for culturing donor cells (e.g., fetal fibroblasts), generating knockout vectors, transfecting the donor cells with the knockout vectors (e.g., transfection in the presence of spermidine), and/or transferring the genetic material from the knockout cells into an oocyte for generation of a transgenic ungulate can be used.

For targeting the second allele of each locus, it may be necessary to assemble a new targeting construct containing a different selectable marker, if the first selectable marker remains in the cell. As described in Table 5, a variety of selection strategies are available and may be compared and the appropriate selection system chosen. Initially, the second allele is targeted by raising the drug concentration (for example, by doubling the drug concentration). If that is not successful, a new targeting construct may be employed.

TABLE 5

Selectable markers and drugs for selection

| Gene | Drug |
| --- | --- |
| Neo$^r$ | G418 |
| Hph | Hygromycin B |
| Puro | Puromycin |
| Ecogpt | Mycophenolic acid |
| Bsr | Blasticidin S |
| HisD | Histidinol |
| DT-A | Diphtheria toxin |

The additional mutations or the gene inactivation mentioned above may be incorporated into the ungulates of the present invention using various methodologies. Once a transgenic ungulate cell line is generated for each desired mutation, crossbreeding may be used to incorporate these additional mutations into the ungulates of the present invention. Alternatively, fetal fibroblast cells that have these additional mutations can be used as the starting material for the knockout of endogenous Ig genes and/or the introduction of xenogenous Ig genes. Also, fetal fibroblast cells having a knockout mutation in endogenous Ig genes and/or containing xenogenous Ig genes can be uses as a starting material for these additional mutations or inactivations.

Targeted Deletion of Ig Loci

Targeting constructs are introduced into embryonic fibroblasts, e.g., by electroporation. The cells that incorporate the targeting vector are selected by the use of the appropriate antibiotic. Clones that are resistant to the drug of choice will be selected for growth. These clones are then subjected to negative selection with gancyclovir, which will select those clones that have integrated appropriately. Alternatively, clones that survive the drug selection are selected by PCR. It is estimated that it will be necessary to screen at least 500-1000 clones to find an appropriately targeted clone. The inventors' estimation is based on Kitamura (Kitamura et al., Nature 350:423-426, 1991), who found that when targeting the membrane domain of IgM heavy chain constant region approximately 1 in 300 neo resistant clones were properly targeted. Thus, it is proposed to pool clones into groups of 10 clones in a 96 well plate and screen pools of 10 clones for the targeted clones of choice. Once a positive is identified, single clones isolated from the pooled clone will be screened. This strategy should enable identification of the targeted clone.

Because fibroblasts move in culture it is difficult to distinguish individual clones when more than approximately ten clones are produced per dish. Further, strategies may be developed for clonal propagation with high efficiency transfection. Several reasonable strategies, such as dilution cloning, may be used.

Cre/Lox Excision of the Drug Resistance Marker

As shown above, exemplary targeting constructs contain selectable markers flanked by loxp sites to facilitate the efficient deletion of the marker using the cre/lox system. Fetal fibroblasts carrying the targeting vector are transfected via electroporation with a Cre containing plasmid. A recently described Cre plasmid that contains a GFPcre fusion gene (Gagneten et al., Nucleic Acids Res. 25:3326-31, 1997) may be used. This allows the rapid selection of all clones that contain Cre protein. These cells are selected either by FACS sorting or by manual harvesting of green fluorescing cells via micromanipulation. Cells that are green are expected to carry actively transcribed Cre recombinase and hence delete the drug resistance marker. Cells selected for Cre expression are cloned and clones analyzed for the deletion of the drug resistance marker via PCR analysis. Those cells that are determined to have undergone excision are grown to small clones, split and one aliquot is tested in selective medium to ascertain with certainty that the drug resistance gene has been deleted. The other aliquot is used for the next round of targeted deletion.

Application of Targeting Strategies to Altering Immunoglobulin Genes of Other Ungulates To alter immunoglobulin genes of other ungulates, targeting vectors are designed to contain three main regions. The first region is homologous to the locus to be targeted. The second region is a drug selection marker that specifically replaces a portion of the targeted locus. The third region, like the first region, is homologous to the targeted locus but is not contiguous with the first region in the wild type genome. Homologous recombination between the targeting vector and the desired wild type locus results in deletion of locus sequences between the two regions of homology represented in the targeting vector and replacement of that sequence with a drug resistance marker. In preferred embodiments, the total size of the two regions of homology is approximately 6 kilobases, and the size of the second region that replaces a portion of the targeted locus is approximately 2 kilobases. This targeting strategy is broadly useful for a wide range of species from prokaryotic cells to human cells. The uniqueness of each vector used is in the locus chosen for gene targeting procedures and the sequences employed in that strategy. This approach may be used in all ungulates, including, without limitation, goats (*Capra hircus*), sheep (*Ovis aries*), and the pig (*Sus scrufa*), as well as cattle (*Bos taurus*).

The use of electroporation for targeting specific genes in the cells of ungulates may also be broadly used in ungulates. The general procedure described herein is adaptable to the introduction of targeted mutations into the genomes of other ungulates. Modification of electroporation conditions (voltage and capacitance) may be employed to optimize the number of transfectants obtained from other ungulates.

In addition, the strategy used herein to target the heavy chain locus in cattle (i.e., removal of all coding exons and intervening sequences using a vector containing regions homologous to the regions immediately flanking the removed exons) may also be used equally well in other ungulates. For example, extensive sequence analysis has been performed on the immunoglobulin heavy chain locus of sheep (*Ovis aries*), and the sheep locus is highly similar to the bovine locus in both structure and sequence (GenBank accession numbers Z71572, Z49180 through Z49188, M60441, M60440, AF172659 through AF172703). In addition to the large number of cDNA sequences reported for rearranged *Ovis aries* immunoglobulin chains, genomic sequence information has been reported for the heavy chain locus, including the heavy chain 5' enhancer (GenBank accession number Z98207), the 3' mu switch region (Z98680) and the 5' mu switch region (Z98681). The complete mRNA sequence for the sheep secreted form of the heavy chain has been deposited as accession number X59994. This deposit contains the entire sequence of four coding exons, which are very homologous to the corresponding bovine sequence.

Information on the sheep locus was obtained from GenBank and used to determine areas of high homology with bovine sequence for the design of primers used for PCR analysis. Because non-isogenic DNA was used to target bovine cells, finding areas of high homology with sheep sequence was used as an indicator that similar conservation of sequences between breeds of cow was likely. Given the similarity between the sequences and structures of the bovine and ovine immunoglobulin loci, it would be expected that the targeting strategies used to remove bovine immunoglobulin loci could be successfully applied to the ovine system. In addition, existing information on the pig (*Sus scrofa*, accession number S42881) and goat (*Capra hircus*, accession number AF140603) indicates that the immunoglobulin loci of both of these species are also sufficiently similar to the bovine loci to utilize the present targeting strategies.

EXAMPLE 5

Bovine IgM Knockout

The following procedures were used to generate bovine fibroblast cell lines in which one allele of the immunoglobulin heavy chain (mu) locus is disrupted by homologous recombination. A DNA construct for effecting an IgM knockout was generated by the removal of exons 1-4 of the Mu locus (corresponds to IgM heavy chain gene), which were replaced with a copy of a neomycin resistance gene. Using this construct, neomycin resistant cell lines have been obtained which were successfully used in nuclear transfer procedures, and blastocysts from these cell lines have been implanted into recipient cows. Additionally, some of these blastocysts were tested to confirm that targeted insertion occurred appropriately in the mu locus using PCR procedures. Blastocysts resulting from nuclear transfer procedures from several of the cell lines obtained indicated that heterozygous IgM-knockout fetuses were in gestation. Additionally, both male and female cell lines that comprise a single IgM heavy chain (mu) knockout have been produced. It is anticipated that mating of animals cloned from these cell lines will give rise to progeny wherein both copies of mu are inactivated. As described herein, the progeny can be mated with prion knockout ungulates to produce offspring with mutations in the IgM and prion genes. Alternatively, a cell from the progeny can be genetically modified to inactivate one or both alleles of the prion gene as described in Example 1. These procedures are discussed in greater detail below.

DNA Construct

The DNA used in all transfections described in this document was generated as follows. The four main exons (excluding the transmembrane domain exons), CH1-4, are flanked by an XhoI restriction site at the downstream (CH4) end and an XbaI site at the upstream (CH1) end. The construct used for the transfection procedure consisted of 1.5 kb of genomic sequence downstream of the XhoI site and 3.1 Kb of genomic sequence upstream of the XbaI site (FIGS. 3D and 3E). These sequences were isolated as described herein from a Holstein cow from a dairy herd in Massachusetts. A neomycin resistance marker was inserted between these two fragments on a 3.5 Kb fragment, replacing 2.4 Kb of DNA, originally containing CH1-4, from the originating genomic sequence. The backbone of the vector was pBluescriptII SK+ (Stratagene) and the insert of 8.1 Kb was purified and used for transfection of bovine fetal fibroblasts. This construct is shown in FIGS. 3A-3C. Other mu knockout constructs containing other homologous regions and/or containing another antibiotic resistance gene may also be constructed using standard methods and used to mutate an endogenous mu heavy chain gene.

Transfection/Knockout Procedures

Transfection of fetal bovine was performed using a commercial reagent, Superfect Transfection Reagent (Qiagen, Valencia, Calif., USA).

Bovine fibroblasts were generated from disease-tested male Charlais cattle at Hematech's Kansas facility and sent to Hematech's Worcester Molecular Biology Labs for use in all experiments described. Any other ungulate breed, genus, or species may be used as the source of donor cells (e.g., somatic cells such as fetal fibroblasts). The donor cells are genetically modified to contain a mutation that reduces or eliminates the expression of functional, endogenous Ig.

The medium used for culture of bovine fetal fibroblasts consisted of the following components: 500 ml Alpha MEM (Bio-Whittaker #12-169F); 50 ml fetal calf serum (Hy-Clone #A-1111-D); 2 ml antibiotic/antimyotic (Gibco/BRL #15245-012); 1.4 ml 2-mercaptoethanol (Gibco/BRL #21985-023); 5.0 ml L-1-Glutamine (Sigma Chemical #G-3126); and 0.5 ml tyrosine tartrate (Sigma Chemical #T-6134)

On the day prior to transfection procedures, cells were seeded in 60 mm tissue culture dishes with a targeted confluency of 40-80% as determined by microscopic examination.

On the day of transfection, 5 µg of DNA, brought to a total volume of 150 µl in serum-free, antibiotic-free medium, was mixed with 20 µl of Superfect transfection reagent and allowed to sit at room temperature for 5-10 minutes for DNA-Superfect complex formation. While the complex formation was taking place, medium was removed from the 60 mm tissue culture dish containing bovine fibroblasts to be transfected, and cells were rinsed once with 4 ml of phosphate-buffered saline. One milliliter of growth medium was added to the 170 µl DNA/Superfect mixture and immediately transferred to the cells in the 60 mm dish. Cells were incubated at 38.5° C., 50% carbon dioxide for 2.5 hours. After incubation of cells with the DNA/Superfect complexes, medium was aspirated off and cells were washed four times with 4 ml PBS. Five ml of complete medium were added and cultures were incubated overnight at 38.5° C., 5% $CO_2$. Cells were then washed once with PBS and incubated with one ml of 0.3% trypsin in PBS at 37° C. until cells were detached from the plate, as determined by microscopic observation. Cells from each 60 mm dish were split into 24 wells of a 24 well tissue culture plate (41.7 ul/well). One milliliter of tissue culture medium was added to each well and plates were allowed to incubate for 24 hours at 38.5° C. and 5% $CO_2$ for 24 hours.

During all transfection procedures, sham transfections were performed using a Superfect/PBS mixture containing no DNA, as none of those cells would be expected to contain the neomycin resistance gene and all cells would be expected to die after addition of G418 to the tissue culture medium. This served as a negative control for positive selection of cells that received DNA.

After the 24 hour incubation, one more milliliter of tissue culture medium containing 400 µg G418 was added to each well, bringing the final G418 concentration to 200 µg/ml. Cells were placed back into the incubator for 7 days of G418 selection. During that period, both transfected and sham transfection plates were monitored for cell death and over 7 days, the vast majority of wells from the sham transfections contained few to no live cells while plates containing cells that received the DNA showed excellent cell growth.

After the 7 day selection period, the cells from wells at 90-100% confluency were detached using 0.2 ml 0.3% trypsin in PBS and were transferred to 35 mm tissue culture plates for expansion and incubated until they became at least 50% confluent, at which point, cells were trypsinized with 0.6 ml 0.3% trypsin in PBS. From each 35 mm tissue culture plate, 0.3 ml of the 0.6 ml cell suspension was transferred to a 12.5 $cm^2$ tissue culture flask for further expansion. The remaining 0.3 ml was reseeded in 35 mm dishes and incubated until they attained a minimal confluency of approximately 50%, at which point cells from those plates were processed for extraction of DNA for PCR analysis. Flasks from each line were retained in the incubator until they had undergone these analyses and were either terminated if they did not contain the desired DNA integration or kept for future nuclear transfer and cryopreservation.

Screening for Targeted Integrations

As described above the DNA source for screening of transfectants containing the DNA construct was a 35 mm tissue culture dish containing a passage of cells to be analyzed. DNA was prepared as follows and is adapted from a procedure published by Laird et al., Nucleic Acids Res., 19:4293). Briefly, DNA was prepared as follows. A cell lysis buffer was prepared with the following components: 100 mM Tris-HCl buffer, pH 8.5; 5 mM EDTA, pH 8.0; 0.2% sodium dodecyl sulfate; 200 mM NaCl; and 100 µg/ml Proteinase K.

Medium was aspirated from each 35 mm tissue culture dish and replaced with 0.6 ml of the above buffer. Dishes were placed back into the incubator for three hours, during which time cell lysis and protein digestion were allowed to occur. Following this incubation, the lysate was transferred to a 1.5 ml microfuge tube and 0.6 ml of isopropanol was added to precipitate the DNA. Tubes were shaken thoroughly by inversion and allowed to sit at room temperature for 3 hours, after which the DNA precipitates were spun down in a microcentrifuge at 13,000 rpm for ten minutes. The supernatant from each tube was discarded and the pellets were rinsed with 70% ethanol once. The 70% ethanol was aspirated off and the DNA pellets were allowed to air-dry. Once dry, each pellet was resuspended in 30-50 ul of Tris (10 mM)-EDTA (1 mM) buffer, pH 7.4 and allowed to hydrate and solubilize overnight. 5-7 microliters of each DNA solution was used for each polymerase chain reaction (PCR) procedure.

Two separate PCR procedures were used to analyze transfectants. The first procedure used two primers that were expected to anneal to sites that are both located within the DNA used for transfection. The first primer sequence is homologous to the neomycin resistance cassette of the DNA construct and the second is located approximately 0.5 Kb away, resulting in a short PCR product of 0.5 Kb. In particular, primers Neo1 (5'-CTT GAA GAC GAA AGG GCC TCG TGA TAC GCC-3'; SEQ ID NO: 42) and IN2521 (5'-CTG AGA CTT CCT TTC ACC CTC CAG GCA CCG-3'; SEQ ID NO: 43) were used. A Qiagen PCR kit was used for this PCR reaction. The PCR reaction mixture contained 1 pmole of each primer, 5 ul of 10× reaction buffer, 10 µl of Q solution, 5 µl of DNA, and 1 µl of dNTP solution. The reaction mixture was brought to a total volume of 50 µl with $H_2O$. This PCR amplification was performed using an initial denaturing incubation at 94° C. for two minutes. Then, 30 cycles of denaturation, annealing, and amplification were performed by incubation at 94° C. for 45 seconds, 60° C. for 45 seconds, and 72° C. for two minutes. Then, the reaction mixture was incubated at 72° C. for five minutes and at 4° C. until the mixture was removed from the PCR machine. Alternatively, any other primers that are homologous to the region of the knockout construct that integrates into the genome of the cells may be used in a standard PCR reaction under appropriate reaction conditions to verify that cells surviving G418 selection were resistant as a result of integration of the DNA construct.

Because only a small percentage of transfectants would be expected to contain a DNA integration in the desired location (the Mu locus), another pair of primers was used to determine not only that the DNA introduced was present in the genome of the transfectants but also that it was integrated in the desired location. The PCR procedure used to detect appropriate integration was performed using one primer located within the neomycin resistance cassette of the DNA construct and one primer that would be expected to anneal over 1.8 Kb away, but only if the DNA had integrated at the appropriate site of the IgM locus (since the homologous region was outside the region included in the DNA construct used for transfection). The primer was designed to anneal to the DNA sequence immediately adjacent to those sequences represented in the DNA construct if it were to integrate in the desired location (DNA sequence of the locus, both within the region present in the DNA construct and adjacent to them in the genome was previously determined). In particular, primers Neo1 and OUT3570 (5'-CGA TGA ATG CCC CAT TTC ACC CAA GTC TGT C-3, SEQ ID NO: 44) were used for this analysis. This PCR reaction was performed using a Qiagen PCR kit as described above for the first PCR reaction to confirm the integration of the targeting construct into the cells. Alternatively, this PCR analysis may be performed using any appropriate reaction conditions with any other primer that is homologous to a region of the knockout construct that integrates into the genome of the cells and any other primer that is homologous to a region in the genome of the cells that is upstream or downstream of the site of integration.

Using these methods, 135 independent 35 mm plates were screened for targeted integration of the DNA construct into the appropriate locus. Of those, DNA from eight plates was determined to contain an appropriately targeted DNA construct and of those, three were selected for use in nuclear transfer procedures. Those cells lines were designated as "8-1C", "5-3C" and "10-1C." Leftover blastocysts not used for transfer into recipient cows were used to extract DNA which was subjected to additional PCR analysis. This analysis was effective using a nested PCR procedure using primers that were also used for initial screening of transfected lines.

As noted above, three cell lines were generated using the gene targeting construct designed to remove exons 1-4 of the mu locus. These lines all tested positive for targeted insertions using a PCR based test and were used for nuclear transfers. Leftover blastocysts resulting from those nuclear transfers were screened by PCR testing the appropriately targeted construct. The following frequencies of positive blastocysts were obtained:

Cell Line 8-1C: 6/8

Cell Line 10-1C: 2/16

Cell Line 5-3C: 0/16

Although at forty days of gestation, 11 total pregnancies were detected by ultrasound, by day 60, seven fetuses had died. The remaining four fetuses were processed to regenerate new fetal fibroblasts and remaining organs were used to produce small tissue samples for PCR analysis. The results of the analyses are below:

Line 8-1C: two fetuses, one fetus positive for targeted insertion by PCR

Line 10-1C: one fetus, positive for targeted insertion by PCR

Line 5-3C: one fetus, negative for targeted insertion by PCR

Surprisingly, although the frequency of 10-1C blastocysts testing positive for targeted insertion was only 2/16, the one viable 60-day fetus obtained from that cell line was positive as determined by PCR. A positive fetus from 8-1C was also obtained. Southern blot analysis of DNA of all tissue samples is being effected to verify that the construct not only targeted correctly at one end (which is determined by PCR of the shorter region of homology present in the original construct) but also at the other end. Based on results to date, it is believed that two heavy chain knockout fetuses from two independent integration events have been produced. Also, since these fetuses were derived from two different lines, at least one is likely to have integrated construct correctly at both ends.

Once the Southern blot analyses have confirmed appropriate targeting of both ends of targeting construct, further nuclear transfers is performed to generate additional fetuses that are carried to term.

Nuclear Transfer and Embryo Transfer

Nuclear transfers were performed with the K/O cell line (8-1-C (18)) and eight embryos were produced. A total of six embryos from this batch were transferred to three disease free recipients at Trans Ova Genetics ("TOG"; Iowa).

Frozen embryos have been transferred to ten disease free recipients to obtain disease free female fibroblast cell lines. Fetal recoveries are scheduled after confirming the pregnancies at 35-40 days.

Pregnancy Diagnosis and Fetal Recovery

Pregnancy status of the eighteen recipients transferred with cloned embryos from knockout fetal cells was checked by ultrasonography. The results are summarized in Table 6.

TABLE 6

Pregnancy at 40 days using mu heavy chain knockout donor cells

| Clone ID | No of recips transferred | Pregnancy at 40 days (%) |
| --- | --- | --- |
| 8-1-0C | 5 | 4 (80) |
| 10-1-C | 6 | 4 (67) |
| 5-3-C | 5 | 3 (60) |
| Total | 16 | 11 (69) |

Pregnancy Diagnosis

Pregnancy status of the three recipients to whom cloned embryos were transferred from knockout cells (8-1C) was checked; one was open and the other two required reconfirmation after one month.

Fetal Recoveries and Establishment of Cell Lines

Eleven pregnancies with the K/O embryos at 40 days were obtained. Four live fetuses were removed out of these at 60 days. Cell lines were established from all four and cryopreserved for future use. Also we collected and snap froze tissue samples from the fetuses and sent them to Hematech molecular biology laboratory for PCR/Southern blot analysis.

All four of the cell lines were male. In order to secure a female cell line, cell lines were established and cryopreserved for future establishment of K/O cells from the fetuses (six) collected at 55 days of gestation from the pregnancies established at Trans Ova Genetics with disease free recipients. Recently, the existence of a female cell line containing a mu knockout was confirmed. This female cell line may be used to produce cloned animals which may be mated with animals generated from the male cell lines, and progeny screened for those that contain the double mu knockout.

If desired, a cell from the resulting knockout fetus or knockout offspring can be used in a second round of nuclear transfer to generate additional cloned offspring. Cells from the initial knockout fetus or knockout offspring may also be frozen to form a cell line to be used as a source of donor cells for the generation of additional knockout ungulates.

EXAMPLE 6

Transgenic Ungulates Having Reduced α-1,3-galactosyltransferase Activity

If desired, transgenic ungulates in which α-1,3-galactosyltransferase is mutated can be generated to prevent undesired glycosylation of xenogenous antibodies with a galactose α(1, 3)-galactose epitope. Bovine fibroblast cell lines in which one allele of the α-1,3-galactosyltransferase locus is mutated were generated by homologous recombination. The DNA construct for generating the α-galactosyltransferase knock-out cells was used to prevent transcription of functional, full-length α-galactosyltransferase mRNA by inserting both a puromycin-resistance gene euro, described herein) and a transcription termination cassette (STOP) in exon 9, which contains the catalytic domain. Thus, the resulting immature α-galactosyltransferase transcripts lack the catalytic domain. The DNA construct (i.e., the α-galactosyltransferase knock-out vector) was electroporated into three independent bovine fibroblast cell lines, and then puromycin-resistant colonies were isolated. Based on PCR analysis, homologous recombination in the exon 9 region occurred in some colonies. Thus, bovine fibroblast cell lines in which one allele of α1,3-galactosyltransferase locus is mutated were generated. If desired, the second allele can be mutated by using the same knockout vector and a higher concentration of antibiotic to select for homozygous knockout cells or using another knockout vector with a different antibiotic resistance gene. This method may also be applied to cells from other ungulates to generate transgenic cells for use in the nuclear transfer methods described herein to produce transgenic ungulates of the present invention.

These methods are described further below.

Construction of an α-1,3-galactosyltransferase Knockout Vector

Figure 23:
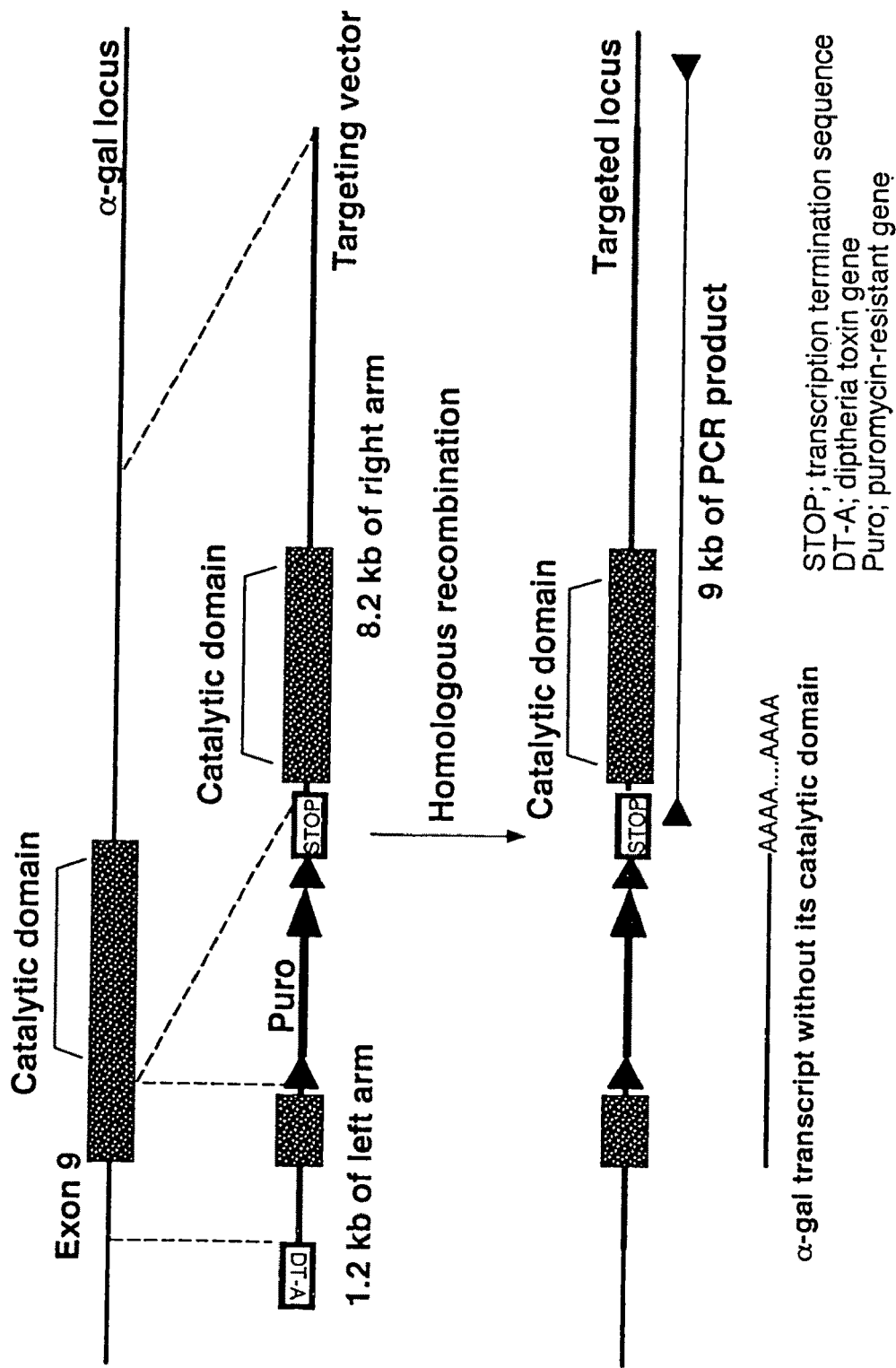
FIG. 23 is a schematic illustration of the α-(1,3)-galactosyltransferase knockout vector used to insert a puromycin resistance gene and a transcription termination sequence into the endogenous α-(1,3)-galactosyltransferase gene in bovine cells.

The α-1,3-galactosyltransferase knockout vector was generated as follows (FIG. 23). To isolate genomic DNA around exon 9 of the α-1,3-galactosyltransferase gene, a DNA probe was amplified by PCR using the following primer pair: 5'-gat gat gtc tcc agg atg cc-3' (SEQ ID NO: 61) and 5'-gac aag ctt aat atc cgc agg-3' (SEQ ID NO: 62). Using this probe, a bovine genomic λ phage library was screened, and 7 positive λ phage clones were identified. One clone, which contained DNA from a male Charolais bovine fibrolast cell, was analyzed further by restriction mapping. The NotI-XhoI genomic fragment containing exon 9 was subcloned into pBluescript II SK(−), and then both puro and STOP cassettes were inserted at the AviI site in the NotI-XhoI genomic fragment that is 5' to the catalytic domain. A diphtheria toxin gene (DT-A, Gibco) was also added to the vector construct to kill cells in which the targeting cassette was integrated nonhomologously.

Transfection/Knockout Procedures

Transfection of three fetal fibroblasts cell lines (two from a male Jersey bovine and one from a female Jersey bovine) was performed using a standard electroporation protocol as follows. The medium used to culture the bovine fetal fibroblasts contained 500 ml Alpha MEM (Gibco, 12561-049), 50 ml fetal calf serum (Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a targeted confluency of 80-100%, as determined by microscopic examination. On the day of transfection, about $10^7$ bovine fibroblasts cells were trypsinized and washed once with alpha-MEM medium. After resuspension of the cells in 800 μl of alpha-MEM, 30 μg of DNA was added to the cell suspension and mixed well by pipetting. The cell-DNA suspension was transferred into an electroporation cuvette and electroporated at 1,000 V and 50 μF. After that, the electroporated cells were plated onto twenty 24-well plates with the alpha-MEM medium supplemented with the serum. After a 48 hour-culture, the medium was replaced with medium containing 1 μg/ml of puromycin, and the cells were cultured for 2-3 weeks to select puromycin resistant cells. After selection, all colonies that reached close to 100% confluency were picked, and genomic DNA was extracted from the colonies to screen for the desired homologous recombination events by PCR.

Screening for Targeted Integrations

As described above, the genomic DNA was extracted from each 24-well independently using the PUREGENE DNA isolation Kit (Gentra Systems) according to the manufacturer's protocol. Each genomic DNA sample was resuspended in 20 μl of 10 mM Tris-Cl (p H8.0) and 1 mM EDTA (EDTA). Screening by PCR was performed using the following primer pair 5'-aag aag aga aag gta gaa gac ccc aag gac-3' (SEQ ID NO: 63) and 5'-cct ggg tat aga cag gtg ggt att gtg c-3' (SEQ ID NO: 64). The sequence of one primer is located in the alpha-1,3-galactosyltransferase knockout vector, and the sequence of the other primer is located just outside of the integrated vector in the targeted endogenous locus (FIG. 23). Therefore, the expected PCR product should be detected only when the knockout vector is integrated into the targeted locus by homologous recombination.

The PCR reaction mixtures contained 18.9 μl water, 3 μl of 10×LA PCR buffer II ($Mg^{2+}$ plus), 4.8 μl of dNTP mixture, 10 pmol forward primer, 10 pmol of reverse primer, 1 μl of genomic DNA, and 0.3 μl of LA Taq. Forty cycles of PCR were performed by incubating the reaction mixtures at the following conditions: 85° C. for three minutes, 94° C. for one minute, 98° C. for 10 seconds, and 68° C. for 15 minutes. After PCR, the reaction mixtures were analyzed by electrophoresis. Puromycin-resistant clones that generated PCR products of the expected size were selected (FIG. 23). Thus, bovine fibroblast cell lines in which one allele of the α-1,3-galactosyltransferase locus is mutated by the knockout vector were successfully generated.

EXAMPLE 7

Alternative Method for Producing Transgenic Ungulates Using Adeno-Associated Viruses to Mutate an Endogenous Gene Adeno-associated virus (AAV) can be used for specific replacement of targeted sequences present in the genome of cells (Inoue et al., Mol. Ther. 3: 526-530, 2001); Hirata et al., J. Virol. 74: 16536-16542, 2000); Inoue et al, J. Virol. 73: 7376-7380, 1999); and Russell et al., Nat. Genet. 18: 325-330, 1998)). The gene targeting rate is highly efficient in comparison to more conventional gene targeting approaches. AAV has a broad range of host and tissue specificities, including specificity for both bovine and human skin fibroblasts. Thus, AAV can be used to produce transgenic ungulate cells containing one or more mutations in an endogenous immunoglobulin (e.g., mu heavy chain, lambda light chain, kappa light chain, or J chain), alpha-(1,3)-galactosyltransferase, or prion gene. These transgenic cells can then be used in the nuclear transfer methods described herein to produce transgenic ungulates of the present invention.

Using AAV resulted in homologous recombination of the bovine immunoglobulin heavy chain locus at higher frequencies than previously obtained using traditional gene targeting strategies (i.e., electroporation and lipofection procedures). In the first round of gene targeting experiments, five appropriately targeted fibroblast clones were obtained out of 73 stable transductants containing the DNA introduced through an AAV vector.

These experiments were carried out as follows.

AAV Knockout Vectors

Figure 24:
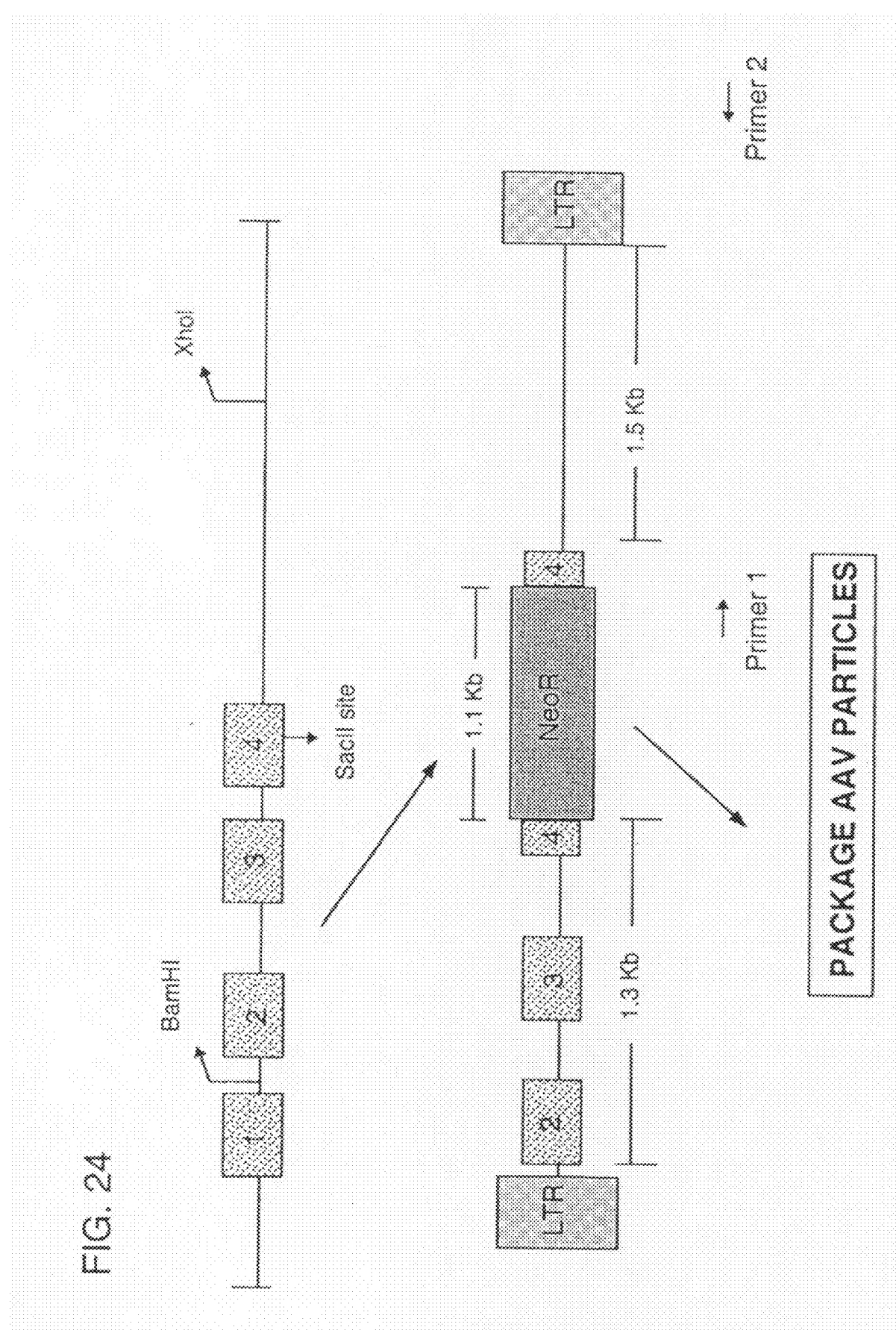
FIG. 24 is a schematic illustration of a BamHI-XhoI fragment containing exons 2, 3, and 4 that was used as a backbone for the AAV targeting vector. A neomycin resistance marker was used for insertional mutagenesis of the locus by insertion into exon 4. The location of the annealing sites for the PCR primers that were used for subsequent confirmation of appropriate targeting is indicated.

AAV constructs can disrupt a gene either by simple insertion of foreign sequences or replacement of endogenous sequences with new sequence present in the AAV vector. FIG. 24 shows an AAV construct in which all four coding exons of the bovine immunoglobulin heavy chain mu constant region are present on a 2822 base pair BamHI-XhoI fragment. A 1.16 Kb fragment containing a neomycin resistance marker present in the commercially available vector, pMC1Neo, was inserted into a SacI site present in exon 4 of the mu heavy chain locus from a Holstein bovine. This locus is the one contained in the phage clone isolated to generate the knockout vector described in Example 3. To generate the AVV vector, the SacII site in the mu heavy chain locus was filled in to create blunt ends, which were then ligated to blunt SalI linkers (New England Biolabs). Then, the XhoI fragment of pMC1Neo, which contains the neomycin resistance gene, was ligated to the SalI site added to the locus through the SalI linker. This ligation can be performed because the XhoI and SalI restriction sites have compatible ends. This knockout vector causes a disruptional insertion of the neomycin resistance gene into the endogenous mu heavy chain gene, thereby inactivating the mu heavy chain gene. This gene inactivation occurs without deleting regions of the endogenous mu locus.

Figure 25:
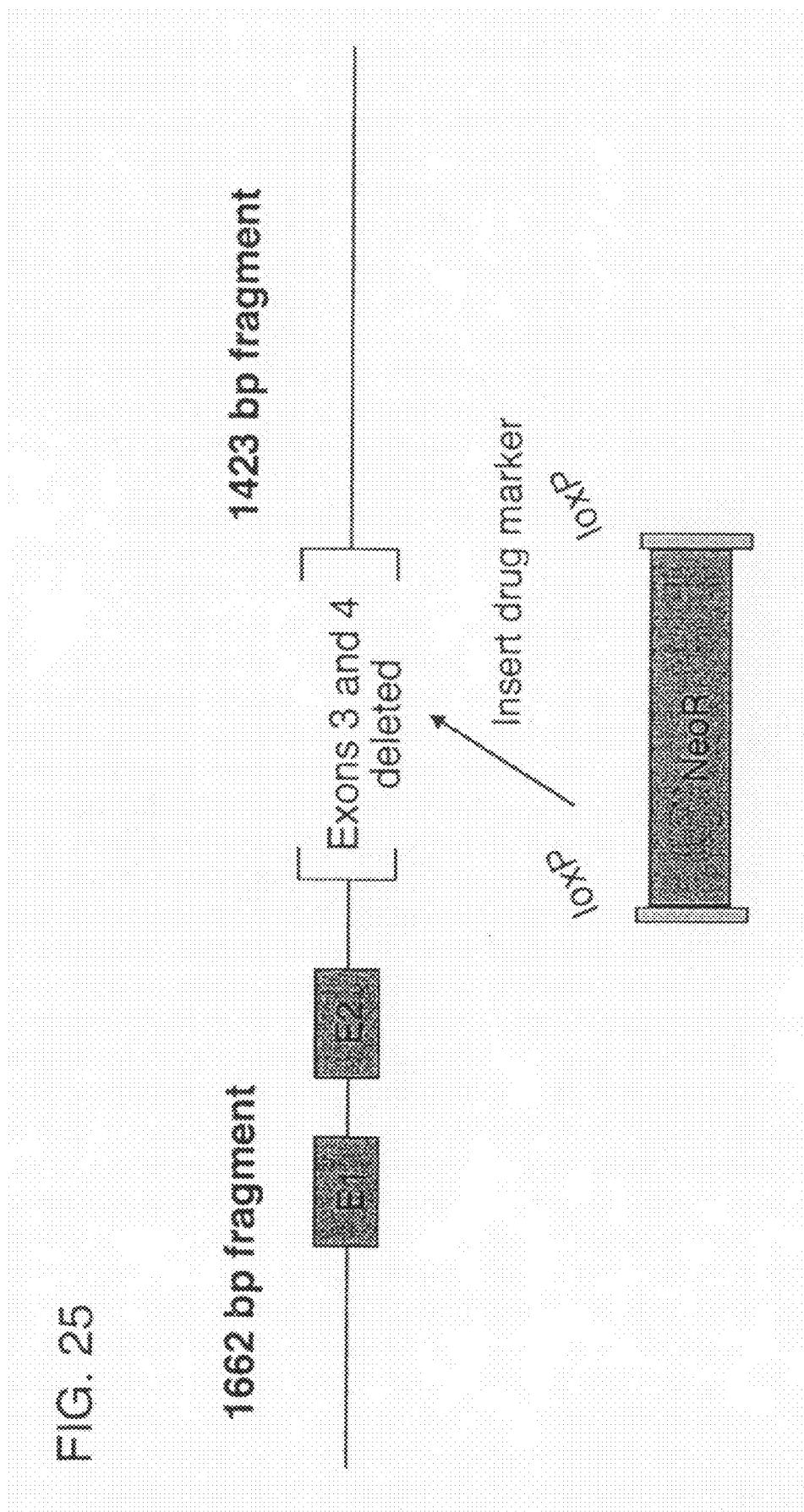
FIG. 25 is a schematic illustration of the construction of an adeno-associated viral construct designed to remove endogenous bovine IgH sequence.

An alternative vector was designed to remove exons 3 and 4 from the endogenous locus during targeting, resulting in the replacement of these two exons with a functional copy of the neomycin resistance gene (FIG. 25). This construct was generated using PCR amplification of genomic DNA from a female Jersey bovine. In particular, the 3' region of homology was amplified using the following primers: 5'-GGG GTC TAG Agc aga cac tac act gat ggg ccc ttg gtc c-3' (SEQ ID NO: 65), which adds an XbaI restriction site, and 5'-GGG GAA GCT Tcg tgt ccc tgg tcc tgt ctg aca cag-3' (SEQ ID NO: 66), which adds a HindIII restriction site. The 5' region of homology was amplified with primers 5'-GGG GCT CGA Ggt cgg cga agg atg ggg gga ggt g-3' (SEQ ID NO: 67), which adds a XhoI restriction site, and 5'-GGG GGG TAC Cgc tgg gct gag ctg ggc aga gtg gg-3' (SEQ ID NO: 68), which adds a KpnI restriction site. The capitalized nucleotides in these primer sequences are nucleotides that do not anneal to the mu heavy chain locus but are included in the primers to add restriction sites to facilitate later subcloning steps. The first four guanines are added to separate the restriction sites from the very end of the primers because restriction enzymes do not cleave sites that are at the very end of primers as well as internal sites. The 5' region of homology is 1.5 Kb long and contains exons 1 and 2. The 5' region of homology also contains the first 25 nucleotides of exon 3 to maintain the splice acceptor site of exon 3. The splice acceptor site allows exon 3 to be used for splicing and thus prevents the possible splicing of exons 1 and 2 to the downstream transmembrane domain to form an aberrant membrane-bound product. The 3' region of homology is 1.24 Kb long and contains the region immediately downstream of exon 4.

For the construct shown in FIG. 24, the targeting cassette was inserted into the AAV vector reported by Ryan et al. (J. Virol. 70:1542-1553, 1996), which contains viral long terminal repeat (LTR) sequences, using standard methods. The AAV vector was packaged into capsids using the TtetA2 packaging cell line as previously described (Inoue and Russell, J. Virol. 72: 7024-7031, 1998) and purified as previously described (Zolotukhin et al., Gene Therapy, 6: 973-985, 1999). For the construct shown in FIG. 25, the above method or any other standard method can be used to insert the targeting-cassette into the AAV vector described by Ryan et al. or any other AAV vector (such as a commercially available vector from Stratagene) and generate viruses containing the vector.

Transduction Procedures

Fibroblasts from a female Jersey bovine were seeded into one well of a 48-well tissue culture plate at 40,000 cells per well and cultured in complete medium at 38.5° C. and 5% $CO_2$ until cells attached to the bottom surface of the well. Once cells adhered, the medium was removed and replaced with 0.2 ml of fresh medium containing AAV particles with the vector shown in FIG. 24 at a multiplicity of infection (MOI) of 500-20,000 particles/cell. The MOI was chosen based on pilot experiments that determined the resulting numbers of colonies and the spacing of the colonies during the drug selection phase. Plates were incubated overnight. After this incubation, the transduced wells were rinsed with calcium and magnesium-free PBS and detached from the wells using either trypsin or the cell dissociation buffer described above. A uniform cell suspension was obtained by gentle pipetting of the detached cells, and the cells from the well were redistributed among ten 100 mm tissue culture dishes. Dishes were incubated with complete medium overnight.

Following this incubation of the 100 mm dishes, the medium was replaced with selective medium containing G418 at a concentration of 350 micrograms/ml. Selective medium was changed every 2-3 days until colonies were macroscopically visible on the surface of the dish. At that point, individual colonies were picked and transferred into their own vessels.

Regions containing colonies were marked on the outer surface of the tissue culture dish. Once all colonies were circled, medium was aspirated off the plates, and the plates were washed three times with calcium and magnesium-free PBS. After washing, the plates were flooded with a 1:25 dilution of 1× trypsin and allowed to sit at room temperature until the colonies had visibly begun to detach from the surface of the plate. Plates were kept stationary to prevent detached colonies from floating to another location of the plate. A pipet tip was used to pick up cell clumps in a volume of 50 microliters, and the contents of the pipet tip were transferred into one well of a 24 well tissue culture plate. Once all colonies were transferred, complete medium containing G418 was added, and the isolated clones were allowed to proliferate to near confluency.

When an individual well was close to confluency, it was washed twice with calcium and magnesium free PBS. Cells were detached using 0.2 ml of cell dissociation buffer. Of this cell suspension, 20 µl was transferred to a new 24 well plate, and the remaining cells were allowed to reattach to the surface of the original 24 well plate following the addition of 2.0 ml of complete medium. The original plate was incubated to 100% confluency. The new plate serves as a source of appropriately targeted cells for future bovine cloning procedures.

When a well from the original 24 well plate became 100% confluent, the medium was removed, and the cells were washed once with PBS. PBS was removed and replaced with a cell lysis buffer adopted from Laird et al. (Nucleic Acids Res. 19:4293, 1991). Briefly, 0.2 ml of lysis buffer containing 200 mM NaCl, 100 mM Tris-HCl pH 8.5, 5 mM EDTA, 0.2% SDS, and 100 ug/ml proteinase K was added to the well. The plate was returned to the incubator for between three hours and overnight. The viscous cell lysate was then transferred to a microfuge tube. An equal volume of isopropanol was added to precipitate DNA. Following a 10 minute spin in a microfuge, the supernatant was discarded, and the pellet was washed once with 0.5 ml of 70% ethanol. After removal of the ethanol, the DNA pellet was air-dried and resuspended in 35 microliters of TE buffer (10 mM Tris pH 8 and 1 mM EDTA). Aliquots of 3 µl were used for PCR analysis.

PCR Analysis

DNA samples from drug resistant clones transduced with AAV particles were screened for appropriate targeting of the vector using PCR analysis. This screening strategy used one primer that anneals within the DNA encoding the drug selection marker and another primer that anneals within the targeted locus, but outside the sequence present in the AAV targeting particles. PCR products are only detected if the AAV targeting DNA has integrated into the desired location of the endogenous genome.

Figure 26:
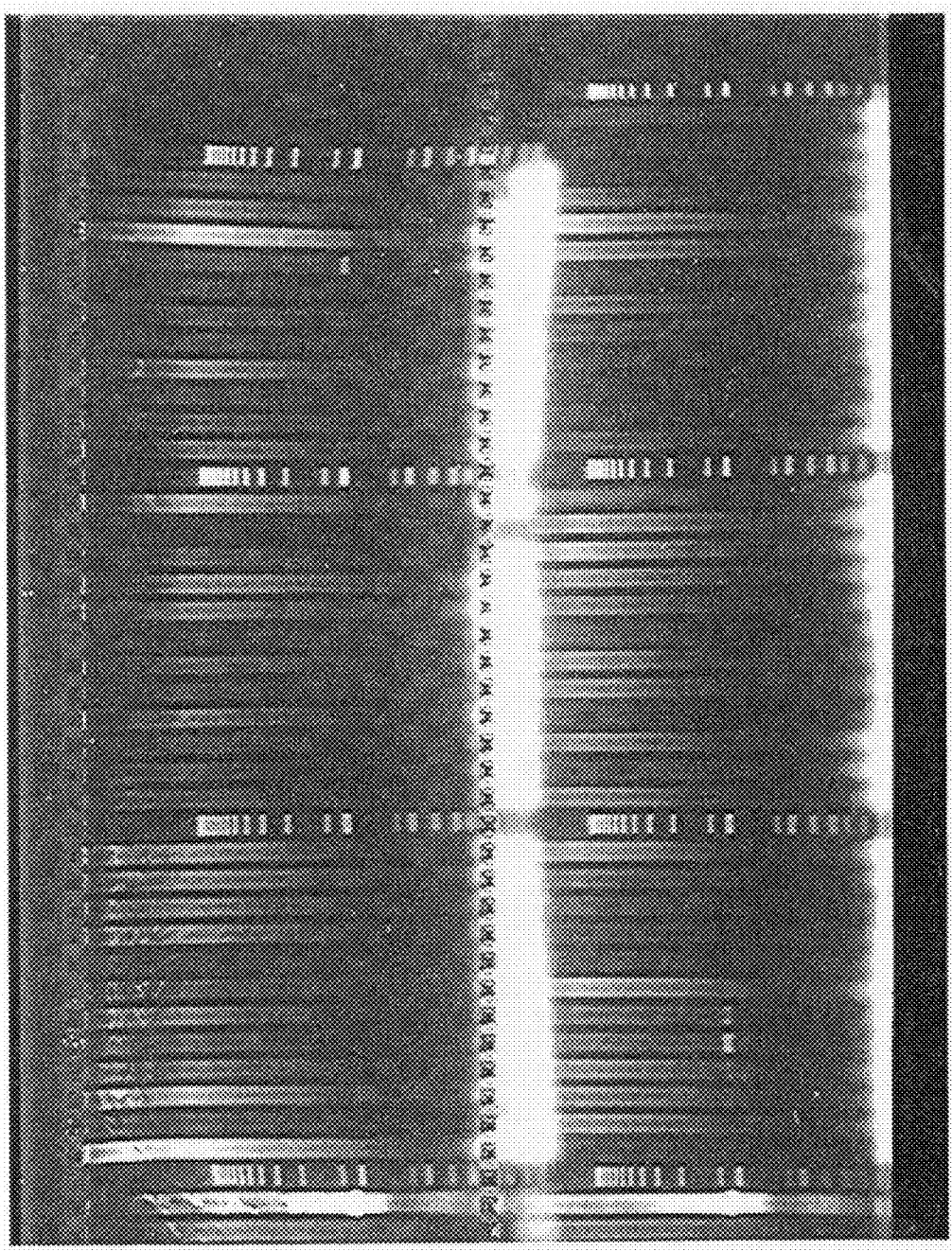
FIG. 26 is a photograph of an agarose gel showing the PCR analysis of individually transduced clones for appropriate targeting events. The vector used in this experiment is shown in FIG. 25. PCR products indicative of appropriate targeting are marked with asterisks.
Figures 28A, 28B:
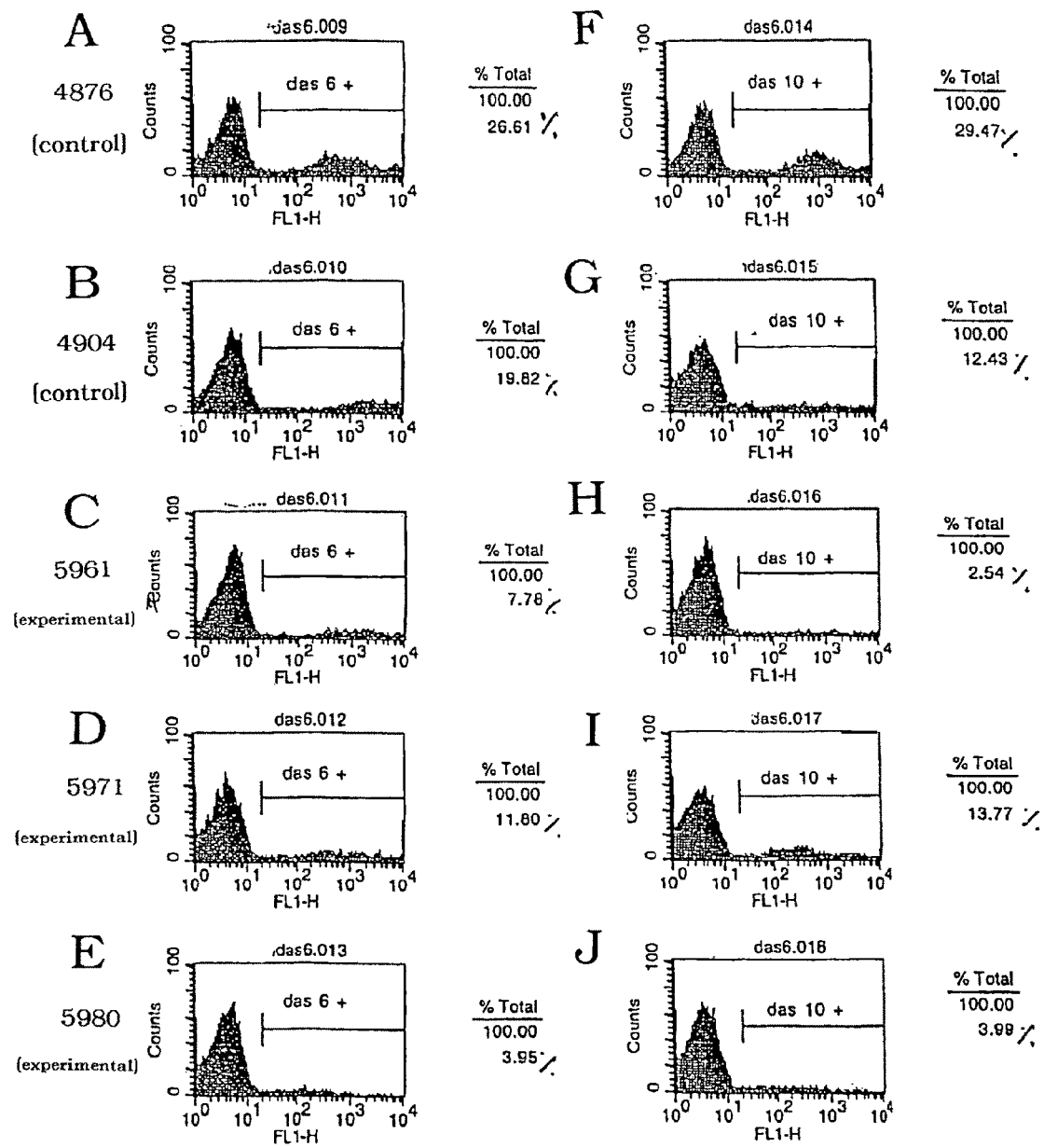

Results from a single targeting experiment using these AAV particles are shown in FIG. 26. Based on this analysis, five out of 73 independent clones contained the appropriate targeted vector DNA.

This method may also be used with the AAV vector shown in FIG. 25 or with any other appropriate adenovirus or adeno-associated viral vector. If desired, the second mu heavy chain allele can be mutated in the isolated colonies by transducing them with an AAV vector with a different antibiotic resistance gene (i.e., a gene other than a neomycin resistance gene). To select the resulting homozygous knockout cells, the infected cells are cultured in the presence of the corresponding antibiotic. Alternatively, the isolated colonies can be transduced with an AAV vector containing a neomycin resistance gene and cultured in the presence of a high concentration of antibiotic (i.e., a concentration of antibiotic that kills heterozygous knockout cells but not homozygous knockout cells).

EXAMPLE 8

Evidence for Nuclear Reprogramming Deficiencies in Traditional Bovine Nuclear Transplant Embryos Traditional nuclear transplant techniques generally produce a low percentage of live births. As described below, this in efficiency may be due to, at least in part, the inability of the reconstituted oocyte to reprogram the donor cell or donor nucleus to promote the transcription of genes desirable for development of the oocyte and to inhibit the transcription of genes undesirable for development. Examples 11 and 12 describe improved cloning methods that can be used to produce transgenic ungulates with a mutation in a prion gene and optionally with a xenogenous Ig gene in the methods of the present invention.

Distribution of Nuclear Envelope, Nuclear Matrix, and Chromatin-Matrix Interface Components During Bovine Preimplantation Development To determine the distribution of nuclear envelope (B-type and A/C-type lamins), nuclear matrix (NuMA), and chromatin-matrix interface (AKAP95) components in preimplantation embryos, bovine embryos were produced by in vitro fertilization (IVF) and examined by immunofluorescence analysis. Bovine in vitro fertilization was performed as described previously (Collas et al., Mol. Reprod. Devel. 34: 212-223, 1993). Briefly, frozen-thawed bovine sperm from a single bull was layered on top of a 45-90% Percoll gradient and centrifuged for 30 minutes at 700×g. The concentration of sperm in the pellet was determined, and the sperm was diluted such that the final concentration at fertilization was $10^6$ sperm/ml. At 22 hours post maturation, oocytes were washed three times in TL HEPES and placed in 480 µl fertilization medium. Twenty microliters sperm suspension was added at $10^6$ sperm/ml for 50 oocytes. Embryos were placed in culture in four-well tissue culture plates containing a monolayer of mouse fetal fibroblasts in 0.5 ml of embryo culture medium covered with 0.3 ml of embryo tested mineral oil (Sigma). Between 25 and 50 embryos were placed in each well and incubated at 38.5° C. in a 5% $CO_2$ air atmosphere. Fertilization rates were over 90% as determined by pronuclear development.

For the immunofluorescence analysis of these in vitro fertilized bovine embryos, anti-human lamin B antibodies were obtained from Dr. Jean-Claude Courvalin, CNRS, Paris, France. Anti-lamins A/C monoclonal antibodies were purchased from Santa-Cruz Biotechnology, and anti-NuMA antibodies were obtained from Transduction Laboratories. Anti-rat AKAP95 affinity-purified rabbit polyclonal antibodies were obtained from Upstate Biotechnologies. The in vitro fertilized bovine embryos were settled onto poly-L-lysine-coated glass coverslips, fixed with 3% paraformaldehyde for 15 minutes, and permeabilized with 0.1% Triton X-100 for 15 minutes (Collas et al., J. Cell Biol. 135:1715-1725, 1996). The proteins were blocked with 2% BSA in PBS/0.01% Tween 20 (PBST) for 15 minutes. Primary antibodies (anti-AKAP95, anti-lamin B, anti-LBR, anti-NuMA, and anti-lamins A/C) and secondary antibodies were incubated each for 30 minutes and used at a 1:100 dilution in PBST-BSA. DNA was counterstained with 0.1 µg/ml Hoechst 33342 incorporated in the antifade mounting medium. Samples were mounted onto slides and coverslips sealed with nail polish. Immunofluorescence observations were made on an Olympus BX60 epifluorescence microscope and photographs were taken with a JVC CCD camera and AnalySIS software. Images were processed using the Aldus Photostyler software. Relative quantification of fluorescence signals was performed using the AnalySIS quantification program. Data were expressed as mean relative fluorescence intensities.

Immunofluorescence analysis of bovine embryos showed that B-type lamins were detected at the nuclear periphery (FIG. 29A). Lamins A/C, however, were not detected at the pronuclear or 8-cell stage. This failure to detect lamins A/C at these early cell stages is expected for a marker of differentiated cells (Guilli et al., EMBO J. 6:3795-3799, 1987). The nuclear matrix structural protein, NuMA, was detected in all the stages that were examined (FIG. 29A). However, in bovine pronuclear stage embryos, NuMA labeling was restricted to the female pronucleus (FPN), the smallest of both pronuclei (FIG. 29A arrows). AKAP95, which was recently characterized in early mouse embryos (Bomar et al., 2002 manuscript submitted) and detected using affinity-purified anti-rat AKAP95 antibodies, was also restricted to the female pronucleus (FIG. 29A). Nevertheless, intranuclear distribution of AKAP95 was observed in nuclei of all blastomeres in subsequent developmental stages (FIG. 29A).

Figure 29B:
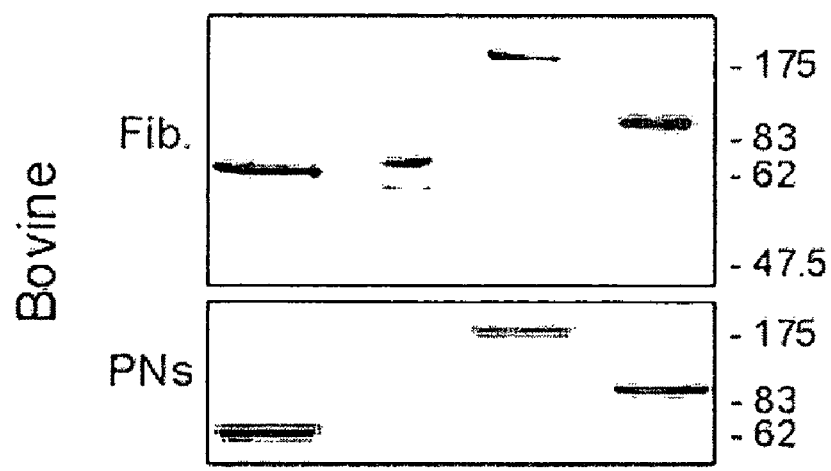

Specificity of immunofluorescence labeling was verified by Western blot analysis of bovine primary fetal fibroblasts and pronuclear stage in vitro fertilized embryos (FIG. 29B). For this analysis, proteins were resolved by 10% SDS-PAGE at 40 mA per gel. Proteins were electrophoretically transferred onto a nitrocellulose membrane in transfer buffer (25 mM TrisHCl, pH 8.3, 192 mM glycine, 20% methanol, and 0.1% SDS) at 100 V for one hour. Membranes were washed for 10 minutes with Tris-buffered saline (TBS; i.e., 140 mM NaCl, 2.7 mM KCl, and 25 mM Tris-HCl at pH 8.0), blocked for one hour with TBST (TBS with 0.05% Tween-20) containing 5% milk, and incubated for 1.5 hours with the following primary antibodies: anti-AKAP95 (1:250 dilution), anti-lamin B (1:1000), anti-LBR (1:500), anti-NuMA (1:500), and anti-lamins A/C (1:500). Blots were washed twice for 10 minutes in TBST and incubated for one hour with horse radish peroxidase (IRP)-conjugated secondary antibodies. Blots were washed twice for 10 minutes in TBS and developed using enhanced chemiluminescence (ECL, Amersham).

All proteins were detected at their expected apparent $M_r$: 68 kDa (B-type lamins), 70 and 60 kDa (lamins A and C, respectively), ~180 kDa (NuMA), and 95 kDa (AKAP95). Altogether, these results indicate that preimplantation bovine embryos express nuclear structural proteins that can be detected with cross-reacting antibodies. Notably, lamins A/C are not immunologically detected in bovine preimplantation embryos. Because lamins A/C are expressed in somatic cells (FIG. 29B), they potentially constitute molecular markers for nuclear reprogramming in nuclear transplant embryos.

Dynamics of Nuclear Envelope, NuMa, and AKAP95 in Nuclear Transplant Bovine Embryos The dynamics of nuclear envelope and nuclear matrix structures was examined during traditional nuclear transplantation procedure in bovine. These structures were investigated using antibodies to lamins A/C and B, NuMA, and AKAP95, respectively. To determine the dynamics of these markers during nuclear remodeling, bovine nuclear transplant embryos were produced using primary fetal fibroblasts, which were isolated as described previously, as the donor cells (Kasinathan et al., Biol. Reprod. 64: 1487-1493, 2001). Briefly, cells were harvested from bovine fetuses by trypsinization using 0.08% trypsin and 0.02% EDTA in PBS (trypsin-EDTA). Cells were seeded in a T75 culture flask (Corning) in α-MEM (Gibco) supplemented with 10% fetal bovine serum (FBS; Hyclone), 0.15 g/ml glutamine (Sigma), 0.003% β-mercaptoethanol (Gibco), and an antibiotic-antimycotic (Gibco). On day three after seeding, cells were harvested with trypsin-EDTA and frozen in α-MEM/DMSO. G1 cells were isolated as described previously (Kasinathan et al., Biol. Reprod. 64: 1487-1493, 2001). Briefly, 24 hours before isolation, $5.0 \times 10^5$ cells were plated in a T75 flask containing 10 ml of MEM/FBS. The following day, the plates were washed with PBS, the culture medium was replaced for 1-2 hours, and the plates were shaken for 30-60 seconds on a Vortex at medium speed. The medium was removed, centrifuged at 500×g for five minutes, and the pellet was resuspended in 250 µl of MEM/FBS. Cell doublets attached by a cytoplasmic bridge were selected using a micropipette and used for nuclear transfer.

Bovine nuclear transfer was carried out as described earlier (Kasinathan et al., Biol. Reprod. 64: 1487-1493, 2001). In vitro-matured oocytes were enucleated 18-20 hours post-maturation. After transferring G1 donor cells into the perivitelline space, they were fused using a single electrical pulse of 2.4 kV/cm for 20 microseconds (Electrocell Manipulator 200, Genetronics). At 28-30 hours post maturation (i.e., 28-30 hours after oocytes were placed in maturation medium after collection from ovaries and at least two hours after fusion with donor cells) reconstituted oocytes and parthenogenetic controls were activated with calcium ionophore (5 µM) for four minutes (Cal Biochem) followed by 10 µg cycloheximide and 2.5 µg cytochalasin D (Sigma) in ACM medium (100 mM NaCl, 3 mM KCl, 0.27 mM $CaCl_2$, 25 mM $NaHCO_3$, 1 mM sodium lactate, 0.4 mM pyruvate, 1 mM L-glutamine, 3 mg/ml BSA, 1%, BME amino acids, and 1% MEM nonessential amino acids, for five hours (Liu et al., Mol. Reprod. Dev. 49: 298-307, 1998). After activation, nuclear transplant embryos or oocytes eggs were washed five times and co-cultured with mouse fetal fibroblasts at 38.5° C. in a 5% $CO_2$ atmosphere.

Figure 30:
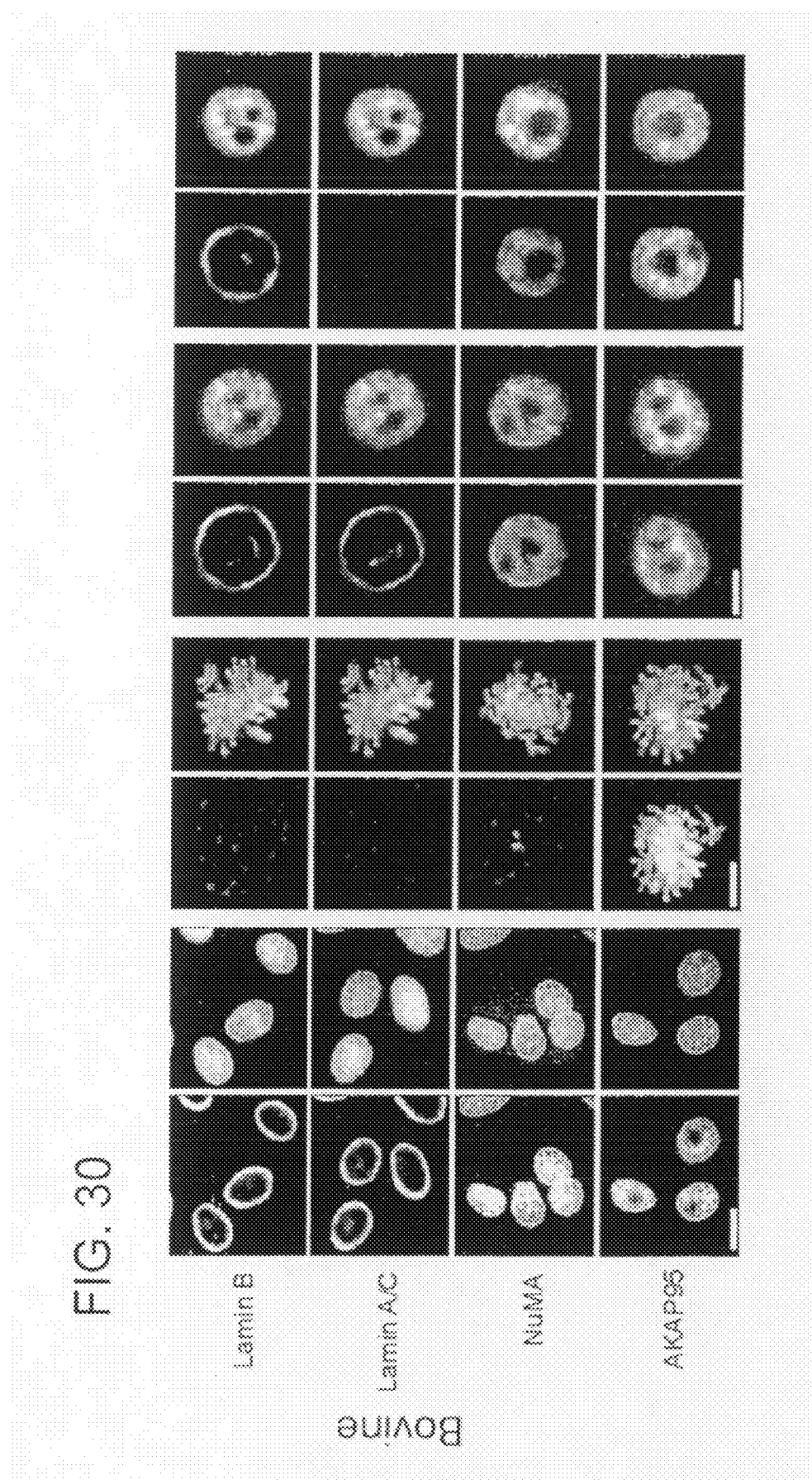
FIG. 30 is a photograph of bovine donor fibroblasts (Donor cell), nuclear transplant embryos at the premature chromatin condensation stage (three hours post-fusion), nuclear transplant embryos at the pronuclear stage (19 hours post-fusion), and parthenogenetic pronuclear stage embryos activated as described herein. Disassembly of the donor nucleus and assembly of the new pronuclei were monitored at the premature chromatin condensation stage three hours post injection "hpi" ("PCC") and seven hours post injection ("NT PN"), using anti-lamin B, lamins A/C, NuMA, and AKAP95 antibodies. Female pronuclei formed after parthenogenetic activation of MII oocytes with 10 mM SrCl$_2$ were also analyzed five hours after start of activation treatment ("Parth. PN"). Lamins A/C were assembled in pronuclei of bovine pronuclear stage nuclear transplant embryos. DNA was counterstained with 0.1 μg/ml Hoechst 33342. TRITC refers to labeling with TRITC-conjugated secondary antibodies (bars, 20 μm).

Reconstituted embryos were activated using standard methods, and three hours post-fusion, embryos at the premature chromatin condensation (PCC) stage were fixed with paraformaldehyde and analyzed by immunofluorescence using antibodies to lamins A/C, lamin B, NuMA, and AKAP95 (FIG. 30, PCC). Furthermore, groups of nuclear transplant embryos that were allowed to progress to the pronuclear (PN) stage (i.e., 15 hour post-fusion bovine embryos) were analyzed similarly (FIG. 30, nuclear transplant-PN). As controls, parthenogenetic oocytes activated as described herein were also examined at the pronuclear stage (FIG. 30, Parth. PN).

As expected, somatic donor cells (bovine fetal fibroblasts, FIG. 30) expressed all markers with a distribution anticipated from the literature. At the premature chromatin condensation stage, distinct condensed chromosome masses were evidenced by DNA staining with Hoechst 33342. Lamins A/C and B were not detected on or near the condensed chromosomes (FIG. 30, PCC), presumably as a result of their dispersal in the egg cytoplasm. Some labeled NuMA was detected; this NuMA was presumably associated with the spindle poles maintaining the condensed chromosomes. AKAP95, in contrast, was associated with the condensed (PCC) chromosomes. This result is reminiscent of AKAP95 labeling in mitotic human cells (Collas et al., J. Cell Biol. 147:1167-1180, 1999; Steen et al., J. Cell Biol. 150:1251-1262, 2000). At the pronuclear stage, all markers were detected. Lamins A/C were present at the pronuclear envelope (FIG. 2, nuclear transplant-PN). This contrasted with their absence from the envelope of control parthenote pronuclei (FIG. 30) and from the envelope of fertilized pronuclei (FIG. 29A). Lamin B was detected in nuclear transplant pronuclei, as in control pronuclei. Likewise, NuMA and AKAP95 decorated the nuclear interior except for the nucleoli. NuMA labeling was consistently brighter in nuclear transplant pronuclei than in control parthenogenetic pronuclei (compare nuclear transplant PN and Parth. PN, FIG. 30). Collectively, these observations indicate that pronuclei of nuclear transplant embryos reassemble the somatic nuclear markers lamins A and C and display strong NuMA staining.

Differential Anchoring of AKAP95 in Pronuclei of Parthenogenetic Embryos and Nuclear Transplant Embryos The A-kinase anchoring protein AKAP95 is a nuclear protein implicated in mitotic chromosome condensation. For use as another molecular marker affecting reprogramming of somatic nuclei after nuclear transplant, the intranuclear anchoring properties of AKAP95 were characterized in bovine nuclear transplant pronuclear stage embryos formed from fetal fibroblasts. Anchoring of AKAP95 in pronuclei from parthenogenetic embryos and nuclei of somatic donor cells was also examined.

Figure 31:
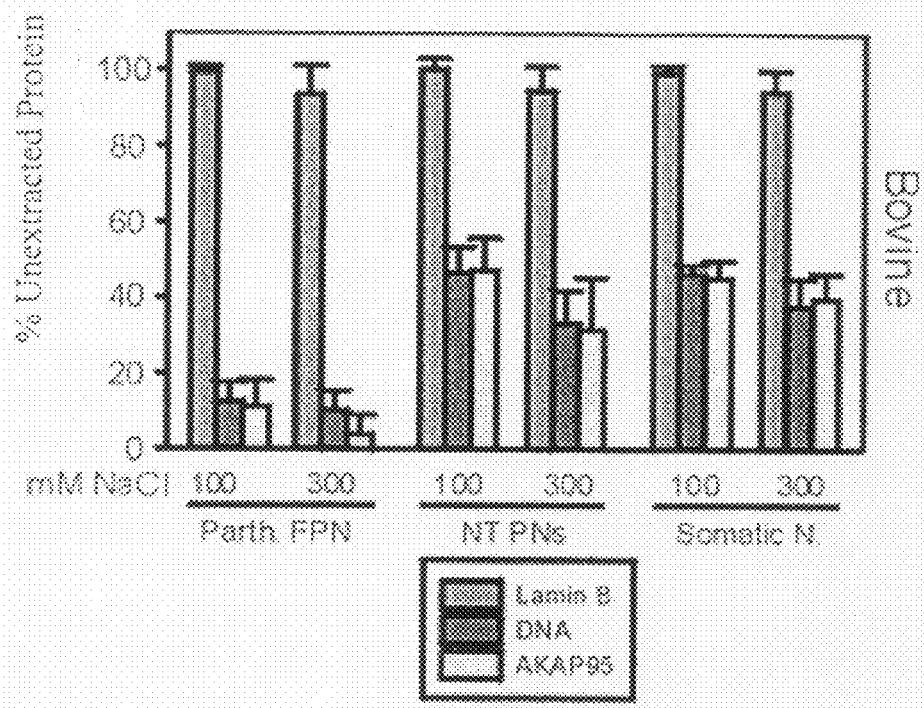
FIG. 31 is a graph demonstrating that AKAP95 is more strongly anchored in pronuclei of nuclear transplant embryos compared to parthenogenetic embryos. This graph shows the relative percent of unextracted lamin B, AKAP95, and DNA labeling in pronuclei of parthenotes, nuclear transplant embryos, and somatic donor nuclei after in situ extraction with 0.1% Triton X-100 and 1 mg/ml DNAse I together with 100 or 300 mM NaCl for 30 minutes at room temperature prior to fixation with 3% paraformaldehyde. Localization of B-type lamins (red) and AKAP95 (green) was examined by double immunofluorescence. Fluorescence labeling intensity in each channel—red, (lamin B), blue (DNA), and green (AKAP95)—was quantified. The reference value (100% unextracted) represents relative amounts of B-type lamins, DNA, and AKAP95 staining in embryos or cells permeabilized with 0.1% Triton X-100 only prior to fixation. Approximately 30 embryos were examined in each group.

Intranuclear anchoring of AKAP95 in pronuclear embryos was examined in situ by extraction of embryos with 0.1% Triton X-100, 1 mg/ml DNAse I, and either 100 or 300 mM NaCl for 30 minutes at room temperature. As noted above, male pronuclei did not harbor any AKAP95. In contrast, a significant amount of AKAP95 and DNA was resistant to DNAse 1 and 300 mM NaCl in pronuclei of nuclear transplant embryos, and in donor nuclei in bovine (FIG. 31). B-type lamins were not extracted by DNAse 1 and 300 mM NaCl in parthenote or nuclear transplant pronuclei (FIG. 31), suggesting that alterations in AKAP95 and DNA distributions did not result from gross changes in nuclear architecture. These data indicate that, as in somatic nuclei, AKAP95 is more tightly anchored to intranuclear structures in nuclear transplant pronuclei than in parthenogenetic pronuclei in the bovine. Whether this association imposes constraints on DNA organization or results from altered genome organization in nuclear transplant embryos remains to be determined. As DNAse I-resistant DNA is transcriptionally silent, incomplete remodeling of AKAP95 anchoring after nuclear transplantation likely impairs expression of developmentally important genes.

Transcriptional Misregulation of Lamins A/C in Nuclear Transplant Bovine Embryos A striking observation was that lamins A/C reassemble at the periphery of pronuclei in bovine nuclear transplant embryos, whereas this somatic-specific marker is absent from in vitro fertilized, and parthenogenetic pronuclei. Thus, we investigated whether reassembly of lamins A/C resulted from (i) re-targeting of somatic lamins disassembled at the premature chromatin condensation stage (FIG. 30), (ii) translation and assembly of lamins from a pool of maternal lamin A/C mRNA, or (iii) de novo transcription of the somatic lamin A (LMNA) gene in nuclear transplant pronuclei.

To distinguish between these possibilities, bovine nuclear transplant embryos were produced by either the "traditional" nuclear transplant procedure as described herein, nuclear transplant followed by activation of reconstituted embryos with the protein synthesis inhibitor cycloheximide (CHX), or by nuclear transplant followed by activation in the presence of the RNA polymerase II (PolII) inhibitor actinomycin D (ActD) to inhibit de novo transcription. For culturing bovine nuclear transplant embryos in cycloheximide, oocytes were activated after nuclear transfer as described above except that oocytes were incubated for 14 hours in cycloheximide (CHX). At 14 hours after activation, oocytes were washed five times and placed in ACM culture medium containing 15 µg/ml Hoechst 33342 (Sigma) for one hour. After incubation, pronuclear development was observed by epifluorescence microscopy. Pronuclear embryos were then fixed in 3% paraformaldehyde in PBS, washed, and mounted on slides. For culturing bovine nuclear transplant oocytes in actinomycin D, oocytes were activated after nuclear transfer as described above except 5 µg/ml actinomycin D (ActD) was added to the cycloheximide incubation step. After five hours, eggs were washed five times and placed in ACM culture medium containing 5 µg/ml actinomycin D. At 14 hours after activation, eggs were washed five times and placed in ACM culture medium containing 15 µg/ml Hoechst 33342 (Sigma) for one hour. After incubation, pronuclear development was observed by epifluorescence microscopy. Pronuclear stage embryos were fixed in 3% paraformaldehyde in PBS, washed, and mounted on slides.

Figure 32:
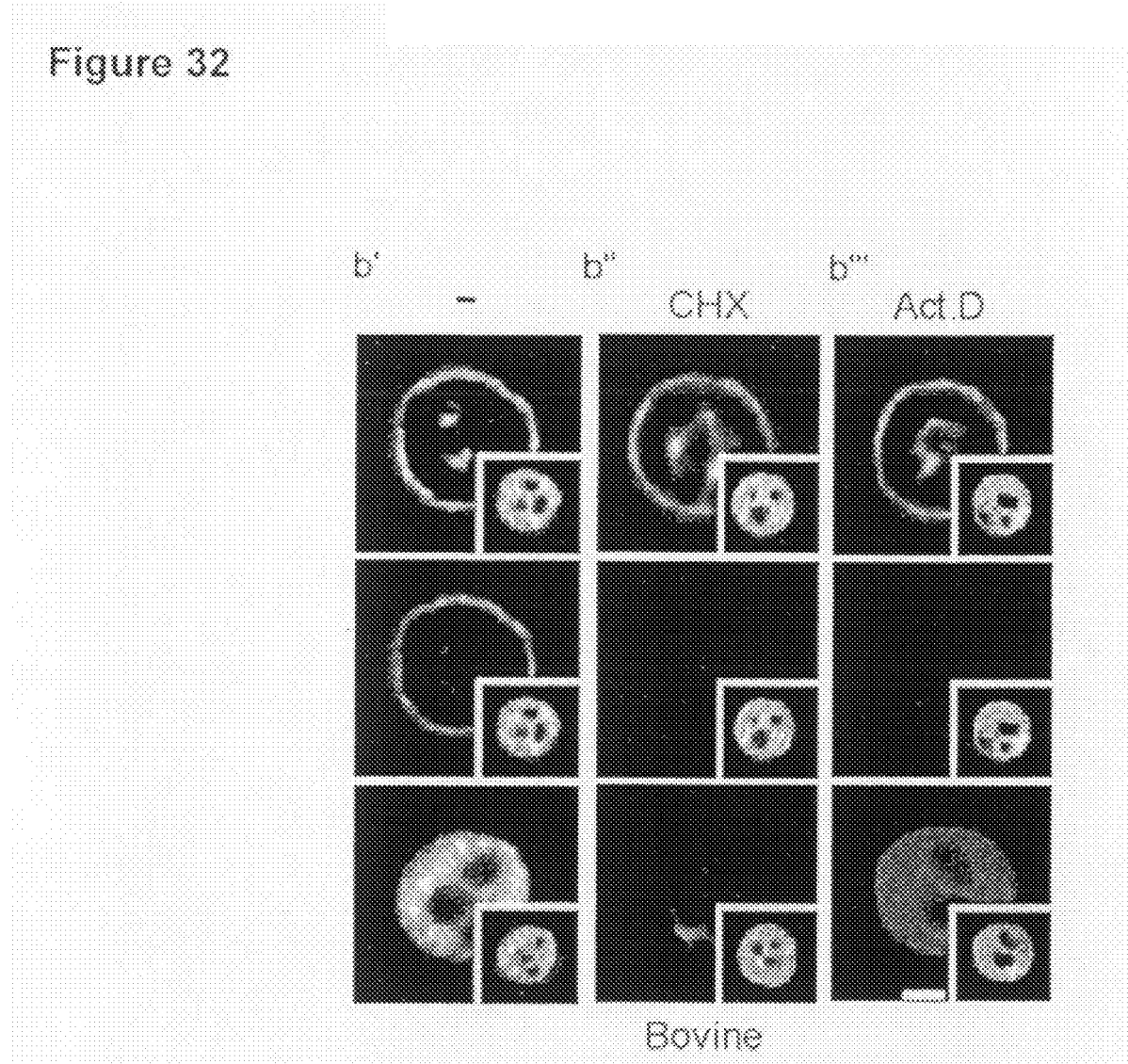
FIG. 32 is a photograph of bovine pronuclear nuclear transplant embryos produced by fibroblast fusion and oocyte activation with either 5 µM ionomycin for four minutes followed by 10 µg/ml cycloheximide/2.5 µg/ml cytochalasin D for four hours (b', -), ionomycin/cycloheximide/cytochalasin D as in (b') followed by an additional nine hours of culture with 10 µg/ml cycloheximide (b", CHX) or incubation as in (b') together with 1 µg/ml actinomycin D during the entire activation treatment (b'"). Anti-lamin B (rabbit polyclonal) and anti-lamins A/C (mAb) antibodies were used on the same preparations. Insets are pictures of DNA labeling with 0.1 µg/ml Hoechst 33342 (bars, 20 µm).

Lamin B assembly around nuclear transplant pronuclei was not affected by either protein or RNA synthesis inhibition. This result indicates that lamin B was reassembled from either a previously disassembled somatic pool and/or from a large pool of lamin B in the oocyte cytoplasm. Lamins A/C, which were detected in nuclear transplant pronuclei (FIG. 30), were absent from nuclei reformed after activation with cycloheximide. This result indicates that lamins A/C assembly requires de novo protein synthesis and that these lamins are not re-targeted from a disassembled somatic pool brought into the oocyte by donor nucleus injection or cell fusion. Furthermore, lamins A/C are not reassembled when embryos are activated in the presence of actinomycin D. This result indicates that lamins A/C reassembly in nuclear transplant pronuclei results from de novo transcription of the LMNA gene in the reconstituted pronucleus. NuMA, which was detected in nuclear transplant pronuclei, is not reassembled in pronuclei of nuclear transplant embryos activated with cycloheximide, but is faintly detected in pronuclei of actinomycin D-treated nuclear transplant embryos. This finding strongly suggests that NuMA reassembly in nuclear transplant pronuclei requires de novo translation that occurs, at least in part, from a pool of maternal NuMA mRNA. The consistent observation that anti-NuMA labeling is weaker in pronuclei of actinomycin D-treated nuclear transplant embryos compared to control untreated nuclear transplant embryos (compare b' and b''' in FIG. 32) suggests that part of NuMA assembly in nuclear transplant pronuclei results from de novo transcription of the NuMA gene at the pronuclear stage.

Collectively, these results indicate that the LMNA gene is not turned off upon nuclear remodeling after nuclear transplantation. Similarly, the NuMA gene apparently remains active in pronuclear nuclear transplant embryos. It is likely that transient inactivation of these genes takes place during premature chromatin condensation, as anticipated from the highly condensed nature of the chromatin (FIG. 30). These results clearly illustrate incomplete nuclear reprogramming in nuclear transplant embryos produced under the conditions described herein. As discussed earlier for AKAP95, we propose that the persistence of lamins A/C in nuclear transplant pronuclei affects gene expression, such as expression of developmentally important genes. The previously reported interactions of lamins A and C with chromatin proteins and DNA, and the association of these lamins with transcription factors also support this hypothesis.

EXAMPLE 9

Exemplary Nuclear Reprogramming Deficiencies in Traditional Bovine Nuclear Transplant Embryos Exemplary differences between naturally-occurring embryos and traditional nuclear transfer embryos are also described below. These differences include differences in pronuclear assembly of differentiated cell-specific A-type nuclear lamins, enhanced pronuclear NuMA and TATA binding protein concentrations, and increased sensitivity of nuclear matrix-chromatin interface component AKAP95 and DNA to extraction with detergent, DNAse and salt.

For these studies, bovine fetal fibroblasts cell lines were established as described previously (Kasinathan et al., Nat. Biotechnol. 19:1176-1178, 2001 and Kasinathan et al., Biol. Reprod. 64:1487-1493, 2001). G1-phase fibroblast doublets were isolated from cultures using a previously described shake-off method (Kasinathan et al., Nat. Biotechnol. 19:1176-1178, 2001). In vitro fertilization with in vitro-matured oocytes was carried out as described previously (Collas et al., Mol. Reprod. Dev. 34:224-231, 1993). For nuclear transplantation (NT) and oocyte activation, nuclear transplantation using G1-phase donor cells was performed at ~20 hours post-maturation (hpm) as reported previously (Kasinathan et al., Nat. Biotechnol. 19:1176-1178, 2001 and Kasinathan et al., Biol. Reprod. 64:1487-1493, 2001). Reconstituted embryos were activated at 28-30 hpm (T=0) with 5 µM calcium ionophore for four minutes followed by 10 µg/ml CHX and 2.5 µg/ml cytochalasin D for five hours. Embryos were washed and co-cultured with mouse fetal fibroblasts (Kasinathan et al., Biol. Reprod. 64:1487-1493, 2001). When reconstituted embryos were cultured in CHX, oocytes were activated as above and cultured with 2.5 µg/ml CHX for another nine hours (total, 14 hours in CHX). Embryos were washed thoroughly and cultured as described (Kasinathan et al., Biol. Reprod. 64:1487-1493, 2001). When reconstituted embryos were exposed to ActD, oocytes were activated as above except that 5 µg/ml ActD was added to the five hour CHX incubation step.

For immunological analysis, cells, oocytes, embryos, nuclei (Example 14), and chromatin masses (Example 14), and were settled onto poly-L-lysine-coated coverslips, fixed with 3% paraformaldehyde for 15 minutes, and permeabilized with 0.1% Triton X-100 for 15 minutes. Proteins were blocked using PBS/2% BSA/0.01% Tween 20. Primary and secondary antibodies (1:100 dilution) were incubated each for 30 minutes. In particular, rabbit polyclonal antibodies against a peptide of human lamin B were used (Chaudhary et al., J. Cell Biol. 122:295-306, 1993). Goat anti-lamin B polyclonal antibodies, anti-lamin A/C monoclonal antibodies, and anti-TBP antibodies from Santa-Cruz Biotechnology were also used. Anti-NuMA monoclonal antibodies were from Transduction Laboratories, and anti-rat AKAP95 affinity-purified polyclonal antibodies were from Upstate Biotechnologies. DNA was counterstained with 0.1 µg/ml Hoechst 33342. Photographs were taken with a JVC CCD camera, and quantification of immunofluorescence intensity was performed using the AnalySIS software. Data were expressed as a mean±SD fluorescence intensity relative to a control in at least three replicates. For in situ extractions, embryos and cells settled on coverslips were incubated for 15 minutes with 0.1% Triton X-100, 1 mg/ml DNAse I, and 300 mM NaCl in Tris-HCl (pH 7.2) prior to immunofluorescence analysis. For immunoblotting, 100 embryos were dissolved in 20 µl SDS sample buffer, proteins resolved by 10% SDS-PAGE, and analyzed with the following antibodies: anti-lamin B, 1:1,000; anti-lamin A/C, 1:250; anti-NuMA, 1:500; anti-AKAP95, 1:250.

Based on the above immunological analysis, the distribution of A/C- and B-type lamins, NuMA and AKAP95 was characterized in bovine fetal fibroblasts commonly used for NT (FIG. 40). In in vitro-produced bovine preimplantation embryos, lamin B was detected at the nuclear periphery as early as the pronuclear (PN) stage (FIG. 40). Lamin A/C was absent, as expected from a marker of differentiated cells. NuMA and AKAP95 were restricted to the female pronucleus at the pronuclear stage but decorated all nuclei in subsequent stages. Specificity of immunofluorescence data was verified on immunoblots (FIG. 40).

Figures 41A, 41B, 41C, 41D:
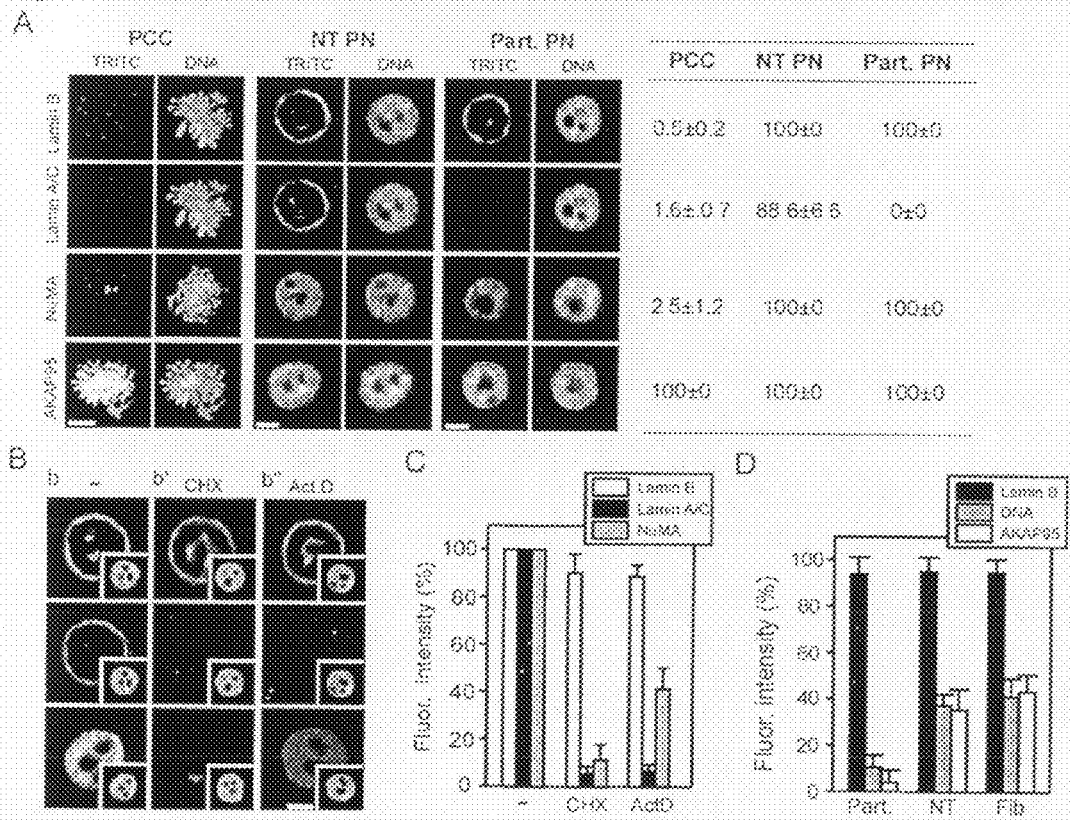
FIGS. 41A-41D illustrate the dynamics of the nuclear envelope, NuMA, and AKAP95 in bovine NT embryos. The disassembly of the donor fibroblast nucleus and assembly of the new pronucleus were immunofluorescently monitored at the PCC and PN stage using indicated antibodies (TRITC) (FIG. 41A). Parthenogenetic pronuclei following a similar activation procedure were also examined (Part. PN). Percent (±SD) embryos labeled with each antibody is shown (n~20 embryos/group in three replicates). Recipient oocytes were activated with either 5 µM ionomycin for four minutes followed by 10 µg/ml CHX/2.5 µg/ml cytochalasin D for four hours (b), ionomycin/CHX/cytochalasin D as in (b) followed by nine hours with 10 µg/ml CHX (b'), or as in (b) together with 5 µg/ml ActD during the activation treatment (b") (FIG. 41B). DNA (insets in B) was labeled with Hoechst 33342.

The dynamics of lamins A/C and B, NuMA, and AKAP95 was examined during morphological nuclear remodeling associated with transplantation of bovine fibroblasts into enucleated oocytes by electrofusion (Kasinathan et al. Biol. Reprod. 64:1487-1493, 2001). Donor nuclei underwent premature chromatin condensation (PCC) within three hours of fusion (FIG. 41A). Nuclear lamins and NuMA were redistributed in the oocyte cytoplasm and were absent from PCC chromosomes (FIG. 41A). AKAP95 was associated with PCC chromosomes, a property reminiscent of mitotic cells. Fourteen hours after start of activation treatment of recipient oocytes, NT embryos displayed fully developed pronuclei (FIG. 41A, NT PN). However, in contrast to pronuclei of parthenogenetic or fertilized embryos, essentially all NT pronuclei expressed strong lamin A/C and NuMA immunoreactivity, two characteristics of the somatic donor cells (FIG. 41A).

Recipient oocyte activation in the presence of 10 µg/ml of the protein synthesis inhibitor cycloheximide (CHX) or 5 ug/ml of the RNA polymerase (Pol) II inhibitor actinomycin D (ActD), both compatible with pronuclear formation, inhibited pronuclear lamin A/C assembly (FIGS. 41B and 41C). This result indicates that assembly of these somatic lamins results from transcription of the somatic lamin A (LMNA) gene. Lamin B assembly was not perturbed by CHX or ActD, indicating that it was re-targeted from a disassembled somatic pool and/or from a maternal pool of B-type lamins (FIGS. 41B and 41C). Essentially no NuMA was detected after CHX exposure; however, 40% of NuMA immunoreactivity in NT pronuclei was detected after ActD treatment (FIGS. 41B and 41C). This result suggests that NuMA assembles as a result of translation from maternal mRNA and of de novo transcription. As lamin A/C and NuMA are abnormally transcribed in NT pronuclei, these proteins can be used as markers to determine the ability of nuclear transfer methods to reprogram the donor genetic material.

Figures 40A, 40B, 40C:
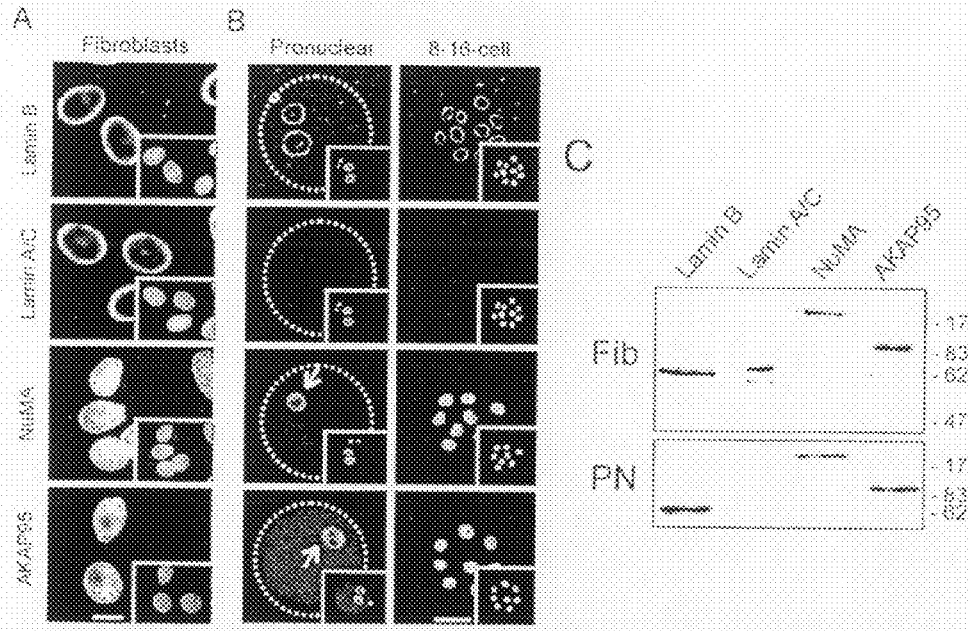
FIGS. 40A-40B illustrate the immunofluorescence distribution of lamin B, lamin A/C, NuMA, and AKAP95 in bovine fetal fibroblasts (FIG. 40A) and pronuclear and 8-16-cell stage bovine embryos cultured in vitro (FIG. 40B). Arrows point to NuMA and AKAP95 labeling in the female pronucleus (the smallest of both pronuclei). Insets, DNA labeled with 0.1 µg/ml Hoechst 33342.
FIG. 40C illustrates the immunoblotting analysis of lamin B, lamin A/C, NuMA, and AKAP95 in bovine fibroblasts (Fib) and pronuclear embryos (PN). Bars, 10 µm (FIG. 40A), 50 µm (FIG. 40B).

As discussed in Example 8, the intranuclear anchoring properties of AKAP95, a structural multivalent protein of the nuclear matrix-chromatin interface (Collas et al., J. Cell Biol. 147:1167-1179, 1999) and enriched in hypoacetylated chromatin, can also be used as a marker for reprogramming of donor genetic material. AKAP95 was the only marker investigated that was detected in somatic donor nuclei on PCC chromosomes and in NT pronuclei with a labeling intensity similar to that of parthenotes (FIG. 41A) and PN embryos (FIG. 40B). AKAP95 association with NT pronuclei was maintained by inhibition of protein or RNA synthesis. Thus, a major fraction of PN AKAP95 in NT embryos is of somatic origin. AKAP95 anchoring was examined by extraction of NT embryos, parthenotes, and donor fibroblasts with 0.1% Triton X-100, 1 mg/ml DNAse 1 and 300 mM NaCl. In parthenotes, 90% of AKAP95 and DNA were extracted; however, 35% of AKAP95 in NT pronuclei resisted extraction (FIG. 41D). Sensitivity of AKAP95 and DNA to DNAse I and NaCl resembled that of fibroblast nuclei (FIG. 41D). Lamin B was not extracted under these conditions, indicating that differences in AKAP95 and DNA extractability did not result from gross alterations in nuclear architecture. These results imply that NT pronuclei are characterized by tight anchoring of AKAP95 and restricted DNA accessibility to DNAse I. Thus, pronuclei produced by somatic NT appear to display structural abnormalities as a result of incomplete morphological remodeling of donor nuclei and/or transcriptional misregulation of somatic genes.

EXAMPLE 10

Exemplary Nuclear Reprogramming Deficiencies in Traditional Bovine Nuclear Transplant Embryos As described in Example 9, expression patterns in Nuclear Transplant (NT) embryos were compared to those in in vitro-produced (IVP) preimplantation embryos. For this comparison, in vitro fertilization was performed, and embryos were cultured as previously described (Collas et al., Mol. Reprod. Dev. 34:224-231, 1993 and Kasinathan et al., Biol. Reprod. 64:1487-1493, 2001). NT was carried out by fusing donor bovine fetal fibroblasts to enucleated oocytes (Kasinathan et al., Nat. Biotechnol. 19:1176-1178, 2001 and Kasinathan et al., Biol. Reprod. 64:1487-1493, 2001). Recipient oocytes were activated at 28-30 hours post-maturation (hpm) with 5 µM calcium ionophore for 4 minutes followed by 10 µg/ml CHX and 2.5 µg/ml cytochalasin D for 5 hours and washed. Embryos were co-cultured with mouse fetal fibroblasts (Kasinathan et al., Biol. Reprod. 64:1487-1493, 2001). For CHX treatment, oocytes were activated as above and embryos were cultured with 2.5 µg/ml CHX for another nine hours before culture. For ActD treatment, oocytes were activated as above except that 5 µg/ml ActD was added to the five-hour CHX incubation step and embryos were maintained in 5 µg/ml ActD for another nine hours prior to culture. NT embryos were cultured to the blastocyst stage in vitro, and two embryos were transferred per recipient female. Pregnancies were monitored by ultrasonography, and C-sections were performed. Calves were scored by veterinarians within 24 hours of birth.

For analysis of protein levels in NT and UVP embryos, anti-lamin B polyclonal antibodies, anti-lamin A/C monoclonal antibodies, and anti-TBP polyclonal or monoclonal antibodies from Santa-Cruz Biotechnology were used. Anti- AKAP95 antibodies were from Upstate Biotechnologies. Immunofluorescence analysis was performed as described (Bomar et al., J. Cell Sci. 115:2931-2940, 2002). Briefly, cells and embryos were settled onto poly-L-lysine-coated coverslips, fixed with 3% paraformaldehyde for 15 minutes, permeabilized with 0.1% Triton X-100 for 15 minutes, and proteins were blocked in PBS/2% BSA/0.01% Tween 20. Samples were incubated with primary and secondary antibodies (1:100 dilutions) each for 30 minutes. DNA was counterstained with 0.1 µg/ml Hoechst 33342. Photographs were taken with a JVC CCD camera, and quantification of immunofluorescence intensity performed using the AnalySIS software. When indicated, samples were extracted on coverslips with a cocktail of 1% Triton X-100, 1 mg/ml DNAse I, and 300 mM NaCl in Tris-HCl (pH 7.2) for 15 minutes prior to immunofluorescence analysis. For immunoblotting, protein samples (30 µg) were resolved by 10% SDS-PAGE, blotted onto nitrocellulose, and probed with indicated antibodies.

Dynamics of the Donor Nucleus in Nuclear Transplant Embryos

Figures 46A, 46B, 46C:
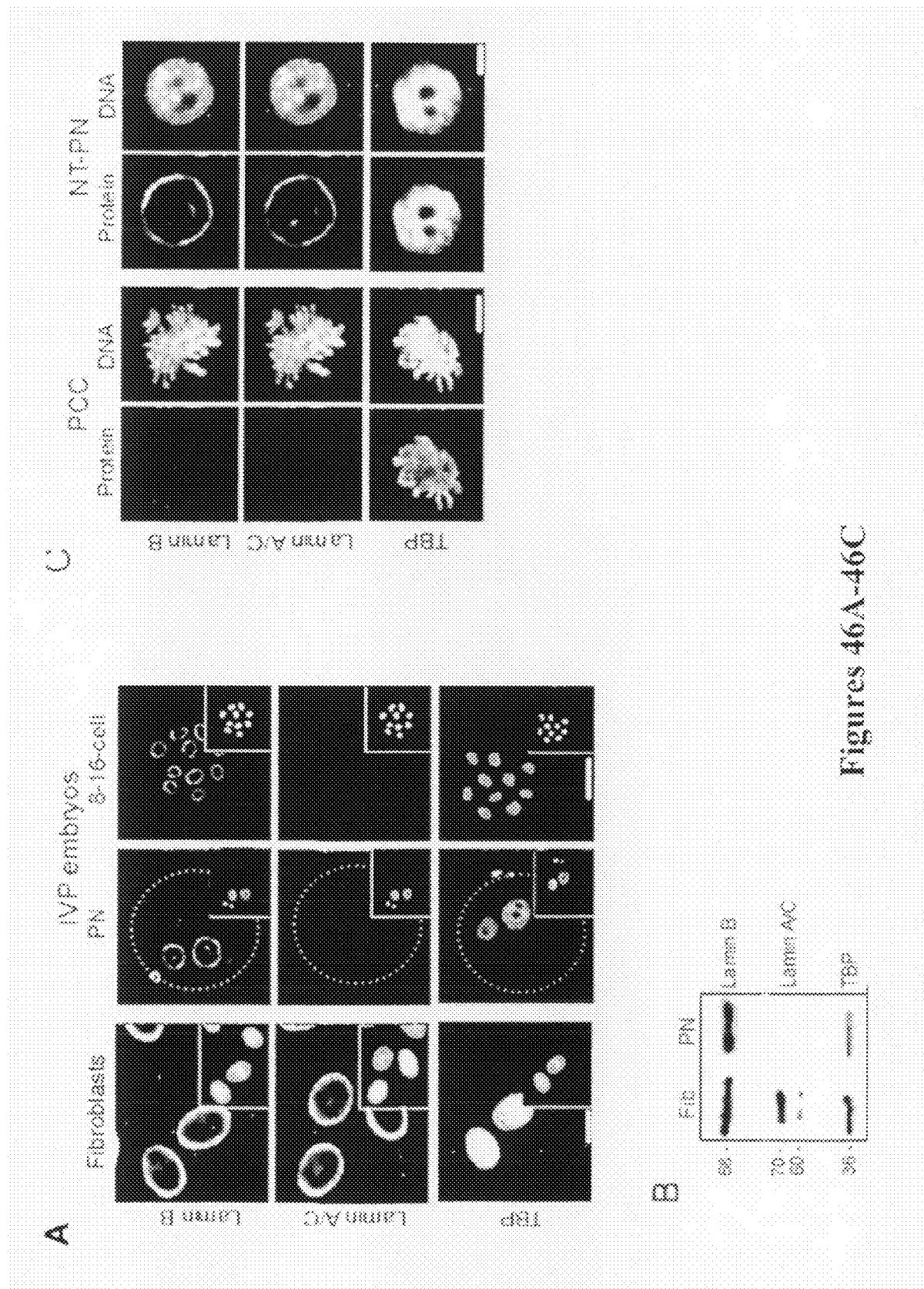
FIGS. 46A-46D depict the dynamics of fibroblast nuclei after NT.

To investigate the dynamics of somatic nuclei during bovine nuclear transplantation (NT), the distribution of two structural components of the nuclear envelope, the ubiquitously expressed B-type lamins (referred to as lamin B) and the differentiated cell-specific A-type lamins (lamin A/C) was examined (Gruenbaum et al., J. Struct. Biol. 129:313-323, 2000). Nuclear lamins anchor nuclear membranes to chromatin and have been suggested to promote nuclear expansion after (pro)nuclear reconstitution in vitro. Lamins have also been shown to be essential for cell survival, as failure to assemble B-type lamins leads to cell death. As a marker of the transcription machinery, the dynamics of the TATA-binding protein, TBP, a transcription factor for virtually all genes, was analyzed. Perinuclear distribution of lamin B and colocalization of TBP with DNA in bovine fetal fibroblasts and in in vitro-produced (IVP) preimplantation embryos were consistent with observations in other species (Holy et al., Dev. Biol. 168:464-478, 1995; Houliston et al., Development 102:271-278, 1988; and Worrad et al., Development 120:2347-2357, 1994). (FIG. 46A). Lamin A/C was not detected during preimplantation development (FIG. 46A) as expected from a marker of differentiated cells. Specificity of immunofluorescence labeling was verified on immunoblots (FIG. 46B).

Figure 46D:
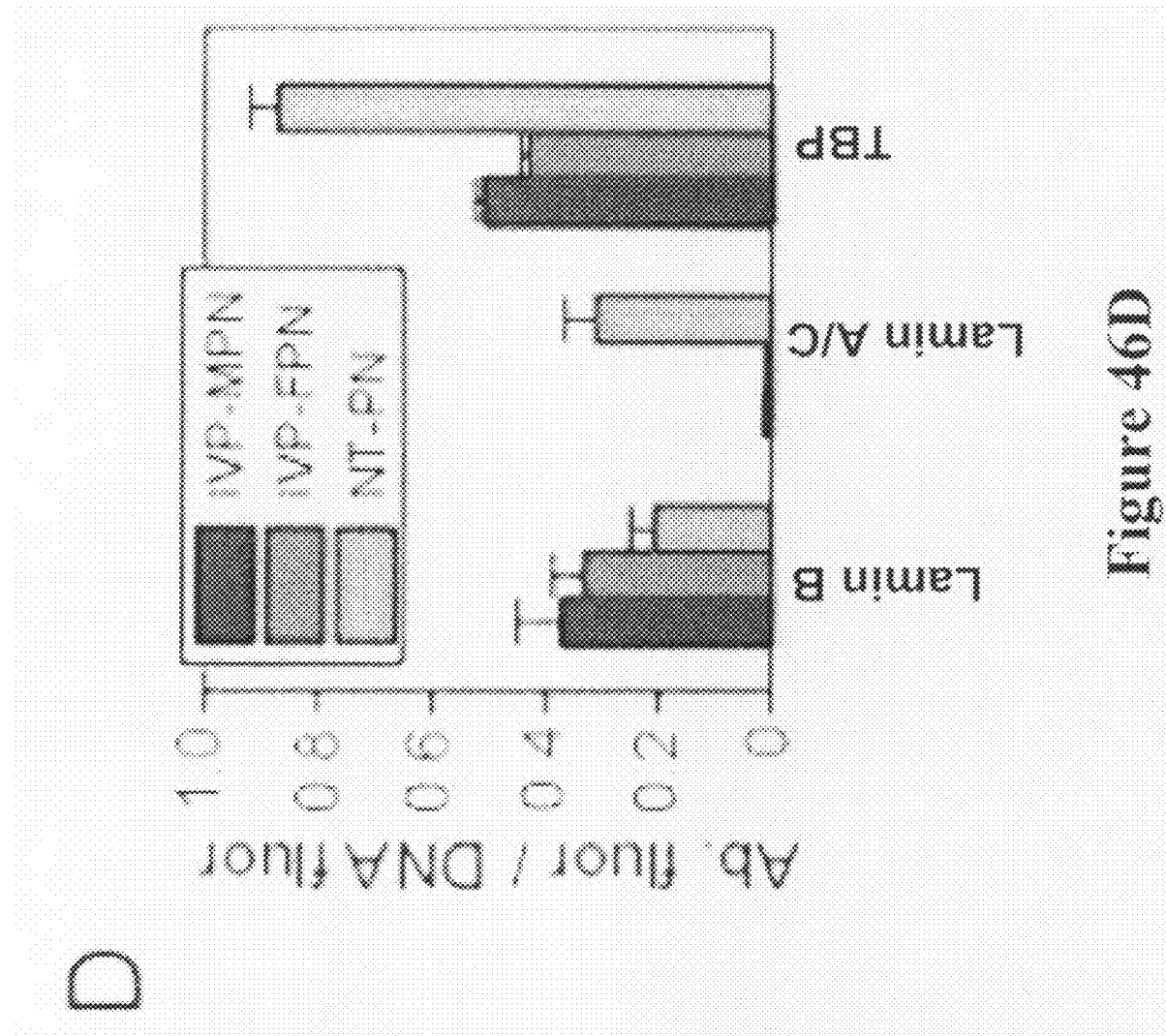

Following transplantation of fibroblast nuclei into enucleated oocytes, both lamins A/C and B were disassembled from the prematurely condensed chromosomes (PCC; three hours post-fusion), while TBP remained associated with the chromosomes (FIG. 46C, PCC). Fourteen hours after initiation of activation of the recipient oocytes, all NT embryos contained fully developed pronuclei with perinuclear lamin B labeling and TBP co-localized with DNA (FIG. 1C, NT-PN). However, in contrast to UVP embryos, 95-99% of NT embryos displayed lamin A/C expression as early as the pronuclear stage (FIG. 46C), and expression persisted during early development (see below). Relative amounts of immunolabeled lamin B, lamin A/C, and TBP in pronuclei of NT and IVP embryos were quantified by measuring the ratio of secondary antibody fluorescence intensity to that of DNA (Hoechst 33342) to account for DNA content (haploid vs diploid) in the nuclei examined. Whereas relative amounts of lamin B were similar in pronuclei of NT and IVP embryos, relative mounts of lamin A/C and TBP were higher in NT pronuclei than in male (MPN) or female (FPN) pronuclei in IVP embryos (FIG. 46D).

TBP, DNA, and A-Type Lamins in Pronuclei of NT Embryos

Figure 47A:
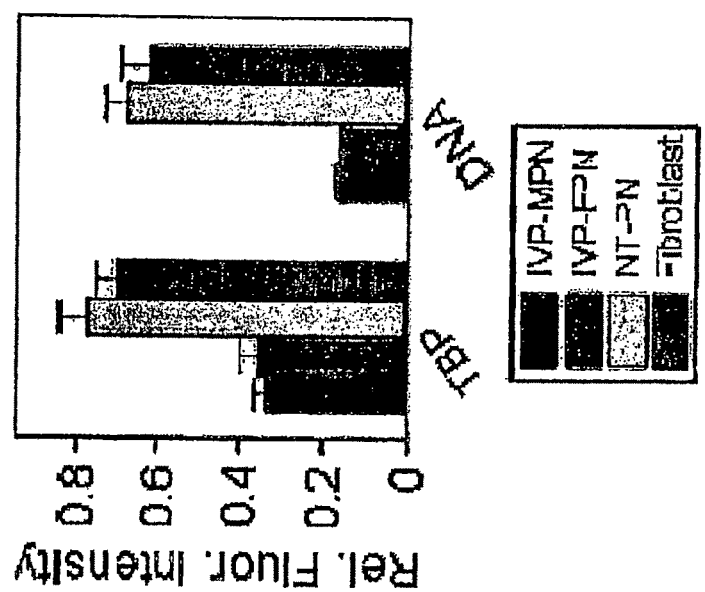
FIGS. 47A-47C illustrate the characterization of pronuclei in NT embryos.

Higher amounts of TBP in NT pronuclei was associated with a greater resistance to in situ extraction with a combination of detergent (1% Triton X-100), nuclease (1 mg/ml DNAse I), and salt (0.3 M NaCl). Quantification of immunofluorescence labeling intensity in extracted embryos relative to that of non-extracted controls shows that 35% of TBP remained unextracted in male (MPN) or female (FPN) pronuclei of IVP embryos (FIG. 47A). However, TBP of NT pronuclei displayed strong resistance to extraction as in fibroblast nuclei (FIG. 47A). Similarly, DNA of NT pronuclei displayed a 4.5-fold increase in resistance to extraction under these conditions compared to pronuclei of IVP embryos (FIG. 47A, DNA), suggestive of a more compact chromatin organization.

Figure 47B:
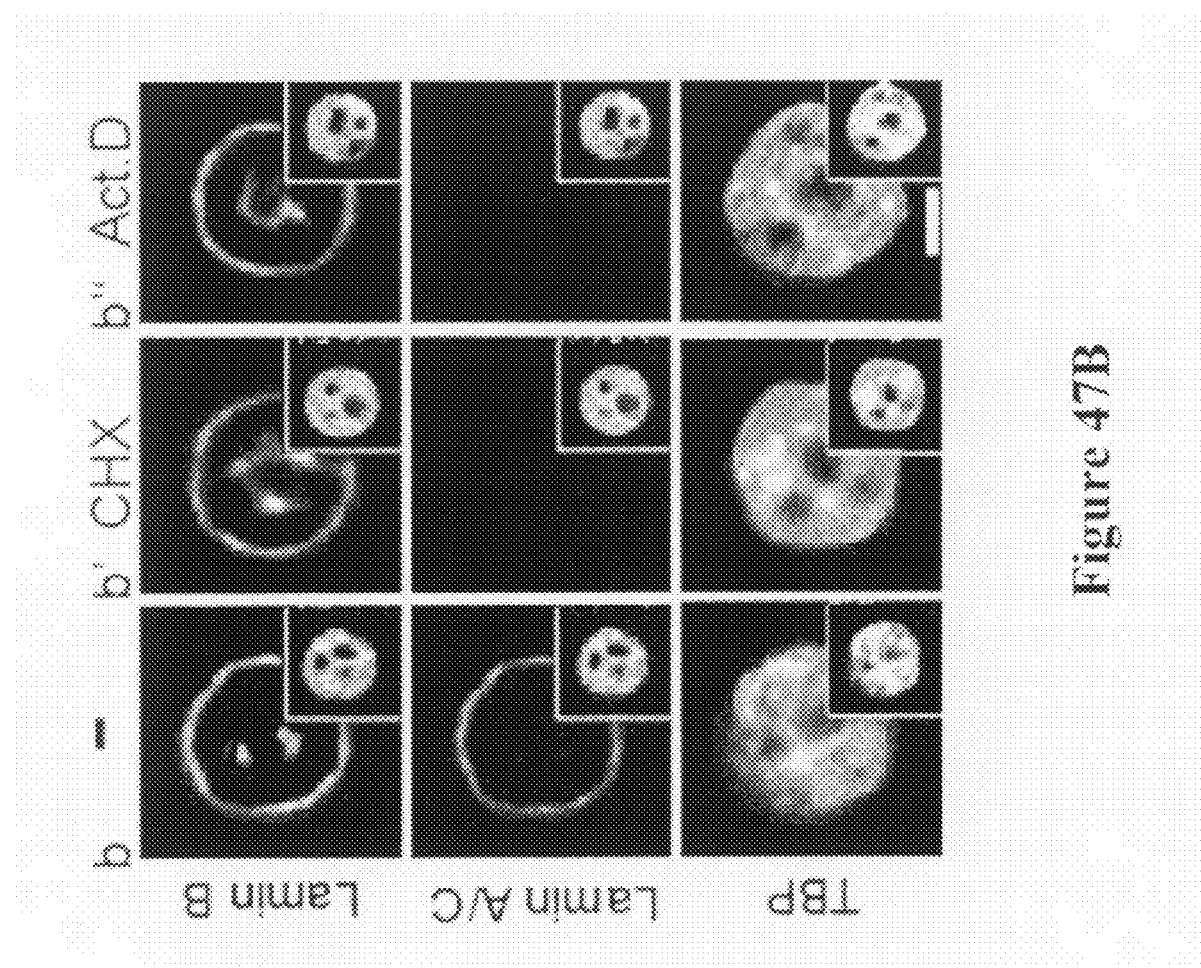
Figure 47C:
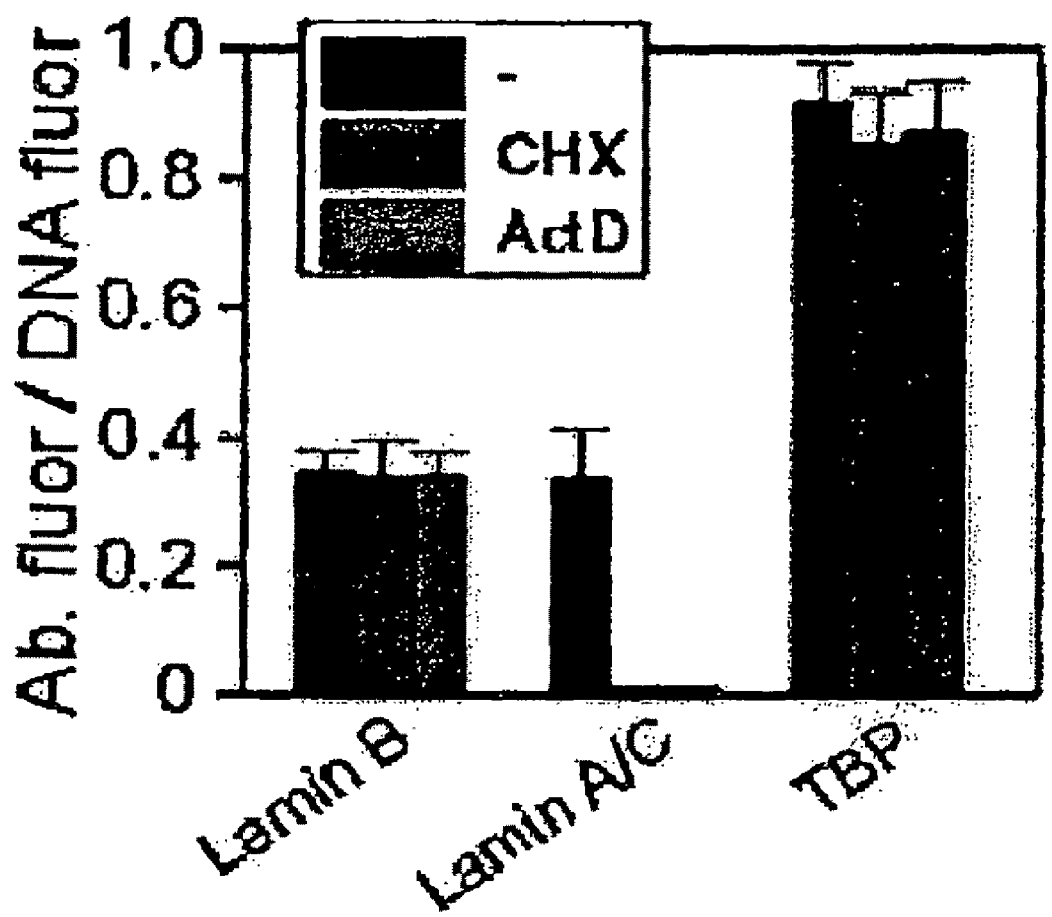
Figure 48:
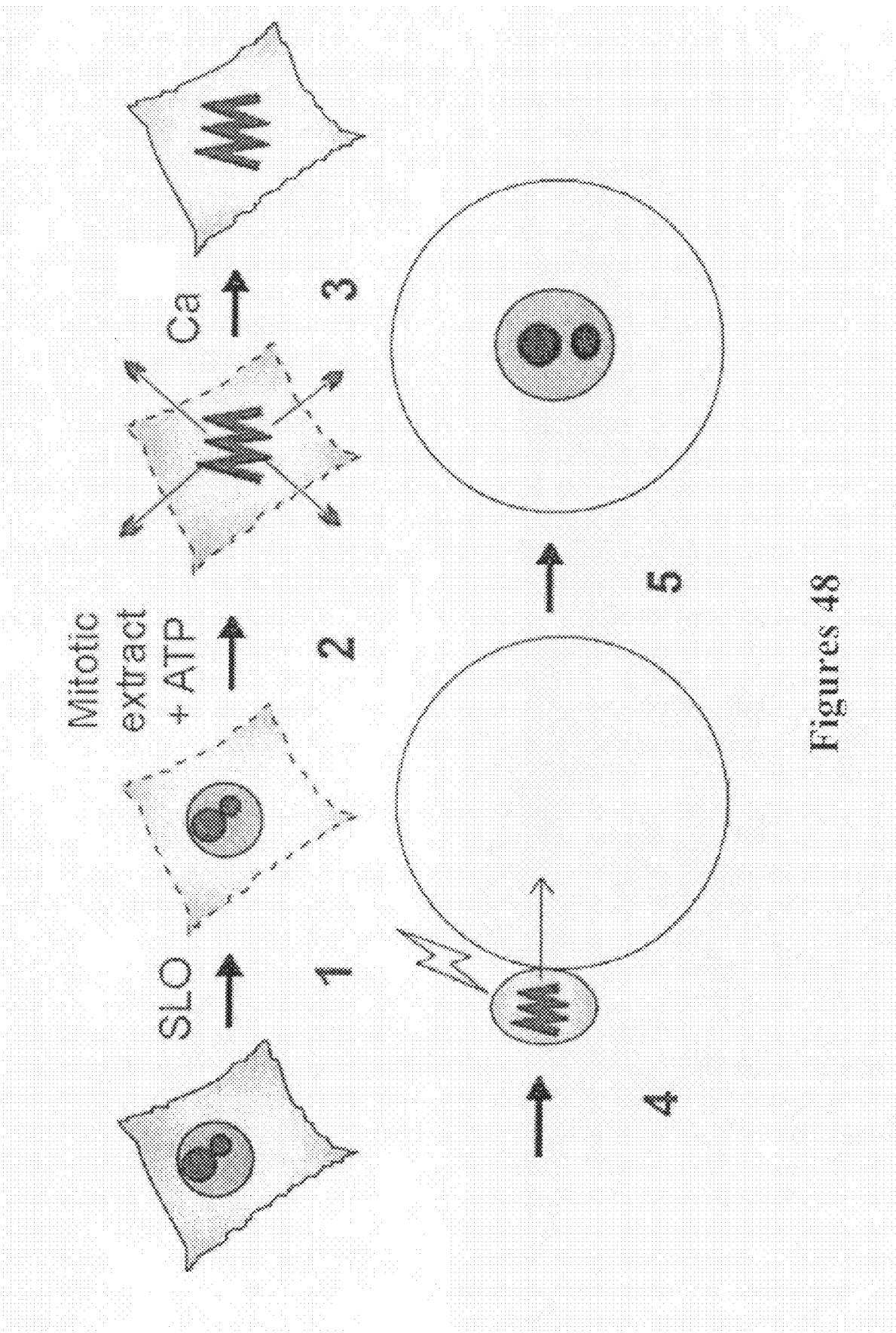
FIG. 48 illustrates the SLOT procedure. In step one, donor fibroblasts are reversibly permeabilized for 30 minutes with 500 ng/ml SLO. In step two, permeabilized cells are washed and incubated in a mitotic extract containing an ATP-regenerating system to elicit chromosome condensation and promote removal of nuclear components (arrows). In step three, the extract is removed, and the cells are optionally resealed in culture with 2 mM $CaCl_2$ for two hours. In step four, cells are fused to enucleated recipient oocytes, and in step five, oocytes are activated as for NT to elicit pronuclear formation and development.

To determine the origin of lamin B, lamin A/C, and TBP in pronuclei of NT embryos, recipient oocytes were activated in the presence of the RNA polymerase (Pol) II inhibitor actinomycin D (ActD; 5 µg/ml) or with the protein synthesis inhibitor cycloheximide (CHX; 10 µg/ml) (Knott et al., Biol. Reprod. 66:1095-1103, 2002) as described herein. Assembly of lamin A/C, lamin B, and TBP was examined by densitometric analysis of immunofluorescently labeled pronuclear embryos. Both inhibitors prevented pronuclear lamin A/C assembly (FIGS. 47B and 48C), suggesting that assembly of these somatic lamins in NT embryos resulted from transcription of the lamin A gene at the pronuclear stage. Lamin B assembly was not perturbed by CHX or ActD treatment (FIGS. 47B and 47C), suggesting that lamin B was assembled from somatic lamins solubilized in the oocyte cytoplasm after NT and/or from a maternal pool of lamins. Similar amounts of TBP were detected in untreated embryos or after inhibition of RNA or protein synthesis (FIGS. 47B and 47C). As TBP associates with condensed chromosomes during PCC, and since the metaphase II oocyte cytoplasm is devoid of detectable TBP, TBP of somatic origin probably remains associated with the donor genome during NT. Thus, in addition to expressing A-type lamins, pronuclei of NT embryos display higher amounts and enhanced intranuclear anchoring of TBP.

EXAMPLE 11

Use of Reprogrammed Donor Chromatin Masses to Clone Mammals

To overcome the problem of incomplete reprogramming in traditional nuclear transfer embryos that was demonstrated in Examples 8-10, new methods were developed to more efficiently reprogram donor chromatin prior to nuclear transfer (PCT/JUS01/50406, filed Dec. 21, 2001). These methods involve incubating a nucleus (e.g., a nucleus that encodes a xenogenous antibody) from a donor cell in a reprogramming media (e.g., a cell extract) that results in nuclear envelope dissolution and possibly chromatin condensation. This nuclear envelope breakdown and chromatin condensation allows the release of transcription regulatory proteins that were attached to the chromosomes and that would otherwise promote the transcription of genes undesirable for oocyte, embryo, or fetus development. Additionally, regulatory proteins from the reprogramming media may bind the chromatin mass and promote the transcription of genes desirable for development.

To generate an ungulate with a mutation in a prion gene and optionally with a xenogenous Ig gene, the donor nucleus or chromatin mass can be modified before, during, or after reprogramming by mutation of one or more alleles of the prion gene and optionally by insertion of one or more nucleic acids encoding a xenogenous antibody. If desired, a cell from the cloned fetus or the cloned offspring can be used in a second round of nuclear transfer to generate additional cloned offspring. Cells from the initial cloned fetus or cloned offspring may also be frozen to form a cell line to be used as a source of donor cells for the generation of additional cloned ungulates.

Bulk Preparation of Donor Nuclei for Use in Cloning

As many as several million nuclei may be isolated from synchronized or unsynchronized cell populations in culture. The cell populations may be synchronized naturally or chemically. Preferably, at least 40, 60, 80, 90, or 100% of the cells in a population are arrested in $G_o$ or $G_1$ phase. To accomplish this, cells may be incubated, for example, in low serum, such as 5%, 2%, or 0% serum, for 1, 2, 3, or more days to increase the percentage of cells in $G_o$ phase. To synchronize cells in $G_1$, the cells may be grown to confluence as attached cells and then incubated in 0.5-1 µg/ml nocodazole (Sigma Chemicals, St. Louis, Mo.) for 17-20 hours, as described previously (see, for example, Collas et al., J. Cell Biol. 147: 1167-1180, 1999 and references therein). The flasks containing the attached cells are shaken vigorously by repeatedly tapping the flasks with one hand, resulting in the detachment of mitotic cells and $G_1$ phase doublets. The $G_1$ phase doublets are pairs of elongated cells at the end of the division process that are still connected by a thin bridge. Detached $G_1$ phase doublets may be isolated from the media based on this characteristic doublet structure. The $G_1$ phase doublets may remain attached or may divide into two separate cells after isolation.

The synchronized or unsynchronized cells are harvested in phosphate buffered saline (PBS) using standard procedures, and several washing steps are performed to transfer the cells from their original media into a hypotonic buffer (10 mM HEPES, pH 7.5, 2 mM $MgCl_2$, 25 mM KCl, 1 mM DTT, 10 µM aprotinin, 10 µM leupeptin, 10 µM pepstatin A, 10 µM soybean trypsin inhibitor, and 100 µM PMSF). For example, the cells may be washed with 50 ml of PBS and pelleted by centrifugation at 500×g for 10 minutes at 4° C. The PBS supernatant is decanted, and the pelleted cells are resuspended in 50 ml of PBS and centrifuged, as described above. After this centrifugation, the pelleted cells are resuspended in 20-50 volumes of ice-cold hypotonic buffer and centrifuged at 500×g for 10 min at 4° C. The supernatant is again discarded and approximately 20 volumes of hypotonic buffer are added to the cell pellet. The cells are carefully resuspended in this buffer and incubated on ice for at least one hour, resulting in the gradual swelling of the cells.

To allow isolation of the nuclei from the cells, the cells are lysed using standard procedures. For example, 2-5 ml of the cell suspension may be transferred to a glass homogenizer and Dounce homogenized using an initial 10-20 strokes of a tight-fitting pestle. Alternatively, the cell suspension is homogenized using a motorized mixer (e.g., Ultraturrax). If desired, cell lysis may be monitored using phase contrast microscopy at 40-fold magnification. During this homogenization, the nuclei should remain intact and most or preferably all of the originally attached cytoplasmic components such as vesicles, organelles, and proteins should be released from the nuclei. If necessary, 1-20 µg/ml of the cytoskeletal inhibitors, cytochalasin B or cytochalasin D, may be added to the aforementioned hypotonic buffer to facilitate this process. Homogenization is continued as long as necessary to lyse the cells and release cytoplasmic components from the nuclei. For some cell types, as many as 100, 150, or more strokes may be required. The lysate is then transferred into a 15 ml conical tube on ice, and the cell lysis procedure is repeated with the remainder of the suspension of swollen cells. Sucrose from a 2 M stock solution made in hypotonic buffer is added to the cell lysate (e.g., ⅛ volume of 2 M stock solution is added to the lysate), resulting in a final concentration of 250 mM sucrose. This solution is mixed by inversion, and the nuclei are pelleted by centrifugation at 400×g in a swing out rotor for 10 to 40 minutes at 4° C. The supernatant is then discarded, and the pelleted nuclei are resuspended in 10-20 volumes of nuclear buffer (10 mM HEPES, pH 7.5, 2 mM $MgCl_2$, 250 mM sucrose, 25 mM KCl, 1 mM DTT, 10 µM aprotinin, 10 µM leupeptin, 10 µM pepstatin A, 10 µM soybean trypsin inhibitor, and 100 µM PMSF). The nuclei are sedimented and resuspended in 1-2 volumes of nuclear buffer, as described above. The freshly isolated nuclei may either be used immediately for in vitro reprogramming and nuclear transfer as described below or stored for later use. For storage, the nuclei are diluted in nuclear buffer to a concentration of approximately $10^6$/ml. Glycerol (2.4 volumes of 100% glycerol) is added and mixed well by gentle pipetting. The suspension is aliquoted into 100-500 µl volumes in 1.5-ml tubes on ice, immediately frozen in a methanol-dry ice bath, and stored at −80° C. Prior to use, aliquots of the nuclei are thawed on ice or at room temperature. One volume of ice cold nuclear buffer is added, and the solution is centrifuged at 1,000×g for 15 minutes in a swing out rotor. The pelleted nuclei are resuspended in 100-500 µl nuclear buffer and centrifuged as described above. The pelleted nuclei are then resuspended in a minimal volume of nuclear buffer and stored on ice until use.

Preparation of Mitotic Extract or Media for Use in Reprogramming Donor Genetic Material For the preparation of a mitotic extract, a somatic cell line (e.g., fibroblasts) is synchronized in mitosis by incubation in 0.5-1 µg/ml nocodazole for 17-20 hours (see, e.g., Collas et al., J. Cell Biol. 147:1167-1180, 1999 and references therein) and the mitotic cells are detached by vigorous shaking, as described above. The detached $G_1$ phase doublets may be discarded, or they may be allowed to remain with the mitotic cells that constitute the majority off the detached cells (typically at least 80%). The harvested detached cells are centrifuged at 500×g for 10 minutes in a 10 ml conical tube at 4° C. Several cell pellets are pooled, resuspended in a total volume of 50 ml of cold PBS, and centrifuged at 500×g for 10 minutes at 4° C. This PBS washing step is repeated. The cell pellet is resuspended in approximately 20 volumes of ice-cold cell lysis buffer (20 mM HEPES, pH 8.2, 5 mM $MgCl_2$, 10 mM EDTA, 1 mM DTT, 10 µM aprotinin, 10 µM leupeptin, 10 µM pepstatin A, 10 µM soybean trypsin inhibitor, 100 µM PMSF, and optionally 20 µg/ml cytochalasin B), and the cells are sedimented by centrifugation at 800×g for 10 minutes at 4° C. The supernatant is discarded, and the cell pellet is carefully resuspended in no more than one volume of cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract.

The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 µl pipette tip, and the supernatant from several tubes is pooled and placed on ice. This supernatant is the "mitotic cytoplasmic" or "MS15" extract. This cell extract may be aliquoted into 50 µl or 10 µl volumes of extract per tube on ice, depending on whether the regular or micromethod for generation of chromatin masses will be used. The extracts are immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the MS15 extract. At the end of centrifugation, the oil is discarded. The supernatant is carefully collected, pooled if necessary, and placed in a cold 1.5 ml tube on ice. This supernatant is referred to as "MS200" or "mitotic cytosolic" extract. The extract is aliquoted and frozen as described for the MS15 extract.

If desired, the extract can be enriched with additional nuclear factors. For example, nuclei can be purified from cells of the cell type from which the reprogramming extract is derived or from cells of any other cell type and lysed by sonication as described above. The nuclear factors are extracted by a 10-60 minute incubation in nuclear buffer containing NaCl or KCl at a concentration of 0.15-800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the nuclei for reprogramming.

Mitotic extracts can also be prepared from germ cells, such as oocytes or male germ cells. For example, metaphase II oocytes that are naturally arrested at this stage can be harvested, washed, and lysed as described above for the generation of an oocyte extract. To prepare a male germ cell extract, germ cells are isolated from testes obtained from the abattoir by mincing the organ and by differential centrifugation of the harvested cells on a sucrose or percoll gradient. Germ cells are separated from somatic (Leydig and Sertoli) cells, washed by suspension, and sedimentation in PBS. The cells are then washed once in ice-sold cell lysis buffer as described above and lysed by sonication. The lysate is cleared by centrifugation at 15,000×g for 15 minutes at 4° C., and the supernatant (i.e., the germ cell extract) is aliquoted and snap-frozen in liquid nitrogen.

As an alternative to a cell extract, a reprogramming media can also be formed by adding one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) to a solution, such as a buffer. Preferably, one or more of the factors are specific for oocytes or stem cells.

Formation of Condensed Chromatin Masses

An aliquot of MS15 or MS200 extract or the mitotic media is thawed on ice. An ATP-generating system (0.6 µl) is added to 20 µl of extract or media and mixed by vortexing. For the preparation of the ATP-generating system, equal proportions of 100 mM ATP stock, 1 M creatine phosphate, and 2.5 mg/ml creatine kinase stock solutions (100×) made in $H_2O$ are mixed and stored on ice until use. After addition of the ATP generating system to the extract, the final concentrations are 1 mM ATP, 10 mM creatine phosphate, and 25 µg/ml creatine kinase.

The nuclei suspension is added to the extract or media at a concentration of 1 µl nuclei per 10 µl of extract or media, mixed well by pipetting, and incubated in a 30, 33, 35, 37, or 39° C. water bath. The tube containing the mixture is tapped gently at regular intervals to prevent chromosomes from clumping at the bottom of the tube. Nuclear envelope breakdown and chromosome condensation is monitored at regular intervals, such as every 15 minutes, under a microscope. When the nuclear envelope has broken down and chromosomes have started to condense, the procedure for recovery of chromatin masses from the extract or media is started.

Alternatively, chromatin masses that are not condensed or only partially condensed may be formed by performing the above procedure after pre-loading the isolated nuclei with an antibody to the nuclear matrix protein NuMA (Steen et al., J. Cell Biol. 149, 531-536, 2000). This procedure allows the removal of nuclear components from chromatin by the dissolution of the nuclear membrane surrounding the donor nuclei; however, the condensation step is inhibited by addition of the anti-NuMA antibody. Preventing chromosome condensation may reduce the risk of chromosome breakage or loss while the chromosomes are incubated in the mitotic extract.

For this procedure, purified cell nuclei (2,000 nuclei/µl) are permeabilized in 500 µl nuclear buffer containing 0.75 µg/ml lysolecithin for 15 minutes at room temperature. Excess lysolecithin is quenched by adding 1 ml of 3% BSA made in nuclear buffer and incubating for 5 minutes on ice. The nuclei are then sedimented and washed once in nuclear buffer. The nuclei are resuspended at 2,000 nuclei/µl in 100 µl nuclear buffer containing an anti-NuMA antibody (1:40 dilution; Transduction Laboratories). After a one hour incubation on ice with gentle agitation, the nuclei are sedimented at 500×g through 1 M sucrose for 20 minutes. The nuclei are then resuspended in nuclear buffer and added to a mitotic extract or media containing an ATP regenerating system, as described in the previous section. Optionally, the anti-NuMA antibody may be added to the extract or media to further prevent chromosome condensation.

Chromatin masses that are not condensed or only partially condensed may also be formed by exposure to a detergent or protein kinase. Detergent may be used to solubilize nuclear components that are either unbound or loosely bound to the chromosomes in the nucleus, resulting in the removal of the nuclear envelope. For this procedure, purified cell nuclei (2,000-10,000 nuclei/µl) are incubated in nuclear buffer supplemented with a detergent, such as 0.1% to 0.5% Triton X-100 or NP-40. To facilitate removal of the nuclear envelope, additional salt, such as NaCl, may be added to the buffer at a concentration of approximately 0.1, 0.15, 0.25, 0.5, 0.75, or 1 M. After a 30-60 minute incubation on ice with gentle shaking, the nuclei are sedimented by centrifugation at 1,000×g in a swing-out rotor for 10-30 minutes, depending on the total volume. The pelleted nuclei are resuspended in 0.5 to 1 ml nuclear buffer and sedimented as described above. This washing procedure is repeated twice to ensure complete removal of the detergent and extra salt.

Alternatively, the nuclear envelope may be removed using recombinant or naturally-occurring protein kinases, alone or in combination. Preferably, the protein kinases are purified using standard procedures or obtained in purified form from commercial sources. These kinases may phosphorylate components of the nuclear membrane, nuclear matrix, or chromatin, resulting in removal of the nuclear envelope (see, for example, Collas and Courvalin, Trends Cell Biol. 10: 5-8, 2000). Preferred kinases include cyclin-dependent kinase 1 (CDK1), protein kinase C (PKC), protein kinase A (PKA), MAP kinase, calcium/calmodulin-dependent kinase (CamKII), and CK1 casein kinase, or CK2 casein kinase. For this method, approximately 20,000 purified nuclei are incubated in 20 µl of phosphorylation buffer at room temperature in a 1.5 ml centrifuge tube. A preferred phosphorylation buffer for CDK1 (Upstate Biotechnology) contains 200 mM NaCl, 50 mM Tris-HCl (pH 7.2-7.6), 10 mM $MgSO_4$, 80 mM β-glycerophosphate, 5 mM EGTA, 100 µM ATP, and 1 mM DTT. For PKC, a preferred buffer contains 200 mM NaCl, 50 mM Tris-HCl (pH 7.2-7.6), 10 mM $MgSO_4$, 100 µM $CaCl_2$, 40 µg/ml phosphatidylserine, 20 µM diacylglycerol, 100 µM ATP, and 1 mM DTT. If both PKC and CDK1 are used simultaneously, the CDK1 phosphorylation buffer supplemented with 40 µg/ml phosphatidylserine and 20 µM diacylglycerol is used. A preferred phosphorylation buffer for PKA includes 200 mM NaCl, 10 mM MgSO4, 10 mM Tris, pH 7.0, 1 mM EDTA, and 100 µM ATP. For MAP kinase, the PKA phosphorylation buffer supplemented with 10 mM $CaCl_2$, and 1 mM DTT may be used. For CamKII, either PKA buffer supplemented with 1 mM DTT or a Cam Kinase assay kit from Upstate Biotechnology (Venema et al. J. Biol. Chem. 272: 28187-90, 1997) is used.

The phosphorylation reaction is initiated by adding a protein kinase to a final amount of 25-100 ng. The reaction is incubated at room temperature for up to one hour. Nuclear envelope breakdown may be monitored by microscopy during this incubation, such as at 15 minute intervals. After nuclear envelope breakdown, nuclei are washed three times, as described above for the removal of the detergent solution.

Recovery of Chromatin Masses

The extract or solution containing the condensed, partially condensed, or not condensed chromatin masses is placed under an equal volume of 1 M sucrose solution made in nuclear buffer. The chromatin masses are sedimented by centrifugation at 1,000×g for 10-30 minutes depending on the sample volume in a swing out rotor at 4° C. The supernatant is discarded, and the pelleted chromatin masses are carefully resuspended by pipetting in 0.1-1.0 ml nuclear buffer or lipofusion buffer (150 mM NaCl, 10 µM aprotinin, 10 µM leupeptin, 10 µM pepstatin A, 10 µM soybean trypsin inhibitor, and 100 µM PMSF in either 20 mM HEPES around pH 7.0 or pH 7.5 or 20 mM MES around pH 6.2) and centrifuged at 1,000×g for 10-30 minutes. The supernatant is discarded, and the pelleted chromatin masses are resuspended in nuclear buffer or lipofusion buffer and stored on ice until use. Each chromatin mass is transferred to a 20 µl drop of HEPES-buffered medium under oil in a micromanipulation dish. One chromatin mass is inserted into each enucleated oocyte, as described below.

Micromethod for Preparation of Chromatin Masses

A 10-20 µl drop of MS15 or MS200 extract or mitotic media containing an ATP generating system, a detergent and/or salt solution, or a protein kinase solution as described above is placed in a petri dish. A 50-µl drop of isolated $G_1$ phase cell doublets or $G_0$ phase cells in culture medium, a separate 50 µl "lysis" drop of HEPES- or bicarbonate-buffered medium containing 0.1% Triton X-100 or NP-40 for use in facilitating cell lysis, and a 50-µl drop of oocyte injection medium is then added. Each of these drops is covered with $CO_2$ equilibrated mineral oil. A 50 µl "wash drop" of culture medium is also added to the petri dish for use in washing the lysed cells or nuclei.

Cells are transferred to the lysis drop using a micropipette. The cell membranes are lysed in the pipette by gentle repeated aspirations. When the cell is lysed, the lysate is gently expelled into the wash drop, and the nucleus is immediately reaspirated to remove detergent. Optionally, the nuclei may be permeabilized and incubated with anti-NuMA antibodies prior to being added to the mitotic extract or media. The nucleus is then expelled into the drop of MS15, MS200, or media, detergent and/or salt solution, or protein kinase solution. Nuclear breakdown and chromosome condensation is monitored as described above. Once the nuclear envelope has broken down and, if a mitotic extract without anti-NuMA antibodies was used, the chromosomes have started to condense, a single intact chromatin mass is isolated with a micropipette and transferred to an enucleated recipient oocyte, as described below.

Enucleation of Oocytes

Preferably, the recipient oocyte is a metaphase II stage oocyte. At this stage, the oocyte may be activated or is already sufficiently activated to treat the introduced chromatin mass as it does a fertilizing sperm. For enucleation of the oocyte, part or preferably all of the DNA in the oocyte is removed or inactivated. This destruction or removal of the DNA in the recipient oocyte prevents the genetic material of the oocyte from contributing to the growth and development of the cloned mammal. One method for destroying the pronucleus of the oocyte is exposure to ultraviolet light (Gurdon, in *Methods in Cell Biology, Xenopus Laevis: Practical Uses in cell and Molecular Biology*, Kay and Peng, eds., Academic Press, California, volume 36:pages 299-309, 1991). Alternatively, the oocyte pronucleus may be surgically removed by any standard technique (see, for example, McGrath and Solter, Science 220:1300-1319, 1983). In one possible method, a needle is placed into the oocyte, and the nucleus is aspirated into the inner space of the needle. The needle may then be removed from the oocyte without rupturing the plasma membrane (U.S. Pat. Nos. 4,994,384 and 5,057,420).

Lipofusion for Insertion of Chromatin Masses into Oocytes

Chromatin may be introduced into recipient oocytes by lipofusion as described below or by standard microinjection or electrofusion techniques (see, for example, U.S. Pat. Nos. 4,994,384 and 5,945,577). The following lipofusion method may also be used in other applications to insert chromosomes into other recipient cells.

Chromatin masses are isolated from the mitotic extract, detergent and/or salt solution, or protein kinase solution by centrifugation, and then washed with lipofusion buffer, as described above. The chromatin masses may be in stored in ice-cold lipofusion buffer until use. Alternatively, the chromatin masses are aliquoted, frozen in liquid nitrogen or in a methanol-dry ice bath, and stored frozen at −80° C. The lipofusion solution is prepared by mixing one or more fusigenic reagents with the lipofusion buffer in respective proportions ranging from 5:1 to 1:10 approximately. The fusigenic reagents consist of, but are not limited to, polyethylene glycol (PEG) and lipophilic compounds such as Lipofectin®, Lipofectamin®, DOTAP®& {N-[1-(2,3-Dioleoyloxy)propyl]-N,N,N-trimethylamonium methylsulfate; $C_{43}H_{83}NO_8S$}, DOSPA® {2,3-dioleyloxy-N-[2(sperminecarboxamido)ethyl]-N,N-dimethyl-1-propanaminium trifluoroacetate}, and DOPE® (dioleoyl phosphatidylethanolamine).

Other preferred lipids include neutral and monovalent or multivalent cationic lipids, such as those containing quaternary ammonium groups. Additional preferred lipids have a cholesterol moiety such as that formed from the reaction of the hydroxyl group in cholesterol with a group in the lipid. Still other preferred lipids have a saturated or unsaturated fatty acid that preferably contains between 5 and 10, 10 and 15, 15 and 20, or 20 and 30 carbon atoms, inclusive. These lipids may be synthesized using standard chemical synthesis techniques, obtained from naturally-occurring sources, or purchased from commercially available source (Summers et al., Biophys J. 71: 3199-3206, 1996; Nabekura et al., Pharm Res. 13: 1069-1072, 1996; Walter et al., Biophys J. 66: 366-376, 1994; Yang et al., Biosci Rep. 13: 143-157, 1993; Walter and Siegel, Biochemistry. 6:32: 3271-3281, 1993). Other preferred fusigenic compounds are phospholipids such as membrane vesicle fractions from sea urchin eggs or any other source (Collas and Poccia, J. Cell Science 109: 1275-1283, 1996). Preferably, contacting chromosomes with the membrane vesicle fraction does not result in the chromosomes being encapsulated by an intact membrane.

For example, a cationic lipid, such as DOTAP®, may be used at a concentration of approximately 0.1 to 30 µg/ml in lipofusion buffer. Alternatively, a liposome formulation consisting of a mixture of a cationic lipid and a neutral lipid, such as DOPE®, may be used.

The chromatin masses, either freshly prepared or frozen and thawed, are mixed with the lipofusion solution to allow coating of the chromatin masses with the compound. Incubation takes place at a temperature of 20-30° C. for a period of approximately 10-30 minutes. Microdrops containing the chromatin masses in the lipofusion solution are placed under $CO_2$ equilibrated mineral oil. A drop containing the enucleated recipient oocytes is also prepared. The chromatin masses coated with the lipofusion reagent are picked up in a micropipette and inserted in the perivitellin space, between the oocyte cytoplasm and the zona pellucida. The chromatin mass is placed next to the oocyte membrane to ensure contact with the oocyte. The chromatin mass-oocyte complexes are maintained at a temperature of 20-30° C., and fusion is monitored under the microscope. Once fusion has occurred, reconstituted oocytes are activated as described below.

Activation, Culturing, and Transplantation of Reconstituted Oocytes

To prevent polar body extrusion and chromosome loss, the oocyte may be activated in the presence of cytochalasin B, or cytochalasin B may be added immediately after activation (Wakayama et al., PNAS 96: 14984-14989, 1999; Wakayama et al., Nature Genetics 24: 108-109, 2000). Either electrical or non-electrical means may be used for activating reconstituted oocytes. Electrical techniques for activating cells are well known in the art (see, for example, U.S. Pat. Nos. 4,994,384 and 5,057,420). Non-electrical means for activating cells may include any method known in the art that increases the probability of cell division. Examples of non-electrical means for activating an oocyte include incubating the oocyte in the presence of ethanol; inositol trisphosphate; $Ca^{++}$ ionophore and a protein kinase inhibitors; a protein synthesis inhibitor; phorbol esters; thapsigargin, or any component of sperm. Other non-electrical methods for activation include subjecting the oocyte to cold shock or mechanical stress. Alternatively, one to three hours after nuclear transfer, oocytes may be incubated for approximately six hours in medium containing $Sr^{2+}$ to activate them and cytochalasin B to prevent cytokinesis and polar body extrusion (Wakayama et al., PNAS 96: 14984-14989, 1999; Wakayama et al., Nature Genetics 24: 108-109, 2000). Depending on the type of mammal cloned, the preferred length of activation may vary. For example, in domestic animals such as cattle, the oocyte activation period generally ranges from about 16-52 hours or preferably about 28-42 hours.

After activation, the oocyte is placed in culture medium for an appropriate amount of time to allow development of the resulting embryo. At the two-cell stage or a later stage, the embryo is transferred into a foster recipient female for development to term. For bovine species, the embryos are typically cultured to the blastocyst stage (e.g., for approximately 6-8 days) before being transferred to maternal hosts. For other cloned animals, an appropriate length for in vitro culturing is known by one skilled in the art or may be determined by routine experimentation.

Methods for implanting embryos into the uterus of a mammal are also well known in the art. Preferably, the developmental stage of the embryo is correlated with the estrus cycle of the host mammal. Once the embryo is placed in the uterus of the mammal, the embryo may develop to term. Alternatively, the embryo is allowed to develop in the uterus until a chosen time, and then the embryo (or fetus) is removed using standard surgical methods to determine its health and viability. Embryos from one species may be placed into the uterine environment of an animal from another species. For example, bovine embryos can develop in the oviducts of sheep (Stice and Keefer, Biology of Reproduction 48: 715-719, 1993). Any cross-species relationship between embryo and uterus may be used in the methods of the invention.

Lipofusion of Nuclei with Oocytes or Other Recipient Cells

The lipofusion solution is prepared by mixing one or more fusigenic reagents with lipofusion buffer in respective proportions ranging from approximately 5:1 to 1:10, as described above. Nuclei, either freshly prepared or frozen and thawed as described above, are mixed with the lipofusion solution to allow coating of the nuclei with the compound. Incubation takes place at a temperature of 20-30° C. for a period of approximately 10-30 minutes. Microdrops containing nuclei in the lipofusion solution are placed under $CO_2$ equilibrated mineral oil. A drop containing the recipient cell, preferably an enucleated cell, is also prepared. Enucleated recipient cells are prepared by physically removing the chromosomes or the nucleus by micromanipulation or by damaging the genetic material by exposure to UV light, as described above. For insertion into oocytes, the nuclei coated with the lipofusion reagent are picked up in a micropipette and inserted in the perivitellin space, between the oocyte cytoplasm and the zona pellucida. For insertion into other recipient cells, the coated nuclei are preferably placed next to the cell membrane to ensure contact with the cell. The nucleus-cell complexes are maintained at a temperature of 20-30° C., and fusion is monitored using a microscope. Once fusion has occurred, reconstituted oocytes are activated as described above.

EXAMPLE 12

Use of Reprogrammed Permeabilized Cells to Clone Mammals

Cells may also be reprogrammed without requiring the isolation of nuclei or chromatin masses from the cells. In this method, cells are permeabilized and then incubated in an interphase or mitotic reprogramming media under conditions that allow the exchange of factors between the media (e.g., a cell extract) and the cells. If an interphase media is used, the nuclei in the cells remain membrane-bounded; if a mitotic media is used, nuclear envelope breakdown and chromatin condensation may occur. After the nuclei are reprogrammed by incubation in this media, the plasma membrane is preferably resealed, forming an intact reprogrammed cell that contains desired factors from the media. If desired, the media can be enriched with additional nuclear factors as described in Example 11. The reprogrammed cells are then fused with recipient oocytes, and embryos formed from the reconstituted oocytes are inserted into maternal recipient mammals for the generation of cloned mammals.

For the production of an ungulate with a mutation in a prion gene and optionally with a xenogenous Ig gene, the donor cells are modified before, during, or after reprogramming by mutation of one or more alleles of the prion gene and optionally by insertion of one or more nucleic acids encoding a xenogenous antibody. If desired, a cell from the cloned fetus or the cloned offspring can be used in a second round of nuclear transfer to generate additional cloned offspring. Cells from the initial cloned fetus or cloned offspring may also be frozen to form a cell line to be used as a source of donor cells for the generation of additional cloned ungulates.

Permeabilization of Cells

Cells that may be reprogrammed using this procedure include unsynchronized cells and cells synchronized in $G_o$, $G_1$, S, $G_2$, or M phase or a combination of these phases. The cells are permeabilized using any standard procedure, such as permeabilization with digitonin or Streptolysin O. Briefly, cells are harvested using standard procedures and washed with PBS. For digitonin permeabilization, cells are resuspended in culture medium containing digitonin at a concentration of approximately 0.001-0.1% and incubated on ice for 10 minutes. For permeabilization with Streptolysin O, cells are incubated in Streptolysin O solution (see, for example, Maghazachi et al., FASEB J. 11: 765-774, 1997, and references therein) for ~15, 30, or 60 minutes at room temperature. After either incubation, the cells are washed by centrifugation at 400×g for 10 minutes. This washing step is repeated twice by resuspension and sedimentation in PBS. Cells are kept in PBS at room temperature until use. Preferably, the permeabilized cells are immediately added to the interphase or mitotic media for reprogramming, as described below.

Preparation of the Reprogramming Media

To prepare an interphase reprogramming extract, interphase cultured cells are harvested using standard methods and washed by centrifugation at 500×g for 10 minutes in a 10 ml conical tube at 4° C. The supernatant is discarded, and the cell pellet is resuspended in a total volume of 50 ml of cold PBS. The cells are centrifuged at 500×g for 10 minutes at 4° C. This washing step is repeated, and the cell pellet is resuspended in approximately 20 volumes of ice-cold interphase cell lysis buffer (20 mM HEPES, pH 8.2, 5 mM $MgCl_2$, 1 mM DTT, 10 μM aprotinin, 10 μM leupeptin, 10 μM pepstatin A, 10 μM soybean trypsin inhibitor, 100 μM PMSF, and optionally 20 μg/ml cytochalasin B). The cells are sedimented by centrifugation at 800×g for 10 minutes at 4° C. The supernatant is discarded, and the cell pellet is carefully resuspended in no more than one volume of interphase cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract.

The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 μl pipette tip, and the supernatant from several tubes is pooled and placed on ice. This supernatant is the "interphase cytoplasmic" or "IS15" extract. This cell extract may be aliquoted into 20 μl volumes of extract per tube on ice and immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the IS15 extract. At the end of centrifugation, the oil is discarded. The supernatant is carefully collected, pooled if necessary, and placed in a cold 1.5 ml tube on ice. This supernatant is referred to as "IS200" or "interphase cytosolic" extract. The extract is aliquoted and frozen as described for the IS15 extract.

If desired, the extract can be enriched with additional nuclear factors. For example, nuclei can be purified from cells of the cell type from which the reprogramming extract is derived or from cells of any other cell type and lysed by sonication as described above. The nuclear factors are extracted by a 10-60 minute incubation in nuclear buffer containing NaCl or KCl at a concentration of 0.15-800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the cells for reprogramming.

Interphase extracts can also be prepared from germ cells, such as oocytes or male germ cells. For example, oocytes are activated as described above and cultured for five hours to allow entry into interphase. Oocytes are then treated as described in Example 11 for metaphase II oocyte extracts except that EDTA is omitted from the lysis buffer. Male germ cell extracts can be prepared as described in Example 11.

As an alternative to a cell extract, a reprogramming media can also be formed by adding one or more naturally-occurring or recombinant factors (e.g., nucleic acids or proteins such as DNA methyltransferases, histone deacetylases, histones, protamines, nuclear lamins, transcription factors, activators, repressors, chromatin remodeling proteins, growth factors, interleukins, cytokines, or other hormones) to a solution, such as a buffer. Preferably, one or more of the factors are specific for oocytes or stem cells.

Reprogramming of Cells in a Media

The permeabilized cells are suspended in an interphase reprogramming media described above or one of the mitotic reprogramming medias described in Example 11 at a concentration of approximately 100-1,000 cells/μl. The ATP generating system and GTP are added to the extract as described above, and the reaction is incubated at 30-37° C. for up to two hours to promote translocation of factors from the extract into the cell and active nuclear uptake or chromosome-binding of factors. The reprogrammed cells are centrifuged at 800×g, washed by resuspension, and centrifuged at 400×g in PBS. If desired, the cells are resuspended in culture medium containing 20-30% fetal calf serum (FCS), RPMI1640 containing 2 mM $CaCl_2$ (added from a 1 M stock in $H_2O$), or in α-MEM medium containing 2 mM $CaCl_2$ and incubated for 1-3 hours at 37° C. in a regular cell culture incubator to allow resealing of the cell membrane. The cells are then washed in regular warm culture medium (10% FCS) and cultured further using standard culturing conditions. As described in Example 17, the reprogrammed permeablized cells may also be used for genetic transfer to oocytes without resealing the cell membrane.

Alternative Method of Reprogramming Permeabilized Cells

Alternatively, the cells can be permeabilized while placed on coverslips to minimize the handling of the cells and to eliminate the centrifugation of the cells, thereby maximizing the viability of the cells. Cells (e.g., fibroblasts) are grown on 16-mm poly-L-lysine-coated coverslips in RPMI1640 to 50,000-100,000 cells/coverslip in 12-well plates. Cells are permeabilized in 200 ng/ml Streptolysin O in $Ca^{2+}$-free Hanks Balanced Salt Solution (Gibco-BRL) for 50 minutes at 37° C. in regular atmosphere. If desired, the percent of cells that are permeabilized under these conditions can be measured based on propidium iodide uptake. Streptolysin O is aspirated; coverslips are overlaid with 80-100 μl of reprogramming media; and the cells are incubated for thirty minutes to one hour at 37° C. in $CO_2$ atmosphere. The reprogramming media preferably contains the ATP generating system and 1 mM each of ATP, CTP, GTP and UTP. To optionally reseal plasma membranes, α-MEM medium containing 2 mM $CaCl_2$, medium containing 20-30% fetal calf serum, or RPMI1640 containing 2 mM $CaCl_2$ is added to the wells, and the cells are incubated for two hours at 37° C. Alternatively, the plasma membrane is not resealed.

Effect of Streptolysin O Treatment on the Percentage of Permeabilized and Resealed Cells To assess the percent of permeabilized and resealed cells, dose and time titrations of Streptolysin O incubation were performed (Table 7). Permeabilization of cells was assessed by uptake of 0.1 μg/ml of the DNA stain propidium iodide at the end of Streptolysin O treatment. Resealing was assessed similarly at the end of the resealing treatment in a separate group of cells.

TABLE 7

Permeabilization and resealing of Streptolysin O (SLO)-treated bovine fibroblasts

| ng/ml SLO | Permeabilization | | Resealing | |
|---|---|---|---|---|
| | N | % pemeabilized +/− sd | N | % Resealed +/− sd |
| 0 | 563 | 1 +/− 2.8 | 560 | 89.9 +/− 4.9 |
| 100 | 404 | 48.6 +/− 4.2 | 810 | 86.1 +/− 8.3 |
| 200 | 548 | 79.2 +/− 1.4 | 478 | 84.9 +/− 1.5 |
| 500 | 495 | 88.7 +/− 1.6 | 526 | 87.6 +/− 0.5 |
| 1000 | 425 | 84.9 +/− 0.7 | 544 | 86.4 +/− 1.4 |
| 2000 | 315 | 96.6 +/− 2.2 | 425 | 10.7 +/− 1 |
| 4000 | 200 | 99 +/− 1.4 | 200 | 11.2 +/− 5.3 |

Assessment of Viability of Bovine Fibroblasts Permeabilized with Streptolysin O Treatment and Exposed to Mitotic Extract TUNEL analysis was performed to evaluate apoptosis in cells permeabilized with 0 or 500 ng/ml Streptolysin O and resealed, or in cells permeabilized with Streptolysin O, exposed to mitotic extract for 30 or 60 minutes, and resealed. TUNEL-positive cells are cells undergoing apoptosis (i.e., cell death). The data show that Streptolysin O itself does not induce apoptosis (Table 8). Exposure of Streptolysin O-treated cells to the mitotic extract for 60 minutes, but not 30 minutes, induces a 10% increase in apoptotic rate, based on TUNEL analysis (Table 8). Based on these data, a 30-minute incubation of donor cells in the extract is more preferable than a 60-minute incubation. Thirty-minute incubations were shown by immunofluorescence analysis of cells to induce nuclear envelope breakdown in the majority of nuclei examined (~90%, n>100).

Additionally, purified nuclei incubated in extract and washed in either buffer N or TL-HEPES and sucrose as described in Example 11 for the chromatin transfer method do not undergo apoptosis (2/34 and 3/47 TUNEL positive, respectively).

TABLE 8

TUNEL analysis of Streptolysin O and Streptolysin O plus extract-treated bovine fibroblasts

| ng/ml SLO | N | % TUNEL pos. +/− sd |
|---|---|---|
| 0-Input cells | 400 | 7.7 +/− 1.7 |
| 0 | 800 | 6.5 +/− 0.17 |
| 500 | 892 | 7.3 +/− 3.41 |
| 0 + extract 30' | 400 | 5.5 +/− 1.12 |
| 500 + extract 30' | 400 | 8.2 +/− 1.1 |
| 0 + extract 60' | 784 | 6.5 +/− 4.0 |
| 500 + extract 60' | 691 | 16.9 +/− 1.9 |

The permeabilization method chosen for these cloning methods was 500 ng/ml SLO for 30 minutes at 38° C. The resealing method chosen for forming an intact membrane surrounding the reprogrammed cells was a two hour incubation in α-MEM medium containing 2 mM $CaCl_2$.

Alternatively Cell Permeabilized Method Using a Protease

In an exemplary cell permeabilization method using a protease, cells (e.g., fibroblasts) are grown to confluency in a 35 mm plate overnight. The fibroblasts are removed from the plate using the normal trypsin-EDTA (0.5%-5.3 mM) procedure for five minutes. The fibroblasts are washed in PBS and then resuspended in 1 ml TL Hepes. One ml of 3 mg/ml protease in TL Hepes is added to 1 ml of cell suspension (final protease concentration is 1.5 mg/ml) and incubated at room temperature for one minute. The cells are washed in 10 ml HBSS and resuspended in 1 ml HBSS and counted. Approximately $10^5$ cells in minimal volume are used for mitotic extract incubation. Forty ul of MS-15 mitotic extract is placed on the cells for 30 minutes at 37° C. Cells are then washed in TL Hepes and used in one of the nuclear transfer procedures described herein.

These cells show signs of permeabilization because after incubation in the mitotic extract, 70-80% of the cells have undergone nuclear envelope breakdown and premature chromosome condensation, indicating that MPF (maturation promoting factor) from the extract or some component of MPF has traversed the membrane. This cell permeabilization method can be used with a variety of proteases such as trypsin and with a variety of germ, somatic, embryonic, fetal, adult, differentiated, and undifferentiated cells.

Formation, Activation, Culturing, and Transplantation of Reconstituted Oocytes

The reprogrammed cells are inserted into, or fused with, recipient oocytes using standard microinjection or electrofusion techniques (see, for example, U.S. Pat. Nos. 4,994,384 and 5,945,577). For example, the cells can be placed next to the oocytes in standard cell medium in the presence or absence of sucrose (e.g., 2.5% sucrose), and the cells can be drawn into an injection pippette. The pipette is then aspirated a few times to lyse the cells and remove cytoplasmic components from the nucleus which is then injected into the oocyte. The reconstituted oocytes are then activated, cultured, and transplanted into maternal recipient mammals using standard methods such as those described in Example 11 to produce cloned mammals.

EXAMPLE 13

Evidence for More Complete Nuclear Reprogramming Using Chromatin Transfer and Streptolysin O-Transfer As illustrated in Examples 8-10, incomplete nuclear remodeling and reprogramming occurs in traditional nuclear transplant pronuclear stage embryos. This finding was demonstrated by the assembly of lamins A/C in the nuclear envelope of pronuclear nuclear transplant embryos and excess NuMA immunofluorescence labeling. More complete nuclear reprogramming was achieved using the chromatin mass transfer method described in Example 11 and the cell permeabilization and reprogramming method (also referred to as SLOT) described in Example 12.

In particular, the cloning methods of the present invention produced embryos with protein expression patterns that more closely resembled in vitro fertilized embryos than cloned embryos produced using traditional cloning methods. As illustrated in Examples 8-10, chromatin transfer embryos expressed much less lamin A/C protein than traditional nuclear transfer embryos. Lamins A/C are somatic-specific components of the nuclear lamina that are naturally expressed in differentiated cells, but not expressed in embryos. Because of the reported interaction of lamins with transcription factors, chromatin proteins, and DNA, it is likely that the expression of lamins A/C in traditional nuclear transfer embryos promotes the expression of proteins specific for somatic cells that are undesirable for embryo development. Thus, the chromatin transfer embryos of the present invention may express fewer undesirable somatic-specific proteins than traditional nuclear transfer embryos. Additionally, the chromatin transfer embryos had expression patterns for NuMA, a main component of the nuclear matrix that is implicated in transcriptional regulation, that more closely resembled in vitro fertilized embryos than traditional nuclear transplant embryos. This result also indicates that chromatin transfer embryos are more efficiently reprogrammed than traditional nuclear transplant embryos.

Assessment of In Vitro Nuclear Breakdown of Bovine Fibroblast Nuclei

Figure 33:
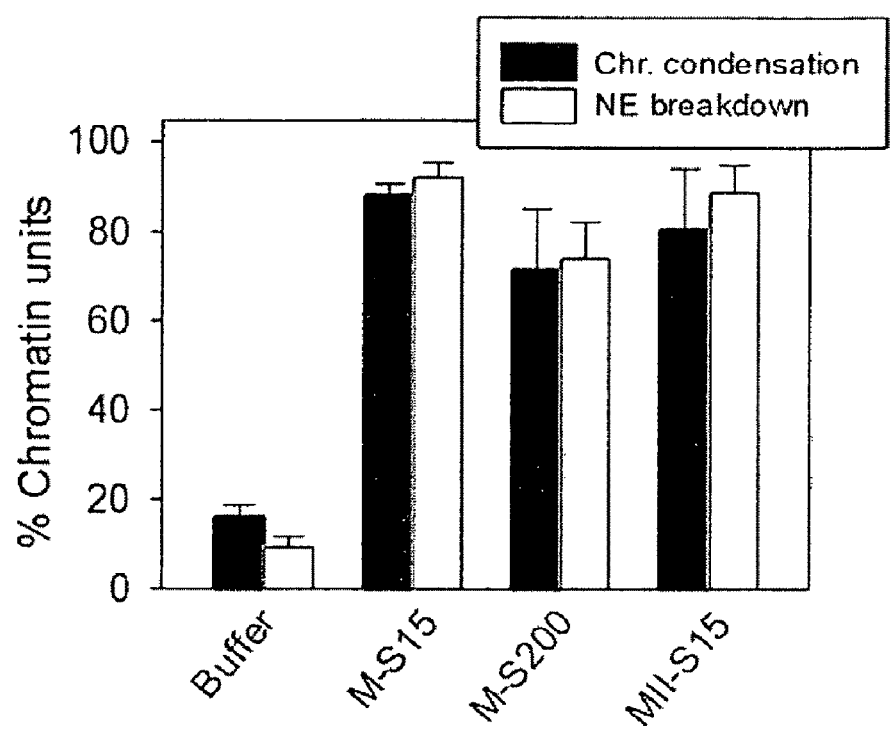
FIG. 33 is a graph of chromosome condensation and nuclear envelope breakdown in mitotic cytoplasmic extract (M-S15), mitotic cytosolic extract (M-S200), and oocyte extract (MII-S15) (n=300-400 nuclei examined in 3-5 replicates).

Extracts prepared from mitotic bovine fibroblasts consistently supported breakdown of 80% of input purified fibroblast nuclei (FIG. 33). An extract from metaphase II oocytes (i.e., an extract from oocytes naturally arrested in metaphase II prior to fertilization) also successfully supported nuclear breakdown (75% of nuclei within 30 minutes).

Figure 34:
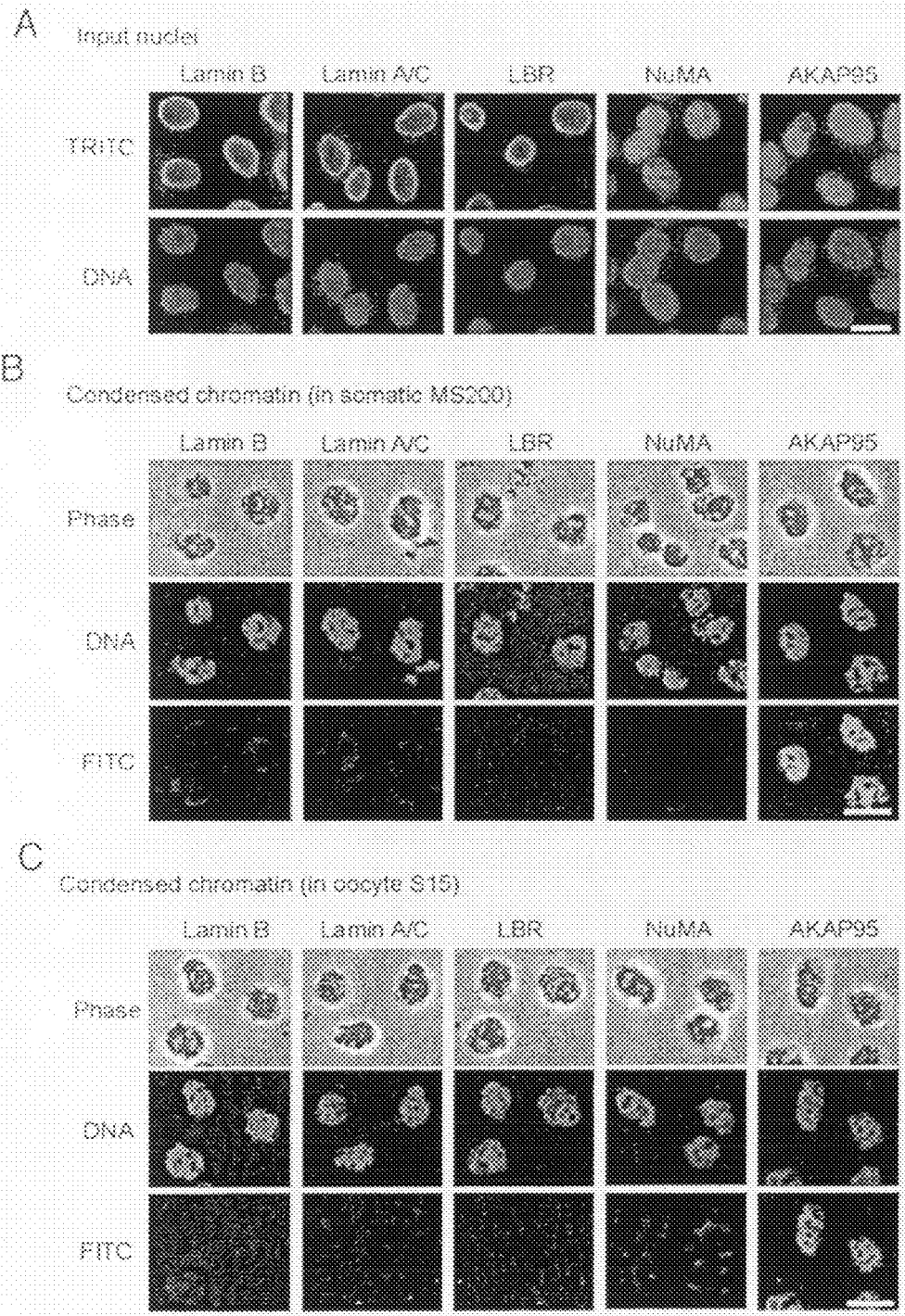
FIGS. 34A-34C are sets of pictures of immunofluorescence analysis of purified input bovine fibroblast nuclei (FIG. 34A) and condensed chromatin produced in mitotic cytosolic extract (FIG. 34B) and oocyte extract (FIG. 34C). The indicated nuclear markers were examined. DNA was counterstained with propidium iodide (red) (bars, 10 µm).
Figure 35:
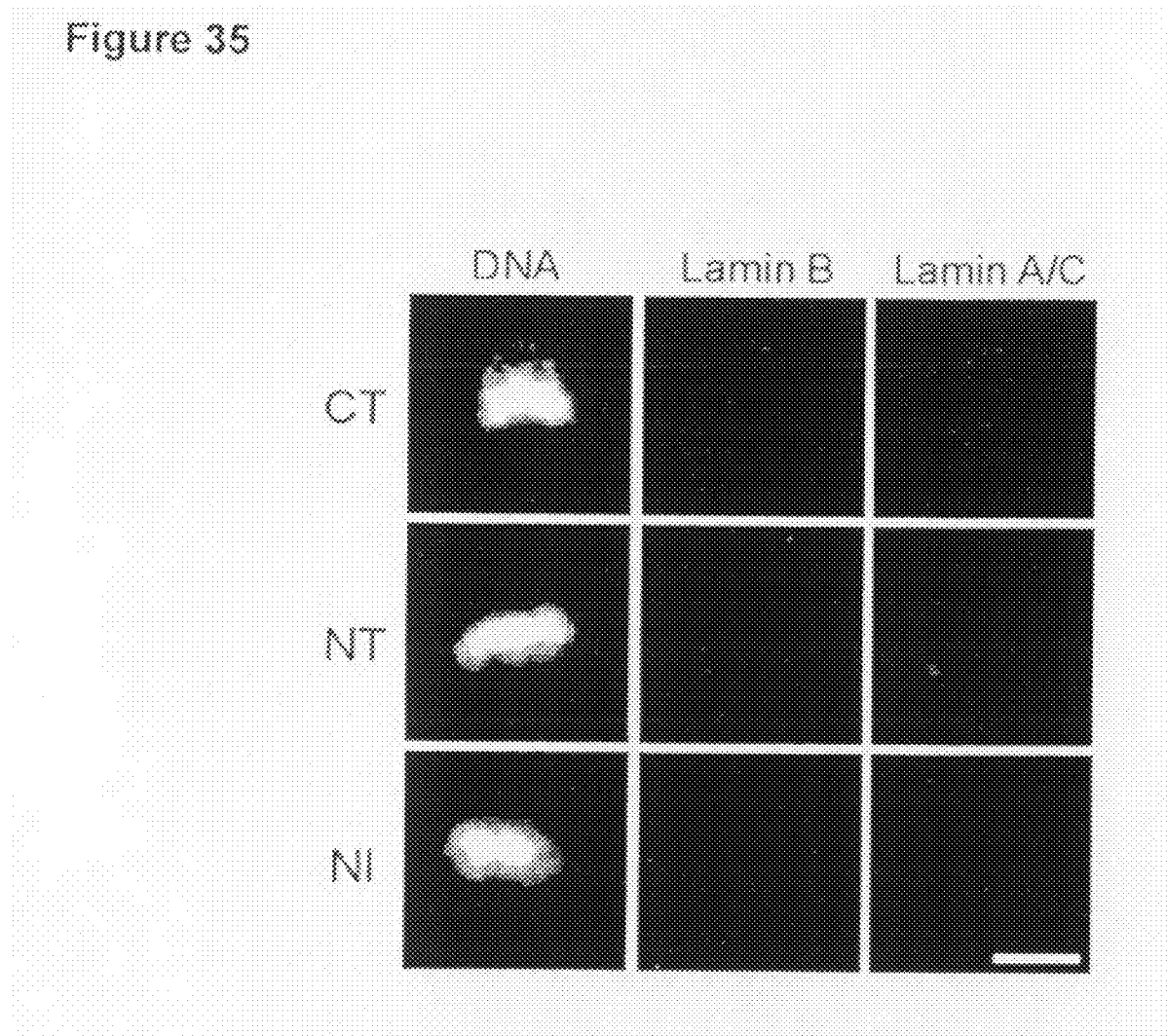
FIG. 35 is a series of photographs of immunofluorescence analysis of condensed chromatin obtained in oocytes following conventional nuclear transplant (NT) or nuclear injection (NI) methods and following injection of chromatin masses into oocytes (CT) using the methods of the present invention. Both detectable lamins B and A/C appear to be solubilized (bar, 10 µm).

Input interphase nuclei (FIG. 34A), chromatin masses obtained from nuclei incubated in a MS15 mitotic extract (FIG. 34B), and chromatin masses obtained from nuclei incubated in an oocyte extract (FIG. 34C) were examined for the expression of the following markers: lamin B receptor (LBR), an integral protein of the inner nuclear membrane (membrane marker); lamin B, a ubiquitous component of the nuclear lamina; lamins A/C, a somatic-specific component of the nuclear lamina present only in differentiated cells and absent in embryos; NuMA, a main component of the nuclear matrix; AKAP95, a PKA-anchoring protein of the nucleus; and DNA. Both somatic cytosolic MS15 and oocyte MS15 extracts induced solubilization of lamin B, lamins A/C, LBR, and NuMA in ~100% of chromatin units examined (FIGS. 34B and 34C). As expected, AKAP95 remained associated with chromosomes, as observed previously in mitotic human cells (Collas et al., J. Cell Biol. 147:1167-1180, 1999). This result was also described in Example 8 for bovine nuclear transplant embryos at the premature chromatin condensation stage. Both the mitotic extract and the oocyte extract appeared to be as efficient as intact oocytes in promoting nuclear envelope solubilization, regardless of the method used, i.e., traditional nuclear transplant, nuclear injection (NI), or chromatin transfer (FIG. 35).

Comparison of Pronuclear Embryos Produced by Chromatin Transfer and Pronuclei from Nuclear Transplant and Nuclear Injection Embryos To generate chromatin transfer embryos, in vitro-matured oocytes were enucleated about 18-20 hours post maturation. Nuclei from interphase bovine fetal fibroblasts were incubated in a MS15 mitotic extract that was prepared from bovine fetal cells as described herein. Chromatin masses were isolated from the extract when after nuclear envelope breakdown had occurred and before chromatin condensation was completed. In particular, the chromatin masses were isolated when the chromatin was approximately 50-60% condensed, compared to the level of condensation of chromosomes in interphase (designated 0% condensed) and the maximum level of condensation of chromosomes in mitosis (designated 100% condensed.) At this stage, individual chromosomes in the chromatin mass could not be distinguished and the edges of the chromatin mass had an irregular shape. Chromatin masses that had been isolated from the mitotic extract were placed in a microdrop of TL HEPES with 2.5% sucrose along with enucleated oocytes. The sucrose was added to the buffer to minimize damage to the ooctyes from the subsequent injection procedure. Chromatin masses were injected into the oocytes using a beveled microinjection pipette using a Burleigh Piezo Drill (Fishers, N.Y.) (frequency 2 Hz for 75 microseconds at an amplitude of 70 V). Typically multiple pulses, such as 2, 3, 4, or 5 pulses, were performed so that the needle sufficiently penetrated the oocyte for injection. After injection, oocytes were washed in serial dilutions of TL HEPES in sucrose to minimize osmotic shock. At 28-30 hours post maturation (i.e., 28-30 hours after oocytes were placed in maturation medium after collection from ovaries, which is also at least two hours after injection of chromatin masses), reconstructed oocytes and controls for parthenogenetic development were activated with calcium ionophore (5 µM) for four minutes (Cal Biochem, San Diego, Calif.) and 10 µg/ml cycloheximide and 2.5 µg/ml cytochalasin D (Sigma) in ACM culture medium (100 mM NaCl, 3 mM KCl, 0.27 mM $CaCl_2$, 25 mM $NaHCO_3$, 1 mM sodium lactate, 0.4 mM pyruvate, 1 mM L-glutamine, 3 mg/ml BSA (fatty acid free), 1% BME amino acids, and 1% MEM nonessential amino acids (Sigma)), for five hours as described earlier (Liu et al., Mol. Reprod. Dev. 49: 298-307, 1998). After activation, eggs were washed five times and placed in culture in four-well tissue culture plates containing mouse fetal fibroblasts and 0.5 ml of embryo culture medium covered with 0.3 ml of embryo tested mineral oil (Sigma). Between 25 and 50 embryos were placed in each well and incubated at 38.5° C. in a 5% $CO_2$ air atmosphere. If desired, calcium (e.g., ~.0.5, 1.0, 1.5, 2.0, 2.5, 3, 3.5, 5 mM, or more $CaCl_2$) can be added to the culture medium for ~0.5, 1.0, 1.5, 2.0, 2.5, 3.0, or more hours to promote resealing of the oocyte after injection. The resealed oocytes are likely to have increased survival rates due to the intact layer surrounding the oocytes when they are implanted into the recipient mammal using the standard methods described herein.

Nuclear injection embryos were formed as described above for chromatin transfer embryos, except that interphase bovine fetal fibroblasts nuclei that had not been incubated in an extract were injected into the oocytes instead of chromatin masses. Nuclear transplant embryos were generated using the conventional methods described in Example 8.

Figure 36A:
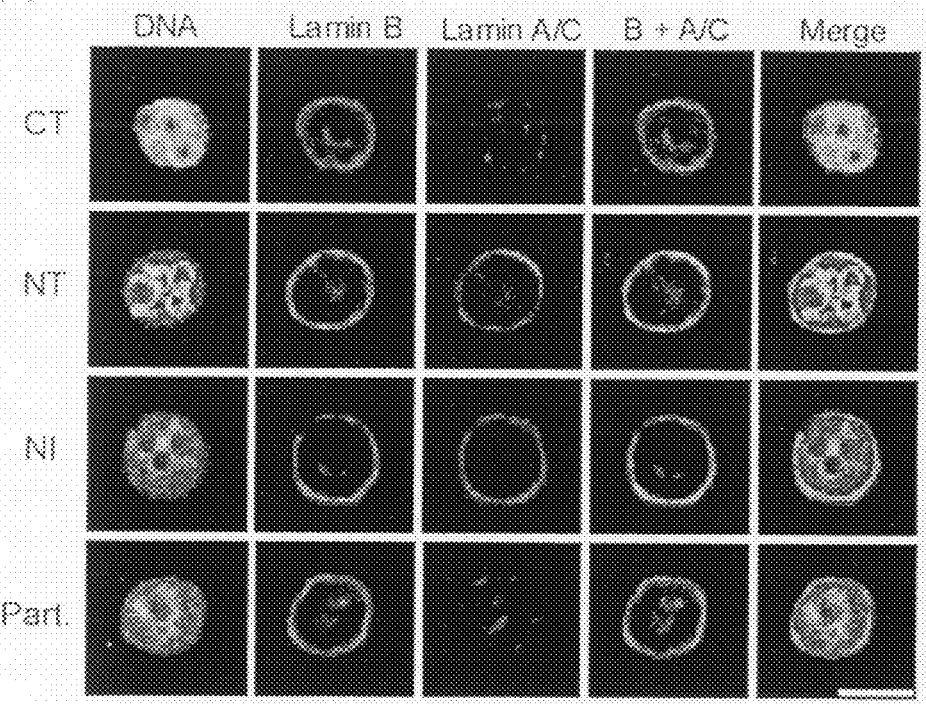
FIGS. 36A-36B are a series of photographs of immunofluorescence analysis of pronuclei resulting from chromatin transfer, nuclear transplant, or nuclear injection. Embryos were fixed at 19 hours post nuclear transplant, nuclear injection, or chromatin transfer and labeled. Control parthenogenetic pronuclei (Part.) were also examined.
Figure 36B:
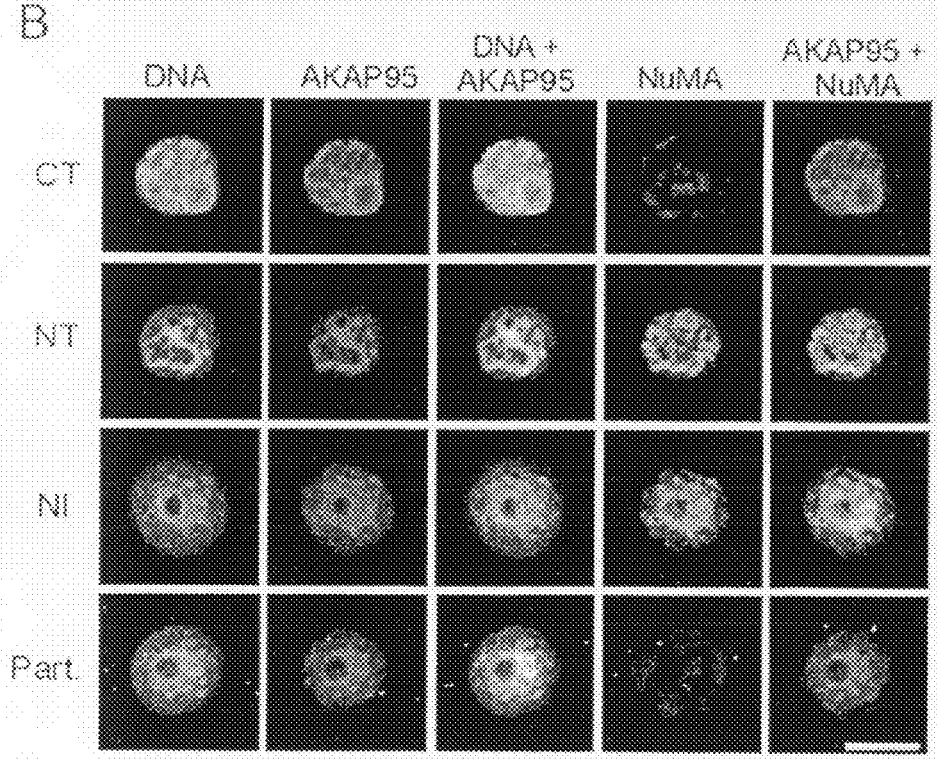

Nuclear transplant, nuclear injection, and chromatin transfer pronuclei reassemble lamin B (FIG. 36A, red label) and AKAP95 (FIG. 36B, red label) as anticipated. Nuclear transplant and nuclear injection pronuclei also reassemble lamins A/C, a somatic-specific component (FIG. 36A, green label), consistent with the results reported above for nuclear transplant embryos. However, chromatin transfer pronuclei and control parthenote pronuclei do not reassemble lamins A/C (FIG. 36A). Nuclear transplant pronuclei also contain NuMA (green label), unlike most chromatin transfer or parthenote pronuclei (FIG. 36B, green label). A proportion of parthenote nuclei and chromatin transfer nuclei assemble a low level of NuMA, as reported above.

In vitro disassembly of nuclei followed by chromatin transfer results in pronuclei that are morphologically similar to control parthenote pronuclei. In contrast, nuclear transplant and nuclear injection pronuclei harbor somatic-specific components (lamins A/C and extensive NuMA labeling). This result is indicative of incomplete nuclear remodeling after traditional nuclear transplant or nuclear injection procedures. As described above, lamins A/C detected in nuclear transplant and nuclear injection pronuclei originate from lamins transcribed de novo at the pronuclear stage. Because nuclear lamins and possibly NuMA are implicated in transcription regulation and disease in humans, persistence of lamins A/C in conventional nuclear transplant pronuclei might be indicative of improper functional reprogramming. We conclude that in vitro nuclear disassembly and chromatin transfer produces more normal pronuclei than traditional nuclear transplant or nuclear injection.

Cloning Efficiency Using Reprogrammed Chromatin Masses or Permeabilized Cells as Donor Source As described in Example 12, a cloning procedure denoted "SLOT" was developed that involves Streptolysin O (SLO)-induced permeabilization of primary fetal bovine fibroblasts, exposure of permeabilized cells to a reprogramming media (e.g., a mitotic extract) for 30 minutes, optional resealing of the fibroblasts with 2 mM calcium in culture, and transfer of the chromatin into oocytes using standard cell fusion methods.

For this cloning method, a vial of Streptolysin O (Sigma S-5265; 25,000 units stored in store powder form at 4° C.) was dissolved in 400 µl $H_2O$ and mixed well. All contents were transferred to a 15-ml conical tube, and then 3.6 ml $H_2O$ was added and mixed by vortexing. Aliquots of 10 µl were frozen at −20° C. at a stock concentration of 0.062 U/µl. Cells (~100,000) were suspended in 100 µl HBSS (Gibco BRL, cat. No. 14170-120) at room temperature. These cells were confluent, and thus ~80-85% of the cells were in G1 phase, and the majority of the other cells were in S phase. Streptolysin O stock solution (5 µl) (i.e., 500 ng/ml or 0.3 U/µl final concentration) was added, and the mixture was incubated at 38° C. for 25 minutes in a water bath. The tube was gently tapped 2-3 times during incubation to ensure that the cells remained in suspension. Room temperature PBS (200 µl) was added and mixed well by gentle pipetting. The cells were centrifuged cells at 5,000 rpm for five minutes at room temperature in a tabletop centrifuge. All the supernatant was discarded. At this stage, the pellet is small and may not be clearly visible. Mitotic extract containing the ATP-generating system (40 µl, "MS15") was added and mixed well. The extract was prepared during the centrifugation of the cells by thawing one vial of 40 µl extract and adding 1.2 µl of ATP-generating system, mixing well, and incubating at room temperature. This mitotic extract was the same extract used for the generation of chromatin masses in the section above. The mixture was incubated at 38° C. in water bath for 30 minutes, and the tube was occasionally gently tapped. Room temperature resealing medium (RM, 500 µL) (complete α-MEM [Bio-Whittaker] medium supplemented with $CaCl_2$ to 2 mM from a 1 M stock) was added. The tube was left open and incubated in a $CO_2$ incubator for two hours with occasional tapping of the tube to ensure that the cells remained in suspension. The cells were centrifuged at 5,000 rpm for five minutes at room temperature in a tabletop centrifuge. The cell pellet was resuspended in 100 µl of room temperature TL HEPES (Bio-Whittaker, cat. No. 04-616F), and another 900 µl TL HEPES was added. The nuclear transfer was performed using standard procedures. Oocytes were activated and transferred to recipient mammals as described in the previous section for chromatin transfer.

The development of embryos formed using this SLOT method and the chromatin transfer method of the present invention is summarized in Table 7. Development to the blastocyst stage was slightly lower for SLOT embryos compared to conventional nuclear transfer embryos. The differences between SLOT and nuclear transfer development at the blastocyst stage could be due to the effect of using a greater percentage of cells in the G1 phase of the cell cycle for nuclear transfer than for SLOT. The survival rate was lower for chromatin transfer embryos, which is expected for an invasive procedure.

Pregnancy rates were comparable for nuclear transfer and SLOT embryos at 40 days of gestation (Table 9). Survival from 40 days of pregnancy to 60 days tended to be higher for SLOT embryos than for nuclear transfer embryos produced using conventional methods.

TABLE 9

Development of chromatin transfer nuclear transplant, and SLOT-produced bovine embryo clones

|  | No. transferred | No. Survived (%) | No. PN stage (%) | No. Cleaved (%) | No. Blastocysts (%) | No. 40 day Preg. (%) | No. Survived 40-60 days/total (%) |
|---|---|---|---|---|---|---|---|
| CT | 1503 | 736 (49) | 355 (23.5) | 81 (5.3) | 3 | 0 | ND |
| SLOT | 1884 | 1802 (97) | ND | 575 (30.5) | 156 (8.3) | 24/65 (37) | 7/10 (70) |
| nuclear transplant | 1821 | 1682 (92) | ND | 764 (41.9) | 235 (12.9) | 39/103 (36) | 8/16 (50) |

As noted above, the survival rate for chromatin transfer embryos may be increased by incubating the reconstituted oocytes in calcium for a few hours to allow the oocytes to reseal prior to be inserted into recipient mammals. Survival rates for SLOT embryos may also be increased by reducing the amount of time between when the cells are taken out of culture and when they are fused with oocytes. For example, the length of time for the incubation in Streptolysin O, the incubation in the reprogramming medium, and/or the incubation in the resealing medium may be decreased. In particular, the incubation in the resealing medium may be decreased to approximately one hour or less. This shortened resealing treatment may be performed in the presence of 2 mM calcium as described above or in the presence of a higher concentration of calcium (e.g., 2.5, 3.0, 3.5, 4.0, 4.5, 5.0, or 6.0 mM calcium) to increase the rate of resealing. By reducing the amount of time the cells are treated prior to being fused with oocytes, the cells are less likely to enter S phase and begin DNA replication which reduces the survival rate of the reconstituted oocyte.

EXAMPLE 14

Evidence for More Complete Nuclear Reprogramming Using Chromatin Transfer

As discussed in Example 11, a strategy was developed to enhance remodeling of donor nuclei, promote repression of somatic genes, and produce embryos with a pronuclear architecture similar to that of fertilized zygotes. In a particular example of this general chromatin transfer method, isolated intact bovine fibroblast nuclei were incubated in a cytoplasmic extract of mitotic bovine fibroblasts in the presence of an ATP-generating system, which was required to drive nuclear disassembly.

To generate a mitotic reprogramming extract for conversion of donor nuclei into chromatin masses, fibroblasts were synchronized in mitosis with 0.5 µg/ml nocodazole for ~18 hours, harvested by mitotic shake-off, and washed twice in ice-cold PBS and once in ice-cold cell lysis buffer (20 mM Hepes, pH 8.2, 5 mM $MgCl_2$, 10 mM EDTA, 1 mM DTT, and protease inhibitors) (Collas et al., J. Cell Biol. 147:1167-1179, 1999). Packed cells were resuspended one volume of cell lysis buffer, allowed to swell on ice for one hour and Dounce-homogenized on ice using a tight fitting pestle until all cells were lysed. The lysate was centrifuged at 15,000×g for 15 minutes at 4° C., and the supernatant (mitotic extract) was collected, aliquoted, and snap-frozen in liquid nitrogen and stored at –80° C.

To generate donor chromatin, unsynchronized confluent fibroblasts were harvested, washed, and resuspended in ~20 volumes of ice-cold hypotonic nuclear isolation buffer (10 mM Hepes, pH 7.5, 2 mm $MgCl_2$, 25 mM KCl, 1 mm DTT, and a cocktail of protease inhibitors) (Collas et al., J. Cell Biol. 147:1167-1179, 1999). After one hour on ice, cells were Dounce-homogenized with a tight-fitting pestle. Sucrose was added from a 2 M stock to a concentration of 250 mM and nuclei sedimented at 400×g for 10 minutes at 4° C. Nuclei were washed in nuclear isolation buffer (same buffer as above but with 250 mM sucrose) and were either used fresh or frozen in nuclear isolation buffer/70% glycerol (Collas et al., J. Cell Biol. 147:1167-1179, 1999).

For reprogramming, isolated fibroblast nuclei were incubated in 40111 of mitotic extract containing an ATP-generating system (1 mM ATP, 10 mM creatine phosphate, and 25 µg/ml creatine kinase) at 4,000 nuclei/µl for 30 minutes in a 38° C. $H_2O$ bath. Nuclear envelope breakdown and chromatin condensation were monitored by phase contrast microscopy. At the end of incubation, the reaction mix was diluted with 500 µl TL Hepes containing 2.5% sucrose, and chromatin was recovered by sedimentation at 2,000×g for five minutes. Chromatin masses were resuspended in TL Hepes/sucrose and transferred to TL Hepes/sucrose under mineral oil together with enucleated oocytes. Individual chromatin masses were injected into in vitro-matured oocytes enucleated at 20 hpm with a beveled microinjection pipette using a Burleigh Piezo Drill (Fishers, N.Y.) (2 Hz, 2 µs, 70 V). After injection, oocytes were washed in serial dilutions of sucrose in TL Hepes to minimize osmotic shock and cultured. At 28 hpm, reconstructed oocytes and parthenogenetic controls were activated as described for NT and cultured ((Kasinathan et al., Nat. Biotechnol. 19:1176-1178, 2001 and Kasinathan et al., Biol. Reprod. 64:1487-1493, 2001). For nuclear injections (NI), purified fibroblast nuclei were exposed to cell lysis buffer instead of mitotic extract and injected into enucleated oocytes as for CT.

Figure 42A:
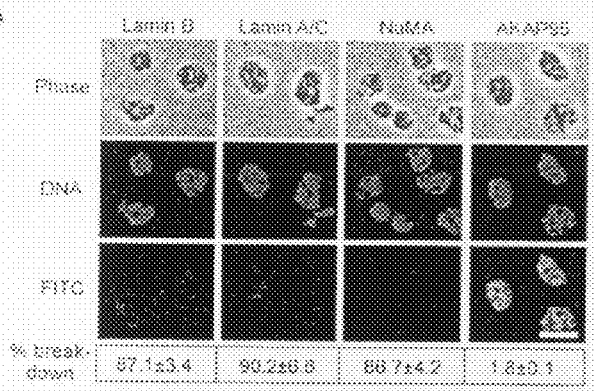
FIGS. 42A-42D demonstrate that CT produces embryos devoid of lamin A/C and NuMA. Redistribution of lamins A/C and B, NuMA and AKAP95 was monitored by immunofluorescence in bovine fibroblast nuclei incubated in extract from mitotic bovine fibroblasts (Chaudhary et al., J. Cell Biol. 122:295-306, 1993) (FIG. 42A). DNA was labeled with 0.1 μg/ml propidium iodide. Percentages of nuclei displaying disassembly (disappearance of labeling) of indicated markers are shown (n>200 nuclei/marker in three replicates). PN embryos were produced by CT, NT, NI, or parthenogenesis, and distribution of lamins A/C and B, NuMA and AKAP95 was examined by immunofluorescence 14 hours after start of activation (Poccia et al., Trends Biochem. Sci. 17:223-227, 1992 and Chaudhary et al., J. Cell Biol. 122:295-306, 1993) (FIG. 42B). DNA was labeled with Hoechst 33342. Mean±SD immunofluorescence intensity of indicated markers in CT, NI, or parthenogenetic embryos relative to fluorescence intensity in PN-stage NT embryos (NT, 100% fluorescence; n=15-20 embryos/marker in three replicates) (FIG. 42C). Immunolabeling intensity of lamin B, DNA, and AKAP95 in PN-stage NT and CT embryos after extraction with Triton X-100/DNAse I/NaCl (FIG. 42D). Values are expressed as mean±SD fluorescence intensity relative to non-extracted pronuclear NT and CT embryos, respectively (n~15 embryos/marker/treatment in three replicates). Bars 10 μm (FIG. 42A), 20 μm (FIG. 42B).

As a result of reprogramming, lamin A/C, lamin B, and NuMA were readily disassembled, while AKAP95 remained associated with condensed chromosomes (FIG. 42A). TUNEL analysis showed that no apoptosis occurred in the extract. Similar nuclear breakdown studies with human HeLa nuclei and mitotic extracts indicated that condensed chromatin masses were capable of supporting nuclear reconstitution (Steen et al., J. Cell Biol. 150:1251-1562, 2000) and transcription in interphase cytoplasm. Thus, in vitro nuclear disassembly produces condensed chromatin capable of reforming functional nuclei. Condensed fibroblast chromatin was recovered by sedimentation, and individual chromatin masses were injected into enucleated recipient oocytes. After recovery in culture, oocytes were activated as described in Example 9 for NT oocytes. To control for artifacts generated by handling of nuclei, intact nuclei exposed to extract buffer alone were also injected.

Figure 42B:
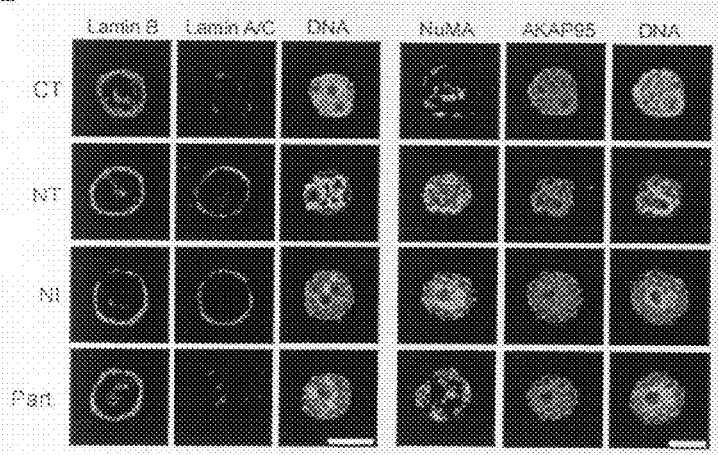
Figure 42C:
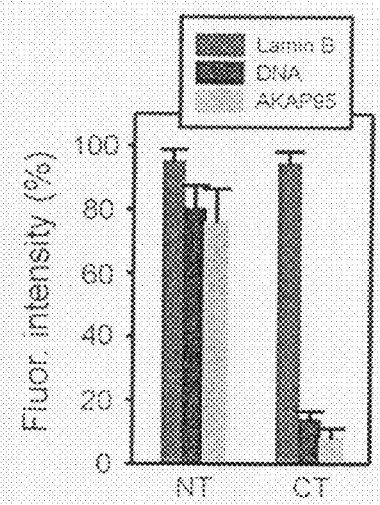
Figure 42D:
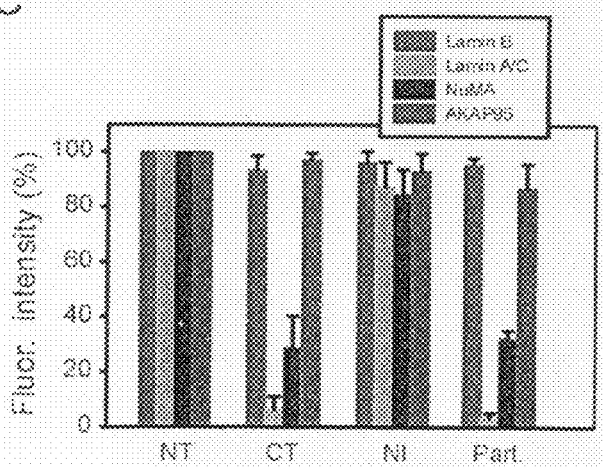

CT and control nuclear injection (NI) results are shown in FIGS. 42A-42D. NI produced pronuclei which, like NT pronuclei, contained lamins A/C and B, NuMA, and AKAP95 (FIGS. 42B and 42C). CT resulted in PN formation in over 80% of embryos that survived injection and activation (~50% of oocytes injected, n>2,000). However, CT pronuclei displayed no detectable lamin A/C and a 3-fold reduction of anti-NuMA immunolabeling compared to NT and NI pronuclei (FIGS. 42B and 42C). This pattern was similar to that of parthenogenetic pronuclei. Extractability of AKAP95 and DNA with Triton X-100/DNAse I/NaCl as described above was enhanced 8-fold in CT pronuclei compared to NT pronuclei, reflecting a beneficial effect of CT on pronuclear AKAP95 anchoring and DNAse I accessibility (FIG. 42D). As chromatin-bound AKAP95 co-fractionates with primarily transcriptionally repressed (hypoacetylated) chromatin, this result suggests that CT enhances formation of euchromatin upon PN assembly.

The dynamics of the TATA binding protein, TBP, was examined during fibroblast donor nucleus remodeling by NT and CT procedures carried out in parallel. TBP facilitates assembly of the general transcription machinery for virtually all genes (Sharp et al., Cell 68:819-821, 1992). TBP co-localized with AKAP95 and DNA in donor fibroblast nuclei (FIG. 43A). PCC chromosomes obtained after NT contained 5-fold more TBP than chromosomes condensed in mitotic extract, as shown by TBP/AKAP95 and TBP/DNA fluorescence intensity ratios (FIG. 43B). TPB labeling intensity of chromosomes condensed in vitro resembled that of mitotic fibroblasts. At the PN stage, TBP was barely detectable in CT embryos but displayed strong immunoreactivity in NT and NI embryos (FIG. 43A). Pronuclear TBP in NT embryos was of somatic origin because inhibition of transcription or translation maintained strong TBP labeling. Pronuclear TBP concentration in the mouse has been shown to increase during progression through interphase (Worrad et al., Development 120:2347-2357, 1994). However, the similarity in kinetics of PN formation from PCC- or in vitro-condensed chromatin between reconstructed NT and CT embryos indicated that the enhanced TBP concentration in NT pronuclei was not due to more a advanced cell cycle stage. Thus, in vitro disassembly of donor nuclei promotes dissociation of TBP from the chromatin, such that resulting CT pronuclei contain ~10-fold less TBP than NT pronuclei at the same stage of reconstitution.

Thus, five structural and functional markers of incomplete reprogramming by NT include pronuclear assembly of lamins A/C, enhanced pronuclear NuMA and TBP concentrations, and increased sensitivity of AKAP95 and DNA to extraction with detergent, DNAse, and salt. In contrast, B-type lamins, essential for proper nuclear reformation and cell survival (Steen et al., J. Cell Biol. 153:621-626, 2001) appear to assemble normally in NT pronuclei, although we were not able to determine whether the pool of assembled B-type lamins was of somatic (and therefore re-targeted) or of maternal origin. The LMNA gene remains active in NT pronuclei, resulting in the assembly of differentiated cell-specific A-type lamins. Through interactions with chromatin and the transcription machinery, nuclear lamins have been suggested to participate in transcription regulation (Cohen et al., Trends Biochem. Sci. 26:41-47, 2001); thus, assembly of the correct set(s) of nuclear lamins is most likely critical for proper pronuclear function in NT embryos.

In the present methods, somatic nuclear components are dispersed in the extract and typically do not come in contact with the oocyte cytoplasm. This prohibits re-targeting of somatic-specific molecules to the developing nucleus, such as B-type lamins whose composition may differ from that of maternal lamins (Cohen et al., Trends Biochem. Sci. 26:41-47, 2001). In vitro chromatin condensation may also promote release of DNA-bound factors such as chromatin remodeling enzymes (Sif et al., Genes Devel. 12:2842-2851, 1998) and transcription factors, thereby "stripping" the donor genome of potentially inhibitory somatic components. In particular, TBP removal may result in inactivation of somatic-specific genes in reconstituted CT pronuclei and duplicate the low transcriptional activity of the male pronucleus after fertilization (Poccia et al., Trends Biochem. Sci. 17:223-227, 1992).

An implication of removing factors from the donor nucleus is that loading of maternal components onto chromatin and remodeling into a physiological pronucleus may be facilitated. CT increases the sensitivity of AKAP95 and DNA to nucleases and salt. DNAse I-resistant DNA is mostly transcriptionally silent; thus, incomplete remodeling of AKAP95 anchoring by NT may impair expression of developmentally important genes, such as genes involved in placental development, maintenance of late pregnancy and post-natal survival of cloned animals.

The following characteristics of CT oocytes indicate that nuclear transfer of a chromatin mass incubated in a mitotic extract significantly improves the functional characteristics of the resulting reconstituted oocyte. A nuclear matrix protein that is expressed at high levels by somatic donor cells, NuMA, was expressed 3-fold less in CT pronuclei (i.e., pronuclei formed after introduction of a chromatin mass into an oocyte) than in NT pronuclei. This result indicates that the level of NuMA in CT oocytes is more similar to the level of NuMA in naturally-occurring oocytes than in NT oocytes. CT pronuclei also expressed 10-fold less of the general transcription factor TBP than NT pronuclei. This removal of TBP from the donor chromatin mass by incubation in the mitotic extract may result in inactivation of undesired, somatic-specific genes in the resulting CT oocyte. Lamin A/C, a nuclear envelope protein that is specific for differentiated cells and is not detected in in vitro fertilized or parthenogenically activated oocytes, was also not detected in CT pronuclei but was detected in NT pronuclei. Because nuclear lamins may regulate transcription, the lack of detectable lamin A/C in CT pronuclei may result in more appropriate regulation of transcription in CT oocytes than in NT oocytes. The sensitivity of AKAP95, a structural protein of the nuclear matrix-chromatin interface which is enriched in transcriptionally repressed (hypoacetylated) chromatin, and DNA to extraction with detergent, DNase, and salt was measured in the pronuclei to characterize the anchoring of AKAP95 to DNA and to characterize DNA accessibility in the pronuclei. Extractability was enhanced 8-fold in CT pronuclei compared to NT pronuclei, reflecting a beneficial effect of incubation of a donor chromatin mass in a mitotic extract on AKAP95 anchoring and morphological remodeling of the donor DNA. Because AKAP95 and DNase I-resistant DNA is associated with transcriptionally repressed or silent DNA, the increased sensitivity of AKAP95 and DNA to nucleases, salt, and detergent suggests that CT oocytes may have increased expression of developmentally important genes.

Similar results are expected with donor nuclei from cells with one or more mutations in a prion gene.

EXAMPLE 15

Evidence for More Complete Nuclear Reprogramming Using Streptolysin O-Transfer

Figure 45A:
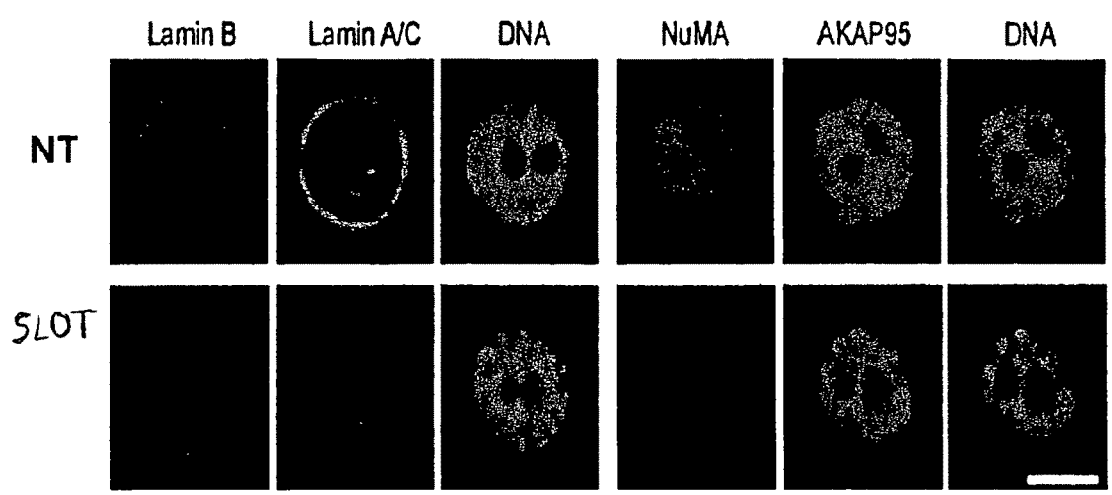
FIG. 45A is a photograph illustrating the level of lamin B, lamin A/C, NuMA, AKAP95, and DNA in pronuclei from NT and SLOT embryos.
Figure 45B:
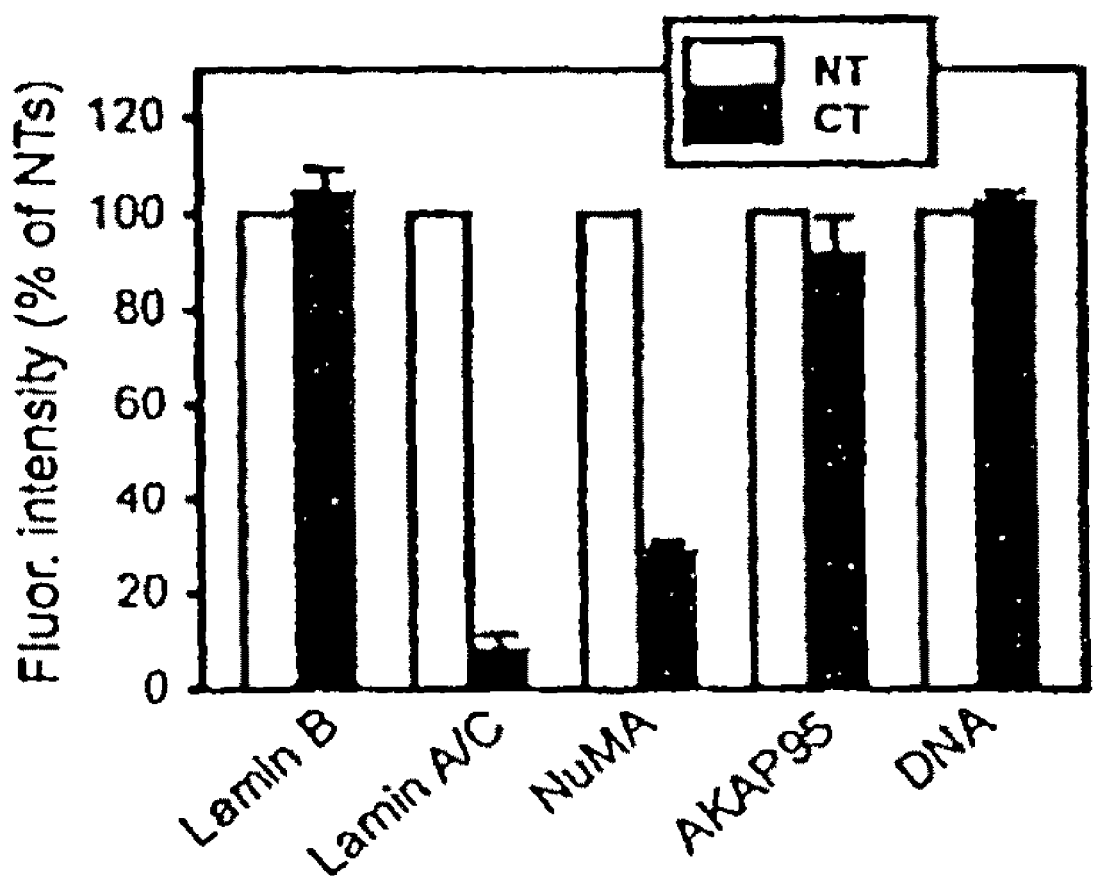
FIG. 45B is a graph of the fluorescence intensity from FIG. 45A.

The reprogramming of a chromatin mass during incubation of a permeabilized cell in a mitotic extract using SLOT is also demonstrated in FIGS. 45A and 45B. In this study, the expression of a nuclear matrix protein that is expressed at high levels by somatic donor cells, NuMA, and the expression of a nuclear envelope protein that is specific for differentiated cells, lamin A/C, was compared for oocytes produced using SLOT and oocytes produced using traditional nuclear transfer of a cell containing a nucleus that has not been incubated in an extract ("NT"). Fourteen hours after activation, the SLOT pronuclei (i.e., pronuclei formed after introduction of a donor cell containing a chromatin mass into an oocyte) expressed significantly less NuMA and lamin A/C than NT pronuclei (n=15-20 embryos/marker in three replicates). These results demonstrate that reconstituted SLOT oocytes are more efficiently reprogrammed than NT oocytes and more closely resemble naturally-occurring, fertilized oocytes. Because nuclear lamins may regulate transcription, the significantly lower level of lamin A/C in SLOT pronuclei may result in more appropriate regulation of transcription in SLOT oocytes than in NT oocytes.

In addition to reducing the expression of undesired factors in the resulting oocyte, SLOT increases the viability of the resulting fetuses compared to traditional nuclear transfer methods (Table 10). Thus, the many structural and functional differences of SLOT donor cells substantially improve the ability of the reconstituted oocytes to form non-human embryos and non-human mammals.

TABLE 10

Development of bovine embryos produced using permeabilized donor cells with a chromatin mass ("SLOT") compared to bovine embryos produced using donor cells with a nucleus ("NT")

|  | No. transferred | No. of Recipients | No. 40 day Preg. (%) | No. 90 day Preg. (%) |
|---|---|---|---|---|
| SLOT | 1955 | 59 | 29/59 (49) | 14/59 (24) |
| NT | 1885 | 95 | 44/95 (46) | 16/95 (17) |

EXAMPLE 16

Exemplary Evidence for More Complete Nuclear Reprogramming Using Streptolysin O-Transfer (SLOT)

As described in Examples 12 and 15, a novel in vitro nuclear remodeling system has been developed. The system involves permeabilization of the donor cell, induction of chromatin condensation in a mitotic cell extract, and washing of the permeabilized cell to remove nuclear factors solubilized during condensation of the chromatin. Pronuclei of bovine chromatin transplant embryos exhibit an expression pattern of several markers that closely resembles that of normal embryos as opposed to nuclear transplant embryos, which resemble somatic cells. Eight healthy calves were produced using this chromatin transfer system. Chromatin transfer shows trends of increased survival to term, lower incidence of large calves, and significantly enhanced survival after birth. The results demonstrate the successful manipulation of a somatic donor nucleus prior to transplantation. As described further below, the disassembly of a somatic nucleus in a mitotic extract followed by transfer of the condensed chromatin into an oocyte enhances nuclear remodeling and shows evidence of improved development and viability of clones. This procedure can be used to further characterize the mechanism of nuclear reprogramming, if desired.

A Chromatin Transfer Strategy

To alleviate defects identified in pronuclear NT embryos, fibroblast nuclei were manipulated in vitro prior to transfer into recipient oocytes. This SLOT system is outlined in FIG. 48. For generation of a mitotic extract, fibroblasts were synchronized in mitosis with 1 μg/ml nocodazole for 18 hours, harvested by mitotic shake-off, and washed twice in phosphate buffered saline and once in cell lysis buffer (20 mM Hepes, pH 8.2, 5 mM $MgCl_2$, 10 mM EDTA, 1 mM DTT and protease inhibitors). Sedimented cells were resuspended in one volume of ice-cold cell lysis buffer, allowed to swell on ice for one hour, and Dounce-homogenized using a tight-fitting glass pestle. The lysate was centrifuged at 15,000×g for 15 minutes at 4° C. and the supernatant (mitotic extract) was aliquoted, frozen in liquid nitrogen, and stored at −80° C. Fresh or frozen extracts were used without noticeable differences on efficiency of nuclear breakdown.

Bovine fetal fibroblasts from confluent cultures were washed in $Ca^{2+}/Mg^{2+}$-free Hank's Balanced Salt Solution (HBSS) and permeabilized by incubation of 100,000 cells in suspension with 31.2 U Streptolysin O (SLO; Sigma) in 100 μl HBSS for 30 minutes in an approximately 38.5° C. $H_2O$ bath. Permeabilization was assessed by uptake of the membrane impermeant DNA stain, propidium iodide (0.1 g/ml). Permeabilized fibroblasts were sedimented, washed, and incubated in 40 μl mitotic extract containing an ATP-generating system (1 mM ATP, 10 mM creatine phosphate, and 25 μg/ml creatine kinase) for 30-45 minutes at approximately 38.5° C. to promote nuclear disassembly and removal of nuclear components. Aliquots were labeled with 0.1 μg/ml Hoechst 33342 to monitor chromatin condensation. After the incubation, fibroblasts were recovered from the extract by sedimentation and washed. The reaction mixture was diluted with 500 μl Alpha MEM/10% fetal bovine serum (Gibco-BRL) containing 2 mM $CaCl_2$ for membrane resealing, and the cells were cultured for two hours at 38.5° C. (Håkelien et al., Nat. Biotechnol. 20:460-466, 2002). Resealing was monitored by propidium iodide uptake. Resealed cells were fused with in vitro-matured oocytes that had been enucleated at 20 hpm; oocytes were activated at 28 hpm, and embryos cultured as described for NT in Example 10.

SLOT embryos were cultured to the blastocyst stage in vitro, and two embryos were transferred per recipient female. Pregnancies were monitored by ultrasonography, and C-sections were performed. Calves were scored by veterinarians within 24 hours of birth.

Breakdown of Fibroblast Nuclei in Mitotic Extract

Figure 49A:
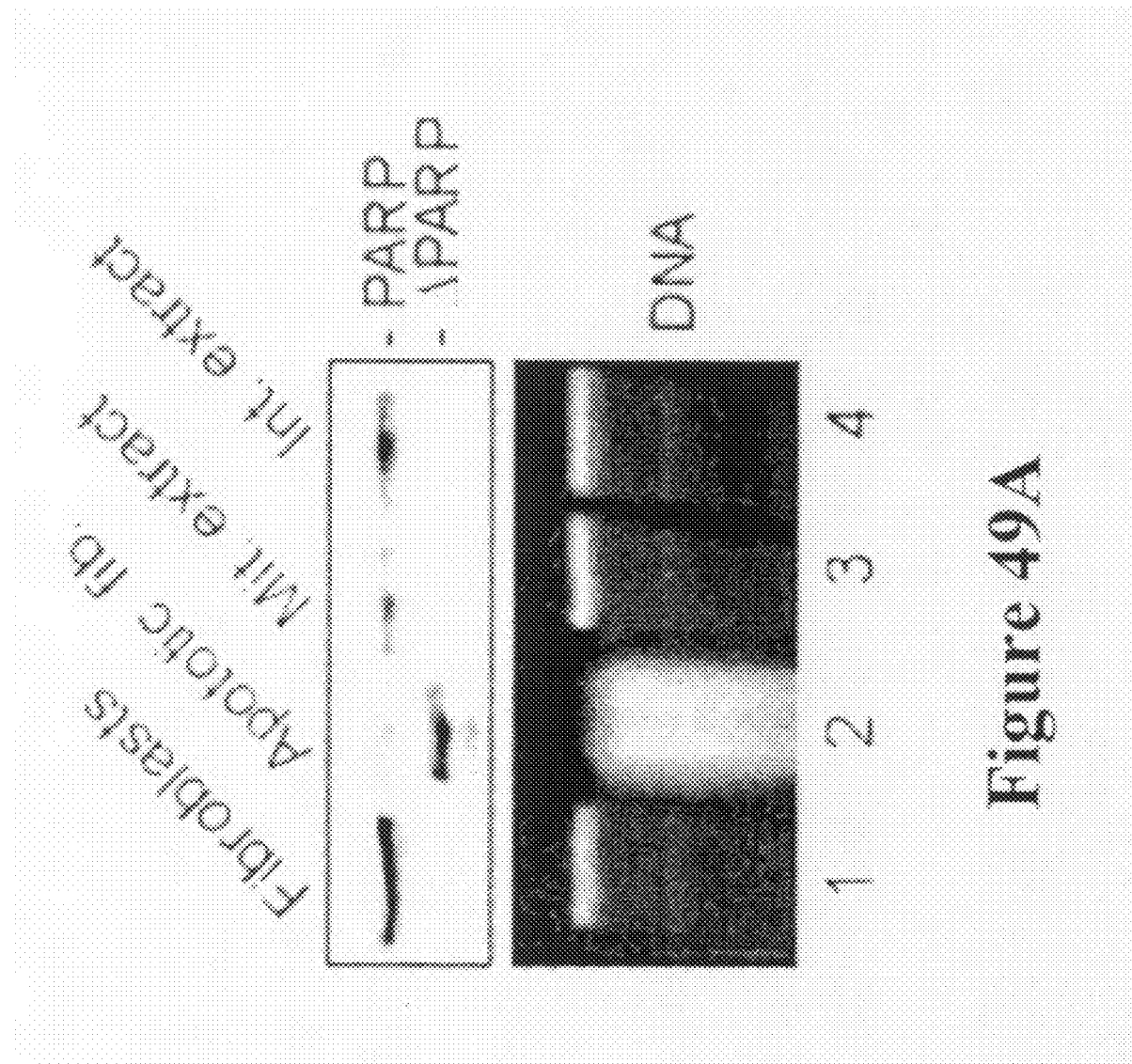
FIGS. 49A-49C show the induction of somatic nuclear breakdown in mitotic extract.

The mitotic extract consisted of a 15,000×g supernatant from a lysate of mitotic bovine fibroblasts and contained an ATP-regenerating system. The extract did not induce apoptosis, as judged by the absence of proteolysis of poly(ADP) ribosyl polymerase (PARP) and DNA fragmentation characteristic of apoptotic fibroblasts (FIG. 49A). Thus, the extract was suitable to promote remodeling of somatic nuclei.

Figure 49B:
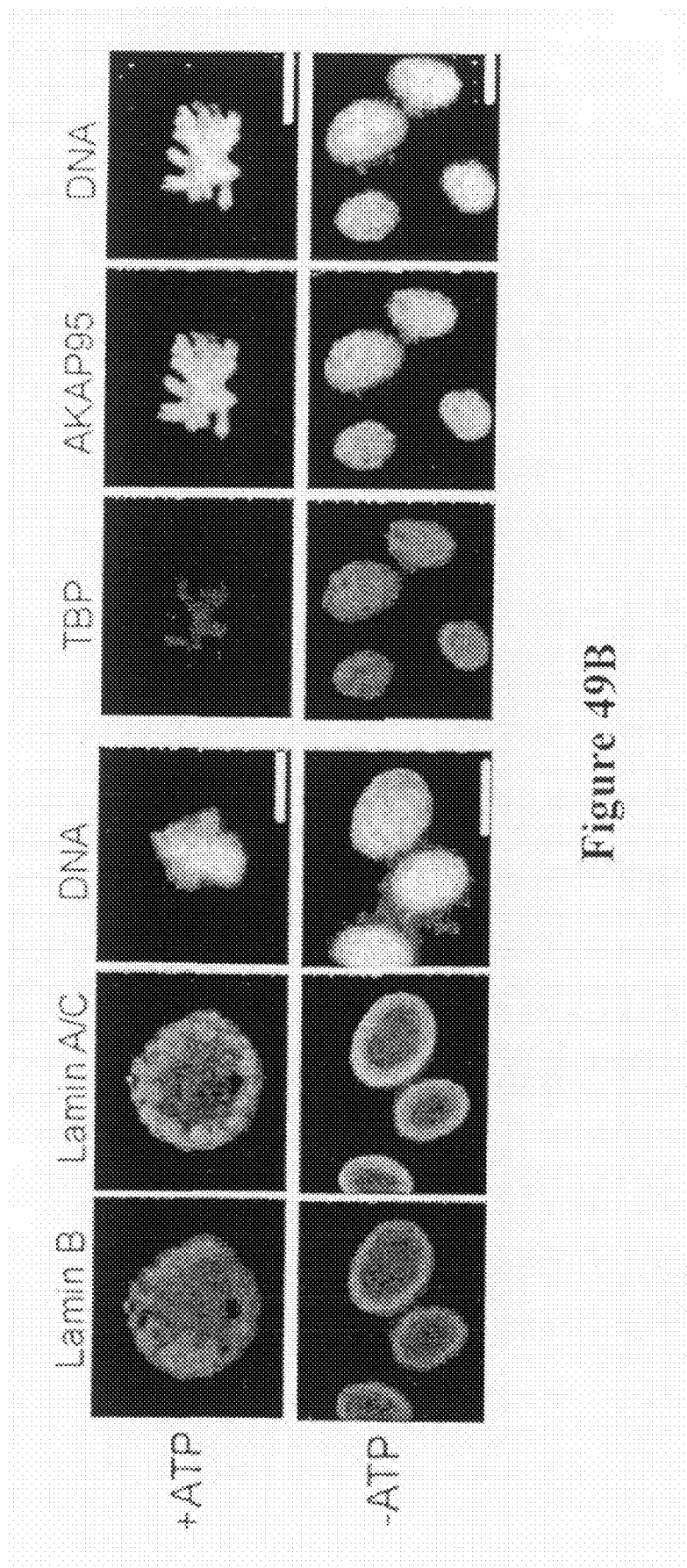
Figure 49C:
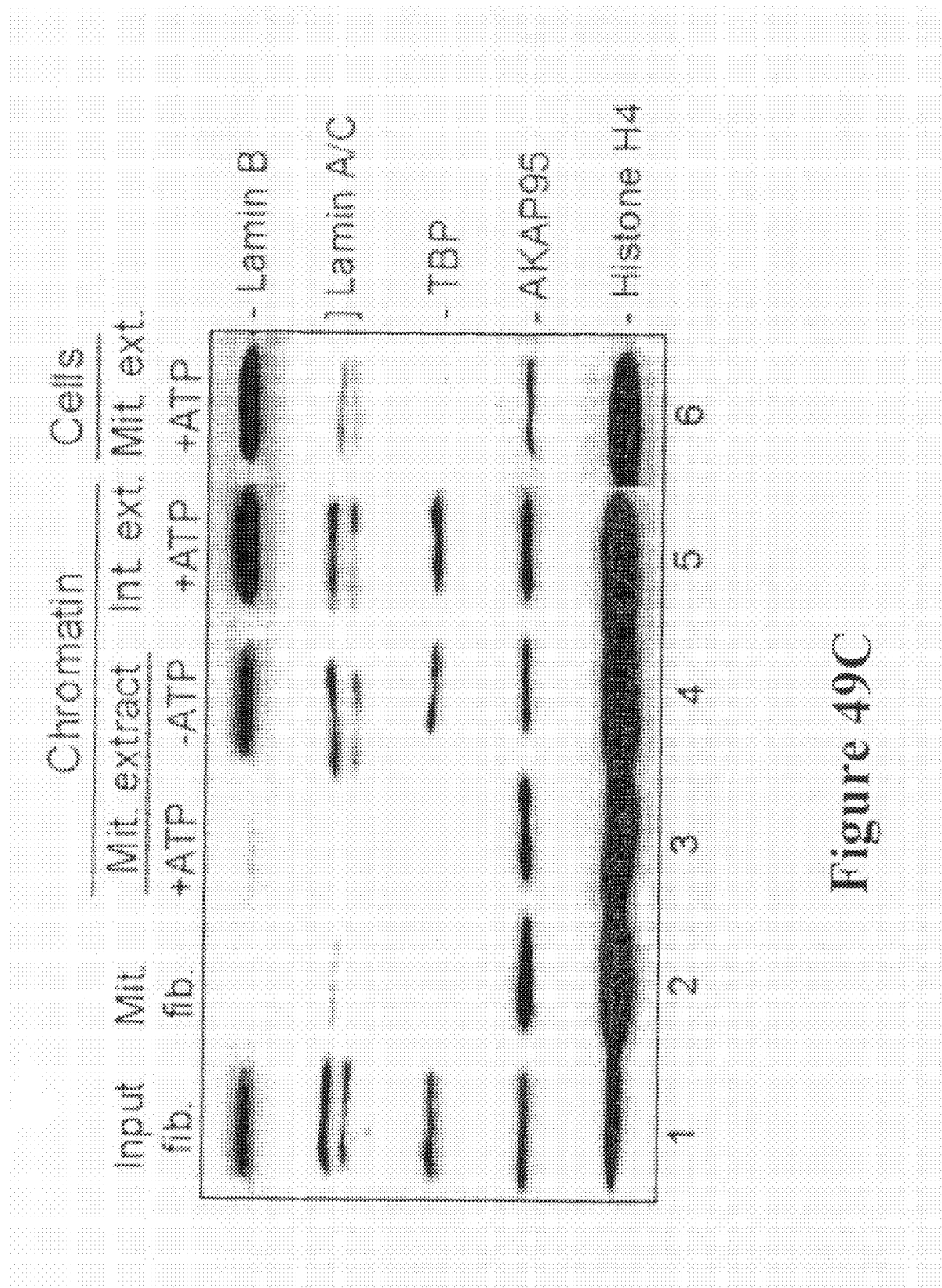

The extract elicited ATP-dependent condensation of chromosomes, disassembly of A/C and B-type lamins from chromatin as judged by cytoplasmic labeling of these lamins, and removal of TBP from chromatin (FIG. 49B). These events were confirmed by immunoblotting analysis of condensed chromatin purified from the fibroblasts after recovery from the mitotic extract (FIG. 49C; compare lanes 1 and 3). In this experiment, the A-kinase anchoring protein AKAP95 was used as a marker of a nuclear component that remains associated with the condensed chromosomes, as normally occurs at mitosis (Collas et al., J. Cell Biol. 147:1167-1180, 1999). Histone H4 was used as a protein loading control in the gel (FIG. 49C). Disassembly of nuclear lamins and TBP from chromatin in mitotic extract was dependent on an ATP-regenerating system (FIGS. 49B and 49C, lanes 3 and 4) and was reminiscent of that occurring in mitotic cells (FIG. 49C, lane 2). Furthermore, immunoblotting analysis of whole permeabilized fibroblasts (as opposed to isolated chromatin) after exposure to mitotic extract showed that a fraction of solubilized lamin A/C and all detectable TBP were eliminated from the cells and/or proteolysed (FIG. 49C, lane 6). Lastly, a control extract from interphase fibroblasts (FIG. 49C, lane 5) or cell lysis buffer alone both containing an ATP-regenerating system failed to promote nuclear disassembly, indicating that nuclear breakdown was ATP-dependent and specific for the mitotic extract. Permeabilized fibroblasts exposed to mitotic extract and resealed with $CaCl_2$ could be cultured over several passages, indicating that membrane permeabilization, incubation of the permeabilized cells in the extract, and membrane resealing were viable procedures.

Characterization of Nuclei in Embryos Produced by Chromatin Transfer

Figures 50A, 50B, 50C, 50D:
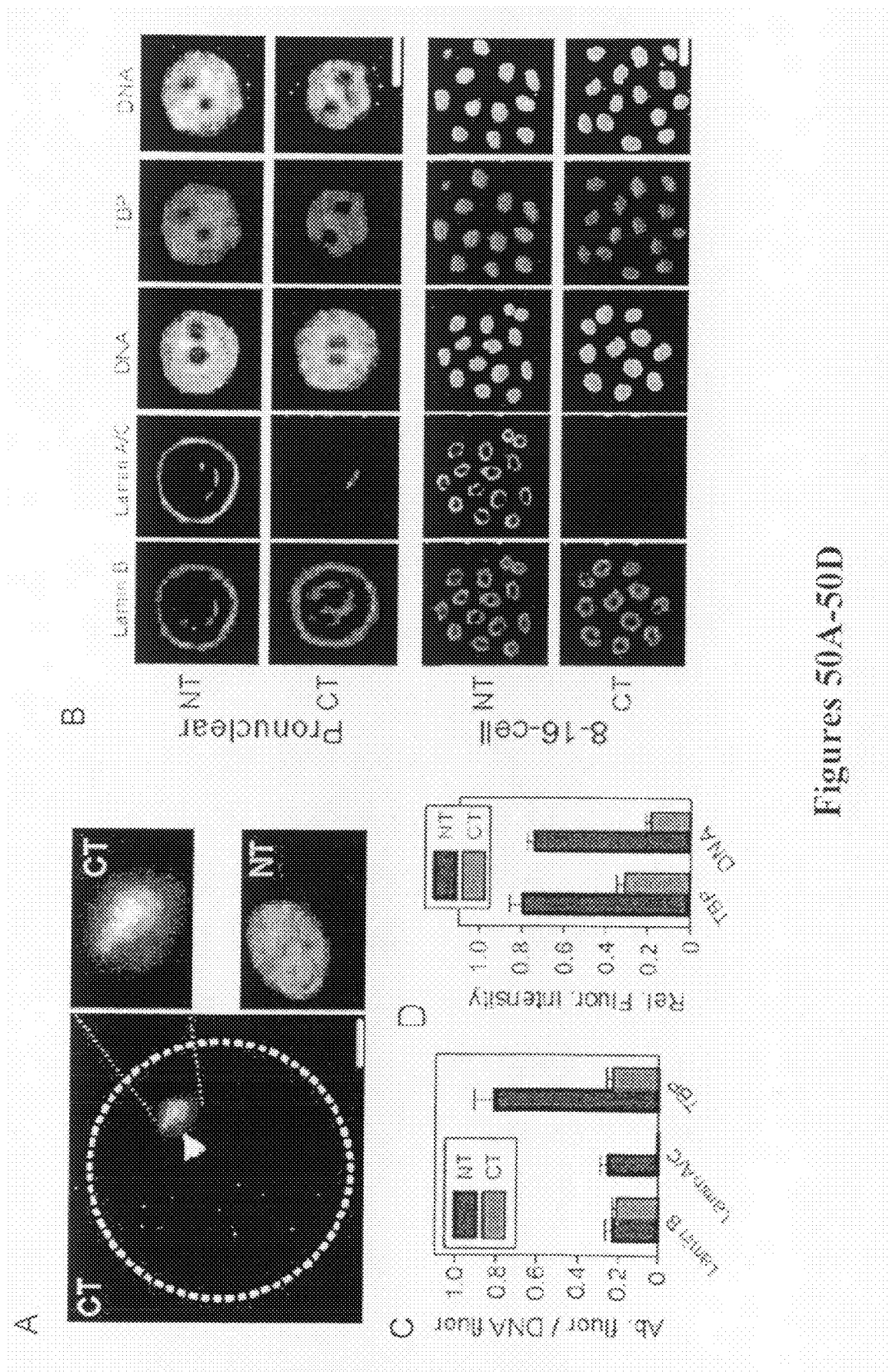
FIGS. 50A-50D demonstrate the characterization of nuclei of SLOT embryos.

Fusion of resealed fibroblasts to recipient oocytes occurred as efficiently (over 70%) as with non-permeabilized cells. The donor chromatin was in a condensed form at the time of introduction into oocytes (FIG. 50A, SLOT). In contrast, chromatin of fibroblasts used for NT was still decondensed within 30 minutes of fusion (FIG. 50A, NT). Thus, resealing of mitotic extract-treated fibroblasts with $CaCl_2$ prior to transfer into oocytes did not promote nuclear reformation in the donor cells. This observation was supported by the absence of a nuclear envelope around the condensed chromatin in SLOT embryos immediately after fusion, as judged by immunofluorescence analysis of several lamina and inner nuclear membrane proteins.

Immunolabeling of nuclear lamins and TBP in nuclei of SLOT and NT embryos, and immunolabeling intensity of these markers relative to DNA fluorescence intensity, are shown in FIGS. 50B and 50C. Perinuclear lamin B labeling intensity was similar in SLOT and NT pronuclei. Remarkably however, in contrast to NT pronuclei, lamin A/C was undetected in pronuclei and up to at least the 8-16-cell stage in SLOT embryos (FIG. 50B). SLOT pronuclei also displayed a 4-fold reduction in TBP labeling compared to NT pronuclei (FIG. 50C). Pronuclear TBP concentration in the mouse has been shown to increase during progression through interphase (Worrad et al., Development 120:2347-2357, 1994). However, as kinetics of pronuclear formation from PCC- or in vitro-condensed chromatin were similar in NT and SLOT embryos, it is unlikely, albeit not formally excluded, that enhanced TBP concentration in NT pronuclei was due to a more advanced cell cycle stage. Resistance of TBP to extraction with 1% Triton X-100, 1 mg/ml DNAse I, and 0.3 M NaCl was decreased by over 2-fold (FIG. 50D), indicating a weaker association of TBP with intranuclear ligands. Likewise, resistance of DNA to DNAse I was reduced nearly 4-fold in SLOT pronuclei, suggesting that SLOT favors the establishment of a looser chromatin configuration in pronuclei (FIG. 50D). Thus, disassembly of fibroblast nuclei in mitotic extract followed by transfer of the condensed chromatin into oocytes enhanced morphological remodeling of the donor nuclei and alleviated defects detected in pronuclei of NT embryos.

Chromatin Transfer Produces Healthy Clones

Figure 51A:
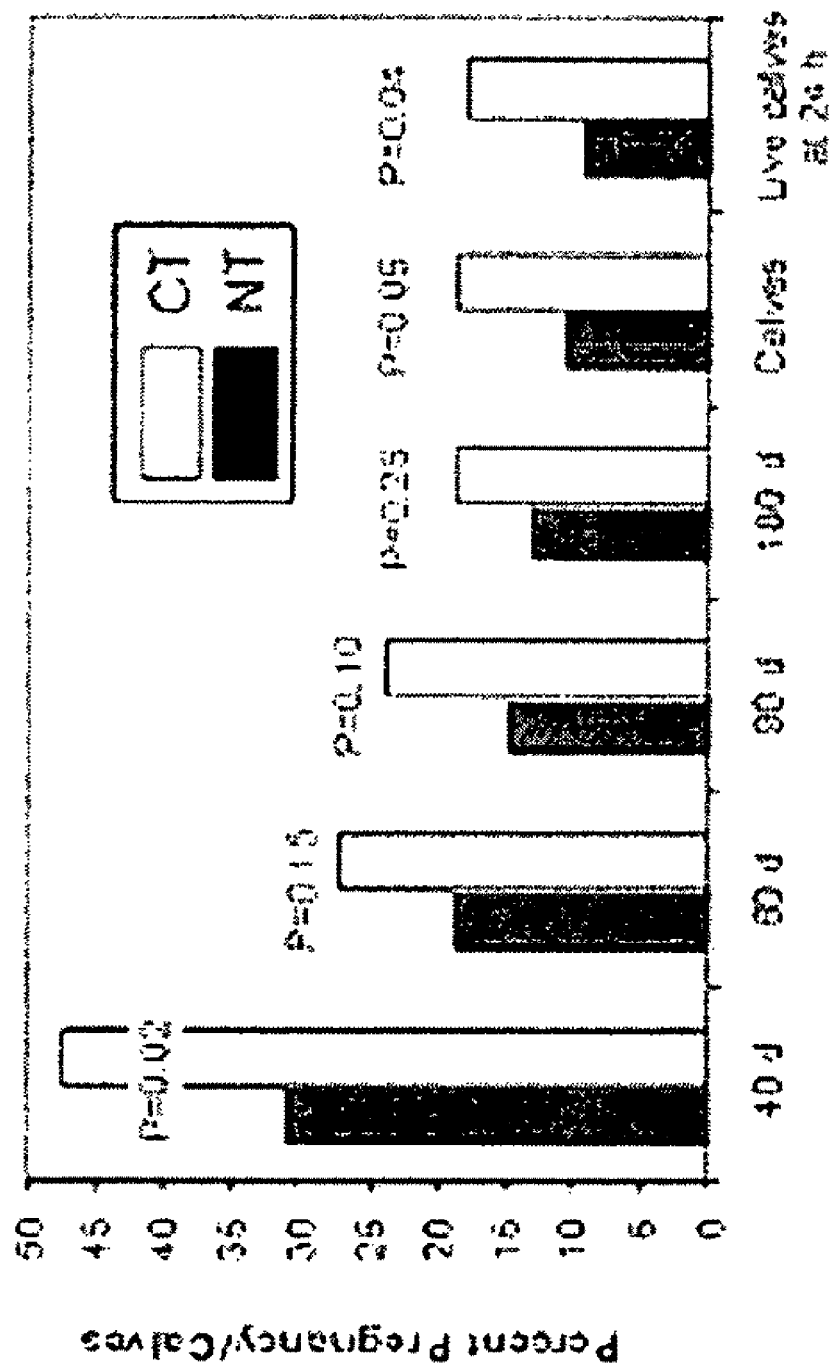
FIGS. 51A-51E illustrate the development and morphological evaluation of SLOT and NT clones.
Figure 51B:
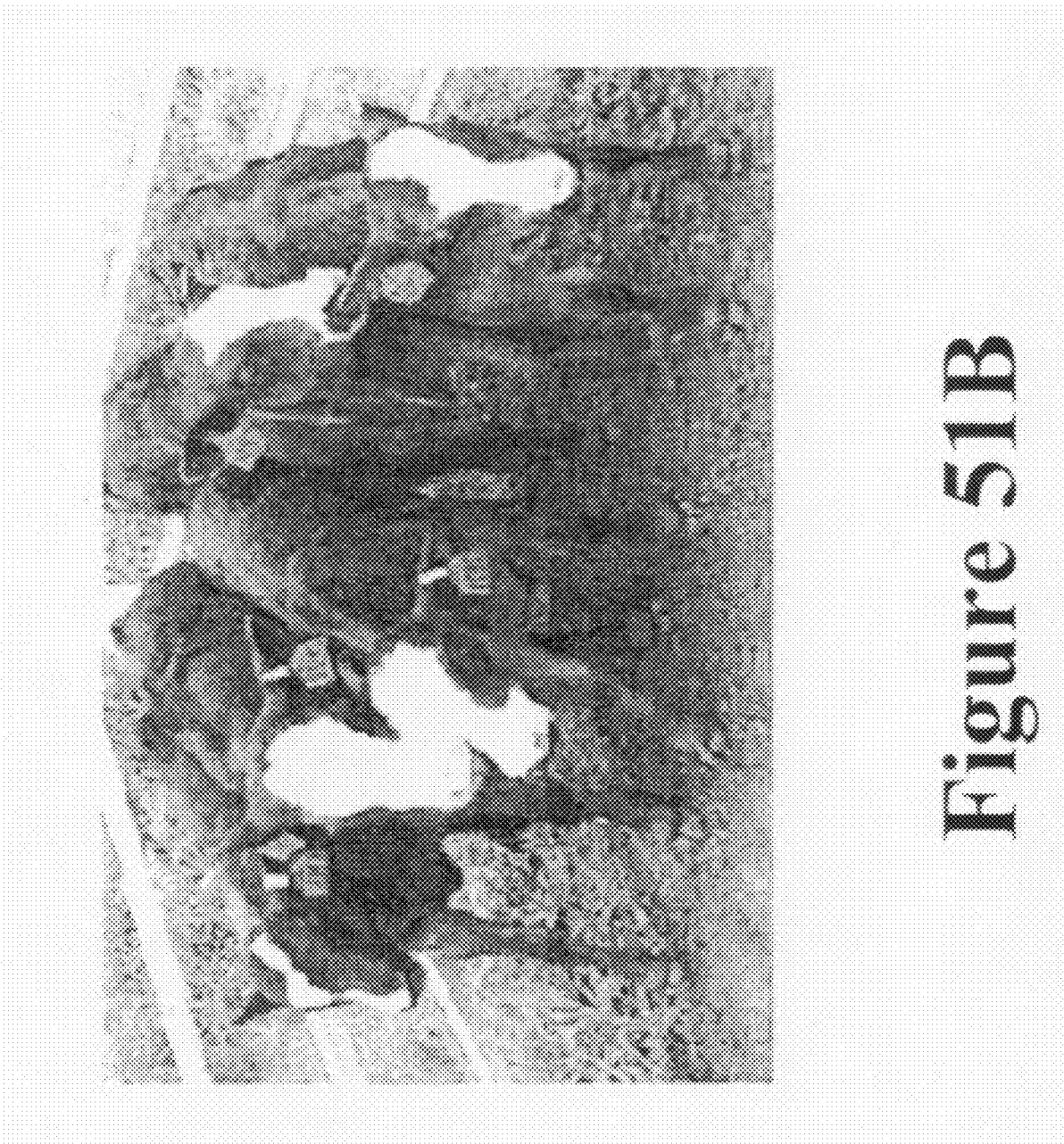

SLOT resulted in development to term of cloned embryos (FIGS. 51A and 51B). Pregnancy rates following transfer of blastocysts into recipient females were significantly higher at 40 days for SLOT embryos than for NT embryos (P=0.02; Fisher's Test), and the trend was maintained up to development to term ($12/59$ and $23/211$ calves born, respectively; P=0.05) (FIG. 51A). Additionally, SLOT enhanced survival rate of clones beyond 24 hours post-partum ($10/59$ and $17/211$, respectively; P=0.04) (FIGS. 51A and 51B).

Figures 51C, 51D:
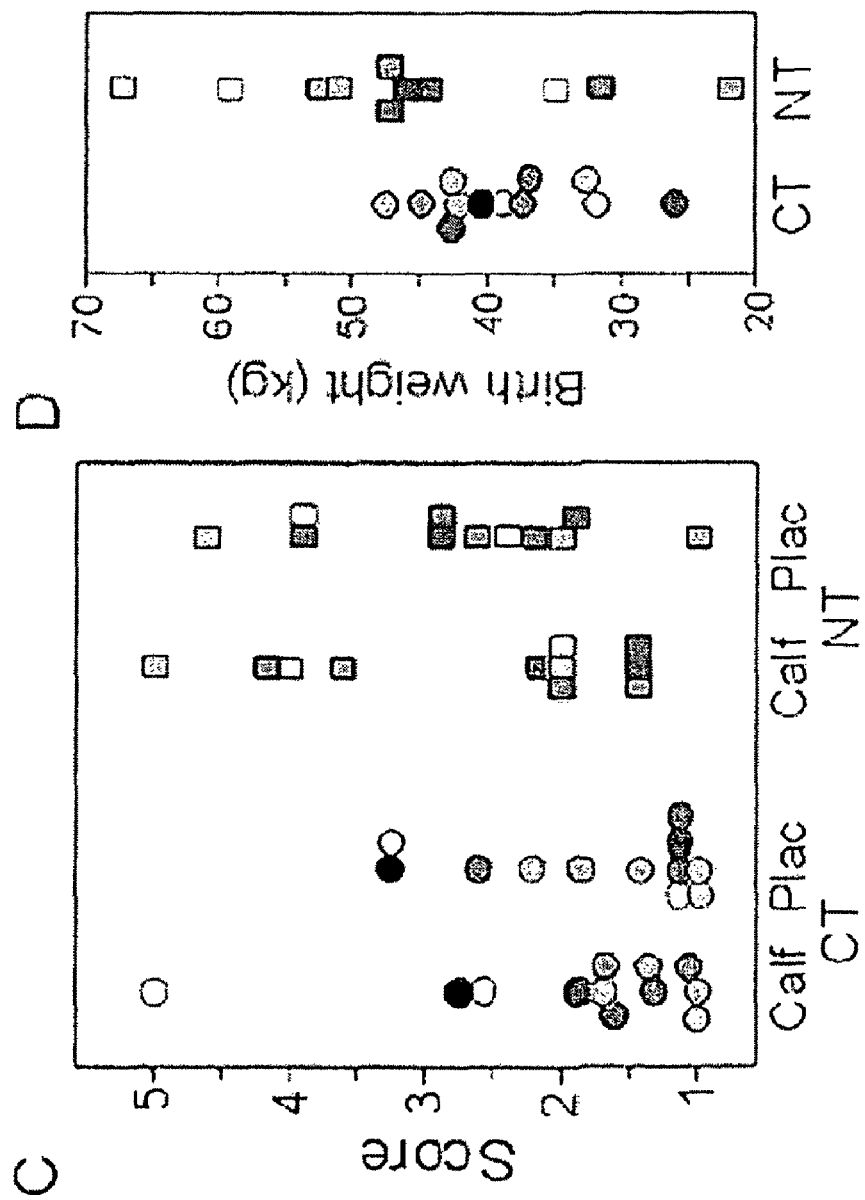
Figure 51E:
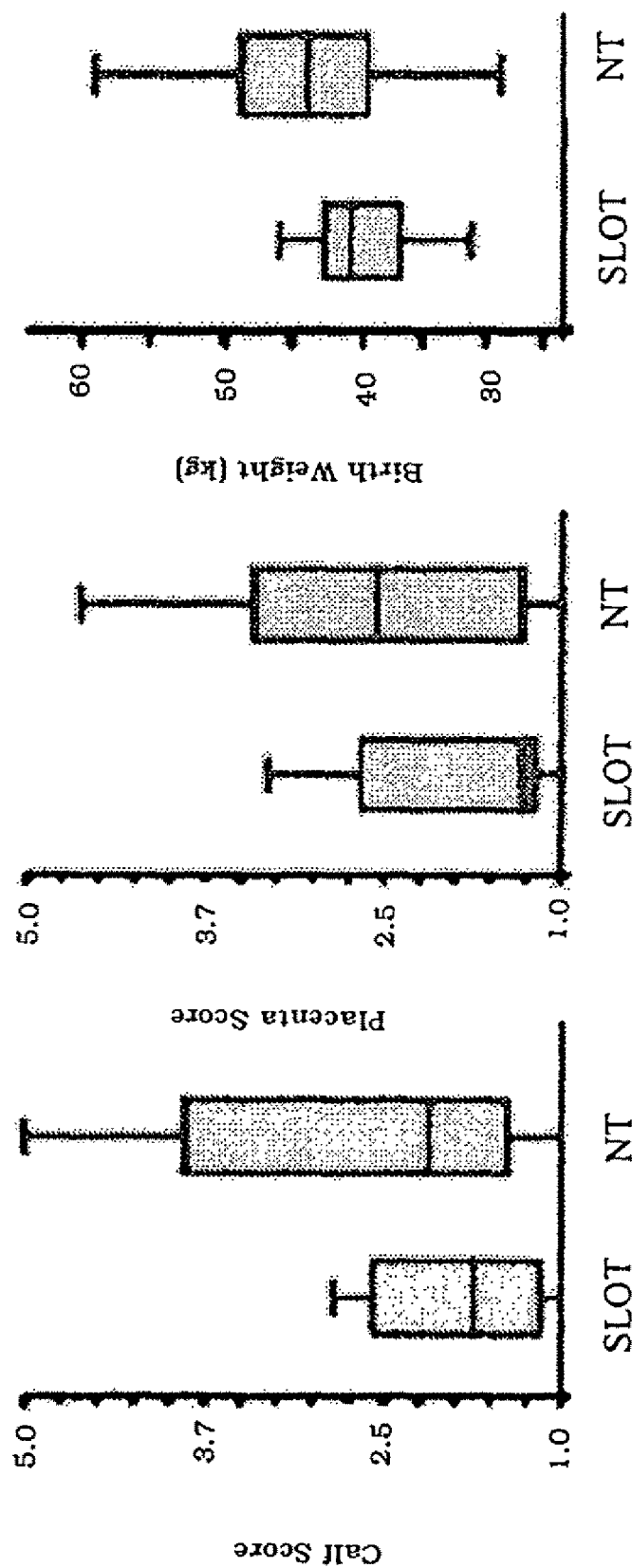

Health of NT (Example 10) and SLOT clones born was evaluated by scoring animals and placentas on a scale of 1 (normal) to 5 (grossly abnormal). Placental scores included parameters such as placental edema, cotyledon number, size and morphology, color of amniotic fluids, morphology of uterus, and umbilicus. Animal scores included functional evaluation and general appearance of respiratory, cardiovascular, digestive, urinary, muscular, skeletal and nervous systems. Data for individual calves are shown in FIG. 51C. Box plot analyses show that scores of animals and placentas derived from NT were more dispersed that those produced by SLOT (FIG. 51E). Mean birth weight of SLOT and NT clones was not significantly different; however, the proportion of SLOT calves over 45 kg at birth was lower (P=0.02; Fisher) than that of NT animals (FIGS. 51D and 51E). Altogether, these results indicate that chromatin transfer produces live offspring and shows evidence of improved development and viability.

In comparison with NT (Example 10) and despite the limited number of SLOT offspring produced (n=8), SLOT significantly enhances pregnancy rates at 40 days (P=0.02) and survival of calves born beyond 24 hours (P=0.04). A trend towards an improvement in the health of animals produced by SLOT is also reflected in box plot analyses. Furthermore, the lower incidence of large (over 45 kg) calves produced by SLOT has practical and economical implications on animal management.

Several nuclear defects have been identified in NT embryos, including assembly of lamin A/C, enhanced pronuclear TBP content and increased resistance of DNA to DNAse I. These defects may result from incomplete remodeling of the fibroblast nuclei and/or from misregulation of expression of differentiated cell-specific (e.g., lamin A) genes. Remodeling of nuclei in vitro and transplantation of condensed chromatin into oocytes alleviates these defects.

Remodeling nuclei through SLOT increases DNA sensitivity to DNAse I and may promote the formation of transcriptionally active (or potentially active) chromatin. This effect may in turn facilitate expression of developmentally important genes, such as genes involved in placental development, maintenance of late pregnancy, and post-natal survival. SLOT also induces repression of lamin A gene expression in cloned embryos. In vitro and in vivo manipulations of nuclear lamina composition have shown that failure to assemble a correct set of lamins invariably leads to apoptosis (Steen et al., J. Cell Biol. 153:621-626, 2001). Moreover, as lamins interact with DNA, chromatin and the transcription machinery, proper lamina reconstitution is likely to be essential for normal nuclear function (Gruenbaum et al., J. Struct. Biol. 129:313-323, 2000 and Cohen et al., Trends Biochem. Sci. 26:41-47, 2001) in cloned embryos.

Chromatin condensation at mitosis or in vitro is associated with the release of DNA-bound components such as chromatin remodeling enzymes, transcription factors (e.g., TBP), or other potentially inhibitory somatic components. Removal of TBP from donor somatic chromatin may facilitate repression or down-regulation of somatic-specific genes in SLOT embryos, which may impair development. An implication of removing factors from the donor nucleus is that loading of maternal components onto chromatin and subsequent remodeling into a physiological pronucleus may be facilitated.

In conclusion, it is possible to directly remodel a somatic nucleus in a cell extract and produce live offspring. In vitro manipulation of nuclei for cloning or transdifferentiation purposes (Landsverk et al., EMBO Rep. 3:384-389, 2002 and Håkelien et al., Nat. Biotechnol. 20:460-466, 2002) is a useful tool for optional further investigation of the mechanisms of nuclear reprogramming. Chromatin transfer shows evidence of improved development to term and viability of clones. Additional manipulation of the system might lead to further improvements in the efficiency of mammalian cloning.

EXAMPLE 17

Additional Evidence for More Complete Nuclear Reprogramming Using Streptolysin O-Transfer (SLOT)

The SLOT method described in Example 12 produced improved results when the donor permeabilized cells were are not resealed prior to genetic transfer. Additionally, use of donor cells in $G_1$ phase instead of confluent cells may result in increased viability of the reconstituted oocyte and resulting embryo. These experiments are described further below.

Preparation of Buffers

A 1 molar DTT solution was prepared by placing 1 ml $H_2O$ in an eppendorf tube, adding 154 mg refrigerated DTT, and mixing well by vortexing. The solution was aliquoted into 10 µl volumes and frozen at –20° C. Aliquots can be thawed and re-frozen several times. A 100 ml volume of cell lysis buffer for preparation of cell extracts for nuclear assembly/disassembly assays contained NaCl (50 mM, 1 ml of 5 M stock), MgCl$_2$, (5 mM, 0.5 ml of 1 M stock), Hepes, pH 8.2 (20 mM, 2 ml of 1 M stock, pH 8.2), and H$_2$O (96.5 ml). The buffer was aliquoted and stored at 4° C. There was a drop of 1 pH unit upon lysate preparation. For preparation of mitotic extracts, 10 mM EGTA was added (1 ml of a 1 M stock) and 95.5 ml H$_2$O was added instead of 96.5 ml. Prior to use, the following were added: DTT (1 µl/ml solution, 1 M stock at −20° C., 1 mM final concentration), PMSF (101/ml solution 100 mM stock, 1 mM final concentration), CAL mix (10 µl CAL cocktail at −20° C. per ml solution, i.e., a final concentration of 10 µg/ml each of chymostatin, aprotinin, and leupeptin), Pepstatin A (10 µl stock at −20° C. per ml solution, 10 µg/ml final concentration), and Cytochalasin D (1 µl/ml from 1 mg/ml stock at −20° C., 1 µg/ml final concentration). For the nocodozole 1000× stock solution, 1 mg/ml of nocodozole in DMSO was prepared and stored in 160 µl aliquots.

To prepare Streptolysin O stock (SLO), a vial of SLO (Sigma S-5265; 25,000 units stored as a powder at 4° C.) was dissolved in 400 µl H$_2$O and mixed well. The entire content was transferred to a 1.5-ml conical tube, divided into 10 µl aliquots, and frozen at −20° C. The stock concentration was "10×." To prepare the protease solution, 3 ml TL Hepes and 9 mg Protease (Sigma P-8811) were added to a 15 ml conical tube and mixed by vortexing. The solution was filtered through a 0.22 um syringe filter directly into TL Hepes. Because the cells doubled the volume, the final concentration was 1.5 mg/ml. For HECM Hepes, NaCl (114 mM, 6.662 g), KCl (3.2 mM, 0.239 g), CaCl$_2$2H$_2$O (2.0 mM, 0.294 g), MgCl$_2$6H$_2$O (0.5 mM, 0.102 g), Pen/Strep (10 ml, Sigma P3539 Pen/Strep, 100 U/ml and 100 ug/ml final concentration), Phenol Red (5 ug/ml, 1 ml), and H$_2$O (in a sufficient amount to increase the total volume to 990 ml) were combined. Then, 100×A.A. (10 ml), Na lactate (10 mM, 1.44 ml), Na pyruvate (0.1 mM, 0.011 g), NaHCO$_3$ (2 mM, 0.168 g), and HEPES (10 mM, 2.38 g) were added. The final solution had an osmolarity of 260-270 mOsM. Then, 3 g bovine serum albumin (Fraction V) was added, and the pH was adjusted to 7.4. The solution was filtered through a 0.22 uM filter and stored at 4° C.

For preparation of the ATP stock solution (Sigma A3377: 100 mM Stock, 100×), H$_2$O (1 ml) and ATP (0.055 g) were combined, and 10 µl aliquots were frozen at −20° C. For preparation of creatine phosphate (Sigma P7936: 1 M stock, 100×), H$_2$O (1 ml) and creatine phosphate (0.255 g) were combined, and 10 µl aliquots were frozen at −20° C. To prepare creatine kinase (Sigma C3755: 2.5 mg/ml stock, 100×), H$_2$O (1 ml) and creatine kinase (0.0025 g) were combined, and 10 µl aliquots were frozen at −20° C. For preparation of the ATP-generating system, equal proportions of 100 mM ATP stock, 1 M creatine phosphate, and 2.5 mg/ml creatine kinase stock solutions (100×) were made using H$_2$O, mixed, and stored as a frozen solution. The ATP generating system was kept on ice until use. The ATP generating system (1.2 µl) was added to the extract (40 µl), and the solution was mixed by vortexing. The final concentration of the ATP generating system in the extract was 1 mM ATP, 10 mM creatine phosphate, and 25 µg/ml creatine kinase.

Preparation of Mitotic Extract

One vial of 1.5 to 2 million cells was thawed. Cells were split into two T75 flasks and grown for two days or until they were confluent. The cells were passaged in 6-8 T75 flasks and grown to confluency. The cells were trypsinized and counted using a hemocytometer, and 3 million cells were added to each of as many T150 flasks as could be used with the number of cells available. The cell line (e.g., fibroblasts such as primary fibroblasts, epithelial cells, or immortalized and disease-free cells such as MDBK cells) was synchronized at 70-80% confluency in mitosis with 0.5-1 µg/ml nocodazole for 17-20 hours using standard procedures (e.g., Collas et al., J. Cell Biol. 147:1167-1180, 1999 and references therein). The synchronized cells were harvested by mitotic shake-off. Each flask containing cells was shaken vigorously by repeatedly tapping it with one hand. The mitotic cells detached and floated in the culture medium. The harvested cells were centrifuged at 500×g for 10 minutes in a 50 ml conical tube at 4° C. The supernatant was discarded, and the cell pellets were resuspended in a total of 50 ml of cold phosphate buffered saline/Ca/Mg Free (PBS). If desired, several cell pellets can be pooled into a single 50 ml tube. The cells were centrifuged at 500×g for 10 minutes at 4° C., and the above washing step was repeated. The volume of the cell pellet was determined, and the cell pellet was resuspended in approximately 20 volumes of ice-cold cell lysis buffer containing protease inhibitors (i.e., DTT and PMSF).

Then, the cells were sedimented at 500×g for five minutes at 4° C. The supernatant was discarded, and the cell pellet volume was determined. The cell pellet was resuspended in no more than one volume of cell lysis buffer containing all of the protease inhibitors. The cells were incubated on ice for one hour to allow swelling of the cells. Using a tip sonicator, the cell suspension was sonicated until all cells were broken open. Cell lysis was monitored under a phase contrast microscope. Desirably, 90% of the cells were lysed before proceeding to the next step. Sonication can be prolonged as long as necessary; the sonication time varies with the cell type used to prepare the extract. Alternatively, cells are lysed by Dounce homogenization using a glass mortar and pestle (homogenizer), desirably until at least 90% of the cells are lysed. The cell lysate was placed in a 1.5-ml centrifuge tube and centrifuged at ~15,000×g for 15 minutes at 4° C. using a table top refrigerated centrifuge. The centrifuge was placed in a cold room or refrigerator and allowed to equilibrate. The tubes were removed from the centrifuge and immediately placed on ice. The supernatant was carefully collected using a 200 µl pipette tip. This supernatant is the mitotic cytoplasmic extract. The extract was placed in another tube on ice. Extracts collected from several tubes were pooled.

Two alternatives exist at this stage. The cell extract was aliquoted into tubes on ice, 41 µl of extract per tube. The extract was immediately snap-frozen in liquid nitrogen and stored in a −80° C. freezer until use. Such extracts prepared from a 15,000×g centrifugation are called MS15 (or mitotic cytoplasmic extract). Alternatively, the MS15 extract is placed in an ultracentrifuge tube on ice (e.g., fitted for an SW55 Ti rotor; Beckman). The tube is overlayed with mineral oil to the top if necessary to prevent collapsing of the tube upon ultracentrifugation. The extract was centrifuged at 200,000×g for three hours at 4° C. to sediment membrane vesicles contained in the MS15. At the end of centrifugation, the oil was discarded. The supernatant was carefully collected and placed in a cold 1.5-ml tube on ice. Several supernatants were used if necessary. This supernatant is referred to as MS200 (or mitotic cytosolic extract). The MS200 extract was aliquoted and frozen as described for the M515 extract.

Chromatin Transfer

On the day before the cloning procedure, one 35 mm Nunc was prepared with 1 million fibroblast cells, or six T75 flasks containing 500,000 cells were prepared for shake-off. On the morning of the cloning procedure, the Alpha MEM with 15% FBS irradiated, complete media in all flasks was changed to remove debris and dead cells. Prior to performing the cell permeabilization and mitotic extract reaction, the lowest concentration of SLO necessary to permeabilize 80-90% of the cells was determined by serial dilution of the SLO stock solution (e.g., dilutions of 1×, 0.5×, 0.3×, and 0.1×), incubating for 30 minutes at approximately 38.5° C. in a water bath, and then staining with propidium iodide.

The cells were dissociated from confluent culture or newly transfected cell culture using trypsin or cell dissociation buffer, placed in 15 ml conical tube, and washed once by centrifugation using Hank's Balanced Salt Solution, Ca/Mg free (HBSS). The cell pellet was resuspended in 1 ml HBSS, and the cells were counted to determine the concentration. Approximately 50,000-100,000 cells were suspended in 100 μl HBSS (Gibco BRL, cat. No. 14170-120) at room temperature. The 5 μl SLO stock solution at the previously determined concentration was added. The mixture was incubated at approximately 38.5° C. for 30 minutes in a water bath. The tube was gently tapped 2-3 times during incubation to ensure that the cells remained in suspension. A 200 μl volume of room temperature PBS (Ca/Mg free) was added and mixed well by gentle pipetting. The cells were centrifuged at 500×g for five minutes at room temperature in table top centrifuge. All of the supernatant was discarded. The pellet was small and may not be clearly visible.

A 40 μl volume of mitotic extract containing the ATP-generating system was added, and the solution was mixed well. The extract was prepared during the minute incubation above. One vial of 40 μl extract was thawed and added to 1.2 μl of ATP-generating system. The solution was mixed well and kept at room temperature. The mixture was incubated at 38.5° C. in a water bath for 30 minutes, and the tube was occasionally gently tapped. A 500 μl volume of room temperature complete media (Alpha MEM+15% Fetal calf serum) was added and stored in an approximately 38.5° C. incubator with the lid open until use. The cells were centrifuged at 500×g for five minutes at room temperature in a table top centrifuge. The cell pellet was resuspended in 1 ml room temperature TL Hepes and transferred to a 15 ml conical tube. A 1 ml volume of 3 mg/ml Protease in TL Hepes (filtered) was added for a final protease concentration on the cells of 1.5 mg/ml, and the mixture was incubated for 30 seconds. TL Hepes was added to fill the 15 ml conical tube, and the tube was capped and centrifuged at 2300 rpm for five minutes. TL Hepes was removed from cells, and 150 ul of TL Hepes was added to cells. The tube was labeled for the appropriate cell line and placed on a warming stage.

During the time that the cells were being prepared, the manipulation station was prepared for cell transfer using an appropriately sized cell transfer pipette. Approximately 50 enucleated oocytes were placed into a 50 ul drop of TL Hepes under heavy mineral oil in a 100 mm dish. The washed cells were placed in a drop with enucleated oocytes. Enough cells were used for genetic transfer to all oocytes. Care was taken to avoid using so many cells that they sterically blocked the manipulation tools. One enucleated oocyte was placed on the holder, and one cell was placed in the perivitellin space under the zona, such that the cell was touching the plasma membrane of the oocyte. To facilitate fusion, the cell was placed adjacent to, or opposite to the polar body. After all enucleated oocytes had cells transferred to them, oocytes were removed from the microdrop and placed in a pre-warmed 35 mm dish of HECM Hepes for fusion.

Results

Comparing the results in Table 12 below for donor cells in which the membrane was not resealed prior to genetic transfer with the results in Table 11 for donor cells in which the membrane was resealed prior to genetic transfer indicates that increased cloning efficiency may be obtained by not resealing the permeablized cell membrane. Additionally, Table 12 demonstrates that the use of donor cells in $G_1$ phase instead of confluent cells may result in increased viability of the reconstituted oocyte and resulting embryo. The data in Table 11 was obtained using an extract from bovine primary fibroblasts and donor bovine fetal fibroblasts. MDBK cells have also been successfully used to generate reprogramming extracts.

TABLE 11

Embryo development with HAC cell lines: NT Vs SLOT with resealed donor cells

| Treatment | Total No | Blast (%) | Recips | Pregnancy at | | | | |
|---|---|---|---|---|---|---|---|---|
| | | | | 40 d (%) | 60 d (%) | 90 d (%) | 120 d (%) | 150 d (%) |
| HAC NTs | 8872 | 1124 (18) | 508 | 170 (34) | 89 (18) | 82 (16) | 76 (15) | 72 (14) |
| HAC SLOTs | 2709 | 223 (12) | 91 | 42 (46) | 22 (24) | 19 (21) | 18 (20) | 17 (19) |
| Total | 11581 | 1347 (17) | 599 | 212 (35) | 111 (19) | 101 (17) | 94 (16) | 89 (15) |

TABLE 12

Embryo development with ΔHAC and ΔΔHAC cell lines: confluent donor cells (CTC) vs $G_1$ donor cells (CTD) without resealing of donor cell membranes

| Treatment | Total No | Blast (%) | Recips | Preg 40 d (%) | Preg 60 d (%) |
|---|---|---|---|---|---|
| ΔHAC CTC | 1729 | 185 (15) | 68 | 14/39 (36) | 5/13 (38) |
| ΔHAC CTD | 1177 | 181 (22) | 68 | 25/44 (56) | 5/22 (33) |
| ΔΔHAC CTC | 1230 | 147 (17) | 60 | | |
| ΔΔHAC CTD | 521 | 95 (26) | 29 | | |
| Total | 4657 | 608 (19) | 225 | | |

EXAMPLE 18

Methods for the Generation of Chimeric Mammals

Many spontaneous abortions that occur using traditional methods to clone mammals are thought to result from placental abnormalities rather than from problems with the fetus. Thus, methods have been developed to produce chimeric embryos with placental tissue primarily from one origin (e.g., an in vitro fertilized, naturally-occurring, or parthenogenetically activated embryo) and fetal tissue primarily from another origin (e.g., a nuclear transfer embryo encoding a xenogenous antibody). Chimeric embryos with placental tissue derived primarily from cells from in vitro fertilized, naturally-occurring, or parthenogenetically activated embryos may better resemble naturally-occurring placental tissue and result in increased production of viable offspring. Preferably, the majority of the cells of the offspring are derived from cells from the nuclear transfer embryo and thus have a genome that is substantially identical to that of the donor cell used to generate the nuclear transfer embryo.

In one such method, cells from an in vitro fertilized embryo are injected into the periphery of a compaction embryo encoding a xenogenous antibody (e.g., between the zona pellucida and the embryo itself) that was produced using traditional nuclear transfer methods or any of the other cloning methods described herein. In an alternative method, cells from a precompaction, in vitro fertilized embryo are incubated with cells from a precompaction embryo encoding a xenogenous antibody produced using one of the cloning methods of the present invention (e.g., using a reprogrammed chromatin mass or a permeabilized cell as the donor source) under conditions that allow cells from each embryo to reorganize to produce a single chimeric embryo (Wells and Powell, Cloning 2:9-22, 2000). In both methods, the cells from the in vitro fertilized embryo are preferentially incorporated into the placenta, and the cells from the nuclear transfer method are preferentially incorporated into the fetal tissue. These methods are described further below. These results were generated using nuclear transfer embryos that do not contain a xenogenous antibody gene; however, similar results are expected for nuclear transfer embryos containing a xenogenous antibody gene and/or containing a mutation in a prion gene.

Isolation of G1 Fibroblasts

For the isolation of G1 fibroblasts as donor cells to produce nuclear transfer embryos, the previously described "shake-off" method was used (Kasinathan et al., Nature biotech 19:1176-1178, 2001). Briefly, 24 hours prior to isolation, $5.0 \times 10^5$ cells were plated onto 100 mm tissue culture plates containing 10 ml of α-MEM plus FCS. The following day, plates were washed with PBS, and the culture medium was replaced for one to two hours before isolation. The plates were then shaken for 30-60 seconds on a Vortex-Genie 2 (Fisher Scientific, Houston, Tex., medium speed). The medium was removed, spun at 500×g for five minutes, and the pellet was re-suspended in 250 µl of MEM plus FCS. This cell suspension consisted of newly divided cell doublets attached by a cytoplasmic bridge, some single cells, and metaphase or anaphase cells. The cell doublets attached by a cytoplasmic bridge were used as donor cells for nuclear transfer.

Nuclear Transplantation, Activation, and Embryo Culture

The nuclear transfer procedure using the isolated G1 fibroblasts was performed essentially as previously described (Cibelli et al, Nature Biotech. 16: 642-646, 1998; Kasinathan et al., Biol. Reprod. 64: 1487-1493, 2000). In vitro matured oocytes were enucleated about 18-20 hours post maturation, and chromosome removal was confirmed by bisBenzimide (Hoechst 33342, Sigma) labeling under UV light. These cytoplast-donor cell couplets were fused using a single electrical pulse of 2.4 kV/cm for 20 microseconds (Electrocell manipulator 200, Genetronics, San Diego, Calif.). At 30 hours past maturation, reconstructed oocytes and controls were activated with calcium ionophore (5 µM) for four minutes (Cal Biochem, San Diego, Calif.) and 10 µg cycloheximide and 2.5 µg cytochalasin D (Sigma) in ACM culture medium (100 mM NaCl, 3 mM KCl, 0.27 Mm $CaCl_2$, 25 mM $NaHCO_3$, 1 mM sodium lactate, 0.4 mM Pyruvate, 1 mM L-glutamine, 3 mg/ml BSA (fatty acid free), 1% BME amino acids, and 1% MEM nonessential amino acids; all from Sigma) for six hours as described previously (Liu et al, Mol. Reprod. Dev. 49:298-307, 1998; Presicce et al., Mol. Reprod. Dev. 38:380-385, 1994). After activation, eggs were washed in HEPES buffered hamster embryo culture medium (HECM-HEPES, 114 mM NaCl, 3.2 mM KCl, 2 mM $CaCl_2$, 10 mM Sodium Lactate, 0.1 mM sodium pyruvate, 2 mM $NaHCO_3$, 10 mM HEPES, and 1% BME amino acids; Sigma) five times and placed in culture in 4-well tissue culture plates containing mouse fetal fibroblasts and 0.5 ml of embryo culture medium covered with 0.2 ml of embryo tested mineral oil (Sigma). Twenty five to 50 embryos were placed in each well and incubated at 38.5° C. in a 5% $CO_2$ in air atmosphere. On day four, 10% FCS was added to the culture medium. On days seven and eight, development to the blastocyst stage was recorded.

Bovine In Vitro Fertilization

In vitro fertilization was performed as described earlier to produce bovine in vitro fertilized embryos (Collas et al., Mol. Reprod. Dev. 34:224-231, 1993). A 45% and 90% isotonic Percoll gradient was prepared with sperm TL stock (Parrish et al., Theriogenology 24:537-549, 1985). Frozen-thawed bovine sperm from a single bull was layered on top of the gradient and centrifuged for 30 minutes at 700×g (2000 rpm using a 6.37 inch tip radius). The concentration of sperm in the pellet was determined, and the sperm was diluted in sperm TL (sperm TL stock, 1 mM pyruvate, 6 mg/ml BSA, and 1% PS) such that the final concentration at fertilization was $10^6$ sperm/ml. At 22 hours post maturation, oocytes were wash three times in TL HEPES and placed in 480 µl of fertilization TL (Bavister et al., Biol. Reprod. 28:235-247, 1983) in Nunc wells containing 6 mg/ml BSA, 0.2 mM pyruvate, 20 uM penicillamine, 10 µM hypotaurine, 1 mM epinepherine (Leibfried et al., J. Reprod. Fertil. 66:87-93, 1982), and 0.004 µg/ml heparin. Twenty microliters of sperm were added to generate a final concentration of $10^6$ sperm/ml to 50 oocytes. Culture conditions were the same as those described above for nuclear transfer. Fertilization rates were over 90% based on pronuclear development.

Chimeric Nuclear Transfer Embryos

In vitro fertilized embryos at 8-cell stage (6-12 blastomeres) were harvested at approximately 96 hours post fertilization, prior to compaction. The zona pellucida was removed with protease (3 mg/ml in TL-HEPES). The zona dissolution was carefully monitored using a dissecting microscope. When the zona first appeared to dissolve (~two minutes), the embryos were removed and washed in TL-HEPES and transferred to 30 mm petri dishes containing Hank's balanced salt solution and incubated at 37.5° C. for 30 minutes. The blastomeres from these precompaction embryos were transferred into microdrops (50 µl) of TL-HEPES under mineral oil in 100 mm petridish. Nuclear transfer embryos on day four at the 8-16 cell stage were selected and transferred into the same microdrops containing the blastomeres. These nuclear transfer embryos included both precompaction embryos (e.g., 8 cell stage embryos) and compaction embryos (e.g., 16 stage embryos). Then 4-6 blatomeres were transferred into the nuclear transfer embryos with the beveled micropipette (35 µm diameter) using standard micromanipulation techniques. After transferring the blastomeres, the embryos were cultured as described for nuclear transfer embryos.

On days seven and eight, the development to blastocyst of the chimeric embryos was evaluated. The blastocysts were also analyzed for the presence of the membrane dye DiI that was added to the cells from the in vitro fertilized embryo before they were injected into the nuclear transfer embryo. The cells were labeled on day four and observed on day seven. This dye is maintained for a few cell divisions in the progeny of the originally dyed cells, allowing the chimeric embryo to be analyzed after a few cell divisions. Based on this analysis, cells from the in vitro fertilized embryo were incorporated into the chimeric embryo. If desired, fluorescence in situ hybridization (FISH) with a probe specific for a nucleic acid in either the in vitro fertilized embryo or the nuclear transfer embryo can be performed using standard methods (see, for example, Ausubel et al., Current Protocols in Molecular Biology, John Wiley & Sons, New York, pp. 14.7.1-14.7.12, 1995). This FISH analysis can be used to determine the distribution of cells derived from each embryo in the chimeric embryo (e.g., to determine what percent of the cells are incorporated into the inner cell mass and what percent are incorporated into the trophectoderm) while it is cultured in vitro and in the fetus or the offspring generated from the embryo. Alternatively, a reporter gene such as green fluorescent protein can be added to cells from one of the embryos and used to monitor the incorporation of the cells into the placenta and various fetal tissues of the chimeric embryo.

Embryo Transfer

Days seven and eight, nuclear transfer blastocysts of grade 1 and 2, derived from nuclear transfer embryos and chimeric nuclear transfer embryos were transferred into day six and seven synchronized recipient heifers. Recipients were synchronized using a single injection of Lutalyse (Parmacia & Upjohn, Kalamazoo, Mich.) followed by estrus detection. The recipients were examined on days 30 and 60 after embryo transfer by ultrasonography for the presence of conceptus and thereafter every 30 days by rectal palpation until 240 days. The pregnancy results at day 40 for the chimeric embryos and for control embryos produced by fusing a transgenic bovine fibroblast with an oocyte are compared in Table 13. These results indicate that a greater number of chimeric embryos survived until day 40.

TABLE 13

Embryo transfers and pregnancies

| Implant | Control Nuclear transfers | | Chimeric Nuclear Transfers | |
| --- | --- | --- | --- | --- |
| | No of recipients | 40 day Pregnancy | No of recipients | 40 day Pregnancy |
| First | 2 | 1 | 2 | 1 |
| Second | 6 | 1 | 4 | 3 |
| Total | 8 | 2 (25%) | 6 | 4 (67%) |

Alternative Methods for Production of Chimeric Embryos

Standard methods can be used to modify the above method for producing chimeric embryos. For example, a naturally-occurring embryo can be surgically isolated from a mammal (e.g., a bovine) or an oocyte can be parthenogenetically activated using standard techniques and used instead of the in vitro fertilized embryo. If desired, fewer cells from the in vitro fertilized, naturally-occurring, or parthenogenetically activated embryos (e.g., 1, 2, 3, 4, or 5 cells) can be injected into the nuclear transfer embryo to reduce the percent of the injected cells and their progeny that become incorporated into fetal tissue. Alternatively, more cells (e.g., 6, 7, 8, 9, 10, 11 or more cells) can be injected to increase the percent of the injected cells and their progeny that are incorporated into placental tissue. Moreover, cells from embryos in other cell stages can be used. For example, in vitro fertilized, naturally-occurring, or parthenogenetically activated embryos at the 4, 8, 16, 32, 64, 128, 256, 512, or later cell stage can be injected into nuclear transfer embryos at the 4, 8, 16, 32, 64, 128, 256, 512, or later cell stage. The injected cells and the nuclear transfer embryo can be at the same cell stage or at different cell stages. In one embodiment, the in vitro fertilized, natu-rally-occurring, or parthenogenetically activated embryo has increased ploidy (e.g., a DNA content of 4n) relative to the nuclear transfer embryo, which further biases the injected cells to the trophectoderm (i.e., the outermost layer of cells of the embryo that primarily forms the placental tissue). If desired, all or part of the zona pellucida can be kept surrounding the injected cells, rather than removed prior to injection.

In other alternative methods, cells from a precompaction or compaction in vitro fertilized, naturally-occurring, or parthenote embryo are incubated with cells from a precompaction nuclear transfer embryo under conditions that allow cells from each embryo to reorganize to produce a single chimeric embryo (Wells and Powell, Cloning 2:9-22, 2000). Cells from in vitro fertilized, naturally-occurring, or parthenote embryo are expected to contribute primarily to the trophectoderm and eventually to the placental tissue, and cells from the nuclear transfer embryo are expected to contribute primarily to the inner cell mass and eventually to the fetal tissue. Cells from both embryos can be at the same cell stage or at different cell stages, and the same or different numbers of cells from each embryo can be combined to form the aggregation embryo.

If desired, a cell from the resulting cloned fetus or the cloned offspring can be used in a second round of nuclear transfer to generate additional cloned offspring. Cells from the initial cloned fetus or cloned offspring may also be frozen to form a cell line to be used as a source of donor cells for the generation of additional cloned ungulates.

EXAMPLE 19

Testing for Human Ig Expression

Testing calves retaining a HAC or other nucleic acid encoding a xenogenous antibody may begin shortly after birth and includes evaluation for (1) xenogenous Ig expression, (2) response to immunization, (3) affinity maturation, and (4) transmission of the HACs to offspring.

Human Ig expression may be monitored by bleeding the animals and assaying for the presence of human heavy and light chain expression by ELISA, RT-PCR, or FACS analysis (see, for example, PCT Publication No. WO01/35735). Once it has been determined that the animals produce human Ig, animals are immunized with tetanus toxoid in adjuvant. Animals are bled once a week following immunization and responses to antigen determined via ELISA or FACS and compared to pre-bleeds collected before immunization. One month after the initial immunization, animals are boosted with an aqueous form of the antigen. One week following the boost, the animals are bled and response to antigen is measured via ELISA or FACS and compared to the prebleed. The ELISA or FACS assay permits measurement of most of the titer of the response as well as the heavy chain isotypes produced. This data allows a determination of an increase in antibody titer as well as the occurrence of class switching. Estimates of average affinity are also measured to determine if affinity maturation occurs during the response to antigen.

After the transgenic bovines have been obtained as described above, they are utilized to produce transgenic Igs, preferably human, but potentially that of other species, e.g. dog, cat, non-human primate, other ungulates such as sheep, pig, goat, murines such as mouse, rat, guinea pig, rabbit, etc. As noted, Ig genes are known to be conserved across species.

Transgenic Antisera and Milk Containing Xenogenous Antibodies

The bovine (or other ungulate) yields transgenic antisera directed to whatever antigen(s) it is endogenously exposed, or to exogenously administered antigen(s). For example, antigens may be administered to the ungulate to produce desired antibodies reactive with the antigens, including antigens such as pathogens (for example, bacteria, viruses, protozoans, yeast, or fungi), tumor antigens, receptors, enzymes, cytokines, etc. Exemplary pathogens for antibody production include, without limitation, hepatitis virus (for example, hepatitis C), immunodeficiency virus (for example, HIV), herpes virus, parvovirus, enterovirus, ebola virus, rabies virus, measles virus, vaccinia virus, Streptococcus (for example, Streptococcus pneumoniae), Haemophilus (for example, Haemophilus influenza), Neisseria (for example, Neisseria meningitis), Coryunebacterium diptheriae, Haemophilus (for example, Haemophilus pertussis), Clostridium (for example, Clostridium botulinium), Staphlococcus, Pseudomonas (for example, Pseudomonas aeruginosa), and respiratory syncytial virus (RSV).

One or more pathogens may be administered to a transgenic ungulate to generate hyperimmune serum useful for the prevention, stabilization, or treatment of a specific disease. For example, pathogens associated with respiratory infection in children may be administered to a transgenic ungulate to generate antiserum reactive with these pathogens (e.g., Streptococcus pneumoniae, Haemophilus influenza, and/or Neissaria meningitis). These pathogens may optionally be treated to reduce their toxicity (e.g., by exposure to heat or chemicals such as formaldehyde) prior to administration to the ungulate.

For the generation of broad spectrum Ig, a variety of pathogens (e.g., multiple bacterial and/or viral pathogens) may be administered to a transgenic ungulate. This hyperimmune serum may be used to prevent, stabilize, or treat infection in mammals (e.g., humans) and is particularly useful for treating mammals with genetic or acquired immunodeficiencies.

In addition, antibodies produced by the methods of the invention may be used to suppress the immune system, for example, to treat neuropathies, as well as to eliminate particular human cells and modulate specific molecules. For example, anti-idiotypic antibodies (i.e., antibodies which inhibit other antibodies) and antibodies reactive with T-cells, B-cells, or cytokines may be useful for the treatment of autoimmune disease or neuropathy (e.g., neuropathy due to inflammation). These antibodies may be obtained from transgenic ungulates that have not been administered an antigen, or they may be obtained from transgenic ungulates that have been administered an antigen such as a B-cell, T-cell, or cytokine (e.g., TNFα).

Transgenic antisera generated from transgenic ungulates that have not been administered an antigen may be used to manufacture pharmaceuticals comprising human polyclonal antibodies, preferably human IgG molecules. These human antibodies may be used in place of antibodies isolated from humans as Intraveneous Immunoglobulin (WIG) therapeutics.

Transgenic antiserum may optionally be enriched for antibodies reactive against one or more antigens of interest. For example, the antiserum may be purified using standard techniques such as those described by Ausubel et al. (Current Protocols in Molecular Biology, volume 2, p. 11.13.1-11.13.3, John Wiley & Sons, 1995). Preferred methods of purification include precipitation using antigen or antibody coated beads, column chromatography such as affinity chromatography, magnetic bead affinity purification, and panning with a plate-bound antigen. Additionally, the transgenic antiserum may be contacted with one or more antigens of interest, and the antibodies that bind an antigen may be separated from unbound antibodies based on the increased size of the antibody/antigen complex. Protein A and/or protein G may also be used to purify IgG molecules. If the expression of endogenous antibodies is not eliminated, protein A and/or an antibody against human Ig light chain lambda (Pharmingen) may be used to separate desired human antibodies from endogenous ungulate antibodies or ungulate/human chimeric antibodies. Protein A has higher affinity for human Ig heavy chain than for bovine Ig heavy chain and may be used to separate desired Ig molecules containing two human heavy chains from other antibodies containing one or two ungulate heavy chains. An antibody against human Ig light chain lambda may be used to separate desired Ig molecules having two human Ig lambda chains from those having one or two ungulate Ig light chains. Additionally or alternatively, one or more antibodies that are specific for ungulate Ig heavy or light chains may be used in a negative selection step to remove Ig molecules containing one or two ungulate heavy and/or light chains.

The resultant antisera may itself be used for passive immunization against an antigen. Alternatively, the antisera has diagnostic, prophylactic, or purification use, e.g. for attaining purification of antigens.

Alternatively, after antisera administration, B-cells may be isolated from the transgenic bovine and used for hybridoma preparation. For example, standard techniques may be used to fuse a B-cell from a transgenic ungulate with a myeloma to produce a hybridoma secreting a monoclonal antibody of interest (Mocikat, J. Immunol. Methods 225:185-189, 1999; Jonak et al., Hum. Antibodies Hybridomas 3:177-185, 1992; Srikumaran et al., Science 220:522, 1983). Preferred hybridomas include those generated from the fusion of a B-cell with a myeloma from a mammal of the same genus or species as the transgenic ungulate. Other preferred myelomas are from a Balb/C mouse or a human. In this instance, hybridomas are provided that make xenogenous monoclonal antibodies against a particular antigen. For example, this technology may be used to produce human, cat, dog, etc. (dependent upon the specific artificial chromosome) monoclonal antibodies that are specific to pathogens. Methods for selecting hybridomas that produce antibodies having desirable properties, i.e., enhanced binding affinity, avidity, are well known.

Alternatively, a B-cell from a transgenic ungulate may be genetically modified to express an oncogene, such as ras, myc, abl, bcl2, or neu, or infected with a transforming DNA or RNA virus, such as Epstein Barr virus or SV40 virus (Kumar et al., Immunol. Lett. 65:153-159, 1999; Knight et al., Proc. Nat. Acad. Sci. USA 85:3130-3134, 1988; Shammah et al., J. Immunol. Methods 160-19-25, 1993; Gustafsson and Hinkula, Hum. Antibodies Hybridomas 5:98-104, 1994; Kataoka et al., Differentiation 62:201-211, 1997; Chatelut et al., Scand. J. Immunol. 48:659-666, 1998). The resulting immortalized B-cells may also be used to produce a theoretically unlimited amount of antibody. Because Ig is also secreted into the milk of ungulates, ungulate milk may also be used as a source of xenogenous antibodies.

Other Embodiments

From the foregoing description, it will be apparent that variations and modifications may be made to the invention described herein to adopt it to various usages and conditions. For example, other incubation times or temperatures (such as 25, 30, 35, 37, 38.5, or 40° C. or a higher or lower temperature) can be used for permeablizing membranes, reprogramming donor genetic material, resealing membranes, and/or transfer of genetic material into oocytes. Such embodiments are also within the scope of the following claims.

All publications mentioned in this specification are herein incorporated by reference to the same extent as if each independent publication or patent application was specifically and individually indicated to be incorporated by reference.

What we claim is:

1. A bovine whose genome comprises a non-naturally occurring mutation in one or both alleles of an endogenous prion nucleic acid, wherein said mutation comprises an insertion of a STOP codon, and wherein said bovine exhibits reduced functional prion production.

2. The bovine of claim 1, wherein said mutation substantially eliminates the expression of functional prion protein.

3. The bovine of claim 1, wherein said mutation is hemizygous.

4. The bovine of claim 1, wherein said mutation is homozygous and said bovine exhibits no functional prion production.

5. The bovine of claim 1, wherein said mutation comprises an insertion of a positive selection marker into a prion nucleic acid.

6. An isolated bovine cell comprising a non-naturally occurring mutation in one or both alleles of an endogenous prion nucleic acid, wherein said mutation comprises an insertion of a STOP codon, and wherein said bovine cell exhibits reduced functional prion production.

7. The cell of claim 6, wherein said mutation is hemizygous.

8. The cell of claim 6, wherein said mutation is homozygous and said bovine cell exhibits no functional prion production.

9. The cell of claim 6, wherein said cell is a fetal fibroblast.

10. The cell of claim 6, wherein said cell is a B-cell.

11. A method for producing an isolated transgenic bovine fibroblast cell having reduced expression of functional prion protein, comprising:
   (a) introducing a first prion gene targeting vector into a bovine fibroblast cell under conditions that allow homologous recombination between said first vector and a first allele of an endogenous prion nucleic acid in said cell, thereby introducing a hemizygous mutation in said cell;
   (b) isolating said bovine fibroblast cell containing said hemizygous mutation; and
   (c) introducing a second prion gene targeting vector having a different selectable marker than said first vector into said bovine fibroblast cell of step (b) under conditions that allow homologous recombination between said second vector and a second allele of an endogenous prion nucleic acid in said cell, thereby introducing a homozygous mutation in said bovine fibroblast cell, wherein said mutation comprises an insertion of a STOP codon.

12. The method of claim 11, wherein said bovine fibroblast cell is a bovine fetal fibroblast.

13. A method for producing a transgenic bovine having reduced expression of functional prion protein, said method comprising the steps of:
   (a) inserting a diploid permeabilized cell into an enucleated metaphase II oocyte, wherein said cell comprises a first non-naturally occurring mutation in an endogenous prion nucleic acid, wherein said mutation comprises an insertion of a STOP codon; and
   (b) transferring said oocyte or an embryo formed from said oocyte into the uterus of a host bovine under conditions that allow said oocyte or said embryo to develop into a fetus, wherein the genome of said fetus comprises said non-naturally occurring mutation in said endogenous prion nucleic acid and wherein said fetus exhibits reduced functional prion production.

14. The method of claim 13, wherein said fetus develops into a viable offspring.

* * * * *